US010835247B2

(12) United States Patent
Shelton, IV et al.

(10) Patent No.: US 10,835,247 B2
(45) Date of Patent: Nov. 17, 2020

(54) LOCKOUT ARRANGEMENTS FOR SURGICAL END EFFECTORS

(71) Applicant: Ethicon Endo-Surgery, LLC, Guaynabo, PR (US)

(72) Inventors: Frederick E. Shelton, IV, Hillsboro, OH (US); Jason L. Harris, Lebanon, OH (US); Gregory J. Bakos, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 580 days.

(21) Appl. No.: 15/386,221

(22) Filed: Dec. 21, 2016

(65) Prior Publication Data

US 2018/0168646 A1     Jun. 21, 2018

(51) Int. Cl.
*A61B 17/072*     (2006.01)
*A61B 17/068*     (2006.01)
(Continued)

(52) U.S. Cl.
CPC .... *A61B 17/07207* (2013.01); *A61B 17/0682* (2013.01); *A61B 34/30* (2016.02);
(Continued)

(58) Field of Classification Search
CPC .............. A61B 17/07207; A61B 90/03; A61B 2017/0688; A61B 2017/07278; A61B 2017/7285; A61B 2017/7271; A61B 2017/0046; A61B 2017/00464; A61B 2017/00309; A61B 2017/07557;
(Continued)

(56) References Cited

U.S. PATENT DOCUMENTS 66,052 A    6/1867   Smith
662,587 A   11/1900   Blake
(Continued)

FOREIGN PATENT DOCUMENTS

AU    2011218702 B2    6/2013
AU    2012200178 B2    7/2013
(Continued)

OTHER PUBLICATIONS

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
(Continued)

*Primary Examiner* — Robert F Long
*Assistant Examiner* — Eduardo R Ferrero

(57) ABSTRACT

Surgical end effectors having an empty and missing cartridge lockout are disclosed. The surgical end effectors can comprise a first jaw, a second jaw rotatably coupled to the first jaw, and a multi-function firing member configured to translate during a firing stroke, wherein the firing member comprises a notch. The surgical end effectors can also include a lockout spring comprising a hook. The notch in the firing member can be aligned to receive the hook during the firing stroke unless an unfired staple cartridge is positioned in the first jaw. A sled assembly of the unfired staple cartridge can be positioned to deflect the hook out of alignment with the notch.

20 Claims, 68 Drawing Sheets

(51) Int. Cl.
*A61B 90/00* (2016.01)
*A61B 34/30* (2016.01)
*A61B 17/00* (2006.01)
*A61B 17/29* (2006.01)

(52) U.S. Cl.
CPC .... *A61B 90/03* (2016.02); *A61B 2017/00017* (2013.01); *A61B 2017/00039* (2013.01); *A61B 2017/0046* (2013.01); *A61B 2017/00309* (2013.01); *A61B 2017/00398* (2013.01); *A61B 2017/00464* (2013.01); *A61B 2017/00473* (2013.01); *A61B 2017/00477* (2013.01); *A61B 2017/00685* (2013.01); *A61B 2017/00734* (2013.01); *A61B 2017/00964* (2013.01); *A61B 2017/0725* (2013.01); *A61B 2017/07214* (2013.01); *A61B 2017/07221* (2013.01); *A61B 2017/07228* (2013.01); *A61B 2017/07242* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2017/2927* (2013.01); *A61B 2017/2929* (2013.01); *A61B 2017/2931* (2013.01); *A61B 2017/2933* (2013.01); *A61B 2090/034* (2016.02); *A61B 2090/065* (2016.02); *A61B 2090/0801* (2016.02); *A61B 2090/0811* (2016.02); *A61B 2090/0814* (2016.02); *A61B 2090/08021* (2016.02)

(58) Field of Classification Search
CPC .... A61B 2017/2927; A61B 2017/2933; A61B 2090/065; A61B 2090/034; A61B 2090/0814; A61B 2090/0811
See application file for complete search history.

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 951,393 A | 3/1910 | Hahn |
| 1,188,721 A | 6/1916 | Bittner |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,037,727 A | 4/1936 | La Chapelle |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Lee |
| 2,441,096 A | 5/1948 | Happe |
| 2,448,741 A | 9/1948 | Scott et al. |
| 2,450,527 A | 10/1948 | Smith |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,957,353 A | 10/1960 | Lewis |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,883,624 A | 5/1975 | McKenzie et al. |
| 3,885,491 A | 5/1975 | Curtis |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |

(56) References Cited

U.S. PATENT DOCUMENTS

| | | |
|---|---|---|
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,981,051 A | 9/1976 | Brumlik |
| 4,025,216 A | 5/1977 | Hives |
| 4,027,746 A | 6/1977 | Kine |
| 4,034,143 A | 7/1977 | Sweet |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,154,122 A | 5/1979 | Severin |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,423,456 A | 12/1983 | Zaidenweber |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,478,220 A | 10/1984 | Di Giovanni et al. |
| 4,480,641 A | 11/1984 | Failla et al. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |

(56) References Cited

U.S. PATENT DOCUMENTS

| | | |
|---|---|---|
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,914 A | 10/1986 | Ueda |
| 4,619,262 A | 10/1986 | Taylor |
| 4,619,391 A | 10/1986 | Sharkany et al. |
| D287,278 S | 12/1986 | Spreckelmeier |
| 4,628,459 A | 12/1986 | Shinohara et al. |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| D298,967 S | 12/1988 | Hunt |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,955,959 A | 9/1990 | Tompkins et al. |
| 4,957,212 A | 9/1990 | Duck et al. |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,973,274 A | 11/1990 | Hirukawa |
| 4,973,302 A | 11/1990 | Armour et al. |
| 4,978,049 A | 12/1990 | Green |
| 4,978,333 A | 12/1990 | Broadwin et al. |

(56) References Cited

U.S. PATENT DOCUMENTS

| | | |
|---|---|---|
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,035,040 A | 7/1991 | Kerrigan et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A * | 4/1992 | Tompkins ........ A61B 17/07207 227/178.1 |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A * | 7/1992 | Schulze ........... A61B 17/07207 227/175.2 |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |

(56) References Cited

U.S. PATENT DOCUMENTS

| | | |
|---|---|---|
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,292,053 A | 3/1994 | Bilotti et al. |
| 5,293,024 A | 3/1994 | Sugahara et al. |
| 5,297,714 A | 3/1994 | Kramer |
| 5,304,204 A | 4/1994 | Bregen |
| D347,474 S | 5/1994 | Olson |
| 5,307,976 A * | 5/1994 | Olson ............ A61B 17/07207 227/175.3 |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A * | 3/1995 | Savage ............ A61B 17/07207 227/175.3 |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,654 A | 7/1995 | Nic |
| 5,431,668 A | 7/1995 | Burbank, III et al. |

(56) References Cited

U.S. PATENT DOCUMENTS

| | | |
|---|---|---|
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,443,197 A | 8/1995 | Malis et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A * | 1/1996 | Olson ............ A61B 17/07207 227/176.1 |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |

(56) References Cited

U.S. PATENT DOCUMENTS

| | | |
|---|---|---|
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| D381,077 S | 7/1997 | Hunt |
| 5,643,291 A | 7/1997 | Pier et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A * | 10/1997 | Bittner ............ A61B 17/07207 227/175.2 |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |

(56) References Cited

U.S. PATENT DOCUMENTS

| | | | |
|---|---|---|---|
| 5,706,998 A | 1/1998 | Plyley et al. | |
| 5,707,392 A | 1/1998 | Kortenbach | |
| 5,709,334 A | 1/1998 | Sorrentino et al. | |
| 5,709,335 A | 1/1998 | Heck | |
| 5,709,680 A | 1/1998 | Yates et al. | |
| 5,709,706 A | 1/1998 | Kienzle et al. | |
| 5,711,472 A | 1/1998 | Bryan | |
| 5,712,460 A | 1/1998 | Carr et al. | |
| 5,713,128 A | 2/1998 | Schrenk et al. | |
| 5,713,505 A | 2/1998 | Huitema | |
| 5,713,895 A | 2/1998 | Lontine et al. | |
| 5,713,896 A | 2/1998 | Nardella | |
| 5,713,920 A | 2/1998 | Bezwada et al. | |
| 5,715,604 A | 2/1998 | Lanzoni | |
| 5,715,987 A | 2/1998 | Kelley et al. | |
| 5,715,988 A * | 2/1998 | Palmer | A61B 17/07207 227/175.3 |
| 5,716,366 A | 2/1998 | Yates | |
| 5,718,359 A * | 2/1998 | Palmer | A61B 17/07207 227/175.2 |
| 5,718,360 A | 2/1998 | Green et al. | |
| 5,718,548 A | 2/1998 | Cotellessa | |
| 5,718,714 A | 2/1998 | Livneh | |
| 5,720,744 A | 2/1998 | Eggleston et al. | |
| D393,067 S | 3/1998 | Geary et al. | |
| 5,724,025 A | 3/1998 | Tavori | |
| 5,725,536 A | 3/1998 | Oberlin et al. | |
| 5,725,554 A | 3/1998 | Simon et al. | |
| 5,728,110 A | 3/1998 | Vidal et al. | |
| 5,728,113 A | 3/1998 | Sherts | |
| 5,728,121 A | 3/1998 | Bimbo et al. | |
| 5,730,758 A | 3/1998 | Allgeyer | |
| 5,732,821 A | 3/1998 | Stone et al. | |
| 5,732,871 A | 3/1998 | Clark et al. | |
| 5,732,872 A | 3/1998 | Bolduc et al. | |
| 5,733,308 A | 3/1998 | Daugherty et al. | |
| 5,735,445 A | 4/1998 | Vidal et al. | |
| 5,735,848 A | 4/1998 | Yates et al. | |
| 5,735,874 A | 4/1998 | Measamer et al. | |
| 5,738,474 A | 4/1998 | Blewett | |
| 5,738,629 A | 4/1998 | Moll et al. | |
| 5,738,648 A | 4/1998 | Lands et al. | |
| 5,741,271 A | 4/1998 | Nakao et al. | |
| 5,743,456 A | 4/1998 | Jones et al. | |
| 5,747,953 A | 5/1998 | Philipp | |
| 5,749,889 A | 5/1998 | Bacich et al. | |
| 5,749,893 A | 5/1998 | Vidal et al. | |
| 5,749,896 A | 5/1998 | Cook | |
| 5,749,968 A | 5/1998 | Melanson et al. | |
| 5,752,644 A | 5/1998 | Bolanos et al. | |
| 5,752,965 A | 5/1998 | Francis et al. | |
| 5,752,970 A | 5/1998 | Yoon | |
| 5,755,717 A | 5/1998 | Yates et al. | |
| 5,758,814 A | 6/1998 | Gallagher et al. | |
| 5,762,255 A | 6/1998 | Chrisman et al. | |
| 5,762,256 A | 6/1998 | Mastri et al. | |
| 5,766,188 A | 6/1998 | Igaki | |
| 5,766,205 A | 6/1998 | Zvenyatsky et al. | |
| 5,769,303 A | 6/1998 | Knodel et al. | |
| 5,769,748 A | 6/1998 | Eyerly et al. | |
| 5,769,791 A | 6/1998 | Benaron et al. | |
| 5,769,892 A | 6/1998 | Kingwell | |
| 5,772,379 A | 6/1998 | Evensen | |
| 5,772,578 A | 6/1998 | Heimberger et al. | |
| 5,772,659 A | 6/1998 | Becker et al. | |
| 5,773,991 A | 6/1998 | Chen | |
| 5,776,130 A | 7/1998 | Buysse et al. | |
| 5,778,939 A | 7/1998 | Hok-Yin | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,396 A | 7/1998 | Mastri et al. | |
| 5,782,397 A | 7/1998 | Koukline | |
| 5,782,748 A | 7/1998 | Palmer et al. | |
| 5,782,749 A | 7/1998 | Riza | |
| 5,782,859 A | 7/1998 | Nicholas et al. | |
| 5,784,934 A | 7/1998 | Izumisawa | |
| 5,785,232 A | 7/1998 | Vidal et al. | |
| 5,785,647 A | 7/1998 | Tompkins et al. | |
| 5,787,897 A | 8/1998 | Kieturakis | |
| 5,791,231 A | 8/1998 | Cohn et al. | |
| 5,792,135 A | 8/1998 | Madhani et al. | |
| 5,792,162 A | 8/1998 | Jolly et al. | |
| 5,792,165 A | 8/1998 | Klieman et al. | |
| 5,792,573 A | 8/1998 | Pitzen et al. | |
| 5,794,834 A | 8/1998 | Hamblin et al. | |
| 5,796,188 A | 8/1998 | Bays | |
| 5,797,536 A | 8/1998 | Smith et al. | |
| 5,797,537 A | 8/1998 | Oberlin et al. | |
| 5,797,538 A | 8/1998 | Heaton et al. | |
| 5,797,637 A | 8/1998 | Ervin | |
| 5,797,906 A | 8/1998 | Rhum et al. | |
| 5,797,927 A | 8/1998 | Yoon | |
| 5,797,941 A | 8/1998 | Schulze et al. | |
| 5,797,959 A | 8/1998 | Castro et al. | |
| 5,799,857 A | 9/1998 | Robertson et al. | |
| 5,800,379 A | 9/1998 | Edwards | |
| 5,800,423 A | 9/1998 | Jensen | |
| 5,804,726 A | 9/1998 | Geib et al. | |
| 5,804,936 A | 9/1998 | Brodsky et al. | |
| 5,806,676 A | 9/1998 | Wasgien | |
| 5,807,376 A | 9/1998 | Viola et al. | |
| 5,807,378 A | 9/1998 | Jensen et al. | |
| 5,807,393 A | 9/1998 | Williamson, IV et al. | |
| 5,809,441 A | 9/1998 | McKee | |
| 5,810,721 A | 9/1998 | Mueller et al. | |
| 5,810,811 A | 9/1998 | Yates et al. | |
| 5,810,846 A | 9/1998 | Virnich et al. | |
| 5,810,855 A | 9/1998 | Rayburn et al. | |
| 5,813,813 A | 9/1998 | Daum et al. | |
| 5,814,055 A | 9/1998 | Knodel et al. | |
| 5,814,057 A | 9/1998 | Oi et al. | |
| 5,816,471 A | 10/1998 | Plyley et al. | |
| 5,817,084 A | 10/1998 | Jensen | |
| 5,817,091 A | 10/1998 | Nardella et al. | |
| 5,817,093 A | 10/1998 | Williamson, IV et al. | |
| 5,817,109 A | 10/1998 | McGarry et al. | |
| 5,817,119 A | 10/1998 | Klieman et al. | |
| 5,820,009 A | 10/1998 | Melling et al. | |
| 5,823,066 A | 10/1998 | Huitema et al. | |
| 5,824,333 A | 10/1998 | Scopelianos et al. | |
| 5,826,776 A | 10/1998 | Schulze et al. | |
| 5,827,271 A | 10/1998 | Buysse et al. | |
| 5,827,298 A | 10/1998 | Hart et al. | |
| 5,829,662 A | 11/1998 | Allen et al. | |
| 5,830,598 A | 11/1998 | Patterson | |
| 5,833,690 A | 11/1998 | Yates et al. | |
| 5,833,695 A | 11/1998 | Yoon | |
| 5,833,696 A | 11/1998 | Whitfield et al. | |
| 5,836,503 A | 11/1998 | Ehrenfels et al. | |
| 5,836,960 A | 11/1998 | Kolesa et al. | |
| 5,839,369 A | 11/1998 | Chatterjee et al. | |
| 5,839,639 A | 11/1998 | Sauer et al. | |
| 5,841,284 A | 11/1998 | Takahashi | |
| 5,843,021 A | 12/1998 | Edwards et al. | |
| 5,843,096 A | 12/1998 | Igaki et al. | |
| 5,843,097 A | 12/1998 | Mayenberger et al. | |
| 5,843,122 A | 12/1998 | Riza | |
| 5,843,132 A | 12/1998 | Ilvento | |
| 5,843,169 A | 12/1998 | Taheri | |
| 5,846,254 A | 12/1998 | Schulze et al. | |
| 5,847,566 A | 12/1998 | Marritt et al. | |
| 5,849,011 A | 12/1998 | Jones et al. | |
| 5,849,020 A | 12/1998 | Long et al. | |
| 5,849,023 A | 12/1998 | Mericle | |
| 5,851,179 A | 12/1998 | Ritson et al. | |
| 5,851,212 A | 12/1998 | Zirps et al. | |
| 5,853,366 A | 12/1998 | Dowlatshahi | |
| 5,855,311 A | 1/1999 | Hamblin et al. | |
| 5,855,583 A | 1/1999 | Wang et al. | |
| 5,860,581 A | 1/1999 | Robertson et al. | |
| 5,860,975 A | 1/1999 | Goble et al. | |
| 5,865,361 A | 2/1999 | Milliman et al. | |
| 5,865,638 A | 2/1999 | Trafton | |

(56) References Cited

U.S. PATENT DOCUMENTS

| | | | |
|---|---|---|---|
| 5,868,361 A | 2/1999 | Rinderer |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A * | 3/2000 | Mastri ............. A61B 17/07207 227/176.1 |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,667 A | 3/2000 | Manna et al. |
| 6,037,724 A | 3/2000 | Buss et al. |
| 6,037,927 A | 3/2000 | Rosenberg |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |

(56) References Cited

U.S. PATENT DOCUMENTS

| | | |
|---|---|---|
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A * | 8/2000 | Alli ................. A61B 17/07207 227/175.2 |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,904 B1 | 3/2001 | Ouchi |
| 6,209,414 B1 | 4/2001 | Uneme |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,270,508 B1 | 8/2001 | Klieman et al. |
| 6,270,916 B1 | 8/2001 | Sink et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |

(56) References Cited

U.S. PATENT DOCUMENTS

| | | |
|---|---|---|
| 6,346,077 B1 | 2/2002 | Taylor et al. |
| 6,348,061 B1 | 2/2002 | Whitman |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,458,077 B1 | 10/2002 | Boebel et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,527,782 B2 | 3/2003 | Hogg et al. |
| 6,527,785 B2 | 3/2003 | Sancoff et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,594,552 B1 | 7/2003 | Nowlin et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,323 B2 | 7/2003 | Melican et al. |

(56) References Cited

U.S. PATENT DOCUMENTS

| | | |
|---|---|---|
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,109 B2 | 4/2004 | Solingen |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |

(56) References Cited

U.S. PATENT DOCUMENTS

| | | |
|---|---|---|
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,775 B2 | 4/2006 | Gadberry et al. |
| 7,028,570 B2 | 4/2006 | Ohta et al. |
| 7,029,435 B2 | 4/2006 | Nakao |

(56) References Cited

U.S. PATENT DOCUMENTS

| | | |
|---|---|---|
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,687 B1 | 5/2006 | Reuss et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 * | 12/2006 | Schwemberger .... A61B 17/072 227/181.1 |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,195,627 B2 | 3/2007 | Amoah et al. |
| 7,196,911 B2 | 3/2007 | Takano et al. |
| D541,418 S | 4/2007 | Schechter et al. |
| 7,199,537 B2 | 4/2007 | Okamura et al. |
| 7,202,576 B1 | 4/2007 | Dechene et al. |
| 7,202,653 B2 | 4/2007 | Pai |

(56) References Cited

U.S. PATENT DOCUMENTS

| | | |
|---|---|---|
| 7,204,404 B2 | 4/2007 | Nguyen et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,045 B2 | 2/2008 | Clermonts |
| 7,336,048 B2 | 2/2008 | Lohr |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,377,918 B2 | 5/2008 | Amoah |
| 7,377,928 B2 | 5/2008 | Zubik et al. |
| RE40,388 E | 6/2008 | Gines |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |

(56) References Cited

U.S. PATENT DOCUMENTS

| | | |
|---|---|---|
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |
| 7,450,010 B1 | 11/2008 | Gravelle et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barley et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,543,730 B1 | 6/2009 | Marczyk |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,578,825 B2 | 8/2009 | Huebner |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| D605,201 S | 12/2009 | Lorenz et al. |
| 7,624,902 B2 | 12/2009 | Marczyk et al. |
| 7,624,903 B2 | 12/2009 | Green et al. |
| 7,625,370 B2 | 12/2009 | Hart et al. |

(56) References Cited

U.S. PATENT DOCUMENTS

| | | |
|---|---|---|
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,712,182 B2 | 5/2010 | Zeiler et al. |
| 7,713,190 B2 | 5/2010 | Brock et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,762,462 B2 | 7/2010 | Gelbman |
| 7,762,998 B2 | 7/2010 | Birk et al. |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |

(56) References Cited

U.S. PATENT DOCUMENTS

| | | |
|---|---|---|
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,085 B2 | 12/2010 | Silverman et al. |
| 7,846,149 B2 | 12/2010 | Jankowski |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,941,865 B2 | 5/2011 | Seman, Jr. et al. |
| 7,942,303 B2 | 5/2011 | Shah |

(56) References Cited

U.S. PATENT DOCUMENTS

| | | |
|---|---|---|
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,563 B2 | 7/2011 | Summerer |
| 7,979,137 B2 | 7/2011 | Tracey et al. |
| 7,980,443 B2 | 7/2011 | Scheib et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |

(56) References Cited

U.S. PATENT DOCUMENTS

| | | |
|---|---|---|
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,236,010 B2 | 8/2012 | Ortiz et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |

(56) References Cited

U.S. PATENT DOCUMENTS

| | | |
|---|---|---|
| 8,257,634 B2 | 9/2012 | Scirica |
| 8,258,745 B2 | 9/2012 | Smith et al. |
| 8,262,560 B2 | 9/2012 | Whitman |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,287,487 B2 | 10/2012 | Estes |
| 8,287,522 B2 | 10/2012 | Moses et al. |
| 8,287,561 B2 | 10/2012 | Nunez et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,801 B2 | 10/2012 | Dejima et al. |
| 8,292,888 B2 | 10/2012 | Whitman |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,343,150 B2 | 1/2013 | Artale |
| 8,347,978 B2 | 1/2013 | Forster et al. |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| D676,866 S | 2/2013 | Chaudhri |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,851 B2 | 3/2013 | Byun |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,222 B2 | 4/2013 | Whitfield et al. |
| 8,409,223 B2 | 4/2013 | Sorrentino et al. |
| 8,411,500 B2 | 4/2013 | Gapihan et al. |

(56) References Cited

U.S. PATENT DOCUMENTS

| | | |
|---|---|---|
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,490,851 B2 | 7/2013 | Blier et al. |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,518,024 B2 | 8/2013 | Williams et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |

(56) References Cited

U.S. PATENT DOCUMENTS

| | | |
|---|---|---|
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 * | 12/2013 | Hueil .............. A61B 17/07207 227/175.2 |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,427 B2 | 12/2013 | Viola |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,211 B2 | 4/2014 | Zemlok et al. |
| 8,708,213 B2 | 4/2014 | Shelton, IV et al. |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak et al. |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |

(56) References Cited

U.S. PATENT DOCUMENTS

| | | |
|---|---|---|
| D711,905 S | 8/2014 | Morrison et al. |
| 8,794,496 B2 | 8/2014 | Scirica |
| 8,794,497 B2 | 8/2014 | Zingman |
| 8,795,276 B2 | 8/2014 | Dietz et al. |
| 8,795,308 B2 | 8/2014 | Valin |
| 8,795,324 B2 | 8/2014 | Kawai et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,498 B2 | 9/2014 | Byrum et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,851,215 B2 | 10/2014 | Goto |
| 8,851,354 B2 | 10/2014 | Swensgard et al. |
| 8,852,174 B2 | 10/2014 | Burbank |
| 8,852,185 B2 | 10/2014 | Twomey |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 * | 12/2014 | Kostrzewski .... A61B 17/07207 227/175.1 |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,986,302 B2 | 3/2015 | Aldridge et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |

(56) References Cited

U.S. PATENT DOCUMENTS

| | | |
|---|---|---|
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,011,439 B2 | 4/2015 | Shalaby et al. |
| 9,011,471 B2 | 4/2015 | Timm et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,241 B2 | 6/2015 | Barner et al. |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,107,663 B2 | 8/2015 | Swensgard |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,769 B2 | 10/2015 | Stoddard et al. |
| 9,161,803 B2 | 10/2015 | Yates et al. |
| 9,161,807 B2 | 10/2015 | Garrison |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,380 B2 | 11/2015 | Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |

(56) References Cited

U.S. PATENT DOCUMENTS

| | | |
|---|---|---|
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,750 B2 | 1/2016 | Weir et al. |
| 9,226,751 B2 | 1/2016 | Shelton, IV et al. |
| 9,226,761 B2 | 1/2016 | Burbank |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,244,524 B2 | 1/2016 | Inoue et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,259,274 B2 | 2/2016 | Prisco |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,784 B2 | 3/2016 | Eggert et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,339,226 B2 | 5/2016 | van der Walt et al. |
| 9,345,477 B2 | 5/2016 | Anim et al. |
| 9,345,480 B2 | 5/2016 | Hessler et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| D758,433 S | 6/2016 | Lee et al. |
| D759,063 S | 6/2016 | Chen |
| 9,358,003 B2 | 6/2016 | Hall et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,364 B2 | 6/2016 | Smith et al. |
| 9,375,206 B2 | 6/2016 | Vidal et al. |
| 9,375,232 B2 | 6/2016 | Hunt et al. |
| 9,375,255 B2 | 6/2016 | Houser et al. |
| 9,381,058 B2 | 7/2016 | Houser et al. |
| 9,386,983 B2 | 7/2016 | Swensgard et al. |

(56) References Cited

U.S. PATENT DOCUMENTS

| | | |
|---|---|---|
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,398,911 B2 | 7/2016 | Auld |
| D763,277 S | 8/2016 | Ahmed et al. |
| 9,402,604 B2 | 8/2016 | Williams et al. |
| 9,402,626 B2 | 8/2016 | Ortiz et al. |
| 9,402,627 B2 | 8/2016 | Stevenson et al. |
| 9,408,604 B2 | 8/2016 | Shelton, IV et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,427,223 B2 | 8/2016 | Park et al. |
| 9,427,231 B2 | 8/2016 | Racenet et al. |
| D767,624 S | 9/2016 | Lee et al. |
| 9,433,411 B2 | 9/2016 | Racenet et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,451,958 B2 | 9/2016 | Shelton, IV et al. |
| D768,152 S | 10/2016 | Gutierrez et al. |
| 9,461,340 B2 | 10/2016 | Li et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| D770,476 S | 11/2016 | Jitkoff et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,492,192 B2 | 11/2016 | To et al. |
| 9,498,213 B2 | 11/2016 | Marczyk et al. |
| 9,498,219 B2 | 11/2016 | Moore et al. |
| 9,504,483 B2 | 11/2016 | Houser et al. |
| 9,504,521 B2 | 11/2016 | Deutmeyer et al. |
| D775,336 S | 12/2016 | Shelton, IV et al. |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,521,996 B2 | 12/2016 | Armstrong |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| D776,683 S | 1/2017 | Gobinski et al. |
| D777,773 S | 1/2017 | Shi |
| 9,532,783 B2 | 1/2017 | Swayze et al. |
| 9,539,726 B2 | 1/2017 | Simaan et al. |
| 9,545,258 B2 | 1/2017 | Smith et al. |
| 9,549,732 B2 | 1/2017 | Yates et al. |
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,554,812 B2 | 1/2017 | Inkpen et al. |
| 9,559,624 B2 | 1/2017 | Philipp |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,062 B2 | 2/2017 | Boudreaux |
| 9,566,065 B2 | 2/2017 | Knodel |
| 9,566,067 B2 | 2/2017 | Milliman et al. |
| 9,572,574 B2 | 2/2017 | Shelton, IV et al. |
| 9,572,577 B2 | 2/2017 | Lloyd et al. |
| 9,572,592 B2 | 2/2017 | Price et al. |
| 9,574,644 B2 | 2/2017 | Parihar |
| D780,803 S | 3/2017 | Gill et al. |
| D781,879 S | 3/2017 | Butcher et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,080 B2 | 4/2017 | Whitfield et al. |
| 9,614,258 B2 | 4/2017 | Takahashi et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,629,652 B2 | 4/2017 | Mumaw et al. |
| 9,629,814 B2 | 4/2017 | Widenhouse et al. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,111 B2 | 5/2017 | Wenchell |
| 9,636,850 B2 | 5/2017 | Stopek et al. |
| 9,641,122 B2 | 5/2017 | Romanowich et al. |
| 9,642,620 B2 | 5/2017 | Baxter, III et al. |
| 9,649,096 B2 | 5/2017 | Sholev |
| 9,649,110 B2 | 5/2017 | Parihar et al. |

(56) References Cited

U.S. PATENT DOCUMENTS

| | | |
|---|---|---|
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,624 B2 | 5/2017 | Shelton, IV et al. |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,675,344 B2 | 6/2017 | Combrowski et al. |
| 9,675,351 B2 | 6/2017 | Hodgkinson et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,321 B2 | 7/2017 | Shelton, IV et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,005 B2 | 7/2017 | Strobl et al. |
| 9,707,026 B2 | 7/2017 | Malackowski et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,713,474 B2 | 7/2017 | Lorenz |
| 9,717,497 B2 | 8/2017 | Zerkle et al. |
| 9,717,498 B2 | 8/2017 | Aranyi et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,635 B2 | 10/2017 | Takei |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,561 B2 | 11/2017 | Forsell |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |

(56) References Cited

U.S. PATENT DOCUMENTS

| | | |
|---|---|---|
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,877,721 B2 | 1/2018 | Schellin et al. |
| 9,877,723 B2 | 1/2018 | Hall et al. |
| 9,883,843 B2 | 2/2018 | Garlow |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,553 B2 | 3/2018 | Cole et al. |
| 9,907,620 B2 | 3/2018 | Shelton, IV et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,924,942 B2 | 3/2018 | Swayze et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,118 B2 | 4/2018 | Shelton, IV et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,955,965 B2 | 5/2018 | Chen et al. |
| 9,955,966 B2 | 5/2018 | Zergiebel |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| D819,680 S | 6/2018 | Nguyen |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,095 B2 | 6/2018 | Chowaniec et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,022,125 B2 | 7/2018 | Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,395 B2 | 8/2018 | Devengenzo et al. |
| 10,058,963 B2 | 8/2018 | Shelton, IV et al. |

(56) References Cited

U.S. PATENT DOCUMENTS

| | | |
|---|---|---|
| 10,064,620 B2 | 9/2018 | Gettinger et al. |
| 10,064,621 B2 | 9/2018 | Kerr et al. |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| D831,209 S | 10/2018 | Huitema et al. |
| 10,085,624 B2 | 10/2018 | Isoda et al. |
| 10,085,728 B2 | 10/2018 | Jogasaki et al. |
| 10,085,748 B2 | 10/2018 | Morgan et al. |
| 10,085,749 B2 | 10/2018 | Cappola et al. |
| 10,085,751 B2 | 10/2018 | Overmyer et al. |
| 10,085,806 B2 | 10/2018 | Hagn et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,642 B2 | 10/2018 | Baxter, III et al. |
| 10,099,303 B2 | 10/2018 | Yoshida et al. |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,111,679 B2 | 10/2018 | Baber et al. |
| 10,111,702 B2 | 10/2018 | Kostrzewski |
| 10,117,649 B2 | 11/2018 | Baxter, III et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,143,474 B2 | 12/2018 | Bucciaglia et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,154,841 B2 | 12/2018 | Weaner et al. |
| 10,159,482 B2 | 12/2018 | Swayze et al. |
| 10,159,483 B2 | 12/2018 | Beckman et al. |
| 10,163,589 B2 | 12/2018 | Zergiebel et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,616 B2 | 1/2019 | Murray et al. |
| 10,172,617 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,188,385 B2 | 1/2019 | Kerr et al. |
| 10,188,393 B2 | 1/2019 | Smith et al. |
| 10,188,394 B2 | 1/2019 | Shelton, IV et al. |
| D839,900 S | 2/2019 | Gan |
| 10,194,904 B2 | 2/2019 | Viola et al. |
| 10,194,910 B2 | 2/2019 | Shelton, IV et al. |
| 10,194,913 B2 | 2/2019 | Nalagatla et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,262 B2 | 2/2019 | Shelton, IV et al. |
| 10,219,832 B2 | 3/2019 | Bagwell et al. |
| 10,220,522 B2 | 3/2019 | Rockrohr |
| 10,226,249 B2 | 3/2019 | Jaworek et al. |
| 10,226,250 B2 | 3/2019 | Beckman et al. |
| 10,231,634 B2 | 3/2019 | Zand et al. |
| 10,231,653 B2 | 3/2019 | Bohm et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,058 B2 | 4/2019 | Omori et al. |
| 10,251,648 B2 | 4/2019 | Harris et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,074 B2 | 4/2019 | Shelton, IV et al. |
| 10,265,090 B2 | 4/2019 | Ingmanson et al. |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| 10,278,697 B2 | 5/2019 | Shelton, IV et al. |
| 10,278,702 B2 | 5/2019 | Shelton, IV et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,705 B2 | 5/2019 | Shelton, IV et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,792 B2 | 5/2019 | Huitema et al. |

(56) References Cited

U.S. PATENT DOCUMENTS

| | | |
|---|---|---|
| 10,299,817 B2 | 5/2019 | Shelton, IV et al. |
| 10,299,818 B2 | 5/2019 | Riva |
| 10,299,878 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,577 B2 | 6/2019 | Laurent et al. |
| 10,314,582 B2 | 6/2019 | Shelton, IV et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,342,533 B2 | 7/2019 | Shelton, IV et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0087048 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0158593 A1 | 10/2002 | Henderson et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1* | 1/2004 | Ehrenfels .......... A61B 17/07207 227/176.1 |
| 2004/0024457 A1 | 2/2004 | Boyce et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0085180 A1 | 5/2004 | Juang |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0232195 A1* | 11/2004 | Shelton, IV ...... A61B 17/07207 227/175.1 |
| 2004/0232200 A1* | 11/2004 | Shelton, IV ...... A61B 17/07207 227/176.1 |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Deli et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |

(56) References Cited

U.S. PATENT DOCUMENTS

| | | |
|---|---|---|
| 2005/0023324 A1* | 2/2005 | Doll .............. A61B 17/07207 227/175.2 |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0173490 A1* | 8/2005 | Shelton, IV ..... A61B 17/07207 227/175.2 |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0022014 A1* | 2/2006 | Shelton, IV ..... A61B 17/07207 227/175.2 |
| 2006/0022015 A1* | 2/2006 | Shelton, IV ..... A61B 17/07207 227/176.1 |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0176031 A1 | 8/2006 | Forman et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0235368 A1 | 10/2006 | Oz |
| 2006/0244460 A1 | 11/2006 | Weaver |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1* | 1/2007 | Shelton, IV ......... A61B 17/072 606/157 |
| 2007/0016235 A1 | 1/2007 | Tanaka et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0102475 A1* | 5/2007 | Ortiz ............. A61B 17/07207 227/175.2 |
| 2007/0106113 A1 | 5/2007 | Ravo |
| 2007/0106317 A1 | 5/2007 | Shelton et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0155010 A1 | 7/2007 | Farnsworth et al. |

(56) References Cited

U.S. PATENT DOCUMENTS

| | | |
|---|---|---|
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0262592 A1 | 11/2007 | Hwang et al. |
| 2007/0275035 A1 | 11/2007 | Herman et al. |
| 2007/0276409 A1 | 11/2007 | Ortiz et al. |
| 2007/0278277 A1 * | 12/2007 | Wixey ............... A61B 17/0686 227/175.2 |
| 2007/0279011 A1 | 12/2007 | Jones et al. |
| 2007/0286892 A1 | 12/2007 | Herzberg et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0042861 A1 | 2/2008 | Dacquay et al. |
| 2008/0051833 A1 | 2/2008 | Gramuglia et al. |
| 2008/0064921 A1 | 3/2008 | Larkin et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0154299 A1 | 6/2008 | Livneh |
| 2008/0154335 A1 | 6/2008 | Thrope et al. |
| 2008/0167670 A1 * | 7/2008 | Shelton ............ A61B 17/07207 606/167 |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0234709 A1 | 9/2008 | Houser |
| 2008/0242939 A1 | 10/2008 | Johnston |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton et al. |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0092651 A1 | 4/2009 | Shah et al. |
| 2009/0099579 A1 | 4/2009 | Nentwick et al. |
| 2009/0099876 A1 | 4/2009 | Whitman |
| 2009/0119011 A1 | 5/2009 | Kondo et al. |
| 2009/0131819 A1 | 5/2009 | Ritchie et al. |
| 2009/0132400 A1 | 5/2009 | Conway |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0221993 A1 | 9/2009 | Sohi et al. |
| 2009/0234273 A1 | 9/2009 | Intoccia et al. |
| 2009/0242610 A1 | 10/2009 | Shelton, IV et al. |
| 2009/0247368 A1 | 10/2009 | Chiang |
| 2009/0247901 A1 | 10/2009 | Zimmer |
| 2009/0248041 A1 | 10/2009 | Williams et al. |
| 2009/0253959 A1 | 10/2009 | Yoshie et al. |
| 2009/0255974 A1 | 10/2009 | Viola |
| 2009/0262078 A1 | 10/2009 | Pizzi |
| 2009/0270895 A1 | 10/2009 | Churchill et al. |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2010/0005035 A1 | 1/2010 | Carpenter et al. |
| 2010/0012703 A1 | 1/2010 | Calabrese et al. |
| 2010/0016888 A1 | 1/2010 | Calabrese et al. |
| 2010/0017715 A1 | 1/2010 | Balassanian |
| 2010/0023024 A1 | 1/2010 | Zeiner et al. |

(56) References Cited

U.S. PATENT DOCUMENTS

| | | |
|---|---|---|
| 2010/0030233 A1 | 2/2010 | Whitman et al. |
| 2010/0036370 A1 | 2/2010 | Mirel et al. |
| 2010/0051668 A1* | 3/2010 | Milliman ............ A61B 17/115 |
| | | 227/175.1 |
| 2010/0057118 A1 | 3/2010 | Dietz et al. |
| 2010/0065604 A1* | 3/2010 | Weng ............. A61B 17/07207 |
| | | 227/175.2 |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0241137 A1 | 9/2010 | Doyle et al. |
| 2010/0249497 A1 | 9/2010 | Peine et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0034910 A1 | 2/2011 | Ross et al. |
| 2011/0036891 A1 | 2/2011 | Zemlok et al. |
| 2011/0046667 A1 | 2/2011 | Culligan et al. |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0095064 A1 | 4/2011 | Taylor et al. |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0121049 A1 | 5/2011 | Malinouskas et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0230713 A1 | 9/2011 | Kleemann et al. |
| 2011/0238044 A1 | 9/2011 | Main et al. |
| 2011/0241597 A1 | 10/2011 | Zhu et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078139 A1 | 3/2012 | Aldridge et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0138660 A1* | 6/2012 | Shelton, IV ......... A61B 17/115 |
| | | 227/176.1 |
| 2012/0171539 A1 | 7/2012 | Rejman et al. |
| 2012/0175398 A1 | 7/2012 | Sandborn et al. |
| 2012/0197272 A1 | 8/2012 | Oray et al. |
| 2012/0211542 A1 | 8/2012 | Racenet |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2012/0303002 A1 | 11/2012 | Chowaniec et al. |
| 2013/0006227 A1 | 1/2013 | Takashino |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098965 A1* | 4/2013 | Kostrzewski .... A61B 17/07207 |
| | | 227/175.2 |
| 2013/0098970 A1 | 4/2013 | Racenet et al. |
| 2013/0105552 A1 | 5/2013 | Weir et al. |
| 2013/0116669 A1 | 5/2013 | Shelton, IV et al. |
| 2013/0123816 A1 | 5/2013 | Hodgkinson et al. |

(56) References Cited

U.S. PATENT DOCUMENTS

| | | |
|---|---|---|
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153636 A1 | 6/2013 | Shelton, IV et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0172878 A1 | 7/2013 | Smith |
| 2013/0175317 A1 | 7/2013 | Yates et al. |
| 2013/0214025 A1 | 8/2013 | Zemlok et al. |
| 2013/0233906 A1 | 9/2013 | Hess et al. |
| 2013/0238021 A1 | 9/2013 | Gross et al. |
| 2013/0245704 A1 | 9/2013 | Koltz et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256379 A1 | 10/2013 | Schmid et al. |
| 2013/0256380 A1 | 10/2013 | Schmid et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0317753 A1 | 11/2013 | Kamen et al. |
| 2013/0324982 A1 | 12/2013 | Smith et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0012289 A1 | 1/2014 | Snow et al. |
| 2014/0012299 A1 | 1/2014 | Stoddard et al. |
| 2014/0014705 A1 | 1/2014 | Baxter, III |
| 2014/0018832 A1 | 1/2014 | Shelton, IV |
| 2014/0039549 A1 | 2/2014 | Belsky et al. |
| 2014/0048580 A1 | 2/2014 | Merchant et al. |
| 2014/0081176 A1 | 3/2014 | Hassan |
| 2014/0094681 A1 | 4/2014 | Valentine et al. |
| 2014/0100558 A1 | 4/2014 | Schmitz et al. |
| 2014/0107640 A1 | 4/2014 | Yates et al. |
| 2014/0110453 A1* | 4/2014 | Wingardner ...... A61B 17/07207 227/175.2 |
| 2014/0110456 A1 | 4/2014 | Taylor |
| 2014/0115229 A1 | 4/2014 | Kothamasu et al. |
| 2014/0131418 A1 | 5/2014 | Kostrzewski |
| 2014/0151433 A1 | 6/2014 | Shelton, IV et al. |
| 2014/0158747 A1 | 6/2014 | Measamer et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0188159 A1 | 7/2014 | Steege |
| 2014/0207124 A1 | 7/2014 | Aldridge et al. |
| 2014/0207125 A1 | 7/2014 | Applegate et al. |
| 2014/0209658 A1 | 7/2014 | Skalla et al. |
| 2014/0224857 A1 | 8/2014 | Schmid |
| 2014/0228867 A1 | 8/2014 | Thomas et al. |
| 2014/0230595 A1 | 8/2014 | Butt et al. |
| 2014/0239041 A1* | 8/2014 | Zerkle ............ A61B 17/07207 227/176.1 |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0249573 A1 | 9/2014 | Arav |
| 2014/0263541 A1 | 9/2014 | Leimbach et al. |
| 2014/0263545 A1* | 9/2014 | Williams ............ A61B 17/068 227/175.2 |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291378 A1* | 10/2014 | Shelton, IV ..... A61B 17/00234 227/175.2 |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0309666 A1 | 10/2014 | Shelton, IV et al. |
| 2014/0330161 A1 | 11/2014 | Swayze et al. |
| 2014/0330579 A1 | 11/2014 | Cashman et al. |
| 2014/0367445 A1 | 12/2014 | Ingmanson et al. |
| 2014/0374130 A1 | 12/2014 | Nakamura et al. |
| 2014/0378950 A1 | 12/2014 | Chiu |
| 2015/0002089 A1 | 1/2015 | Rejman et al. |
| 2015/0008248 A1 | 1/2015 | Giordano et al. |
| 2015/0053737 A1 | 2/2015 | Leimbach et al. |
| 2015/0053742 A1 | 2/2015 | Shelton, IV et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083781 A1 | 3/2015 | Giordano et al. |
| 2015/0083782 A1 | 3/2015 | Scheib et al. |
| 2015/0088547 A1 | 3/2015 | Balram et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0108199 A1 | 4/2015 | Shelton, IV et al. |
| 2015/0122870 A1 | 5/2015 | Zemlok et al. |
| 2015/0134077 A1 | 5/2015 | Shelton, IV et al. |
| 2015/0148830 A1 | 5/2015 | Stulen et al. |
| 2015/0150554 A1 | 6/2015 | Soltz |
| 2015/0150620 A1 | 6/2015 | Miyamoto et al. |
| 2015/0173745 A1* | 6/2015 | Baxter, III ........ A61B 17/07207 227/175.3 |
| 2015/0173746 A1* | 6/2015 | Baxter, III ........ A61B 17/07207 227/180.1 |
| 2015/0173749 A1 | 6/2015 | Shelton, IV et al. |
| 2015/0173755 A1* | 6/2015 | Baxter, III ............ A61B 17/072 227/180.1 |
| 2015/0173756 A1* | 6/2015 | Baxter, III ........ A61B 17/07207 227/177.1 |
| 2015/0173789 A1 | 6/2015 | Baxter, III et al. |
| 2015/0182220 A1 | 7/2015 | Yates et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196348 A1 | 7/2015 | Yates et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0222212 A1 | 8/2015 | Iwata |
| 2015/0223868 A1 | 8/2015 | Brandt et al. |
| 2015/0231409 A1 | 8/2015 | Racenet et al. |
| 2015/0238118 A1 | 8/2015 | Legassey et al. |

(56) References Cited

U.S. PATENT DOCUMENTS

| | | |
|---|---|---|
| 2015/0272557 A1* | 10/2015 | Overmyer .............. A61B 17/068 606/1 |
| 2015/0272571 A1 | 10/2015 | Leimbach et al. |
| 2015/0272576 A1* | 10/2015 | Cappola .............. A61B 17/072 227/175.2 |
| 2015/0272580 A1 | 10/2015 | Leimbach et al. |
| 2015/0272582 A1 | 10/2015 | Leimbach et al. |
| 2015/0272604 A1 | 10/2015 | Chowaniec et al. |
| 2015/0289873 A1* | 10/2015 | Shelton, IV ..... A61B 17/07207 227/176.1 |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1* | 10/2015 | Huitema .............. A61B 17/068 227/176.1 |
| 2015/0297228 A1* | 10/2015 | Huitema .............. G06F 11/1425 227/176.1 |
| 2015/0297229 A1* | 10/2015 | Schellin .............. A61B 17/072 227/177.1 |
| 2015/0297233 A1* | 10/2015 | Huitema .............. A61B 17/0644 227/176.1 |
| 2015/0297234 A1* | 10/2015 | Schellin .............. A61B 17/0682 227/176.1 |
| 2015/0297235 A1* | 10/2015 | Harris .................. A61B 17/105 227/176.1 |
| 2015/0302539 A1 | 10/2015 | Mazar et al. |
| 2015/0303417 A1 | 10/2015 | Koeder et al. |
| 2015/0313594 A1 | 11/2015 | Shelton, IV et al. |
| 2015/0324317 A1* | 11/2015 | Collins .................. G16Z 99/00 710/106 |
| 2015/0327864 A1 | 11/2015 | Hodgkinson et al. |
| 2015/0336249 A1 | 11/2015 | Iwata et al. |
| 2015/0351762 A1 | 12/2015 | Vendely et al. |
| 2015/0351765 A1* | 12/2015 | Valentine .............. A61B 90/90 227/176.1 |
| 2015/0352699 A1 | 12/2015 | Sakai et al. |
| 2015/0366585 A1 | 12/2015 | Lemay et al. |
| 2015/0372265 A1 | 12/2015 | Morisaku et al. |
| 2015/0374361 A1 | 12/2015 | Gettinger et al. |
| 2015/0374363 A1* | 12/2015 | Laurent, IV ......... A61B 17/068 227/175.3 |
| 2015/0374369 A1 | 12/2015 | Yates et al. |
| 2015/0374371 A1 | 12/2015 | Richard et al. |
| 2015/0374372 A1 | 12/2015 | Zergiebel et al. |
| 2015/0374373 A1* | 12/2015 | Rector .............. A61B 17/0644 606/219 |
| 2015/0374375 A1 | 12/2015 | Shelton, IV et al. |
| 2015/0374378 A1 | 12/2015 | Giordano et al. |
| 2016/0000430 A1 | 1/2016 | Ming et al. |
| 2016/0000431 A1 | 1/2016 | Giordano et al. |
| 2016/0000437 A1 | 1/2016 | Giordano et al. |
| 2016/0000438 A1 | 1/2016 | Swayze et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0023342 A1 | 1/2016 | Koenig et al. |
| 2016/0030042 A1 | 2/2016 | Heinrich et al. |
| 2016/0051257 A1 | 2/2016 | Shelton, IV et al. |
| 2016/0058443 A1 | 3/2016 | Yates et al. |
| 2016/0066913 A1 | 3/2016 | Swayze et al. |
| 2016/0069449 A1 | 3/2016 | Kanai et al. |
| 2016/0074040 A1 | 3/2016 | Widenhouse et al. |
| 2016/0074103 A1 | 3/2016 | Sartor |
| 2016/0082161 A1 | 3/2016 | Zilberman et al. |
| 2016/0089137 A1 | 3/2016 | Hess et al. |
| 2016/0089146 A1 | 3/2016 | Harris et al. |
| 2016/0089149 A1 | 3/2016 | Harris et al. |
| 2016/0089198 A1 | 3/2016 | Arya et al. |
| 2016/0095585 A1 | 4/2016 | Zergiebel et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0166248 A1 | 6/2016 | Deville et al. |
| 2016/0166256 A1 | 6/2016 | Baxter, III et al. |
| 2016/0166308 A1 | 6/2016 | Manwaring et al. |
| 2016/0174974 A1 | 6/2016 | Schmid et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192977 A1 | 7/2016 | Manwaring et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199089 A1 | 7/2016 | Hess et al. |
| 2016/0199956 A1 | 7/2016 | Shelton, IV et al. |
| 2016/0206310 A1 | 7/2016 | Shelton, IV |
| 2016/0206314 A1 | 7/2016 | Scheib et al. |
| 2016/0220248 A1 | 8/2016 | Timm et al. |
| 2016/0220266 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235409 A1 | 8/2016 | Shelton, IV et al. |
| 2016/0235467 A1 | 8/2016 | Godara et al. |
| 2016/0235494 A1 | 8/2016 | Shelton, IV et al. |
| 2016/0242777 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249910 A1 | 9/2016 | Shelton, IV et al. |
| 2016/0249922 A1 | 9/2016 | Morgan et al. |
| 2016/0256071 A1 | 9/2016 | Shelton, IV et al. |
| 2016/0256154 A1 | 9/2016 | Shelton, IV et al. |
| 2016/0256159 A1 | 9/2016 | Pinjala et al. |
| 2016/0256160 A1 | 9/2016 | Shelton, IV et al. |
| 2016/0256185 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0270780 A1 | 9/2016 | Hall et al. |
| 2016/0278765 A1 | 9/2016 | Shelton, IV et al. |
| 2016/0287249 A1 | 10/2016 | Alexander, III et al. |
| 2016/0287250 A1 | 10/2016 | Shelton, IV et al. |
| 2016/0287253 A1 | 10/2016 | Shelton, IV et al. |
| 2016/0287279 A1 | 10/2016 | Bovay et al. |
| 2016/0310143 A1 | 10/2016 | Bettuchi |
| 2016/0331375 A1 | 11/2016 | Shelton, IV et al. |
| 2016/0345976 A1 | 12/2016 | Gonzalez et al. |
| 2016/0346034 A1 | 12/2016 | Arya et al. |
| 2016/0354085 A1 | 12/2016 | Shelton, IV et al. |
| 2016/0367122 A1 | 12/2016 | Ichimura et al. |
| 2016/0367246 A1 | 12/2016 | Baxter, III et al. |
| 2016/0367255 A1 | 12/2016 | Wise et al. |
| 2016/0374672 A1 | 12/2016 | Bear et al. |
| 2016/0374675 A1 | 12/2016 | Shelton, IV et al. |
| 2017/0000485 A1 | 1/2017 | Shelton, IV et al. |
| 2017/0007236 A1 | 1/2017 | Shelton, IV et al. |
| 2017/0007237 A1 | 1/2017 | Yates et al. |
| 2017/0007238 A1 | 1/2017 | Yates et al. |
| 2017/0007239 A1 | 1/2017 | Shelton, IV |
| 2017/0007241 A1 | 1/2017 | Shelton, IV et al. |
| 2017/0007243 A1 | 1/2017 | Shelton, IV et al. |
| 2017/0007244 A1 | 1/2017 | Shelton, IV et al. |
| 2017/0007245 A1 | 1/2017 | Shelton, IV et al. |
| 2017/0007246 A1 | 1/2017 | Shelton, IV et al. |
| 2017/0007247 A1 | 1/2017 | Shelton, IV et al. |
| 2017/0007248 A1 | 1/2017 | Shelton, IV et al. |
| 2017/0007249 A1 | 1/2017 | Shelton, IV et al. |
| 2017/0007250 A1 | 1/2017 | Shelton, IV et al. |
| 2017/0007251 A1 | 1/2017 | Yates et al. |
| 2017/0007347 A1 | 1/2017 | Jaworek et al. |
| 2017/0014125 A1 | 1/2017 | Shelton, IV et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0049444 A1 | 2/2017 | Schellin et al. |
| 2017/0049447 A1 | 2/2017 | Barton et al. |
| 2017/0049448 A1 | 2/2017 | Widenhouse et al. |
| 2017/0055986 A1 | 3/2017 | Harris et al. |

(56) References Cited

U.S. PATENT DOCUMENTS

| | | |
|---|---|---|
| 2017/0055991 A1 | 3/2017 | Kang |
| 2017/0055998 A1 | 3/2017 | Baxter, III et al. |
| 2017/0055999 A1 | 3/2017 | Baxter, III et al. |
| 2017/0056000 A1 | 3/2017 | Nalagatla et al. |
| 2017/0056002 A1 | 3/2017 | Nalagatla et al. |
| 2017/0056005 A1 | 3/2017 | Shelton, IV et al. |
| 2017/0056006 A1 | 3/2017 | Shelton, IV et al. |
| 2017/0056007 A1 | 3/2017 | Eckert et al. |
| 2017/0079642 A1 | 3/2017 | Overmyer et al. |
| 2017/0079643 A1 | 3/2017 | Yates et al. |
| 2017/0086827 A1 | 3/2017 | Vendely et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086832 A1 | 3/2017 | Harris et al. |
| 2017/0086836 A1 | 3/2017 | Harris et al. |
| 2017/0086837 A1 | 3/2017 | Vendely et al. |
| 2017/0086838 A1 | 3/2017 | Harris et al. |
| 2017/0086842 A1 | 3/2017 | Shelton, IV et al. |
| 2017/0086843 A1 | 3/2017 | Vendely et al. |
| 2017/0086844 A1 | 3/2017 | Vendely et al. |
| 2017/0095250 A1 | 4/2017 | Kostrzewski et al. |
| 2017/0119386 A1 | 5/2017 | Scheib et al. |
| 2017/0119390 A1 | 5/2017 | Schellin et al. |
| 2017/0119392 A1 | 5/2017 | Shelton, IV et al. |
| 2017/0119397 A1 | 5/2017 | Harris et al. |
| 2017/0135695 A1 | 5/2017 | Shelton, IV et al. |
| 2017/0135697 A1 | 5/2017 | Mozdzierz et al. |
| 2017/0150983 A1 | 6/2017 | Ingmanson et al. |
| 2017/0172382 A1 | 6/2017 | Nir et al. |
| 2017/0172550 A1 | 6/2017 | Mukherjee et al. |
| 2017/0172662 A1 | 6/2017 | Panescu et al. |
| 2017/0172672 A1 | 6/2017 | Bailey et al. |
| 2017/0182211 A1 | 6/2017 | Raxworthy et al. |
| 2017/0189019 A1 | 7/2017 | Harris et al. |
| 2017/0196558 A1 | 7/2017 | Morgan et al. |
| 2017/0196561 A1 | 7/2017 | Shelton, IV et al. |
| 2017/0196562 A1 | 7/2017 | Shelton, IV et al. |
| 2017/0196637 A1 | 7/2017 | Shelton, IV et al. |
| 2017/0196649 A1 | 7/2017 | Yates et al. |
| 2017/0202596 A1 | 7/2017 | Shelton, IV et al. |
| 2017/0209145 A1 | 7/2017 | Swayze et al. |
| 2017/0209146 A1 | 7/2017 | Yates et al. |
| 2017/0209226 A1 | 7/2017 | Overmyer et al. |
| 2017/0215881 A1 | 8/2017 | Shelton, IV et al. |
| 2017/0215943 A1 | 8/2017 | Allen, IV |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224334 A1 | 8/2017 | Worthington et al. |
| 2017/0224335 A1 | 8/2017 | Weaner et al. |
| 2017/0224339 A1 | 8/2017 | Huang et al. |
| 2017/0224342 A1 | 8/2017 | Worthington et al. |
| 2017/0224343 A1 | 8/2017 | Baxter, III et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0238928 A1 | 8/2017 | Morgan et al. |
| 2017/0238929 A1 | 8/2017 | Yates et al. |
| 2017/0245952 A1 | 8/2017 | Shelton, IV et al. |
| 2017/0249431 A1 | 8/2017 | Shelton, IV et al. |
| 2017/0258469 A1 | 9/2017 | Shelton, IV et al. |
| 2017/0265856 A1 | 9/2017 | Shelton, IV et al. |
| 2017/0281155 A1 | 10/2017 | Shelton, IV et al. |
| 2017/0281162 A1 | 10/2017 | Shelton, IV et al. |
| 2017/0281164 A1 | 10/2017 | Harris et al. |
| 2017/0281166 A1 | 10/2017 | Morgan et al. |
| 2017/0281167 A1 | 10/2017 | Shelton, IV et al. |
| 2017/0281168 A1 | 10/2017 | Shelton, IV et al. |
| 2017/0281169 A1 | 10/2017 | Harris et al. |
| 2017/0281171 A1 | 10/2017 | Shelton, IV et al. |
| 2017/0281172 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281177 A1 | 10/2017 | Harris et al. |
| 2017/0281179 A1 | 10/2017 | Shelton, IV et al. |
| 2017/0281180 A1 | 10/2017 | Morgan et al. |
| 2017/0281183 A1 | 10/2017 | Miller et al. |
| 2017/0281184 A1 | 10/2017 | Shelton, IV et al. |
| 2017/0281185 A1 | 10/2017 | Miller et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290584 A1 | 10/2017 | Jasemian et al. |
| 2017/0290585 A1 | 10/2017 | Shelton, IV et al. |
| 2017/0296169 A1 | 10/2017 | Yates et al. |
| 2017/0296170 A1 | 10/2017 | Shelton, IV et al. |
| 2017/0296171 A1 | 10/2017 | Shelton, IV et al. |
| 2017/0296172 A1 | 10/2017 | Harris et al. |
| 2017/0296173 A1 | 10/2017 | Shelton, IV et al. |
| 2017/0296177 A1 | 10/2017 | Harris et al. |
| 2017/0296178 A1 | 10/2017 | Miller et al. |
| 2017/0296179 A1 | 10/2017 | Shelton, IV et al. |
| 2017/0296180 A1 | 10/2017 | Harris et al. |
| 2017/0296185 A1 | 10/2017 | Swensgard et al. |
| 2017/0296189 A1 | 10/2017 | Vendely et al. |
| 2017/0296190 A1 | 10/2017 | Aronhalt et al. |
| 2017/0296191 A1 | 10/2017 | Shelton, IV et al. |
| 2017/0296213 A1 | 10/2017 | Swensgard et al. |
| 2017/0311944 A1 | 11/2017 | Morgan et al. |
| 2017/0311949 A1 | 11/2017 | Shelton, IV |
| 2017/0311950 A1 | 11/2017 | Shelton, IV et al. |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0319207 A1 | 11/2017 | Shelton, IV et al. |
| 2017/0319209 A1 | 11/2017 | Morgan et al. |
| 2017/0325813 A1 | 11/2017 | Aranyi et al. |
| 2017/0333034 A1 | 11/2017 | Morgan et al. |
| 2017/0333035 A1 | 11/2017 | Morgan et al. |
| 2017/0333070 A1 | 11/2017 | Laurent et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0354415 A1 | 12/2017 | Casasanta, Jr. et al. |
| 2017/0360441 A1 | 12/2017 | Sgroi |
| 2017/0360442 A1 | 12/2017 | Shelton, IV et al. |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367698 A1 | 12/2017 | Shelton, IV et al. |
| 2017/0367699 A1 | 12/2017 | Shelton, IV et al. |
| 2017/0367700 A1 | 12/2017 | Leimbach et al. |
| 2017/0367991 A1 | 12/2017 | Widenhouse et al. |
| 2018/0000483 A1 | 1/2018 | Leimbach et al. |
| 2018/0000545 A1 | 1/2018 | Giordano et al. |
| 2018/0008270 A1 | 1/2018 | Moore et al. |
| 2018/0008271 A1 | 1/2018 | Moore et al. |
| 2018/0008356 A1 | 1/2018 | Giordano et al. |
| 2018/0008357 A1 | 1/2018 | Giordano et al. |
| 2018/0028184 A1 | 2/2018 | Shelton, IV et al. |
| 2018/0028185 A1 | 2/2018 | Shelton, IV et al. |
| 2018/0042611 A1 | 2/2018 | Swayze et al. |
| 2018/0049824 A1 | 2/2018 | Harris et al. |
| 2018/0049883 A1 | 2/2018 | Moskowitz et al. |
| 2018/0055513 A1 | 3/2018 | Shelton, IV et al. |
| 2018/0055524 A1 | 3/2018 | Shelton, IV et al. |
| 2018/0055525 A1 | 3/2018 | Shelton, IV et al. |
| 2018/0055526 A1 | 3/2018 | Shelton, IV et al. |
| 2018/0064437 A1 | 3/2018 | Yates et al. |
| 2018/0064440 A1 | 3/2018 | Shelton, IV et al. |
| 2018/0064441 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070939 A1 | 3/2018 | Giordano et al. |
| 2018/0070942 A1 | 3/2018 | Shelton, IV et al. |
| 2018/0078248 A1 | 3/2018 | Swayze et al. |
| 2018/0085116 A1 | 3/2018 | Yates et al. |
| 2018/0085117 A1 | 3/2018 | Shelton, IV et al. |
| 2018/0103952 A1 | 4/2018 | Aronhalt et al. |
| 2018/0103953 A1 | 4/2018 | Shelton, IV et al. |
| 2018/0103955 A1 | 4/2018 | Shelton, IV et al. |
| 2018/0110516 A1 | 4/2018 | Baxter, III et al. |
| 2018/0110518 A1 | 4/2018 | Overmyer et al. |

(56) References Cited

U.S. PATENT DOCUMENTS

| | | |
|---|---|---|
| 2018/0110519 A1 | 4/2018 | Lytle, IV et al. |
| 2018/0110520 A1 | 4/2018 | Shelton, IV et al. |
| 2018/0110521 A1 | 4/2018 | Shelton, IV et al. |
| 2018/0110522 A1 | 4/2018 | Shelton, IV et al. |
| 2018/0110523 A1 | 4/2018 | Shelton, IV |
| 2018/0110574 A1 | 4/2018 | Shelton, IV et al. |
| 2018/0110575 A1 | 4/2018 | Shelton, IV et al. |
| 2018/0114591 A1 | 4/2018 | Pribanic et al. |
| 2018/0116658 A1 | 5/2018 | Aronhalt, IV et al. |
| 2018/0116662 A1 | 5/2018 | Shelton, IV et al. |
| 2018/0116665 A1 | 5/2018 | Hall et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125489 A1 | 5/2018 | Leimbach et al. |
| 2018/0125590 A1 | 5/2018 | Giordano et al. |
| 2018/0126504 A1 | 5/2018 | Shelton, IV et al. |
| 2018/0132845 A1 | 5/2018 | Schmid et al. |
| 2018/0132850 A1 | 5/2018 | Leimbach et al. |
| 2018/0132851 A1 | 5/2018 | Hall et al. |
| 2018/0132952 A1 | 5/2018 | Spivey et al. |
| 2018/0133856 A1 | 5/2018 | Shelton, IV et al. |
| 2018/0140299 A1 | 5/2018 | Weaner et al. |
| 2018/0140368 A1 | 5/2018 | Shelton, IV et al. |
| 2018/0146960 A1 | 5/2018 | Shelton, IV et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168576 A1 | 6/2018 | Hunter et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168581 A1 | 6/2018 | Hunter et al. |
| 2018/0168582 A1 | 6/2018 | Swayze et al. |
| 2018/0168583 A1 | 6/2018 | Hunter et al. |
| 2018/0168584 A1 | 6/2018 | Harris et al. |
| 2018/0168585 A1 | 6/2018 | Shelton, IV et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168595 A1 | 6/2018 | Overmyer et al. |
| 2018/0168596 A1 | 6/2018 | Beckman et al. |
| 2018/0168597 A1 | 6/2018 | Fanelli et al. |
| 2018/0168598 A1 | 6/2018 | Shelton, IV et al. |
| 2018/0168599 A1 | 6/2018 | Bakos et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168611 A1 | 6/2018 | Shelton, IV et al. |
| 2018/0168612 A1 | 6/2018 | Shelton, IV et al. |
| 2018/0168613 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168616 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168620 A1 | 6/2018 | Huang et al. |
| 2018/0168621 A1 | 6/2018 | Shelton, IV et al. |
| 2018/0168622 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168634 A1 | 6/2018 | Harris et al. |
| 2018/0168635 A1 | 6/2018 | Shelton, IV et al. |
| 2018/0168636 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168643 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168646 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0199940 A1 | 7/2018 | Zergiebel et al. |
| 2018/0206843 A1 | 7/2018 | Yates et al. |
| 2018/0206906 A1 | 7/2018 | Moua et al. |
| 2018/0214147 A1 | 8/2018 | Merchant et al. |
| 2018/0221046 A1 | 8/2018 | Demmy et al. |
| 2018/0221050 A1 | 8/2018 | Kostrzewski et al. |
| 2018/0228490 A1 | 8/2018 | Richard et al. |
| 2018/0250001 A1 | 9/2018 | Aronhalt et al. |
| 2018/0256184 A1 | 9/2018 | Shelton, IV et al. |
| 2018/0271520 A1 | 9/2018 | Shelton, IV et al. |
| 2018/0273597 A1 | 9/2018 | Stimson |
| 2018/0280020 A1 | 10/2018 | Hess et al. |
| 2018/0280021 A1 | 10/2018 | Timm et al. |
| 2018/0280023 A1 | 10/2018 | Timm et al. |
| 2018/0286274 A1 | 10/2018 | Kamiguchi et al. |
| 2018/0289369 A1 | 10/2018 | Shelton, IV et al. |
| 2018/0296211 A1 | 10/2018 | Timm et al. |
| 2018/0296215 A1 | 10/2018 | Baxter, III et al. |
| 2018/0296216 A1 | 10/2018 | Shelton, IV et al. |
| 2018/0296217 A1 | 10/2018 | Moore et al. |
| 2018/0303481 A1 | 10/2018 | Shelton, IV et al. |
| 2018/0303482 A1 | 10/2018 | Shelton, IV et al. |
| 2018/0310931 A1 | 11/2018 | Hall et al. |
| 2018/0311002 A1 | 11/2018 | Giordano et al. |
| 2018/0317907 A1 | 11/2018 | Kostrzewski |
| 2018/0317916 A1 | 11/2018 | Wixey |
| 2018/0317917 A1 | 11/2018 | Huang et al. |
| 2018/0317918 A1 | 11/2018 | Shelton, IV |
| 2018/0317919 A1 | 11/2018 | Shelton, IV et al. |
| 2018/0333155 A1 | 11/2018 | Hall et al. |
| 2018/0333169 A1 | 11/2018 | Leimbach et al. |
| 2018/0344319 A1 | 12/2018 | Shelton, IV et al. |
| 2018/0353170 A1 | 12/2018 | Overmyer et al. |
| 2018/0353176 A1 | 12/2018 | Shelton, IV et al. |
| 2018/0353177 A1 | 12/2018 | Shelton, IV et al. |
| 2018/0353178 A1 | 12/2018 | Shelton, IV et al. |
| 2018/0353179 A1 | 12/2018 | Shelton, IV et al. |
| 2018/0360443 A1 | 12/2018 | Shelton, IV et al. |
| 2018/0360444 A1 | 12/2018 | Harris et al. |
| 2018/0360445 A1 | 12/2018 | Shelton, IV et al. |
| 2018/0360446 A1 | 12/2018 | Shelton, IV et al. |
| 2018/0360447 A1 | 12/2018 | Shelton, IV et al. |
| 2018/0360448 A1 | 12/2018 | Harris et al. |
| 2018/0360449 A1 | 12/2018 | Shelton, IV et al. |
| 2018/0360450 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360455 A1 | 12/2018 | Shelton, IV et al. |
| 2018/0360456 A1 | 12/2018 | Shelton, IV et al. |
| 2018/0360469 A1 | 12/2018 | Shelton, IV et al. |
| 2018/0360471 A1 | 12/2018 | Parfett et al. |
| 2018/0360472 A1 | 12/2018 | Harris et al. |

(56) References Cited

U.S. PATENT DOCUMENTS

| | | |
|---|---|---|
| 2018/0360473 A1 | 12/2018 | Shelton, IV et al. |
| 2018/0360549 A1 | 12/2018 | Hares et al. |
| 2018/0368822 A1 | 12/2018 | Shelton, IV et al. |
| 2018/0368833 A1 | 12/2018 | Shelton, IV et al. |
| 2018/0368837 A1 | 12/2018 | Morgan et al. |
| 2018/0368838 A1 | 12/2018 | Shelton, IV et al. |
| 2018/0368839 A1 | 12/2018 | Shelton, IV et al. |
| 2018/0368840 A1 | 12/2018 | Shelton, IV et al. |
| 2018/0368841 A1 | 12/2018 | Shelton, IV et al. |
| 2018/0368842 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368845 A1 | 12/2018 | Bakos et al. |
| 2018/0368846 A1 | 12/2018 | Shelton, IV et al. |
| 2018/0368847 A1 | 12/2018 | Shelton, IV et al. |
| 2019/0000446 A1 | 1/2019 | Shelton, IV et al. |
| 2019/0000447 A1 | 1/2019 | Shelton, IV et al. |
| 2019/0000448 A1 | 1/2019 | Shelton, IV et al. |
| 2019/0000450 A1 | 1/2019 | Shelton, IV et al. |
| 2019/0000454 A1 | 1/2019 | Swayze et al. |
| 2019/0000456 A1 | 1/2019 | Shelton, IV et al. |
| 2019/0000457 A1 | 1/2019 | Shelton, IV et al. |
| 2019/0000458 A1 | 1/2019 | Shelton, IV et al. |
| 2019/0000459 A1 | 1/2019 | Shelton, IV et al. |
| 2019/0000460 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000463 A1 | 1/2019 | Shelton, IV et al. |
| 2019/0000464 A1 | 1/2019 | Shelton, IV et al. |
| 2019/0000465 A1 | 1/2019 | Shelton, IV et al. |
| 2019/0000466 A1 | 1/2019 | Shelton, IV et al. |
| 2019/0000467 A1 | 1/2019 | Shelton, IV et al. |
| 2019/0000469 A1 | 1/2019 | Shelton, IV et al. |
| 2019/0000470 A1 | 1/2019 | Yates et al. |
| 2019/0000471 A1 | 1/2019 | Shelton, IV et al. |
| 2019/0000472 A1 | 1/2019 | Shelton, IV et al. |
| 2019/0000473 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000479 A1 | 1/2019 | Harris et al. |
| 2019/0000525 A1 | 1/2019 | Messerly et al. |
| 2019/0000528 A1 | 1/2019 | Yates et al. |
| 2019/0000530 A1 | 1/2019 | Yates et al. |
| 2019/0000534 A1 | 1/2019 | Messerly et al. |
| 2019/0000565 A1 | 1/2019 | Shelton, IV et al. |
| 2019/0008509 A1 | 1/2019 | Shelton, IV et al. |
| 2019/0008511 A1 | 1/2019 | Kerr et al. |
| 2019/0015096 A1 | 1/2019 | Shelton, IV et al. |
| 2019/0015102 A1 | 1/2019 | Baber et al. |
| 2019/0015165 A1 | 1/2019 | Giordano et al. |
| 2019/0029675 A1 | 1/2019 | Yates et al. |
| 2019/0029676 A1 | 1/2019 | Yates et al. |
| 2019/0029677 A1 | 1/2019 | Yates et al. |
| 2019/0029678 A1 | 1/2019 | Shelton, IV et al. |
| 2019/0029681 A1 | 1/2019 | Swayze et al. |
| 2019/0029682 A1 | 1/2019 | Huitema et al. |
| 2019/0029701 A1 | 1/2019 | Shelton, IV et al. |
| 2019/0033955 A1 | 1/2019 | Leimbach et al. |
| 2019/0038279 A1 | 2/2019 | Shelton, IV et al. |
| 2019/0038281 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0038371 A1 | 2/2019 | Wixey et al. |
| 2019/0046187 A1 | 2/2019 | Yates et al. |
| 2019/0059886 A1 | 2/2019 | Shelton, IV et al. |
| 2019/0090870 A1 | 3/2019 | Shelton, IV et al. |
| 2019/0090871 A1 | 3/2019 | Shelton, IV et al. |
| 2019/0099177 A1 | 4/2019 | Yates et al. |
| 2019/0099178 A1 | 4/2019 | Leimbach et al. |
| 2019/0099179 A1 | 4/2019 | Leimbach et al. |
| 2019/0099180 A1 | 4/2019 | Leimbach et al. |
| 2019/0099181 A1 | 4/2019 | Shelton, IV et al. |
| 2019/0099182 A1 | 4/2019 | Bakos et al. |
| 2019/0099183 A1 | 4/2019 | Leimbach et al. |
| 2019/0099184 A1 | 4/2019 | Setser et al. |
| 2019/0099224 A1 | 4/2019 | Leimbach et al. |
| 2019/0099229 A1 | 4/2019 | Spivey et al. |
| 2019/0102930 A1 | 4/2019 | Leimbach et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105038 A1 | 4/2019 | Schmid et al. |
| 2019/0105039 A1 | 4/2019 | Morgan et al. |
| 2019/0105043 A1 | 4/2019 | Jaworek et al. |
| 2019/0105044 A1 | 4/2019 | Shelton, IV et al. |
| 2019/0105049 A1 | 4/2019 | Moore et al. |
| 2019/0110791 A1 | 4/2019 | Shelton, IV et al. |
| 2019/0110792 A1 | 4/2019 | Shelton, IV et al. |
| 2019/0110793 A1 | 4/2019 | Parihar et al. |
| 2019/0117216 A1 | 4/2019 | Overmyer et al. |
| 2019/0117217 A1 | 4/2019 | Overmyer et al. |
| 2019/0117222 A1 | 4/2019 | Shelton, IV et al. |
| 2019/0117224 A1 | 4/2019 | Setser et al. |
| 2019/0117225 A1 | 4/2019 | Moore et al. |
| 2019/0125343 A1 | 5/2019 | Wise et al. |
| 2019/0125344 A1 | 5/2019 | DiNardo et al. |
| 2019/0125345 A1 | 5/2019 | Baber et al. |
| 2019/0125365 A1 | 5/2019 | Parfett et al. |
| 2019/0125380 A1 | 5/2019 | Hunter et al. |
| 2019/0125475 A1 | 5/2019 | Wise et al. |
| 2019/0133585 A1 | 5/2019 | Smith et al. |
| 2019/0142421 A1 | 5/2019 | Shelton, IV |
| 2019/0183490 A1 | 6/2019 | Shelton, IV et al. |
| 2019/0183491 A1 | 6/2019 | Shelton, IV et al. |
| 2019/0183492 A1 | 6/2019 | Shelton, IV et al. |
| 2019/0183493 A1 | 6/2019 | Shelton, IV et al. |
| 2019/0183494 A1 | 6/2019 | Shelton, IV et al. |
| 2019/0183495 A1 | 6/2019 | Shelton, IV et al. |
| 2019/0183496 A1 | 6/2019 | Shelton, IV et al. |
| 2019/0183497 A1 | 6/2019 | Shelton, IV et al. |
| 2019/0183498 A1 | 6/2019 | Shelton, IV et al. |
| 2019/0183499 A1 | 6/2019 | Shelton, IV et al. |
| 2019/0183500 A1 | 6/2019 | Shelton, IV et al. |
| 2019/0183501 A1 | 6/2019 | Shelton, IV et al. |
| 2019/0183502 A1 | 6/2019 | Shelton, IV et al. |
| 2019/0183503 A1 | 6/2019 | Shelton, IV et al. |
| 2019/0183504 A1 | 6/2019 | Shelton, IV et al. |
| 2019/0183505 A1 | 6/2019 | Vendely et al. |
| 2019/0183592 A1 | 6/2019 | Shelton, IV et al. |
| 2019/0183594 A1 | 6/2019 | Shelton, IV et al. |
| 2019/0183597 A1 | 6/2019 | Shelton, IV et al. |
| 2019/0192137 A1 | 6/2019 | Shelton, IV et al. |
| 2019/0192138 A1 | 6/2019 | Shelton, IV et al. |
| 2019/0192141 A1 | 6/2019 | Shelton, IV et al. |
| 2019/0192144 A1 | 6/2019 | Parfett et al. |
| 2019/0192145 A1 | 6/2019 | Shelton, IV et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192149 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0192152 A1 | 6/2019 | Morgan et al. |
| 2019/0192153 A1 | 6/2019 | Shelton, IV et al. |
| 2019/0192154 A1 | 6/2019 | Shelton, IV et al. |
| 2019/0192155 A1 | 6/2019 | Shelton, IV et al. |
| 2019/0192227 A1 | 6/2019 | Shelton, IV et al. |
| 2019/0192235 A1 | 6/2019 | Harris et al. |
| 2019/0192236 A1 | 6/2019 | Shelton, IV et al. |
| 2019/0200991 A1 | 7/2019 | Moore et al. |
| 2019/0200992 A1 | 7/2019 | Moore et al. |
| 2019/0200993 A1 | 7/2019 | Moore et al. |

FOREIGN PATENT DOCUMENTS

| | | |
|---|---|---|
| CA | 1015829 A | 8/1977 |
| CA | 1125615 A | 6/1982 |
| CA | 2520413 A1 | 3/2007 |
| CA | 2725181 A1 | 11/2007 |
| CA | 2664874 A1 | 11/2009 |
| CA | 2940510 A1 | 8/2015 |

(56) References Cited

FOREIGN PATENT DOCUMENTS

| | | | |
|---|---|---|---|
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 2868212 Y | 2/2007 |
| CN | 200942099 Y | 9/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101522120 A | 9/2009 |
| CN | 101669833 A | 3/2010 |
| CN | 101721236 A | 6/2010 |
| CN | 101828940 A | 9/2010 |
| CN | 101873834 A | 10/2010 |
| CN | 201719298 U | 1/2011 |
| CN | 102038532 A | 5/2011 |
| CN | 201879759 U | 6/2011 |
| CN | 201949071 U | 8/2011 |
| CN | 101779977 B | 12/2011 |
| CN | 101912284 B | 7/2012 |
| CN | 202313537 U | 7/2012 |
| CN | 202397539 U | 8/2012 |
| CN | 202426586 U | 9/2012 |
| CN | 202489990 U | 10/2012 |
| CN | 102835977 A | 12/2012 |
| CN | 203564285 U | 4/2014 |
| CN | 203564287 U | 4/2014 |
| CN | 203597997 U | 5/2014 |
| CN | 103829983 A | 6/2014 |
| CN | 103908313 A | 7/2014 |
| CN | 203736251 U | 7/2014 |
| CN | 103981635 A | 8/2014 |
| CN | 203815517 U | 9/2014 |
| CN | 102783741 B | 10/2014 |
| CN | 102973300 B | 10/2014 |
| CN | 104337556 A | 2/2015 |
| CN | 204158441 U | 2/2015 |
| CN | 102469995 B | 3/2015 |
| CN | 204636451 U | 9/2015 |
| CN | 103860225 B | 3/2016 |
| CN | 103750872 B | 5/2016 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004063606 A1 | 7/2006 |
| DE | 202007003114 U1 | 6/2007 |
| DE | 102010013150 A1 | 9/2011 |
| EP | 0000756 A1 | 2/1979 |
| EP | 0122046 A1 | 10/1984 |
| EP | 0129442 B1 | 11/1987 |
| EP | 0255631 A1 | 2/1988 |
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2606812 A1 | 6/2013 |
| EP | 2649948 A1 | 10/2013 |
| EP | 2649949 A1 | 10/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2842500 A1 | 3/2015 |
| EP | 2853220 A1 | 4/2015 |
| EP | 2298220 B1 | 6/2016 |
| EP | 2510891 B1 | 6/2016 |
| EP | 2364651 B1 | 11/2016 |
| EP | 2747235 B1 | 11/2016 |
| EP | 2789299 B1 | 5/2017 |
| EP | 3363378 A1 | 8/2018 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |

(56) References Cited

FOREIGN PATENT DOCUMENTS

| | | |
|---|---|---|
| GB | 2509523 A | 7/2014 |
| GR | 930100110 A | 11/1993 |
| JP | S4711908 Y1 | 5/1972 |
| JP | S5033988 U | 4/1975 |
| JP | S56112235 A | 9/1981 |
| JP | S62170011 U | 10/1987 |
| JP | S63270040 A | 11/1988 |
| JP | H0129503 B2 | 6/1989 |
| JP | H0378514 U | 8/1991 |
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H 05226945 A | 9/1993 |
| JP | H0630945 A | 2/1994 |
| JP | H06237937 A | 8/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H09-323068 A | 12/1997 |
| JP | H10118090 A | 5/1998 |
| JP | H10-200699 A | 7/1998 |
| JP | H 10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001087272 A | 4/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006346445 A | 12/2006 |
| JP | 2008-220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | 2010069307 A | 4/2010 |
| JP | 2010069310 A | 4/2010 |
| JP | 2010098844 A | 4/2010 |
| JP | 2011072574 A | 4/2011 |
| JP | 4722849 B2 | 7/2011 |
| JP | 2011524199 A | 9/2011 |
| JP | 5154710 B1 | 2/2013 |
| JP | 2014121599 A | 7/2014 |
| JP | 2016-512057 A | 4/2016 |
| KR | 20100110134 A | 10/2010 |
| KR | 20110003229 A | 1/2011 |
| RU | 1814161 A1 | 5/1993 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |

(56) References Cited

FOREIGN PATENT DOCUMENTS

| WO | WO-03094747 A1 | 11/2003 |
|---|---|---|
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006/073581 A2 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008/061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012/013577 A1 | 2/2012 |
| WO | WO-2012044606 A2 | 4/2012 |
| WO | WO-2012166503 A1 | 12/2012 |
| WO | WO-2013151888 A1 | 10/2013 |
| WO | WO-2014004209 A2 | 1/2014 |
| WO | WO-2014/113438 A1 | 7/2014 |
| WO | WO-2015/032797 A1 | 3/2015 |
| WO | WO-2015138760 A1 | 9/2015 |
| WO | WO-2015187107 A1 | 12/2015 |

OTHER PUBLICATIONS

Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
Disclosed Anonymously, "Motor-Driven Surgical Stapler Improvements," Research Disclosure Database No. 526041, Published: Feb. 2008.
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Solorio et al., "Gelatin Microspheres Crosslinked with Genipin for Local Delivery of Growth Factors," J. Tissue Eng. Regen. Med. (2010), 4(7): pp. 514-523.
Pitt et al., "Attachment of Hyaluronan to Metallic Surfaces," J. Biomed. Mater. Res. 68A: pp. 95-106, 2004.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
"Indian Standard: Automotive Vehicles—Brakes and Braking Systems (IS 11852-1:2001)", Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014].
Covidien Brochure "iDrive™ Ultra Powered Stapling System," (6 pages).
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
"Biomedical Coatings," Fort Wayne Metals, Research Products Corporation, obtained online at www.fwmetals.com on Jun. 21, 2010 (1 page).

(56) References Cited

OTHER PUBLICATIONS

The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg—6Zn and Ti—3Al—2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press Ltd, 2012, pp. 1-29.
Youtube.com; video by Fibran (retrieved from URL https://www.youtube.com/watch?v=vN2Qjt51gFQ); (Year: 2018).
"Foot and Ankle: Core Knowledge in Orthopaedics"; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
"Tutorial overview of inductively coupled RFID Systems," UPM, May 2003, pp. 1-7, UPM Rafsec <http://cdn.mobiusconsulting.com/papers/rfidsystems.pdf>.
Schroeter, John, "*Demystifying UHF Gen 2 RFID, HF RFID*," Online Article, Jun. 2, 2008, pp. 1-3, <https://www.edn.com/design/industrial-control/4019123/Demystifying-UHF-Gen-2-RFID-HF-RFID>.
Adeeb, et al., "*An Inductive Link-Based Wireless Power Transfer System for Biomedical Applications*," Research Article, Nov. 14, 2011, pp. 1-12, vol. 2012, Article ID 879294, Hindawi Publishing Corporation.

\* cited by examiner

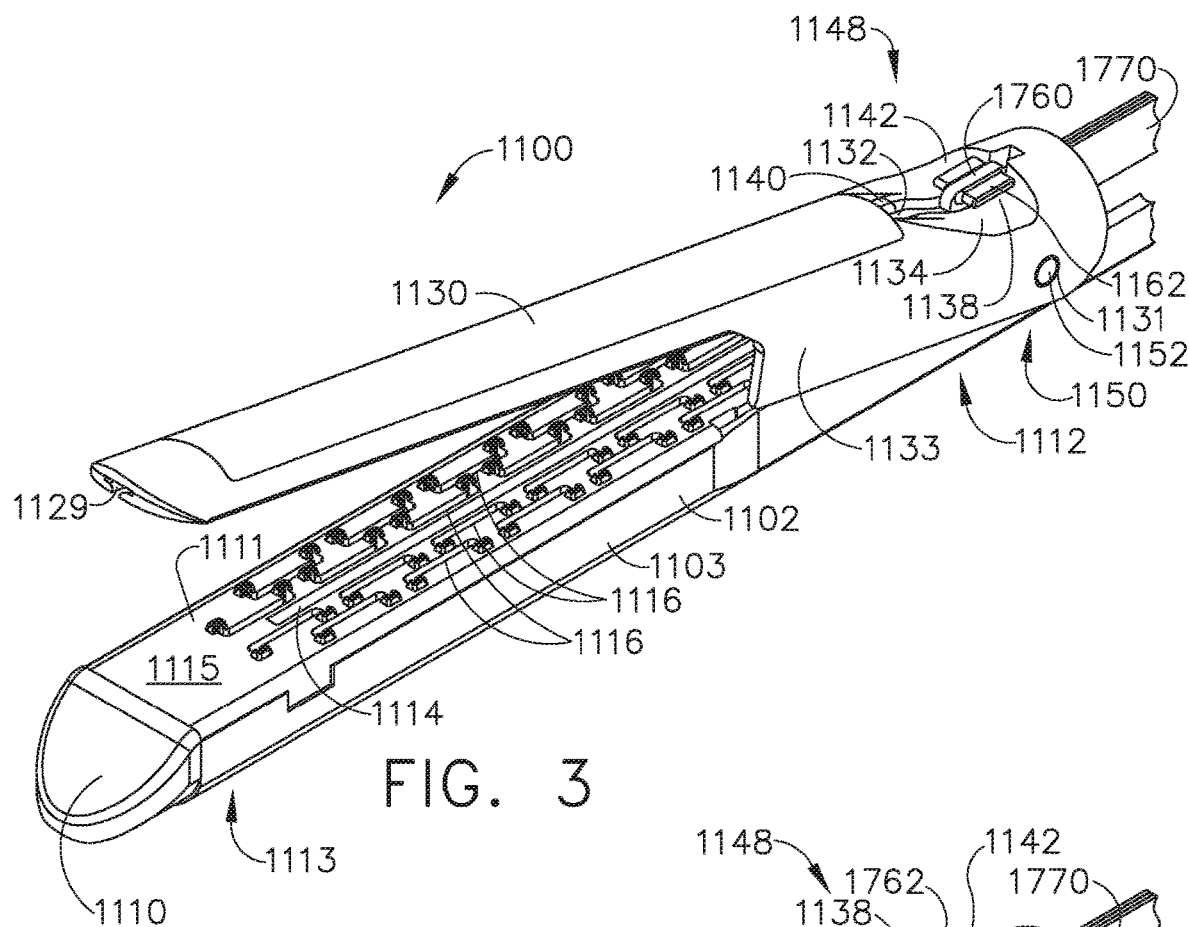
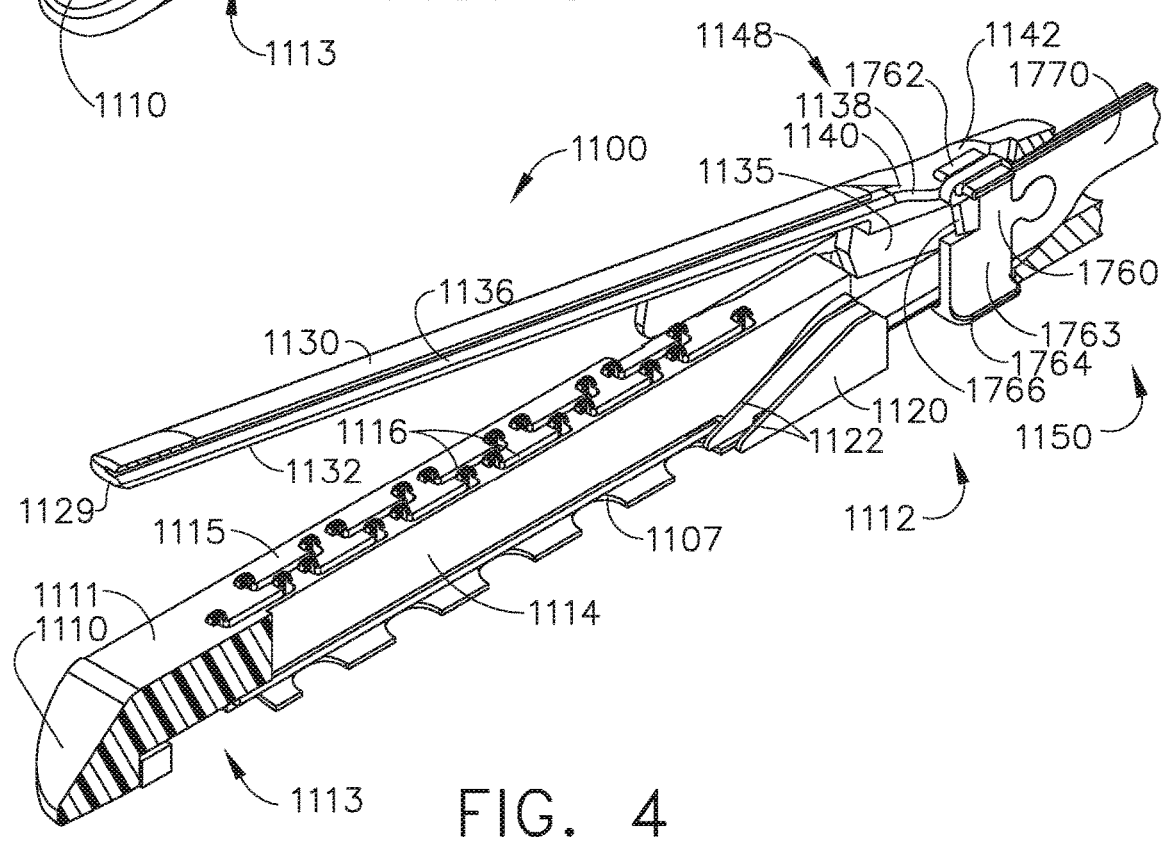

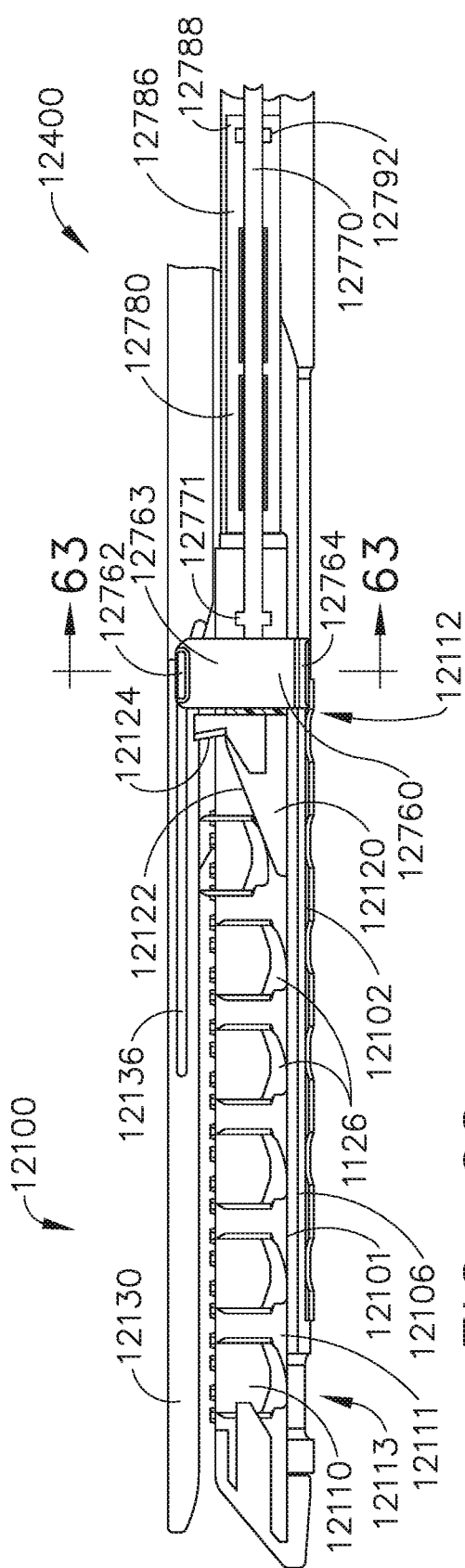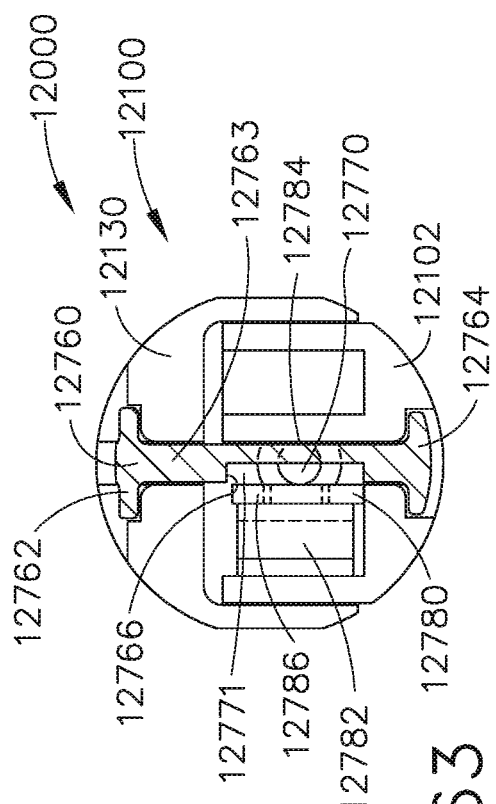
FIG. 62
FIG. 63

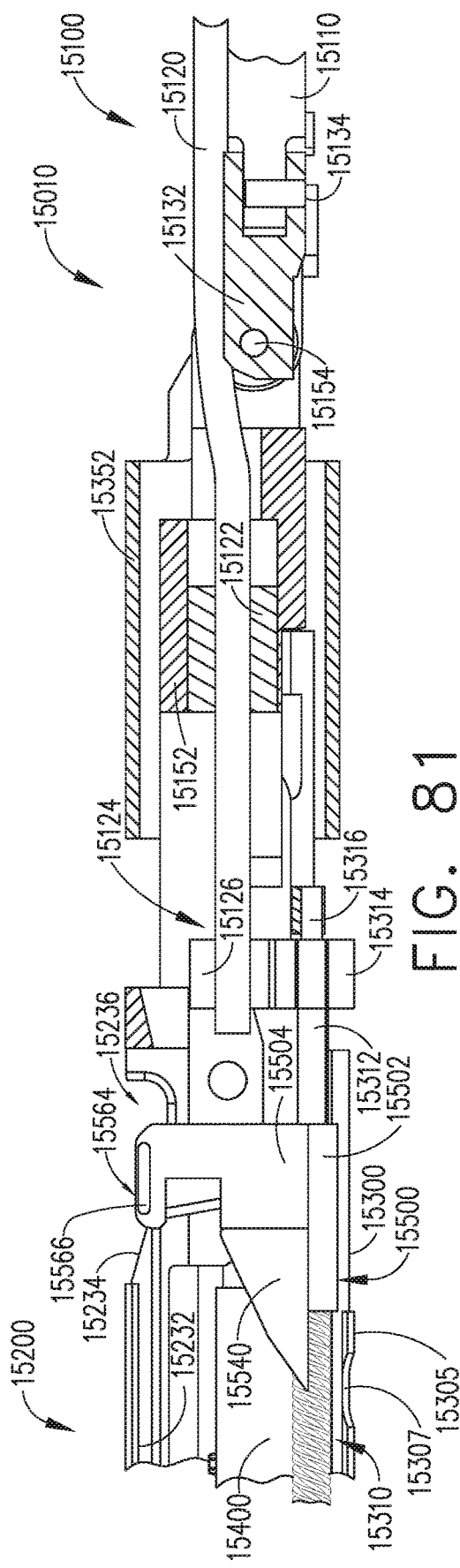
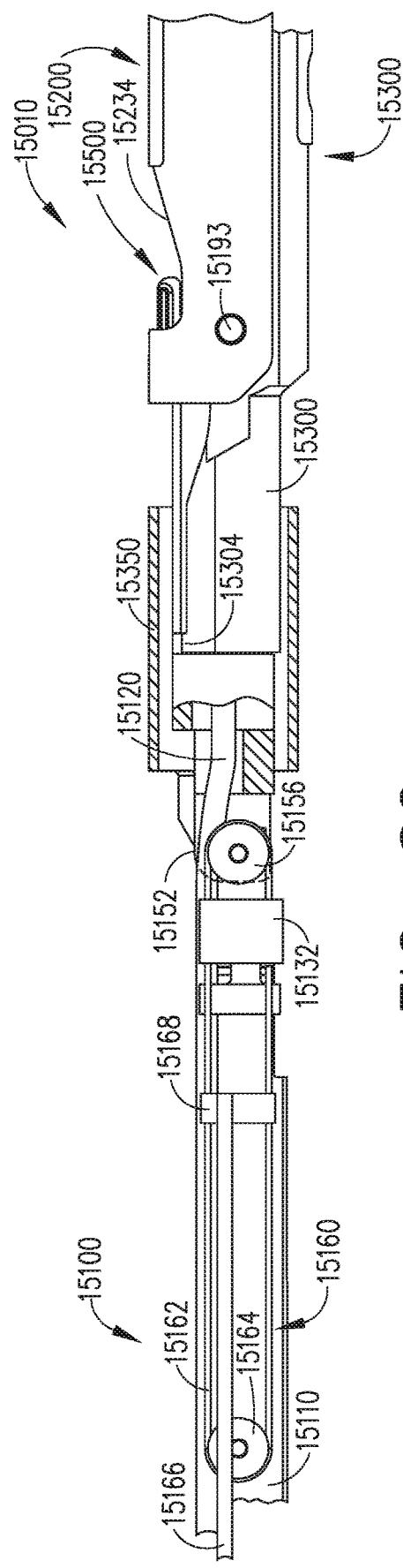
FIG. 81
FIG. 82

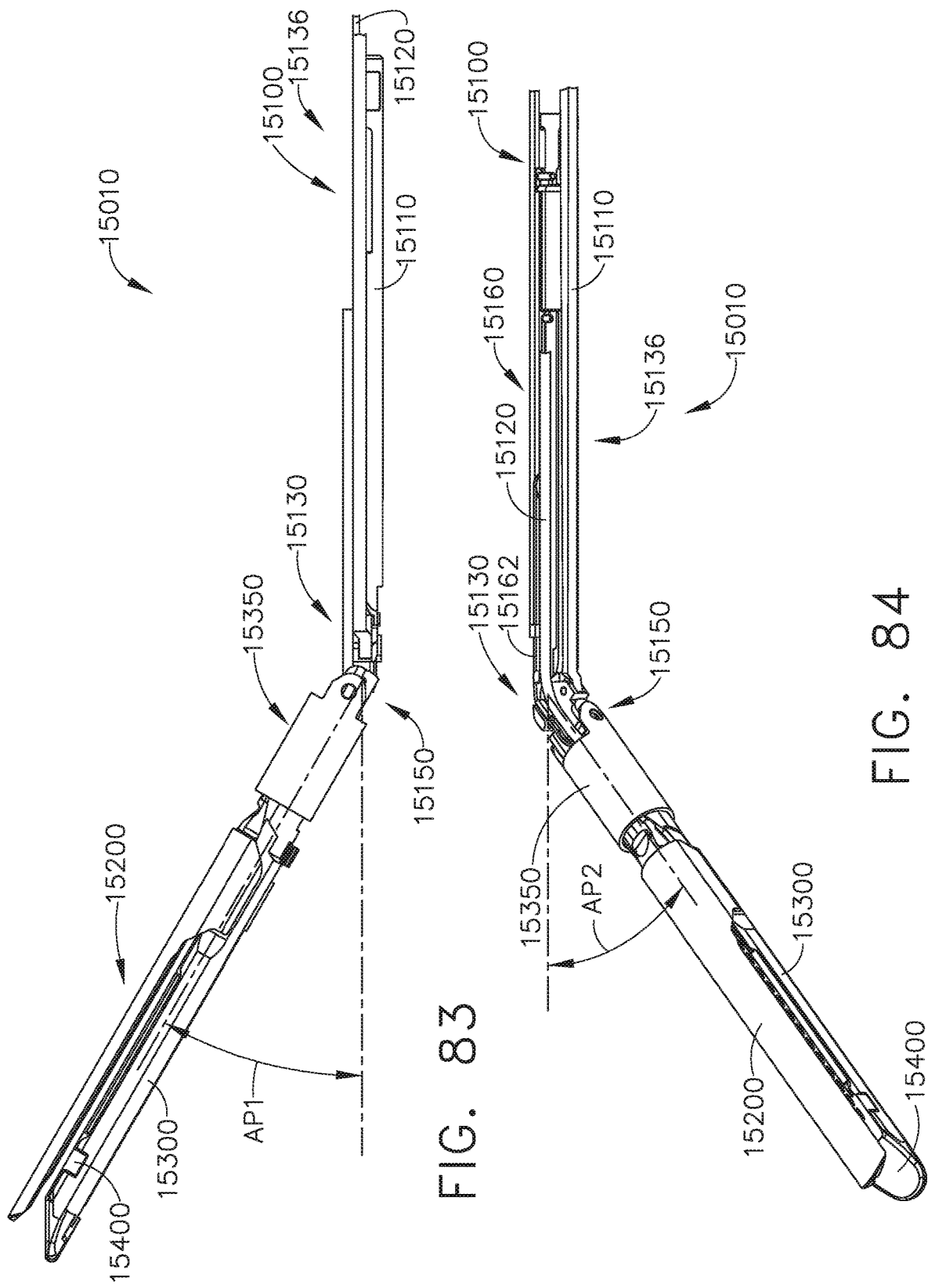

LOCKOUT ARRANGEMENTS FOR SURGICAL END EFFECTORS

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 3 is a perspective view of a distal portion of the interchangeable surgical tool assembly depicted in FIG. 1 with portions thereof omitted for clarity;

FIG. 4 is a perspective cross-sectional view of a distal portion of the interchangeable surgical tool assembly depicted in FIG. 1 taken along the longitudinal axis thereof with portions thereof omitted for clarity;

FIG. 62 is an elevation cross-sectional view of a distal portion of the interchangeable surgical tool assembly of FIG. 56 at the outset of a first firing stroke;

FIG. 63 is an elevation cross-sectional view of the interchangeable surgical tool assembly of FIG. 56 taken along the plane indicated in FIG. 62 at the outset of a first firing stroke;

FIG. 81 is a cross-sectional elevational view of portions of the surgical instrument of FIGS. 75-79;

FIG. 82 is another cross-sectional elevational view of the portions of the surgical instrument depicted in FIG. 81;

FIG. 83 is a partial side elevational view of the surgical instrument of FIGS. 75-79 with an end effector thereof articulated within a first articulation plane relative to the shaft assembly;

FIG. 84 is a partial perspective view of the surgical instrument of FIG. 83 with the end effector thereof articulated in a second articulation plane relative to the shaft assembly;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
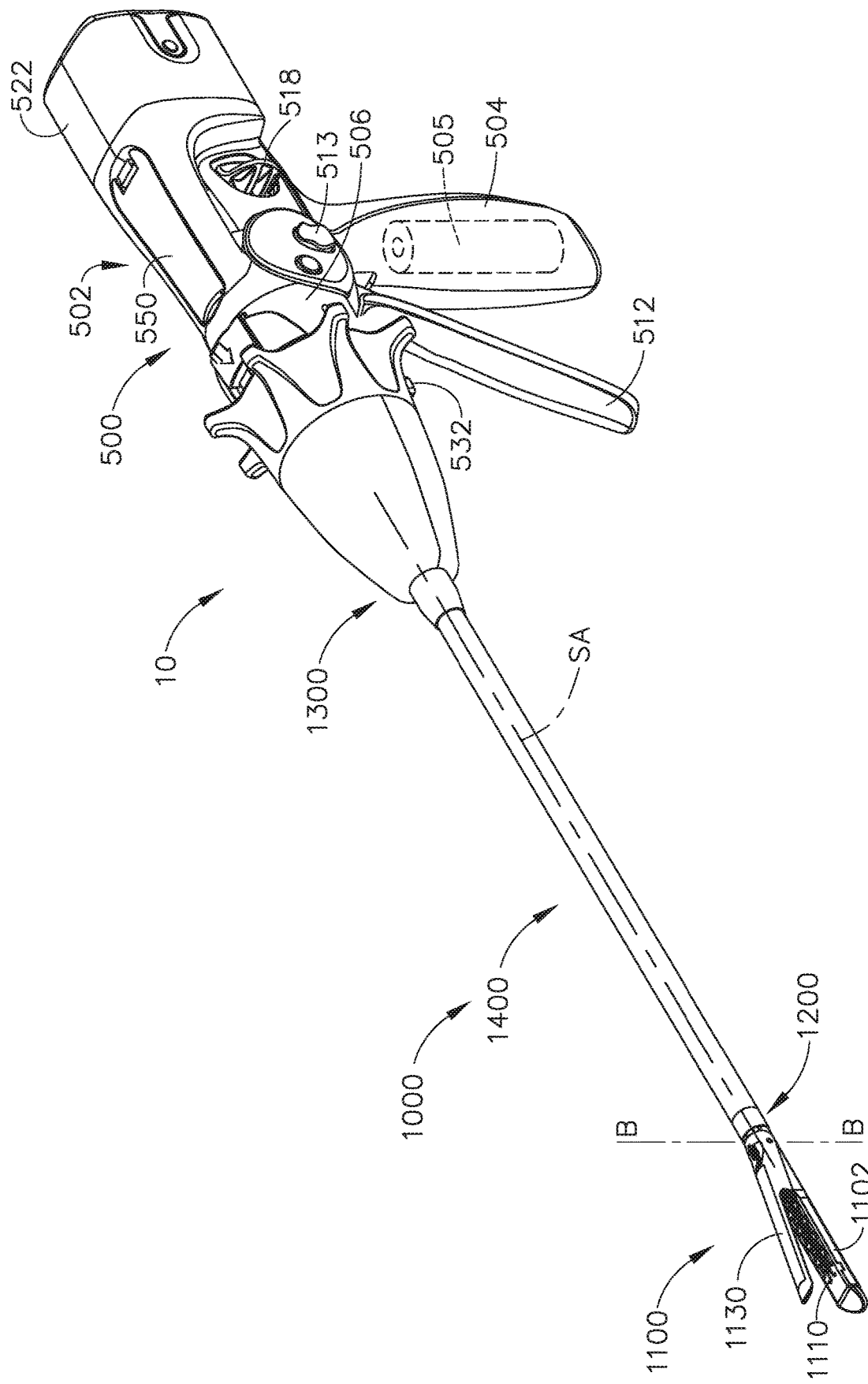
FIG. 1 is a perspective view of an interchangeable surgical tool assembly operably coupled to a handle assembly.

Applicant of the present application owns the following U.S. Patent Applications that were filed on Dec. 21, 2016 and which are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF;

U.S. patent application Ser. No. 15/386,230, entitled ARTICULATABLE SURGICAL STAPLING INSTRUMENTS;

U.S. patent application Ser. No. 15/386,209, entitled SURGICAL END EFFECTORS AND FIRING MEMBERS THEREOF;

U.S. patent application Ser. No. 15/386,198, entitled LOCKOUT ARRANGEMENTS FOR SURGICAL END EFFECTORS AND REPLACEABLE TOOL ASSEMBLIES; and U.S. patent application Ser. No. 15/386,240, entitled SURGICAL END EFFECTORS AND ADAPTABLE FIRING MEMBERS THEREFOR.

Applicant of the present application owns the following U.S. Patent Applications that were filed on Dec. 21, 2016 and which are each herein incorporated by reference in their respective entireties:

U.S. patent application Ser. No. 15/385,939, entitled STAPLE CARTRIDGES AND ARRANGEMENTS OF STAPLES AND STAPLE CAVITIES THEREIN;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS;

U.S. patent application Ser. No. 15/385,943, entitled SURGICAL STAPLING INSTRUMENTS AND STAPLE-FORMING ANVILS;

U.S. patent application Ser. No. 15/385,950, entitled SURGICAL TOOL ASSEMBLIES WITH CLOSURE STROKE REDUCTION FEATURES;

U.S. patent application Ser. No. 15/385,945, entitled STAPLE CARTRIDGES AND ARRANGEMENTS OF STAPLES AND STAPLE CAVITIES THEREIN;

U.S. patent application Ser. No. 15/385,946, entitled SURGICAL STAPLING INSTRUMENTS AND STAPLE-FORMING ANVILS;

U.S. patent application Ser. No. 15/385,951, entitled SURGICAL INSTRUMENTS WITH JAW OPENING FEATURES FOR INCREASING A JAW OPENING DISTANCE;

U.S. patent application Ser. No. 15/385,953, entitled METHODS OF STAPLING TISSUE;

U.S. patent application Ser. No. 15/385,954, entitled FIRING MEMBERS WITH NON-PARALLEL JAW ENGAGEMENT FEATURES FOR SURGICAL END EFFECTORS;

U.S. patent application Ser. No. 15/385,955, entitled SURGICAL END EFFECTORS WITH EXPANDABLE TISSUE STOP ARRANGEMENTS;

U.S. patent application Ser. No. 15/385,948, entitled SURGICAL STAPLING INSTRUMENTS AND STAPLE-FORMING ANVILS;

U.S. patent application Ser. No. 15/385,956, entitled SURGICAL INSTRUMENTS WITH POSITIVE JAW OPENING FEATURES;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT; and U.S. patent application Ser. No. 15/385,947, entitled STAPLE CARTRIDGES AND ARRANGEMENTS OF STAPLES AND STAPLE CAVITIES THEREIN.

Applicant of the present application owns the following U.S. Patent Applications that were filed on Dec. 21, 2016 and which are each herein incorporated by reference in their respective entireties:

U.S. patent application Ser. No. 15/385,896, entitled METHOD FOR RESETTING A FUSE OF A SURGICAL INSTRUMENT SHAFT;

U.S. patent application Ser. No. 15/385,898, entitled STAPLE FORMING POCKET ARRANGEMENT TO ACCOMMODATE DIFFERENT TYPES OF STAPLES;

U.S. patent application Ser. No. 15/385,899, entitled SURGICAL INSTRUMENT COMPRISING IMPROVED JAW CONTROL;

U.S. patent application Ser. No. 15/385,901, entitled STAPLE CARTRIDGE AND STAPLE CARTRIDGE CHANNEL COMPRISING WINDOWS DEFINED THEREIN;

U.S. patent application Ser. No. 15/385,902, entitled SURGICAL INSTRUMENT COMPRISING A CUTTING MEMBER;

U.S. patent application Ser. No. 15/385,904, entitled STAPLE FIRING MEMBER COMPRISING A MISSING CARTRIDGE AND/OR SPENT CARTRIDGE LOCKOUT;

U.S. patent application Ser. No. 15/385,905, entitled FIRING ASSEMBLY COMPRISING A LOCKOUT;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT;

U.S. patent application Ser. No. 15/385,908, entitled FIRING ASSEMBLY COMPRISING A FUSE; and U.S. patent application Ser. No. 15/385,909, entitled FIRING ASSEMBLY COMPRISING A MULTIPLE FAILED-STATE FUSE.

Applicant of the present application owns the following U.S. Patent Applications that were filed on Dec. 21, 2016 and which are each herein incorporated by reference in their respective entireties:

U.S. patent application Ser. No. 15/385,920, entitled STAPLE FORMING POCKET ARRANGEMENTS;

U.S. patent application Ser. No. 15/385,913, entitled ANVIL ARRANGEMENTS FOR SURGICAL STAPLERS;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT;

U.S. patent application Ser. No. 15/385,893, entitled BILATERALLY ASYMMETRIC STAPLE FORMING POCKET PAIRS;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS;

U.S. patent application Ser. No. 15/385,911, entitled SURGICAL STAPLERS WITH INDEPENDENTLY ACTUATABLE CLOSING AND FIRING SYSTEMS;

U.S. patent application Ser. No. 15/385,927, entitled SURGICAL STAPLING INSTRUMENTS WITH SMART STAPLE CARTRIDGES;

U.S. patent application Ser. No. 15/385,917, entitled STAPLE CARTRIDGE COMPRISING STAPLES WITH DIFFERENT CLAMPING BREADTHS;

U.S. patent application Ser. No. 15/385,900, entitled STAPLE FORMING POCKET ARRANGEMENTS COMPRISING PRIMARY SIDEWALLS AND POCKET SIDEWALLS;

U.S. patent application Ser. No. 15/385,931, entitled NO-CARTRIDGE AND SPENT CARTRIDGE LOCKOUT ARRANGEMENTS FOR SURGICAL STAPLERS;

U.S. patent application Ser. No. 15/385,915, entitled FIRING MEMBER PIN ANGLE;

U.S. patent application Ser. No. 15/385,897, entitled STAPLE FORMING POCKET ARRANGEMENTS COMPRISING ZONED FORMING SURFACE GROOVES;

U.S. patent application Ser. No. 15/385,922, entitled SURGICAL INSTRUMENT WITH MULTIPLE FAILURE RESPONSE MODES;

U.S. patent application Ser. No. 15/385,924, entitled SURGICAL INSTRUMENT WITH PRIMARY AND SAFETY PROCESSORS;

U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS;

U.S. patent application Ser. No. 15/385,910, entitled ANVIL HAVING A KNIFE SLOT WIDTH;

U.S. patent application Ser. No. 15/385,903, entitled CLOSURE MEMBER ARRANGEMENTS FOR SURGICAL INSTRUMENTS; and U.S. patent application Ser. No. 15/385,906, entitled FIRING MEMBER PIN CONFIGURATIONS.

Applicant of the present application owns the following U.S. Patent Applications that were filed on Dec. 21, 2016 and which are each herein incorporated by reference in their respective entireties:

U.S. patent application Ser. No. 15/386,188, entitled STEPPED STAPLE CARTRIDGE WITH ASYMMETRICAL STAPLES;

U.S. patent application Ser. No. 15/386,192, entitled STEPPED STAPLE CARTRIDGE WITH TISSUE RETENTION AND GAP SETTING FEATURES;

U.S. patent application Ser. No. 15,386,206, entitled STAPLE CARTRIDGE WITH DEFORMABLE DRIVER RETENTION FEATURES;

U.S. patent application Ser. No. 15/386,226, entitled DURABILITY FEATURES FOR END EFFECTORS AND FIRING ASSEMBLIES OF SURGICAL STAPLING INSTRUMENTS;

U.S. patent application Ser. No. 15/386,222, entitled SURGICAL STAPLING INSTRUMENTS HAVING END EFFECTORS WITH POSITIVE OPENING FEATURES; and U.S. patent application Ser. No. 15/386,236, entitled CONNECTION PORTIONS FOR DISPOSABLE LOADING UNITS FOR SURGICAL STAPLING INSTRUMENTS.

Applicant of the present application owns the following U.S. Patent Applications that were filed on Dec. 21, 2016 and which are each herein incorporated by reference in their respective entireties:

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM;

U.S. patent application Ser. No. 15/385,890, entitled SHAFT ASSEMBLY COMPRISING SEPARATELY ACTUATABLE AND RETRACTABLE SYSTEMS;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM;

U.S. patent application Ser. No. 15/385,894, entitled SHAFT ASSEMBLY COMPRISING A LOCKOUT; and U.S. patent application Ser. No. 15/385,895, entitled SHAFT ASSEMBLY COMPRISING FIRST AND SECOND ARTICULATION LOCKOUTS.

Applicant of the present application owns the following U.S. Patent Applications that were filed on Dec. 21, 2016 and which are each herein incorporated by reference in their respective entireties:

U.S. patent application Ser. No. 15/385,916, entitled SURGICAL STAPLING SYSTEMS;

U.S. patent application Ser. No. 15/385,918, entitled SURGICAL STAPLING SYSTEMS;

U.S. patent application Ser. No. 15/385,919, entitled SURGICAL STAPLING SYSTEMS;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES;

U.S. patent application Ser. No. 15/385,923, entitled SURGICAL STAPLING SYSTEMS;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS;

U.S. patent application Ser. No. 15/385,932, entitled ARTICULATABLE SURGICAL END EFFECTOR WITH ASYMMETRIC SHAFT ARRANGEMENT;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION; and U.S. patent application Ser. No. 15/385,936, entitled ARTICULATABLE SURGICAL INSTRUMENTS WITH ARTICULATION STROKE AMPLIFICATION FEATURES.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES;

U.S. patent application Ser. No. 15/191,807, entitled STAPLING SYSTEM FOR USE WITH WIRE STAPLES AND STAMPED STAPLES;

U.S. patent application Ser. No. 15/191,834, entitled STAMPED STAPLES AND STAPLE CARTRIDGES USING THE SAME;

U.S. patent application Ser. No. 15/191,788, entitled STAPLE CARTRIDGE COMPRISING OVERDRIVEN STAPLES; and U.S. patent application Ser. No. 15/191,818, entitled STAPLE CARTRIDGE COMPRISING OFFSET LONGITUDINAL STAPLE ROWS.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER;

U.S. Design patent application Ser. No. 29/569,227, entitled SURGICAL FASTENER;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entireties:

U.S. patent application Ser. No. 15/089,325, entitled METHOD FOR OPERATING A SURGICAL STAPLING SYSTEM;

U.S. patent application Ser. No. 15/089,321, entitled MODULAR SURGICAL STAPLING SYSTEM COMPRISING A DISPLAY;

U.S. patent application Ser. No. 15/089,326, entitled SURGICAL STAPLING SYSTEM COMPRISING A DISPLAY INCLUDING A RE-ORIENTABLE DISPLAY FIELD;

U.S. patent application Ser. No. 15/089,263, entitled SURGICAL INSTRUMENT HANDLE ASSEMBLY WITH RECONFIGURABLE GRIP PORTION;

U.S. patent application Ser. No. 15/089,262, entitled ROTARY POWERED SURGICAL INSTRUMENT WITH MANUALLY ACTUATABLE BAILOUT SYSTEM;

U.S. patent application Ser. No. 15/089,277, entitled SURGICAL CUTTING AND STAPLING END EFFECTOR WITH ANVIL CONCENTRIC DRIVE MEMBER;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS;

U.S. patent application Ser. No. 15/089,258, entitled SURGICAL STAPLING SYSTEM COMPRISING A SHIFTABLE TRANSMISSION;

U.S. patent application Ser. No. 15/089,278, entitled SURGICAL STAPLING SYSTEM CONFIGURED TO PROVIDE SELECTIVE CUTTING OF TISSUE;

U.S. patent application Ser. No. 15/089,284, entitled SURGICAL STAPLING SYSTEM COMPRISING A CONTOURABLE SHAFT;

U.S. patent application Ser. No. 15/089,295, entitled SURGICAL STAPLING SYSTEM COMPRISING A TISSUE COMPRESSION LOCKOUT;

U.S. patent application Ser. No. 15/089,300, entitled SURGICAL STAPLING SYSTEM COMPRISING AN UNCLAMPING LOCKOUT;

U.S. patent application Ser. No. 15/089,196, entitled SURGICAL STAPLING SYSTEM COMPRISING A JAW CLOSURE LOCKOUT;

U.S. patent application Ser. No. 15/089,203, entitled SURGICAL STAPLING SYSTEM COMPRISING A JAW ATTACHMENT LOCKOUT;

U.S. patent application Ser. No. 15/089,210, entitled SURGICAL STAPLING SYSTEM COMPRISING A SPENT CARTRIDGE LOCKOUT;

U.S. patent application Ser. No. 15/089,324, entitled SURGICAL INSTRUMENT COMPRISING A SHIFTING MECHANISM;

U.S. patent application Ser. No. 15/089,335, entitled SURGICAL STAPLING INSTRUMENT COMPRISING MULTIPLE LOCKOUTS;

U.S. patent application Ser. No. 15/089,339, entitled SURGICAL STAPLING INSTRUMENT;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS;

U.S. patent application Ser. No. 15/089,304, entitled SURGICAL STAPLING SYSTEM COMPRISING A GROOVED FORMING POCKET;

U.S. patent application Ser. No. 15/089,331, entitled ANVIL MODIFICATION MEMBERS FOR SURGICAL STAPLERS;

U.S. patent application Ser. No. 15/089,336, entitled STAPLE CARTRIDGES WITH ATRAUMATIC FEATURES;

U.S. patent application Ser. No. 15/089,312, entitled CIRCULAR STAPLING SYSTEM COMPRISING AN INCISABLE TISSUE SUPPORT;

U.S. patent application Ser. No. 15/089,309, entitled CIRCULAR STAPLING SYSTEM COMPRISING ROTARY FIRING SYSTEM; and U.S. patent application Ser. No. 15/089,349, entitled CIRCULAR STAPLING SYSTEM COMPRISING LOAD CONTROL.

Applicant of the present application also owns the U.S. Patent Applications identified below which were filed on Dec. 31, 2015 which are each herein incorporated by reference in their respective entireties:

U.S. patent application Ser. No. 14/984,488, entitled MECHANISMS FOR COMPENSATING FOR BATTERY PACK FAILURE IN POWERED SURGICAL INSTRUMENTS;

U.S. patent application Ser. No. 14/984,525, entitled MECHANISMS FOR COMPENSATING FOR DRIVETRAIN FAILURE IN POWERED SURGICAL INSTRUMENTS; and U.S. patent application Ser. No. 14/984,552, entitled SURGICAL INSTRUMENTS WITH SEPARABLE MOTORS AND MOTOR CONTROL CIRCUITS.

Applicant of the present application also owns the U.S. Patent Applications identified below which were filed on Feb. 9, 2016 which are each herein incorporated by reference in their respective entireties:

U.S. patent application Ser. No. 15/019,220, entitled SURGICAL INSTRUMENT WITH ARTICULATING AND AXIALLY TRANSLATABLE END EFFECTOR;

U.S. patent application Ser. No. 15/019,228, entitled SURGICAL INSTRUMENTS WITH MULTIPLE LINK ARTICULATION ARRANGEMENTS;

U.S. patent application Ser. No. 15/019,196, entitled SURGICAL INSTRUMENT ARTICULATION MECHANISM WITH SLOTTED SECONDARY CONSTRAINT;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;

U.S. patent application Ser. No. 15/019,215, entitled SURGICAL INSTRUMENTS WITH NON-SYMMETRICAL ARTICULATION ARRANGEMENTS;

U.S. patent application Ser. No. 15/019,227, entitled ARTICULATABLE SURGICAL INSTRUMENTS WITH SINGLE ARTICULATION LINK ARRANGEMENTS;

U.S. patent application Ser. No. 15/019,235, entitled SURGICAL INSTRUMENTS WITH TENSIONING ARRANGEMENTS FOR CABLE DRIVEN ARTICULATION SYSTEMS;

U.S. patent application Ser. No. 15/019,230, entitled ARTICULATABLE SURGICAL INSTRUMENTS WITH OFF-AXIS FIRING BEAM ARRANGEMENTS; and U.S. patent application Ser. No. 15/019,245, entitled SURGICAL INSTRUMENTS WITH CLOSURE STROKE REDUCTION ARRANGEMENTS.

Applicant of the present application also owns the U.S. Patent Applications identified below which were filed on Feb. 12, 2016 which are each herein incorporated by reference in their respective entireties:

U.S. patent application Ser. No. 15/043,254, entitled MECHANISMS FOR COMPENSATING FOR DRIVETRAIN FAILURE IN POWERED SURGICAL INSTRUMENTS;

U.S. patent application Ser. No. 15/043,259, entitled MECHANISMS FOR COMPENSATING FOR DRIVETRAIN FAILURE IN POWERED SURGICAL INSTRUMENTS;

U.S. patent application Ser. No. 15/043,275, entitled MECHANISMS FOR COMPENSATING FOR DRIVETRAIN FAILURE IN POWERED SURGICAL INSTRUMENTS; and U.S. patent application Ser. No. 15/043,289, entitled MECHANISMS FOR COMPENSATING FOR DRIVE-TRAIN FAILURE IN POWERED SURGICAL INSTRUMENTS.

Applicant of the present application owns the following patent applications that were filed on Jun. 18, 2015 and which are each herein incorporated by reference in their respective entireties:

U.S. patent application Ser. No. 14/742,925, entitled SURGICAL END EFFECTORS WITH POSITIVE JAW OPENING ARRANGEMENTS;

U.S. patent application Ser. No. 14/742,941, entitled SURGICAL END EFFECTORS WITH DUAL CAM ACTUATED JAW CLOSING FEATURES;

U.S. patent application Ser. No. 14/742,914, entitled MOVABLE FIRING BEAM SUPPORT ARRANGEMENTS FOR ARTICULATABLE SURGICAL INSTRUMENTS;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT;

U.S. patent application Ser. No. 14/742,885, entitled DUAL ARTICULATION DRIVE SYSTEM ARRANGEMENTS FOR ARTICULATABLE SURGICAL INSTRUMENTS; and U.S. patent application Ser. No. 14/742,876, entitled PUSH/PULL ARTICULATION DRIVE SYSTEMS FOR ARTICULATABLE SURGICAL INSTRUMENTS.

Applicant of the present application owns the following patent applications that were filed on Mar. 6, 2015 and which are each herein incorporated by reference in their respective entireties:

U.S. patent application Ser. No. 14/640,746, entitled POWERED SURGICAL INSTRUMENT, now U.S. Patent Application Publication No. 2016/0256184;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Patent Application Publication No. 2016/0256153;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Patent Application Publication No. 2016/0256187;

U.S. patent application Ser. No. 14/640,817, entitled INTERACTIVE FEEDBACK SYSTEM FOR POWERED SURGICAL INSTRUMENTS, now U.S. Patent Application Publication No. 2016/0256186;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Patent Application Publication No. 2016/0256155;

U.S. patent application Ser. No. 14/640,837, entitled SMART SENSORS WITH LOCAL SIGNAL PROCESSING, now U.S. Patent Application Publication No. 2016/0256163;

U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Patent Application Publication No. 2016/0256162; and U.S. patent application Ser. No. 14/640,780, entitled SURGICAL INSTRUMENT COMPRISING A LOCKABLE BATTERY HOUSING, now U.S. Patent Application Publication No. 2016/0256161.

Applicant of the present application owns the following patent applications that were filed on Feb. 27, 2015, and which are each herein incorporated by reference in their respective entireties:

U.S. patent application Ser. No. 14/633,576, entitled SURGICAL INSTRUMENT SYSTEM COMPRISING AN INSPECTION STATION, now U.S. Patent Application Publication No. 2016/0249919;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Patent Application Publication No. 2016/0249915;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Patent Application Publication No. 2016/0249918;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Patent Application Publication No. 2016/0249908;

U.S. patent application Ser. No. 14/633,548, entitled POWER ADAPTER FOR A SURGICAL INSTRUMENT, now U.S. Patent Application Publication No. 2016/0249909;

U.S. patent application Ser. No. 14/633,526, entitled ADAPTABLE SURGICAL INSTRUMENT HANDLE, now U.S. Patent Application Publication No. 2016/0249945;

U.S. patent application Ser. No. 14/633,541, entitled MODULAR STAPLING ASSEMBLY, now U.S. Patent Application Publication No. 2016/0249927; and U.S. patent application Ser. No. 14/633,562, entitled SURGICAL APPARATUS CONFIGURED TO TRACK AN END-OF-LIFE PARAMETER, now U.S. Patent Application Publication No. 2016/0249917.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Patent Application Publication No. 2016/0174977;

U.S. patent application Ser. No. 14/574,483, entitled SURGICAL INSTRUMENT ASSEMBLY COMPRISING LOCKABLE SYSTEMS, now U.S. Patent Application Publication No. 2016/0174969;

U.S. patent application Ser. No. 14/575,139, entitled DRIVE ARRANGEMENTS FOR ARTICULATABLE SURGICAL INSTRUMENTS, now U.S. Patent Application Publication No. 2016/0174978;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Patent Application Publication No. 2016/0174976;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLOSURE ARRANGEMENTS, now U.S. Patent Application Publication No. 2016/0174983;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Patent Application Publication No. 2016/0174975;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Patent Application Publication No. 2016/0174973;

U.S. patent application Ser. No. 14/574,493, entitled SURGICAL INSTRUMENT ASSEMBLY COMPRISING A FLEXIBLE ARTICULATION SYSTEM, now U.S. Patent Application Publication No. 2016/0174970; and U.S. patent application Ser. No. 14/574,500, entitled SURGICAL INSTRUMENT ASSEMBLY COMPRISING A LOCKABLE ARTICULATION SYSTEM, now U.S. Patent Application Publication No. 2016/0174971.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Patent Application Publication No. 2014/0263539.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAILOUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Patent Application Publication No. 2015/0272583; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Patent Application Publication No. 2016/0066914;

U.S. patent application Ser. No. 14/478,908, entitled MONITORING DEVICE DEGRADATION BASED ON COMPONENT EVALUATION, now U.S. Patent Application Publication No. 2016/0066910;

U.S. patent application Ser. No. 14/478,895, entitled MULTIPLE SENSORS WITH ONE SENSOR AFFECTING A SECOND SENSOR'S OUTPUT OR INTERPRETATION, now U.S. Patent Application Publication No. 2016/0066909;

U.S. patent application Ser. No. 14/479,110, entitled POLARITY OF HALL MAGNET TO DETECT MISLOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Patent Application Publication No. 2016/0066916; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in four longitudinal rows. Two rows of staple cavities are positioned on a first side of a longitudinal slot and two rows of staple cavities are positioned on a second side of the longitudinal slot. Other arrangements of staple cavities and staples may be possible.

The staples are movable between their unfired positions and their fired positions by a sled assembly. The sled assembly is movable between a proximal position adjacent the proximal end and a distal position adjacent the distal end. The sled assembly comprises a plurality of ramped surfaces configured to slide under the staples and lift the staples toward the anvil. Other arrangements may include staple drivers supporting the staples in the staple cavities and, in such arrangements, the sled assembly can slide under and lift the drivers, as well as the staples supported thereon, toward the anvil.

Further to the above, the sled assembly is moved distally by a firing member. The firing member is configured to contact the sled assembly and push the sled assembly toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

In certain instances, the end effectors described herein can define a width equal to or less than 8 mm and a height equal to or less than 8 mm. For example, the end effectors described herein can be 5 mm wide by 8 mm high. In other instances, the end effectors can be 5 mm wide by 5 mm high, for example. The compact end effectors described herein can include various features that contribute to the smaller footprint thereof. For example, such end effectors can include direct-drive staples, such as the staples described in U.S. patent application Ser. No. 14/836,324, entitled SURGICAL STAPLES FOR MINIMIZING STAPLE ROLL, filed Aug. 26, 2015, which is incorporated by reference herein in its entirety. Because drivers are eliminated when a staple is driven directly by a sled assembly, the height of the staple cartridge and, thus, the height of the end effector configured to receive the staple cartridge can be reduced. Additionally or alternatively, such end effectors can include a multifunction firing member. For example, the firing member can drive a sled to fire the staples from the staple cartridge, cut tissue clamped between the jaws, cam the jaws into a clamped configuration, and cam the jaws into an open configuration. Such clamp-fire-open firing members can implement a combination of surgical functions with a single actuation system, which can decrease the independent actuation systems in the end effector and, thus, may reduce the size of the end effector. For example, a translating closure tube that moves around at least a portion of the end effector to effect a closure motion can be eliminated in certain instances.

The compact end effectors described herein can be advantageous for a wide variety of surgical procedures including surgical procedures in which a small surgical footprint is appreciated. For example, in certain thoracic procedures, the end effectors can be utilized to cut and seal vessels such as the pulmonary vessel, for example, which has a small diameter and a high volume of flow. The compact end effectors may require a smaller insertion orifice and can provide increased viewability to the surgeon around the surgical site.

Figure 1A:
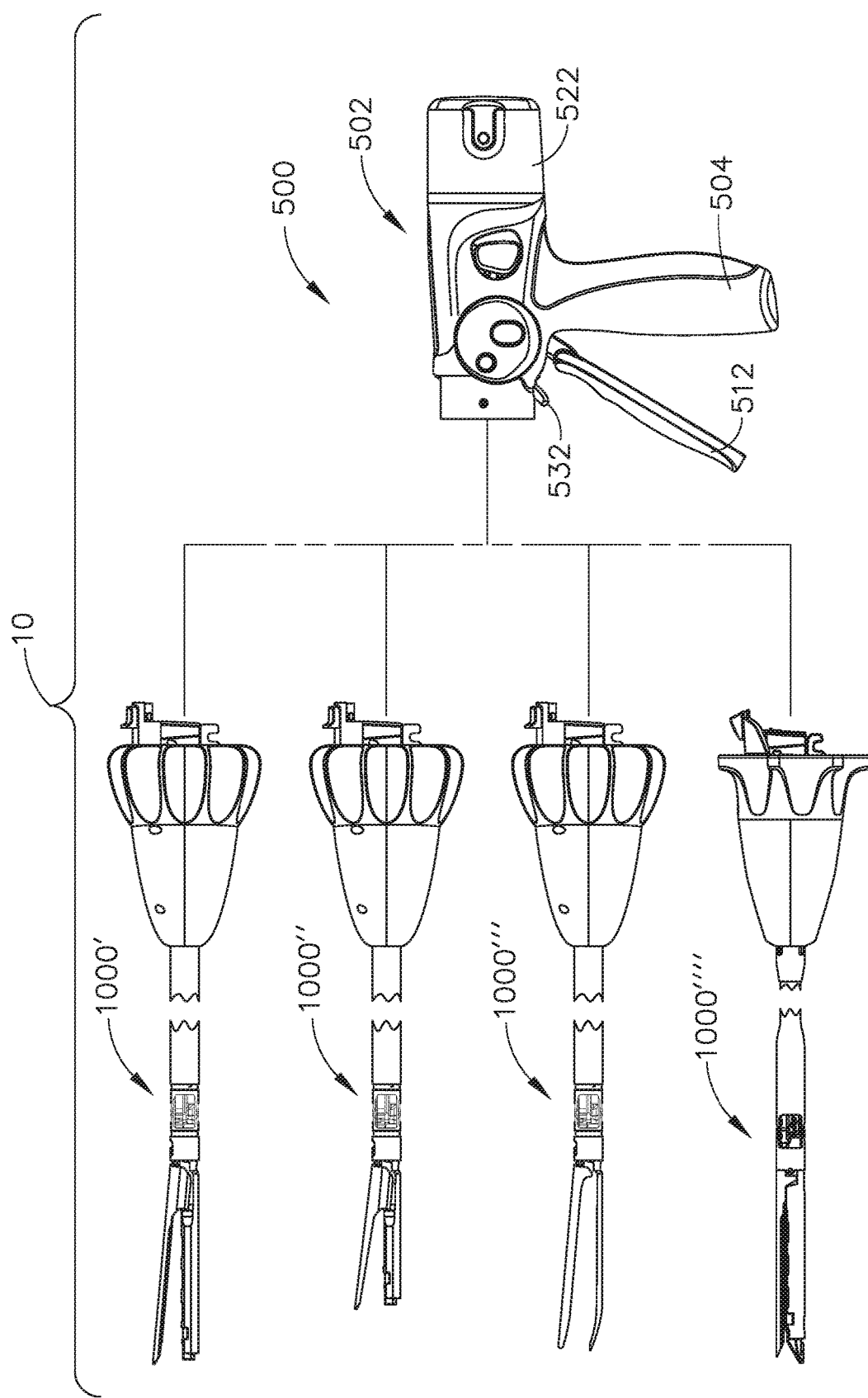
FIG. 1A is an elevation exploded assembly view of the handle assembly of FIG. 1 and a plurality of interchangeable surgical tool assemblies therefor.
Figure 2:
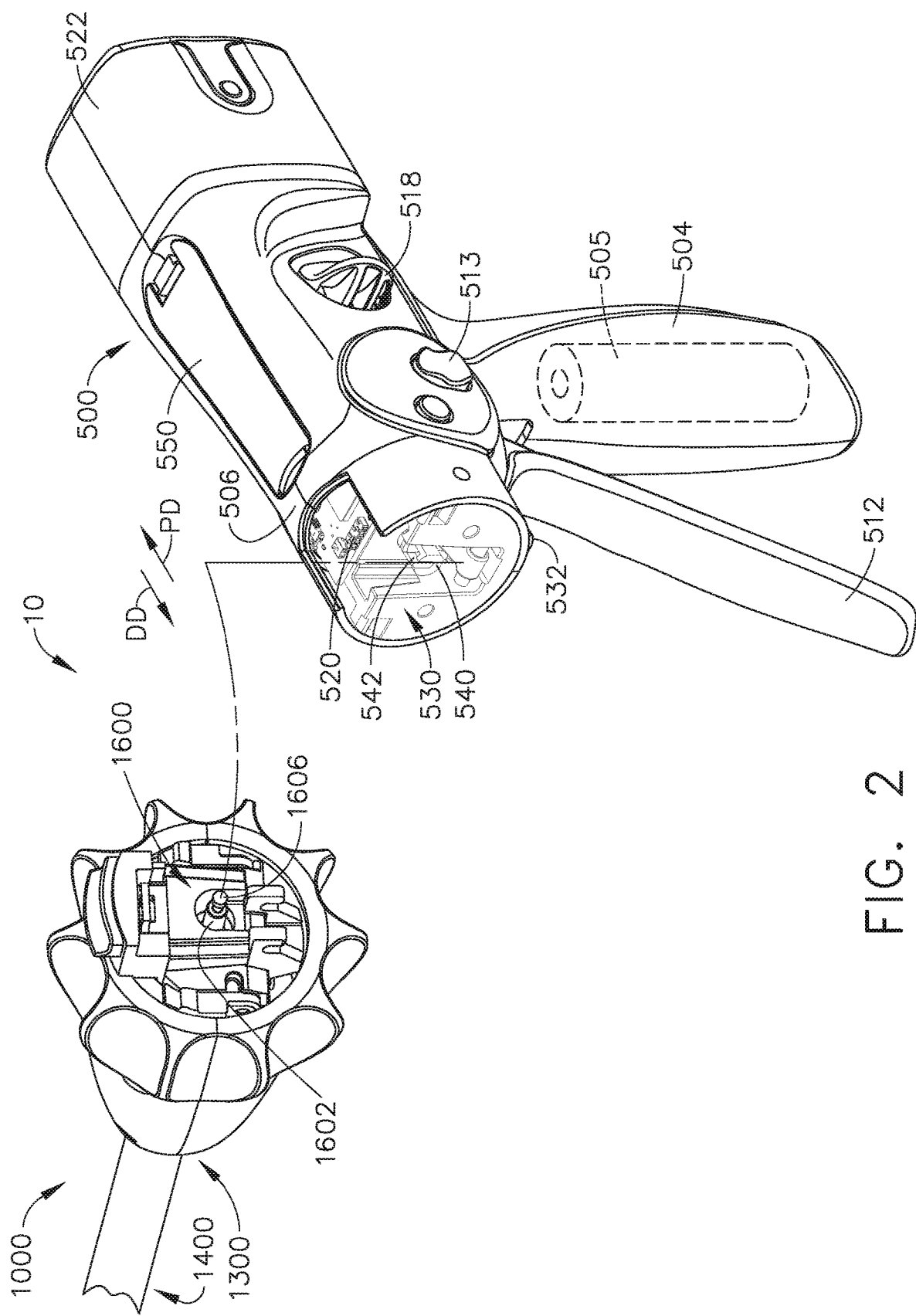
FIG. 2 is a perspective exploded assembly view of the handle assembly and portions of the interchangeable surgical tool assembly of FIG. 1.

FIGS. 1 and 2 depict one form of a surgical instrument 10 including an interchangeable surgical tool assembly 1000 that is operably coupled to a motor driven handle assembly 500. Referring to FIG. 1A, the handle assembly 500 can be compatible with a plurality of different interchangeable surgical tool assemblies in addition to the interchangeable surgical tool assembly 1000. For example, the handle assembly 500 can be compatible with the interchangeable surgical tool assemblies 1000', 1000'', 1000''' and 1000'''' depicted in FIG. 1A. The interchangeable surgical tool assembly 1000 may also be effectively employed with a tool drive assembly of a robotically controlled or automated surgical system. For example, the interchangeable surgical tool assemblies disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety. The handle assembly 500, as well as the tool drive assembly of a robotic system may also be referred to herein as "control systems" or "control units".

FIGS. 1 and 2 illustrate attachment of the interchangeable surgical tool assembly 1000 to the handle assembly 500. The handle assembly 500 may comprise a handle housing 502 that includes a pistol grip portion 504 that can be gripped and manipulated by the clinician. The handle assembly 500 may further include a frame 506 that operably supports at least one drive system.

In at least one form, the handle assembly 500 and the frame 506 may operably support a drive system 530 that is configured to apply closing and firing motions to corresponding portions of the interchangeable surgical tool assembly that is attached thereto. As was described in detail in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, the drive system 530 may employ an electric motor 505 that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries, which may be connected in series, may be used as the power source 522 for the handle assembly 500. In addition, the power source 522 may be replaceable and/or rechargeable.

Referring primarily to FIG. 2, the electric motor 505 is configured to axially drive a longitudinally movable drive member 540 in distal and proximal directions depending upon the polarity of the motor 505. For example, when the motor 505 is driven in one rotary direction, the longitudinally movable drive member 540 will be axially driven in the distal direction "DD". When the motor 505 is driven in the opposite rotary direction, the longitudinally movable drive member 540 will be axially driven in a proximal direction "PD". The handle assembly 500 can include a switch 513 that can be configured to reverse the polarity applied to the electric motor 505 by the power source 522 or otherwise control the motor 505. The handle assembly 500 can also include a sensor or sensors (not shown) configured to detect the position of the drive member 540 and/or the direction in which the drive member 540 is being moved. When the interchangeable surgical tool assembly 1000 is mounted to the handle assembly 500, the drive member 540 of the handle drive system 530 is coupled to a drive member 1602 of a tool drive system 1600 in the interchangeable surgical tool assembly 1000, and the drive member 1602 is connected to a firing member 1760 in the end effector 1100 via a flexible firing bar 1770 (see FIGS. 3-5).

During a firing stroke, the drive member 540 transfers a firing motion to the firing bar 1770 via the drive member 1602 to fire the firing member 1760. For example, actuation of the drive member 540 is configured to displace the firing bar 1770 and the firing member 1760 distally to cut tissue and effect firing of staples from a staple cartridge. Thereafter, the drive member 540 can be retracted proximally to retract the firing bar 1770 and the firing member 1760 proximally. The firing bar 1770 can be comprised of a laminated beam structure including a least two layers. The firing bar 1770 can be configured to flex within an articulation joint 1200. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the firing bar 1770 to be sufficiently flexible to accommodate articulation of the end effector 1100. Various laminated knife bar arrangements are disclosed in U.S. patent application Ser. No. 15/019,245, entitled SURGICAL INSTRUMENTS WITH CLOSURE STROKE REDUCTION ARRANGEMENTS, which is hereby incorporated by reference herein in its entirety. The reader will readily appreciate that various firing members described herein can be coupled to the firing bar 1770 in certain instances.

In various instances, the handle assembly 500 can be configured to detect the type of interchangeable surgical tool assembly 1000 mounted or attached thereto. For example, the handle assembly 500 can include a Hall effect sensor, which can be configured to detect a detectable element, such as a magnetic element, for example, on an interchangeable surgical tool assembly, such as interchangeable surgical tool assembly 1000, for example. Different interchangeable surgical tool assemblies can have different detectable elements and/or arrangements thereof. Various sensors for detecting different interchangeable surgical tool assemblies are described in U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564, which is hereby incorporated by reference herein in its entirety.

Based on the detected type of interchangeable surgical tool assembly 1000, the handle assembly 500 can implement certain surgical functions and/or can lockout certain surgical functions. For example, the handle assembly 500 can include one or more discrete drive systems (e.g. a closure drive system and a firing drive system), however, upon detecting the interchangeable surgical tool assembly 1000, the handle assembly 500 can disarm or deactivate certain drive system(s) (e.g. can deactivate the closure drive system and employ the firing drive system to close and fire the end effector). For example, a handle assembly that includes a plurality of drive systems is described in contemporaneously-filed U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, which is hereby incorporated by reference herein in its entirety.

In at least one form, the longitudinally movable drive member 540 may have a rack of teeth (not shown) formed thereon for meshing engagement with a corresponding drive gear arrangement (not shown) that interfaces with the motor 505. Further details regarding those features may be found in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein. At least one form also includes a manually-actuatable "bailout" assembly that is configured to enable the clinician to manually retract the longitudinally movable drive member 540 should the motor 505 become disabled. The bailout assembly may include a lever or bailout handle assembly that is stored within the handle assembly 500 under a releasable door 550. The lever is configured to be manually pivoted into ratcheting engagement with the teeth in the drive member 540. Thus, the clinician can manually retract the drive member 540 by using the bailout handle assembly to ratchet the drive member 540 in the proximal direction "PD". U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, the entire disclosure of which is hereby incorporated by reference herein, discloses bailout arrangements and other components, arrangements, and systems that may also be employed with the interchangeable surgical tool assembly 1000.

Referring still to FIG. 2, actuation of the motor 505 for the drive system 530 can be controlled by one or more actuators. In at least one form, the drive system 530 may include an actuator in the form of a closure trigger 512 that is pivotally supported by the frame 506. Such an arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly, to a fully compressed or fully actuated position. The closure trigger 512 can be employed to apply closing and, optionally, opening motions to the interchangeable surgical tool assembly 1000 that is operably attached or coupled to the handle assembly 500.

As described in further detail in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, when the clinician fully depresses the closure trigger 512 to attain a "full" closure stroke, the drive system 530 (or another drive system in the handle assembly 500) can be configured to lock the closure trigger 512 into the fully depressed or fully actuated position. When the clinician desires to unlock the closure trigger 512 to permit it to be biased to the unactuated position, the clinician simply activates a closure release button assembly 518, which enables the closure trigger 512 to return to unactuated position. The closure release button assembly 518 may also be configured to interact with various sensors that communicate with a microcontroller 520 (see FIG. 2) in the handle assembly 500 for tracking the position of the closure trigger 512. Further details concerning the configuration and operation of the closure release button assembly 518 may be found in U.S. patent application Ser. No. 14/226,142, entitled SURGICAL INSTRUMENT COMPRISING A SENSOR SYSTEM, now U.S.

Patent Application Publication No. 2015/0272575, which is hereby incorporated by reference in its entirety herein.

In at least one form, the drive system 530 may also include an actuator in the form of a firing trigger 532 that is pivotally supported by the frame 506. The firing trigger 532 may be pivoted between an unactuated position and an actuated position. The firing trigger 532 may be biased into the unactuated position by a spring (not shown) or other biasing arrangement such that when the clinician releases the firing trigger 532, it may be pivoted or otherwise returned to the unactuated position by the spring or biasing arrangement. In at least one form, the firing trigger 532 can be positioned "outboard" of the closure trigger 512. As discussed in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, the handle assembly 500 may be equipped with a firing trigger safety button (not shown) to prevent inadvertent actuation of the firing trigger 532. When the closure trigger 512 is in the unactuated position, the safety button is contained in the handle assembly 500 where the clinician cannot readily access it and move it between a safety position preventing actuation of the firing trigger 532 and a firing position wherein the firing trigger 532 may be fired. As the clinician depresses the closure trigger 512, the safety button and the firing trigger 532 may pivot down wherein they can then be manipulated by the clinician.

As further described herein, the closure trigger 512 can be configured to actuate the motor 505 to drive the drive system 530 a first degree and/or through a first range of motion and the firing trigger 532 can be configured to actuate the motor 505 to drive the drive system 530 a second degree and/or through a second range of motion. In other instances, the handle assembly 500 can include a single actuator for closing and firing the end effector.

Referring primarily to FIG. 2, the interchangeable surgical tool assembly 1000 includes a tool drive system 1600 that is supported for axial travel within the spine assembly 1500. In the illustrated embodiment, the tool drive system 1600 includes a proximal drive shaft segment 1602. The proximal drive shaft segment 1602 can be coupled to an intermediate drive member, such as the drive member 3540 (see FIGS. 30, 31, 33, and 35), and the intermediate drive member can be coupled to a firing bar that terminates in a firing member, such as the firing bar 3770 and the firing member 1760 (see FIGS. 30, 31, 33, and 35). As can be seen in FIG. 2, a proximal attachment lug 1606 protrudes proximally from a proximal end of the proximal drive shaft segment 1602 and is configured to be operably received within the firing shaft attachment cradle 542 in the longitudinally movable drive member 540 that is supported in the handle assembly 500. When assembled, the handle drive member 540 is configured to transfer motion to the proximal drive shaft segment 1602 and ultimately to the firing member 1760 via the intermediate drive member and the firing bar.

Referring still to FIGS. 1 and 2, the interchangeable surgical tool assembly 1000 includes a shaft mounting portion 1300 that is operably attached to an elongate shaft assembly 1400. A surgical end effector 1100 that comprises an elongate channel 1102 that is configured to operably support a staple cartridge 1110 therein is operably attached to the elongate shaft assembly 1400. The end effector 1100 may further include an anvil 1130 that is pivotally supported relative to the elongate channel 1102. The elongate channel 1102/staple cartridge assembly 1110 and the anvil 1130 may also be referred to as "jaws". The interchangeable surgical tool assembly 1000 may further include the articulation joint 1200 (see FIG. 1) and an articulation lock, which can be configured to releasably hold the end effector 1100 in a desired articulated position about an articulation axis B-B which is transverse to a shaft axis SA. Details regarding the construction and operation of the articulation lock may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, the entire disclosure of which is hereby incorporated by reference herein.

Figure 5:
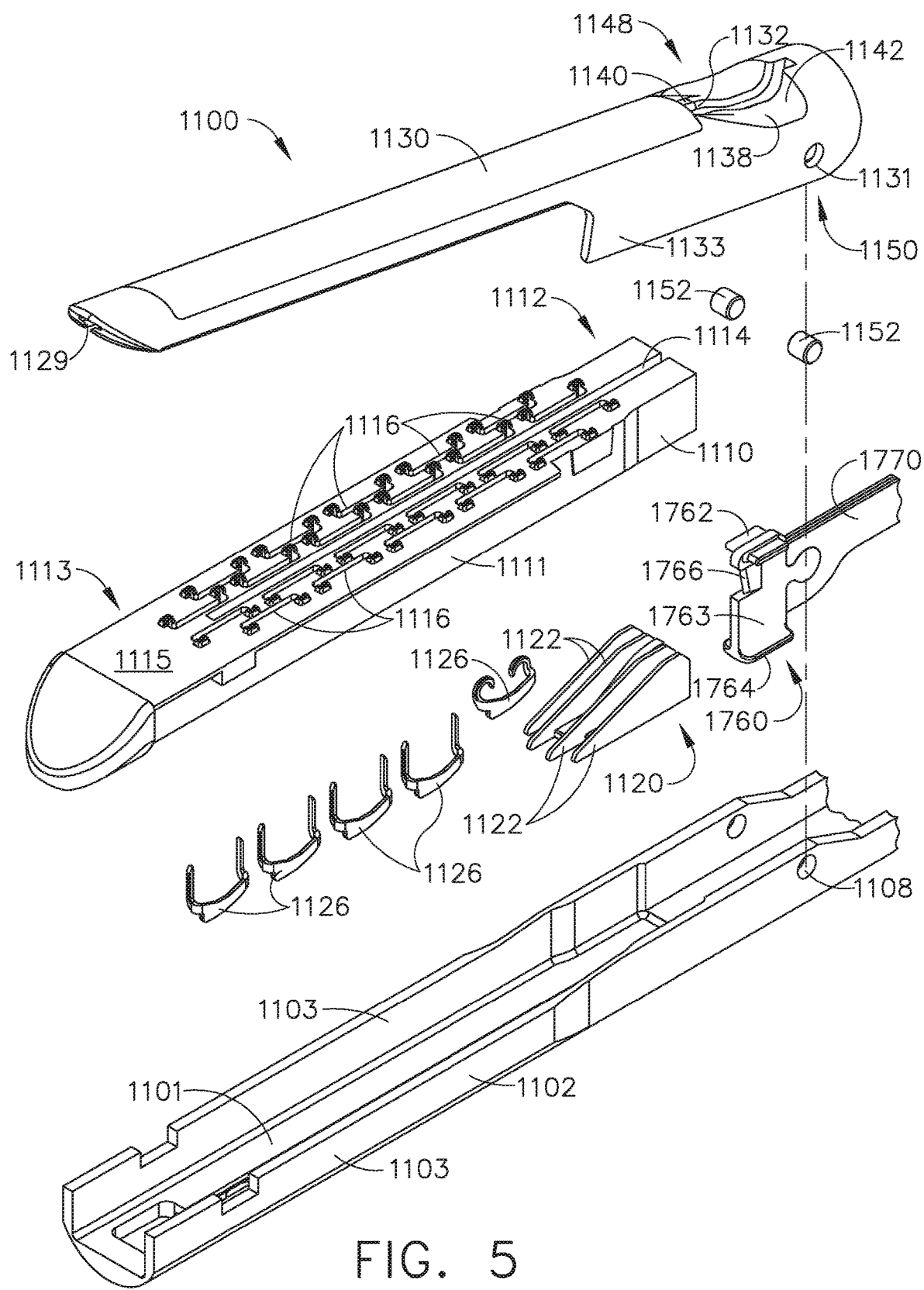
FIG. 5 is an exploded assembly view of a distal portion of the interchangeable surgical tool assembly of FIG. 1.

Referring primarily now to FIGS. 3-5, a firing member 1760 is configured to operably interface with a sled assembly 1120 that is operably supported within the cartridge body 1111 of the surgical staple cartridge 1110. The sled assembly 1120 is slidably displaceable within the surgical staple cartridge body 1111 from a proximal starting position adjacent the proximal end 1112 of the cartridge body 1111 to an ending position adjacent a distal end 1113 of the cartridge body 1111.

Staple pockets or cavities 1116 are aligned in rows on each side of a centrally-disposed slot 1114. The cavities 1116 open through the upper deck surface 1115 of the cartridge body 1111. The centrally-disposed slot 1114 enables the firing member 1760 to pass therethrough and cut the tissue that is clamped between the anvil 1130 and the staple cartridge 1110. A direct-drive surgical staple or fastener 1126 (see FIG. 5) is positioned in each staple cavity 1116. Referring primarily to FIG. 5, the staples 1126 are flat-formed staples, which can be cut and/or stamped from a sheet of material, for example. The sheet of material can be metallic and can comprise stainless steel and/or titanium, for example. In at least one instance, outlines can be traced, etched, and/or cut into the sheet of material which are machined and/or laser cut to form the direct-drive staples 1126 into a manufactured shape.

The staples 1126 comprise a pair of staple legs and a staple base portion, or crown, from which the staple legs extend. Each staple leg comprises a staple tip, or piercing portion, which is configured to pierce the tissue and contact a corresponding forming pocket 1128 (see FIG. 6) of the anvil of the surgical stapling instrument. The staple legs are configured to change shape to achieve a formed configuration to fasten the tissue. The staple base portion defines a first plane and the staple legs define a second plane which is laterally offset from but at least substantially parallel to the first plane. In other instances, the first and second planes may not be parallel.

The staples 1126 include drive surfaces on the base portion or crown. The drive surfaces are configured to receive the driving force from the sled assembly 1120. When the sled assembly 1120 translates distally through the staple cartridge 1110, the sled assembly 1120 contacts the drive surfaces to lift the staple 1126 out of the staple cartridge 1110 and form the staple 1126 into its fired configuration. Direct-drive staples, such as the staples 1126, for example, are further described in U.S. patent application Ser. No. 14/836,324, entitled SURGICAL STAPLES FOR MINI- MIZING STAPLE ROLL, filed Aug. 26, 2015, which is incorporated by reference herein in its entirety.

The sled assembly 1120 includes a plurality of sloped or wedge-shaped cams 1122 wherein each cam 1122 corresponds to a particular line of staples 1126 located on a side of the centrally-disposed slot 1114. When the firing member 1760 is fired or driven distally, the firing member 1760 drives the sled assembly 1120 distally as well. As the firing member 1760 moves distally through the staple cartridge 1110, the tissue cutting feature 1766 cuts the tissue that is clamped between the anvil assembly 1130 and the staple cartridge 1110, and the sled assembly 1120 drives the staples 1126 upwardly in the staple cartridge 1110 and into forming contact with the anvil assembly 1130.

The firing member 1760 defines an I-beam structure that includes a lower flange 1764, an upper flange 1762, and a support portion 1763 extending between the flanges 1762 and 1764. The upper flange 1762 is comprised of horizontal pins extending from the support portion 1763. The lower flange 1764 is comprised of an enlarged or widened foot at the base of the support portion 1763. The tissue cutting feature 1766 is supported by the support portion 1763 between the flanges 1762 and 1764. The support portion 1763 is configured to travel though aligned slots in the elongate channel 1102, the staple cartridge 1110, and the anvil 1130. For example, the support portion 1763 extends through a centrally-disposed longitudinal channel slot 1104 in the elongate channel 1102 such that the lower flange 1764 is movably positioned within a passageway 1106 (see FIGS. 10 and 11) defined by elongate channel 1102. For example, the passageway 1106 can be defined below a cartridge-supporting base 1101 of the elongate channel 1102.

The support portion 1763 also extends through a centrally-disposed anvil slot 1132 in the anvil 1130 such that the upper flange 1762 is movably positioned within a passageway 1136 (see FIGS. 10 and 11) defined by the anvil 1130. For example, the passageway 1136 can be defined through the anvil 1130. The I-beam flanges 1762 and 1764 provide camming surfaces, which interact with the elongate channel 1102 and the anvil 1130, respectively, to open and clamp, or close, the jaws, as further described herein. Moreover, the firing member 1760 is configured to maintain a constant distance between the elongate channel 1102 and the anvil 1130 along the length of the end effector 1100 to ensure an appropriate tissue gap.

Figure 6:
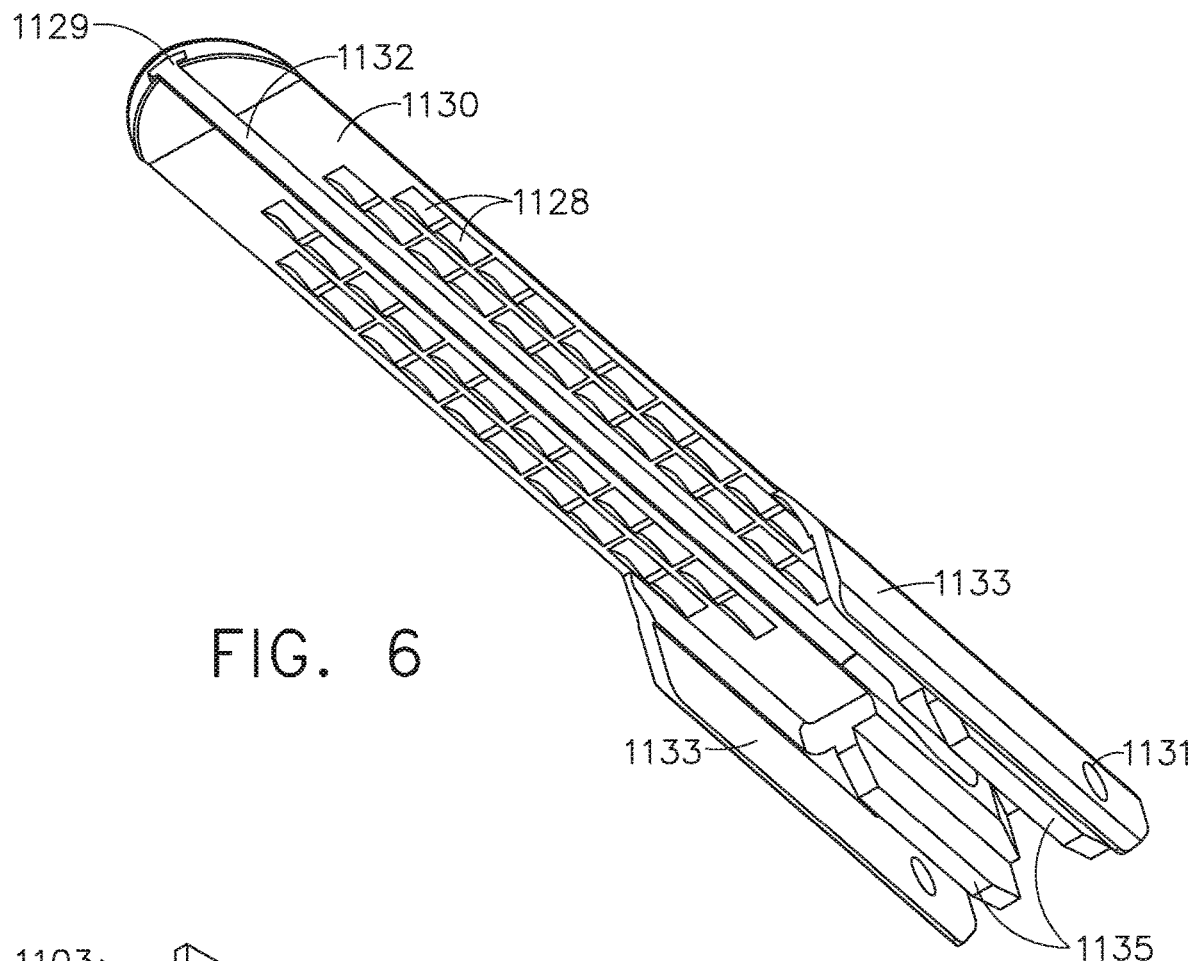
FIG. 6 is a perspective view of an anvil of the interchangeable surgical tool assembly depicted in FIG. 1.

Referring primarily now to FIG. 6, the anvil 1130 includes downwardly-extending sidewalls 1133 commonly referred to as "tissue stops". The tissue stops 1133 are configured to block the target tissue from getting too far proximal between the anvil 1130 and the staple cartridge 1110 (see FIG. 3-5). For example, the tissue stops 1133 extend toward the staple cartridge 1110 (see FIG. 3). When the anvil 1130 is closed toward the staple cartridge 1110, the tissue stops 1133 on either side of the anvil 1130 extend downward past the cartridge deck surface 1115 and form a wall or barrier, which prevents tissue from being positioned too far proximal between the anvil 1130 and the staple cartridge 1110. Additionally or alternatively, the elongate channel 1102 can include upwardly-extending tissue stops for blocking proximal tissue.

The anvil 1130 also includes inner rails 1135, which extend downwardly toward the staple cartridge 1110. The inner rails 1135 extend parallel to the tissue stops 1133 and are positioned laterally inboard of the tissue stops 1133. The inner rails 1135 are configured to guide the anvil 1130 relative to the elongate channel 1102 as the anvil 1130 pivots relative to the elongate channel 1102. For example, the inner rails 1135 can nest within the sidewalls 1103 of the elongate channel 1102 and the tissue stops 1133 can be positioned outside the sidewalls 1103 of the elongate channel 1102 when the anvil 1130 pivots toward a closed position. In various instances, the inner rails 1135 can slide or move adjacent to an inner surface of the sidewalls 1103 of the elongate channel 1102 as the anvil 1130 approaches the staple cartridge 1110 to ensure that the anvil 1130 remains properly aligned with the elongate channel 1102 and the staple cartridge 1110 installed therein.

The slot 1132 in the anvil 1130 extends from the proximal end to the distal end of the anvil 1130. Referring primarily to FIG. 6, the slot 1132 and the passageway 1136 extend to a t-shaped opening 1129 at the distal end of the anvil 1130, which can provide an assembly pathway for the firing member 1760. For example, the firing member 1760 can be inserted into the anvil 1130 from the distal end at the t-shaped opening 1129 and retracted proximally to a home position before the staple cartridge 1110 is inserted in the elongate channel 1102.

Figure 7:
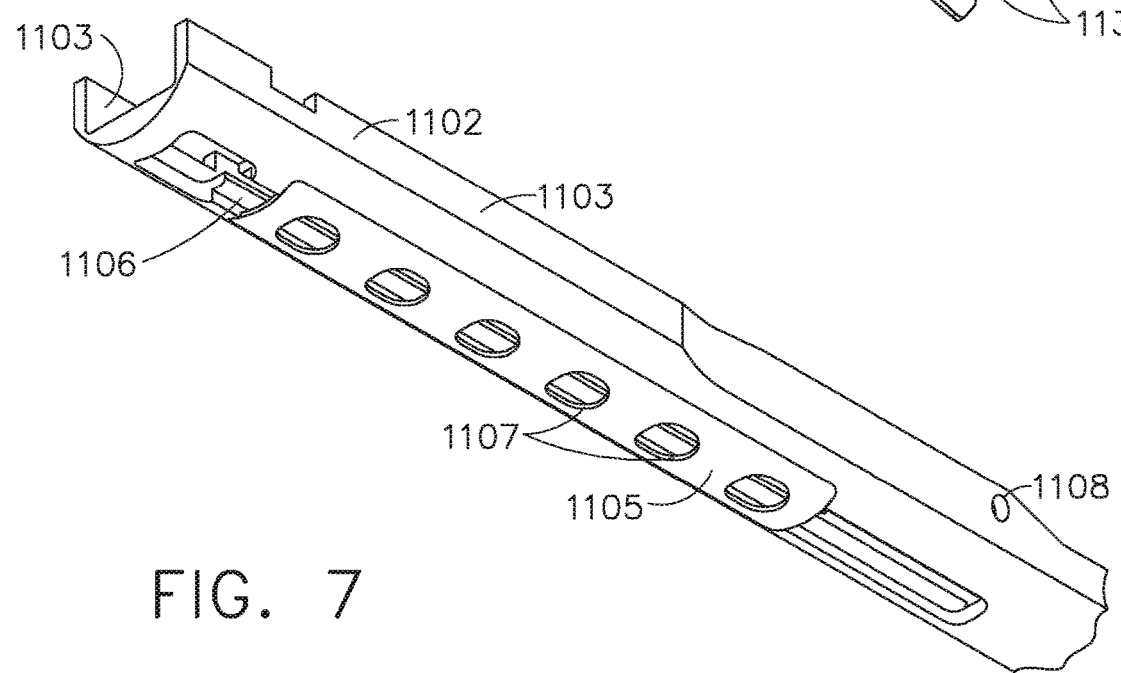
FIG. 7 is a perspective view of an elongate channel of the interchangeable surgical tool assembly depicted in FIG. 1.

Referring primarily now to FIG. 7, the elongate channel 1102 includes the sidewalls 1103 and a pin hole 1108 defined in a proximal portion of each sidewall 1103. The elongate channel 1102 also includes a plate 1105, which is attached to the underside of the cartridge-supporting base 1101 of the elongate channel 1102. The plate 1105 can be laser welded to the elongate channel 1102, for example, and can increase the structural integrity of the elongate channel 1102. For example, the plate 1105 can be configured to prevent and/or limit bending, torqueing and/or deformation of the elongate channel 1102 during a stapling operation. The plate 1105 is positioned over a portion of the longitudinal channel slot 1104 and can define the passageway 1106 through the elongate channel 1102. For example, the passageway 1106 for the lower flange 1764 can be defined by the plate 1105 and the cartridge-supporting base 1101. Openings 1107 in the plate 1105 are positioned along the length thereof to provide views of the firing member as the firing member 1760 traverses the longitudinal channel slot 1104 during a firing stroke. For example, an operator can view the progress of the firing member 1760 through the openings 1107 throughout the firing stroke.

Figure 8:
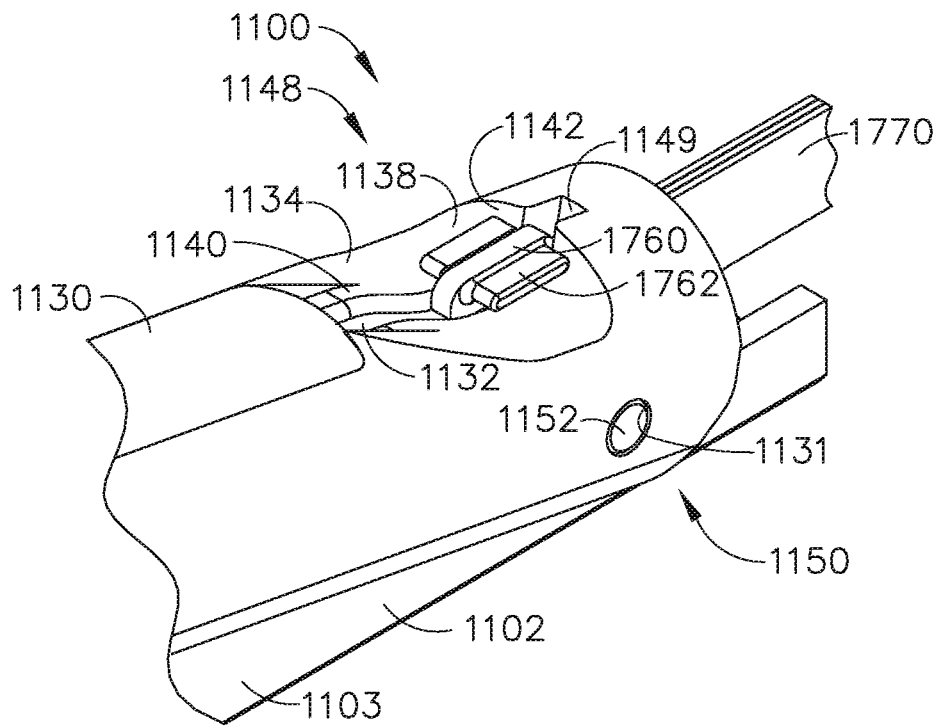
FIG. 8 is a perspective view of a pivot joint of the interchangeable surgical tool assembly of FIG. 1.
Figure 9:
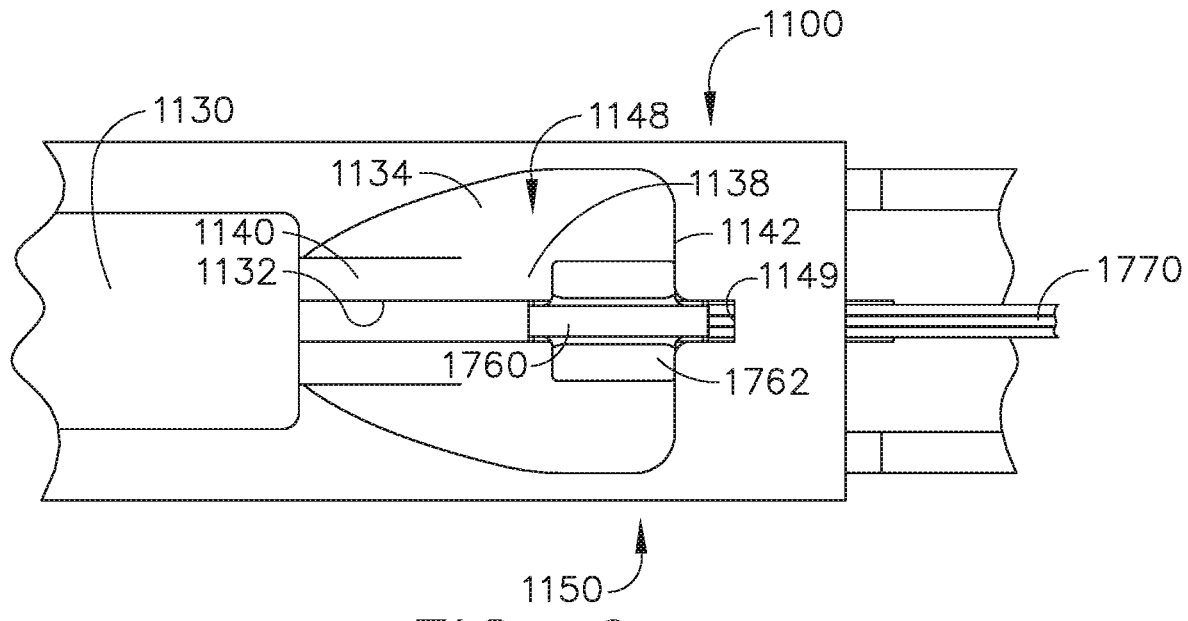
FIG. 9 is a plan view of the pivot joint of FIG. 8.
Figure 10:
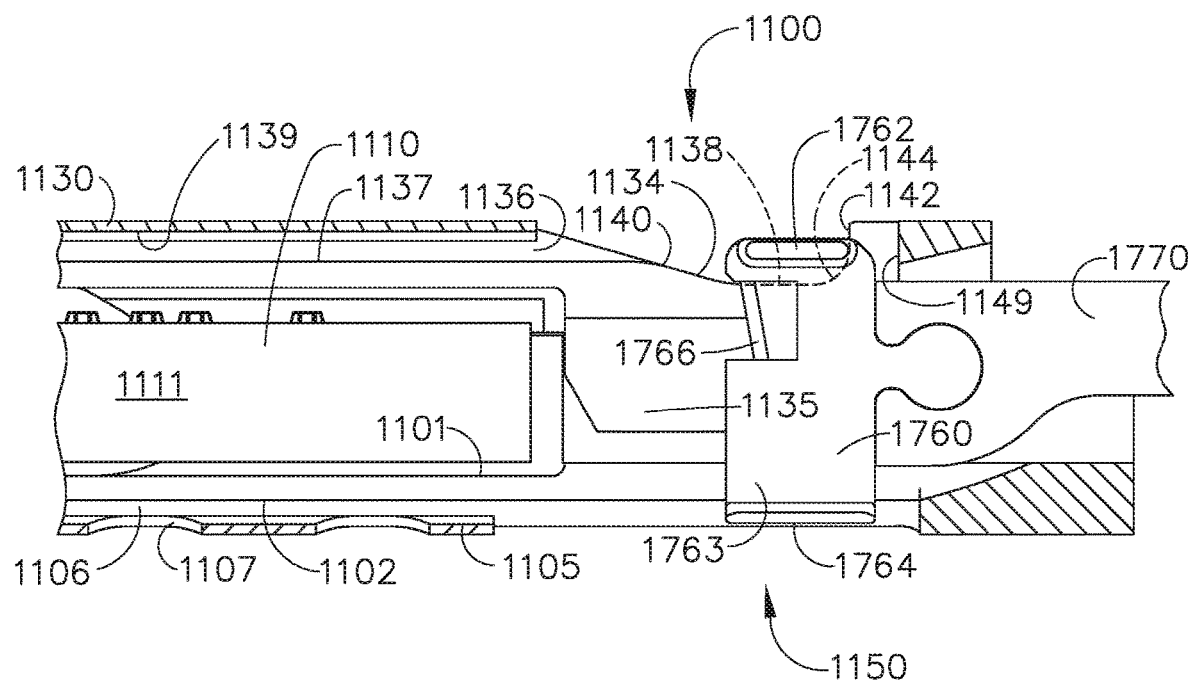
FIG. 10 is an elevation cross-sectional view of a distal portion of the interchangeable surgical tool assembly of FIG. 1 depicting a firing member at the pivot joint of FIG. 8 in an initial position.

Referring primarily now to FIGS. 8-12, a pivot joint 1150 for the end effector 1100 is depicted. The pivot joint 1150 includes pivot pins 1152 (see FIG. 8) at which the anvil 1130 pivots relative to the elongate channel 1102. Although only a single pivot pin 1152 is depicted in FIG. 8, the reader will readily appreciate that symmetrical pivot pins 1152 are positioned on opposite sides of the end effector 1100. The symmetrical pivot pins 1152 are shown in FIG. 5. The pivot pins 1152 extend through apertures 1131 on each side of the anvil 1130 and into the pin holes 1108 on each respective side of the elongate channel 1102. For example, the pivot pins 1152 can be pressed into the apertures 1131. At the outset of the firing stroke, the firing member 1760 is configured to move distally from an initial or home position (FIG. 10). As the firing member 1760 moves distally, the anvil 1130 is pivoted toward a clamped configuration by the I-beam structure of the firing member 1760. More specifically, the lower flanges 1764 of the firing member 1760 move through the passageway 1106 defined by the elongate channel 1102 and the upper flanges 1762 move along a ramped surface 1134 of the anvil 1130 and then through the passageway 1136 defined by the anvil 1130.

Figure 11:
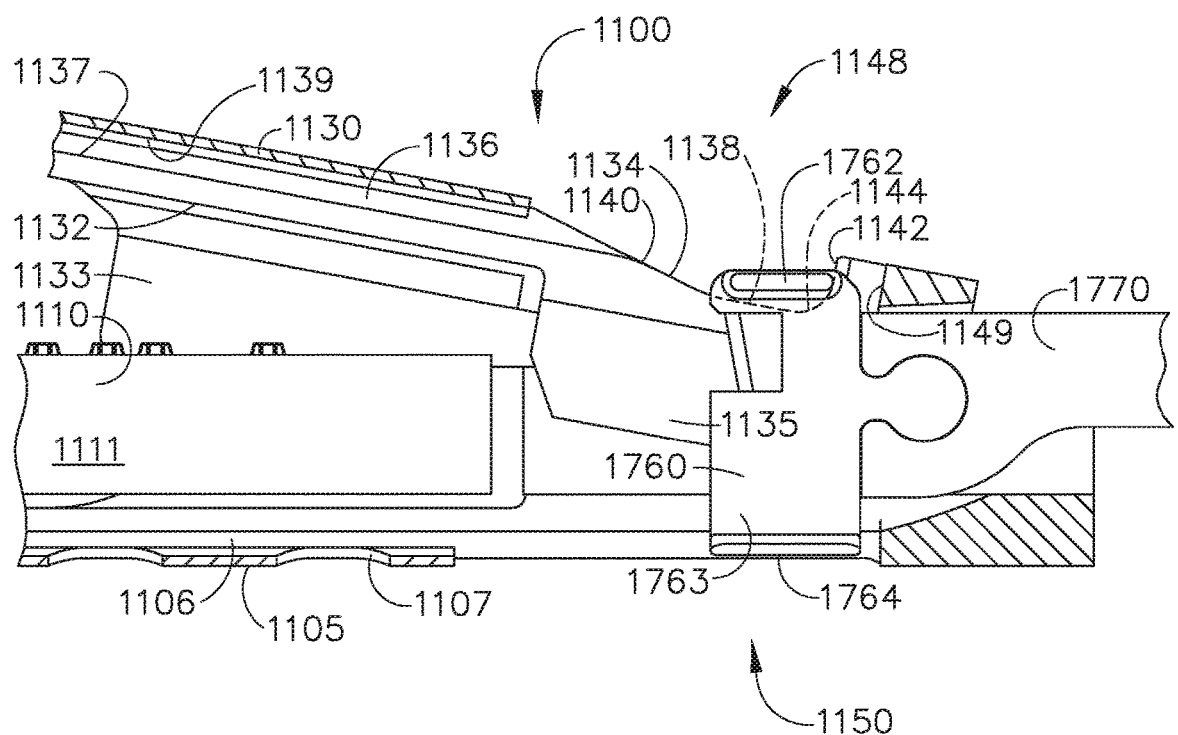
FIG. 11 is an elevation cross-sectional view of a distal portion of the interchangeable surgical tool assembly of FIG. 1 depicting the firing member at the pivot joint of FIG. 8 in a proximally-retracted position from the initial position.

Referring primarily to FIGS. 10 and 11, the ramped surface 1134 defines an open-close cavity 1148 in the anvil 1130 through which a portion of the firing member 1760 extends during a portion of the firing stroke. For example, the upper flanges 1762 protrude from the anvil 1130 via the open-close cavity 1148 during a portion of the firing stroke. The ramped surface 1134 slopes downward along a proximal opening surface 1142, extends along an intermediate portion 1138, and slopes upward along a distal closure ramp 1140. When the firing member 1760 is in an initial position or home position (see FIG. 10), the upper flanges 1762 are spaced apart from the intermediate portion 1138. In other words, the upper flanges 1762 are not cammingly engaged with the open-close cavity 1148. In the home position, the firing member 1760 can dwell or hover with respect to the open-close cavity 1148 such that neither an opening force nor a closing force is applied to the anvil 1130 by the firing member 1760.

From the home position (see FIG. 10), the firing member 1760 can be retracted proximally. A retracted position of the firing member 1760 is depicted in FIG. 11. As the firing member 1760 continues to move proximally, the upper flanges 1762 of the firing member 1760, which are engaged with the proximal opening surface 1142, are configured to exert an opening force on the proximal opening surface 1142. As the upper flanges 1762 move against the proximal opening surface 1142, the proximal opening surface 1142 pivots, which causes the pivoting, opening motion of the anvil 1130. The proximal opening surface 1142 is positioned proximal to the pivot joint 1150. As a result, as the upper flanges 1762 exert a downward force on the proximal opening surface 1142, the anvil 1130 is pushed upward by the leveraging action on the proximal opening surface 1142.

The ramped surface 1134 also includes a fillet 1144 between the intermediate portion 1138 and the proximal opening surface 1142. In certain instances, the proximal end of the open-close cavity 1148 can include an opening ramp, which can extend to a protruding tail. The upper flange 1762 of the firing member 1760 can be configured to camming engage the opening ramp and/or the protruding tail to generate an opening motion for the end effector 1100. In certain instances, the upper flange 1762 can also include a proximally-extending boss, which can be configured to generate an additional opening motion, as further described herein.

From the retracted position (see FIG. 11), the firing member 1760 can be advanced distally to return to the home position (see FIG. 10). To close the end effector, the firing member 1760 can be further advanced from the home position to an advanced position depicted in FIG. 12. For a portion of the firing motion intermediate the retracted position and the advanced position, the upper flanges 1762 are spaced apart from the ramped surface 1134. For example, the upper flanges 1762 hover or dwell above the intermediate portion 1138 as the firing member 1760 shifts between a closure motion (see FIG. 12) and an opening motion (see FIG. 11). The dwell portion of the firing motion can be configured to prevent jamming of the opening and/or closing motions, for example.

Figure 12:
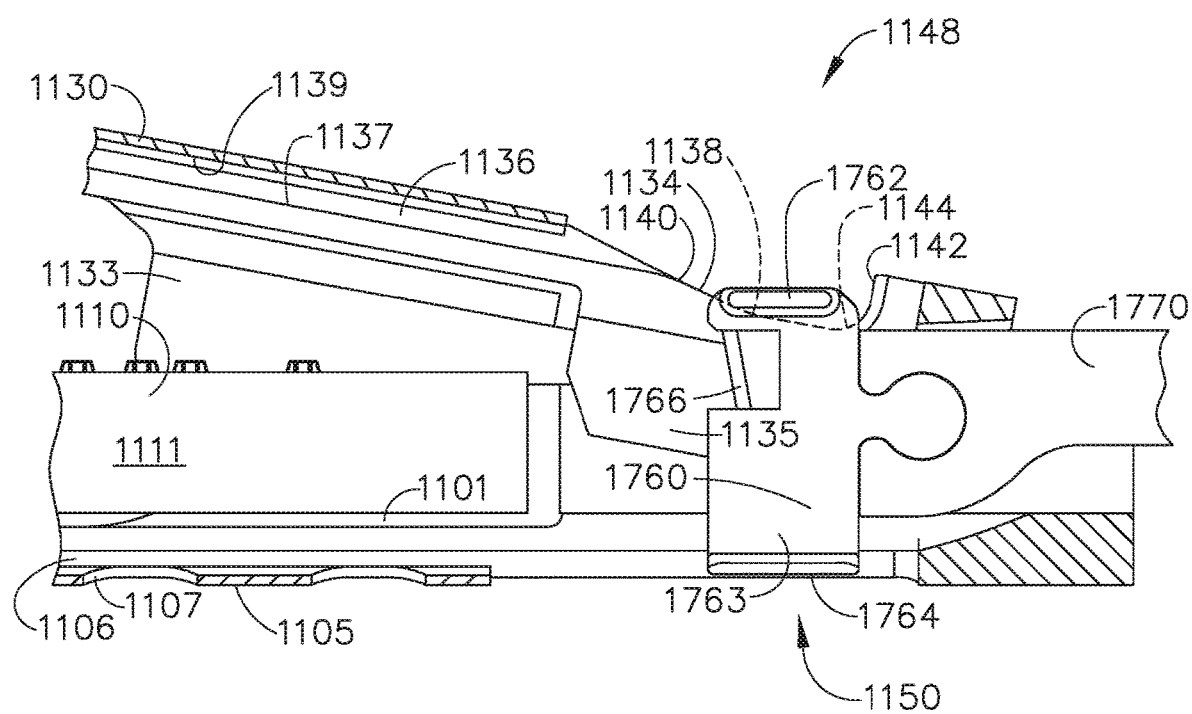
FIG. 12 is an elevation cross-sectional view of a distal portion of the interchangeable surgical tool assembly of FIG. 1 depicting the firing member at the pivot joint of FIG. 8 in a distally-advanced position from the initial position.

The firing member 1760 moves into contact with the ramped surface 1134 and the distal closure ramp 1140 thereof in the advanced position depicted in FIG. 12. As the firing member 1760 is advanced farther distally, the upper flanges 1762 move along the distal closure ramp 1140 to clamp the anvil 1130 relative to the elongate channel 1102. The distal closure ramp 1140 is positioned distal to the pivot joint 1150. As a result, as the upper flanges 1762 exert a downward force on the distal closure ramp 1140, the anvil 1130 is pushed downward.

As the firing member 1760 continues to progress distally, the upper flanges 1762 move through the passageway 1136 to ensure a constant distance between the anvil 1130 and the elongate channel 1102 along the length of the end effector 1100. For example, the passageway 1136 includes a lower ledge 1137 and an upper cap 1139, which define the lower and upper limits of the passageway 1136. The upper flanges 1762 are constrained within those lower and upper limits during the firing stroke. The upper flanges 1762 can be dimensioned to fit snuggly within the confines of the passageway 1136. In other instances, as further described herein, the upper flanges 1762 can be configured to float and/or adjust vertically within a clearance provided by the passageway 1136 or a portion thereof.

The firing member 1760 is a multi-function firing member. For example, the firing member 1760 is configured to drive the sled assembly 1120 in order to fire the direct-drive staples 1126 from the staple cartridge 1110, to cut tissue clamped between the jaws 1102 and 1130, to cam the jaws 1102 and 1130 into a clamped configuration at the outset of the firing stroke, and to cam the jaws 1102 and 1130 into an open configuration at the completion of the firing stroke. In other words, the firing member 1760 is configured to implement a combination of surgical functions with a single actuation system. As a result, the independent actuations systems required to fit within the footprint of the end effector 1100 can be minimized by the multi-function firing member 1760.

In other instances, an interchangeable surgical tool assembly can include a closure tube for opening and closing the jaws of an end effector. A closure tube can be configured to translate relative to the end effector. As the closure tube translates over the end effector, for example, the closure tube can be configured to bias the jaws of the end effector closed. In certain instances, a spring can be configured to bias the jaws of the end effector toward an open configuration and the closure tube can overcome the spring bias in order to close the jaws.

An interchangeable surgical tool assembly 7000 including an end effector 7100 and a distal closure tube 7430 is depicted in FIGS. 13-17. The end effector 7100 includes an anvil 7130 and an elongate channel 7102, which are similar to the anvil 1130 and the elongate channel 1102, respectively. A closure assembly 7406 is utilized to close and/or open the anvil 7130 and the elongate channel 7102 of the end effector 7100. The closure assembly 7406 includes an intermediate closure member 7410 and a distal closure member 7430. The intermediate closure member 7410 and the distal closure member 7430 are coupled together by an upper double pivot link 7220.

In the illustrated arrangement, the distal closure member 7430 comprises a hollow tubular member that is slidably supported relative to the end effector 7100. Hence, the distal closure member 7430 may also be referred to herein as the distal closure tube. Actuation of a closure trigger 512 (see FIGS. 1 and 2) on the handle assembly 500 of the surgical instrument can result in the axial movement of the closure assembly 7406 including the distal closure tube 7430. A closure spring (not shown) may also be journaled on the closure assembly 7406 and serves to bias the closure assembly 7406 in the proximal direction "PD" which can serve to pivot closure trigger 512 into the unactuated position when the interchangeable surgical tool assembly 7000 is operably coupled to the handle assembly 500. In use, the closure assembly 7406 is configured to be translated distally (direction DD) to close the anvil 7130, for example, in response to the actuation of the closure trigger 512.

Figure 13:
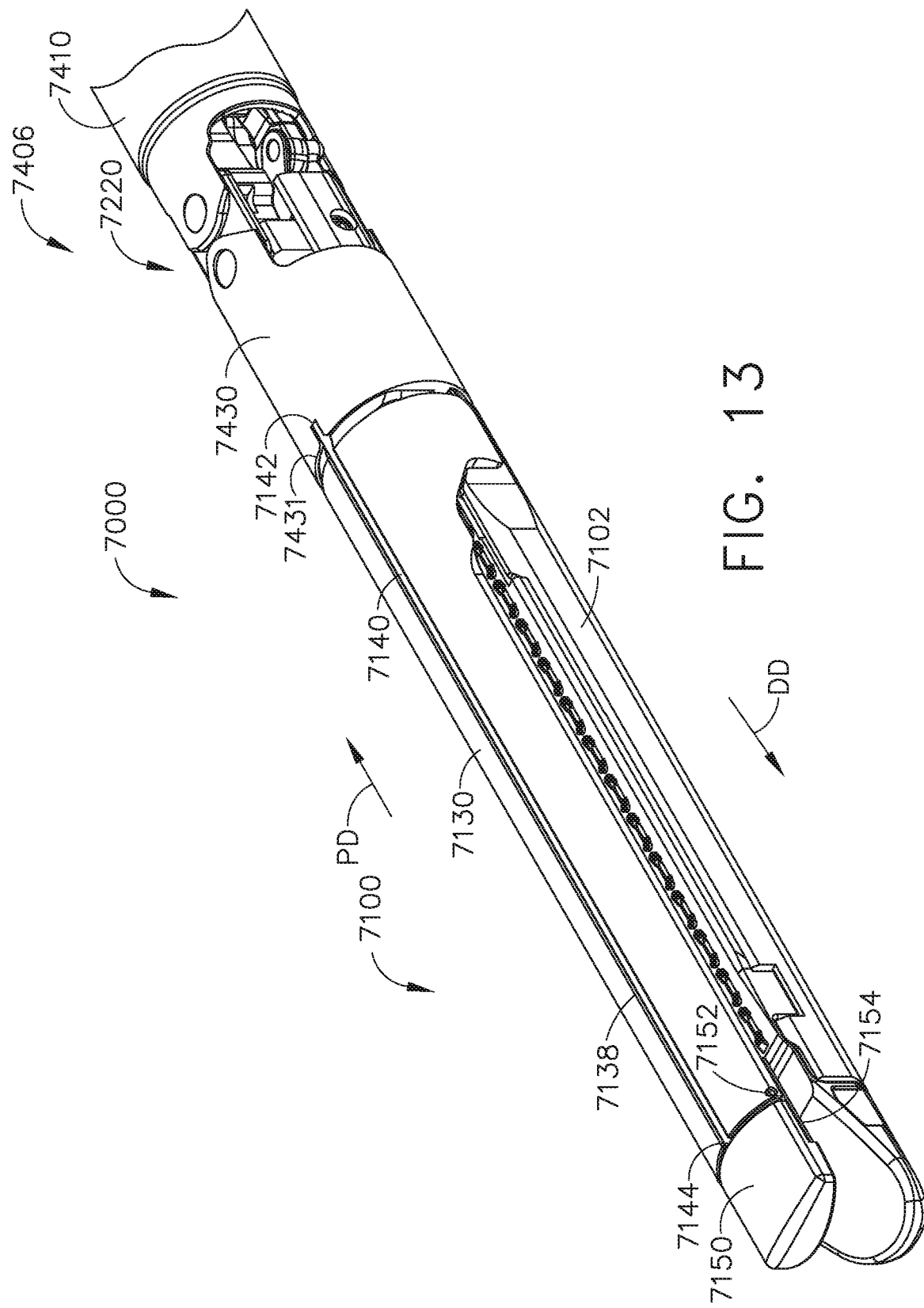
FIG. 13 is a perspective view of a distal portion of an interchangeable surgical tool assembly depicting a distal nose portion thereof in an initial configuration.
Figure 14:
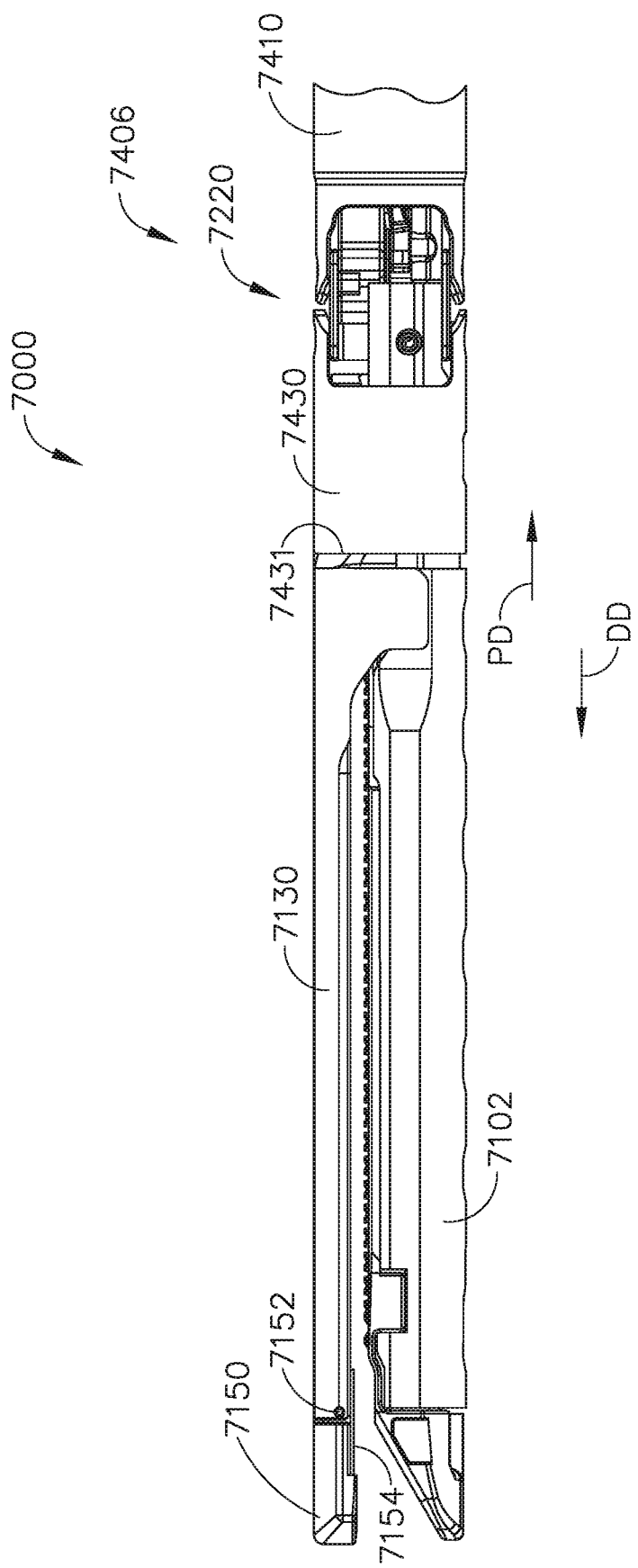
FIG. 14 is an elevation view of a distal portion of the interchangeable surgical tool assembly of FIG. 13 depicting the distal nose portion in the initial configuration.

FIGS. 13 and 14 illustrate the anvil 7130 and the elongate channel 7102 (the "jaws") in the closed position. As the distal closure member 7430 is advanced in the distal direction DD, the distal end 7431 of the distal closure member 7430 can be configured to travel up closure cam surfaces formed on the anvil mounting walls and up closure cam surfaces formed on the proximal end of the elongate channel 7102. When the clinician desires to move the anvil 7130 and the elongate channel 7102 to the open position, the distal closure member 7430 is moved in the proximal direction PD. Actuation of a closure trigger and closure assembly including a distal closure tube thereof is described in contemporaneously-filed U.S. patent application Ser. No. 15/385,956, entitled SURGICAL INSTRUMENTS WITH POSITIVE JAW OPENING FEATURES, which is hereby incorporated by reference herein in its entirety.

Figure 17:
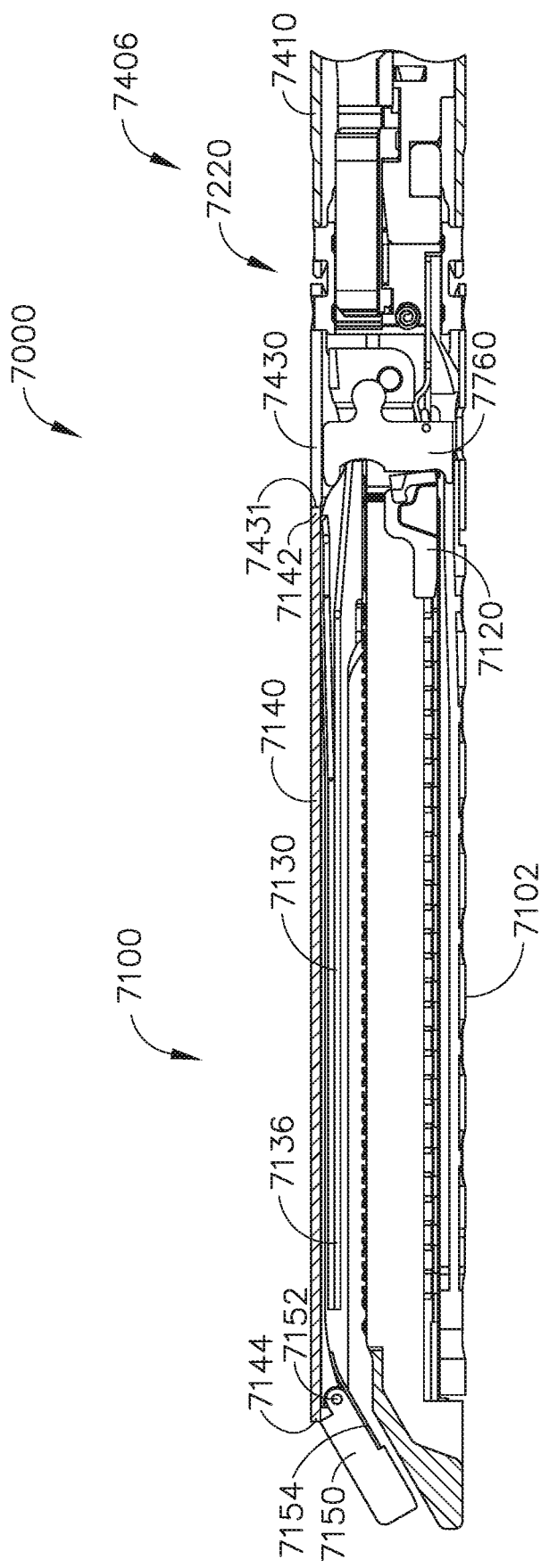
FIG. 17 is an elevation cross-sectional view of the end effector of FIG. 13 depicting the distal nose portion in the pivoted configuration.

Referring primarily now to FIG. 17, a firing member 7760 is positioned in the end effector 7100. The firing member 7760 is configured to translate through the end effector 7100 during a firing stroke to move a sled assembly 7120 through the end effector 7100 and cut tissue clamped between the jaws of the end effector 7100. The anvil 7130 includes a passageway 7136, which is configured to receive a portion of the firing member 7760 during the firing stroke. For example, an upper flange on the firing member 7760 can be movably positioned in the passageway 7136.

Figure 15:
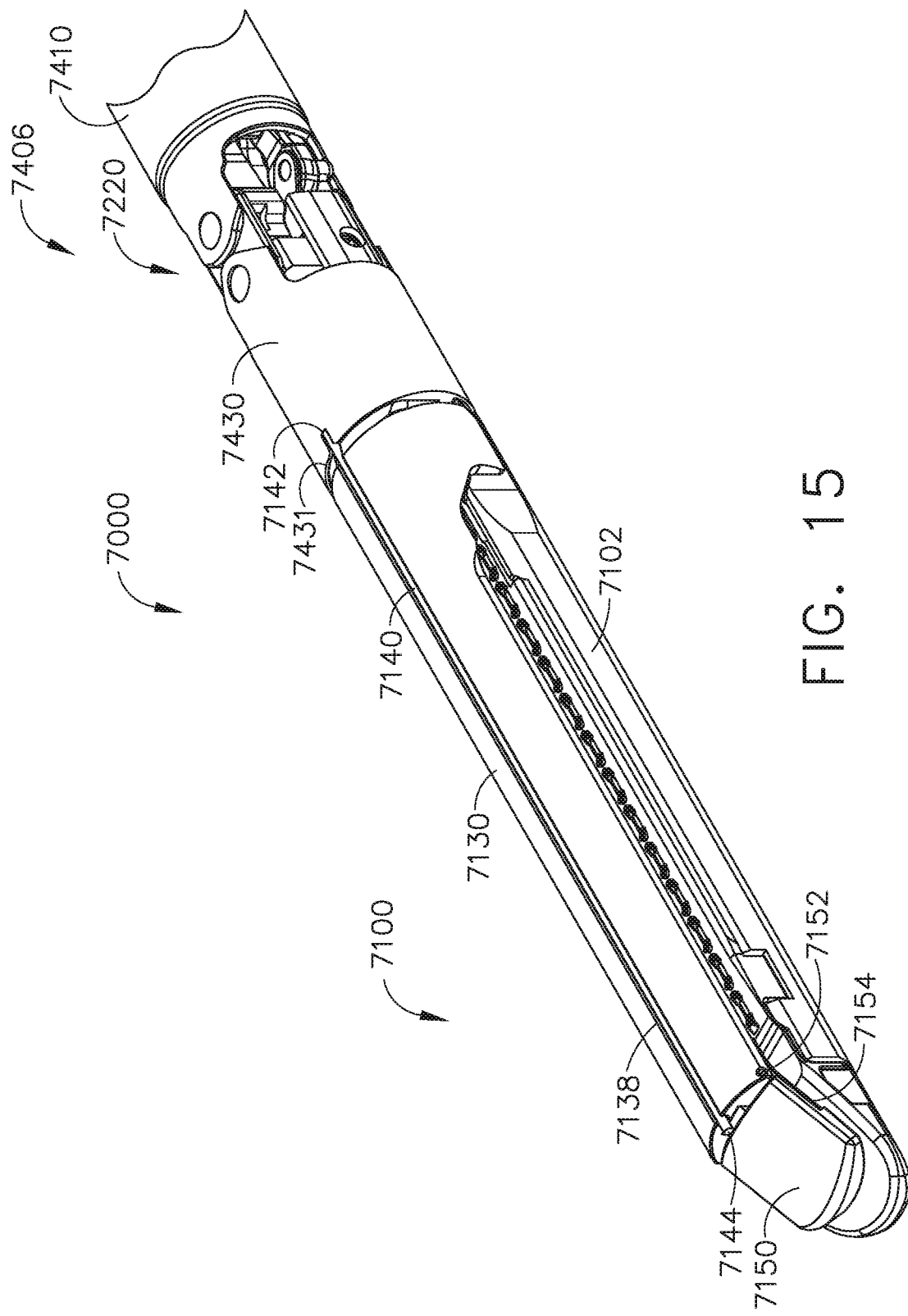
FIG. 15 is a perspective view of a distal portion of the interchangeable surgical tool assembly of FIG. 13 depicting the distal nose portion in a pivoted configuration.
Figure 16:
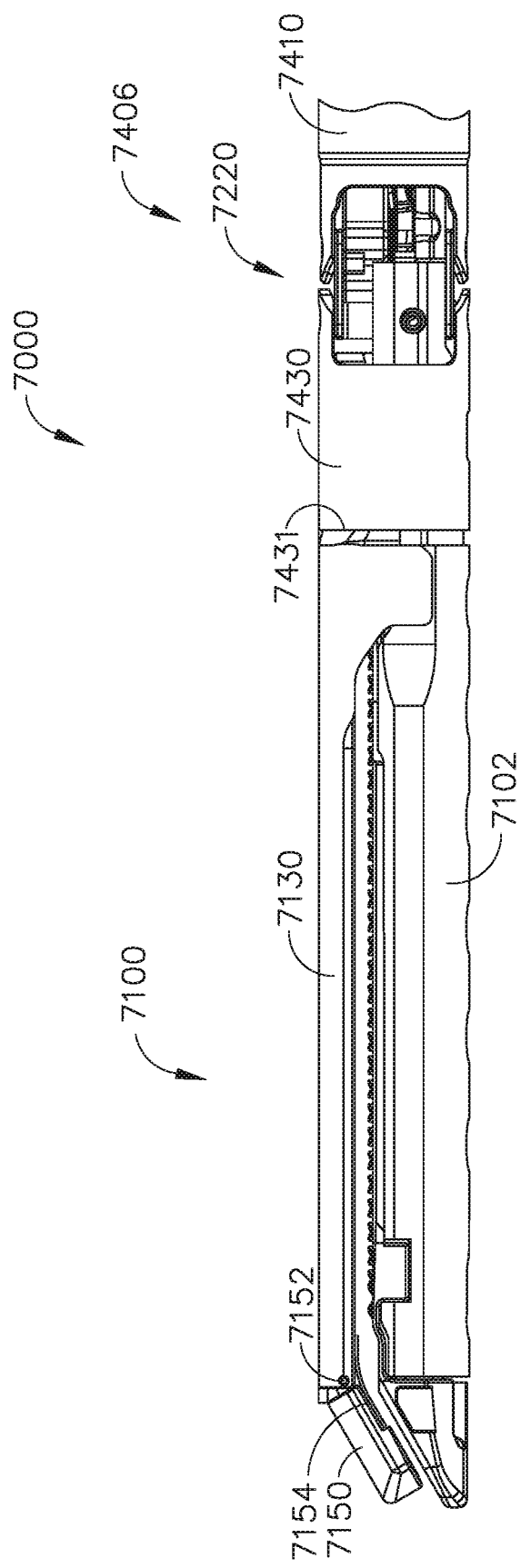
FIG. 16 is an elevation view of a distal portion of the interchangeable surgical tool assembly of FIG. 13 depicting the distal nose portion in the pivoted configuration.

The anvil 7130 also includes a channel 7138 (see FIGS. 13 and 15) through which a rod 7140 extends. Referring primarily to FIG. 17, the rod 7140 includes a proximal end 7142 and a distal end 7144. The distal end 7144 is operably positioned to engage a distal nose 7150 of the anvil 7130, as further described herein. The proximal end 7142 is operably positioned in abutting contact with the distal end 7431 of the distal closure tube 7430. When the distal closure tube 7430 is moved distally to complete the closure of the anvil 7130, the distal end 7431 of the distal closure tube 7430 can be moved into abutting contact with the proximal end 7142 of the rod 7140. As a result, at the completion of the closure motion, the rod 7140 is extended or pushed distally, which causes pivoting of the distal nose 7150. Referring primarily to FIGS. 15-17, the rod 7140 is pushed distally by the closure tube 7430 to pivot the distal nose 7150 after the anvil 7130 has been moved to a closed configuration by the distal closure tube 7430.

Referring again to FIGS. 13 and 15, the channel 7138 extends from a proximal portion of the anvil 7130 to the distal nose 7150. The distal nose 7150 is pivotably connected to the body of the anvil 7130 at a pivot joint 7152. A resilient support 7154 is configured to hold the distal nose 7150 in a linear, or non-pivoted, position (see FIGS. 13 and 14). The resilient support 7154 can be an elastic member or a spring, such as a leaf spring or hairpin spring, for example. When the rod 7140 is extended distally, the distal end 7144 thereof engages the distal nose 7150 and overcomes the resilient support 7154. For example, the rod 7140 has been extended in FIGS. 15-17 to pivot the distal nose 7150 to a pivoted position. In the pivoted position, the distal nose 7150 is configured to clamp tissue against a distal nose portion of the staple cartridge. Such a clamping feature is configured to trap or hold a distal portion of tissue and to limit tissue flow during a firing stroke. For example, increased clamping pressure can be applied by the end effector 7100 at the distal end portion thereof.

As described above, in certain instances, the upper flange 1762 of a firing member can hover out of contact with the ramped surface 1134 for a portion of the firing motion (see FIG. 10). For example, the ramped surface 1134 can include the intermediate surface 1138 extending between the distal closure ramp 1140 and the proximal closure surface 1142. The intermediate surface 1124 can separate the distal closure ramp 1140 from the proximal closure surface 1142 such that the surfaces 1140 and 1142 are separate and distinct.

For example, though the closure trigger 512 (see FIGS. 1 and 2) may be pivoting within a range of motion to displace the firing member 1760, the pivoting motion is not configured to cause a corresponding pivoting motion of the anvil 1130. In other words, during a range of motion of the closure trigger 512, the actuation of the closure trigger 512 is non-proportional to the closing and opening motion of the anvil 1130. In certain instances, it is desirable to provide feedback to the anvil 1130, i.e., effect pivoting thereof, throughout the firing motion including while the upper flange 1762 hovers above the intermediate surface 1138 between engagement with the distal closure ramp 1140 and engagement with the proximal closure surface 1142. For example, a spring assembly can be configured to exert a biasing force on the anvil 1130 during the dwell portion of the firing stroke.

Figure 54:
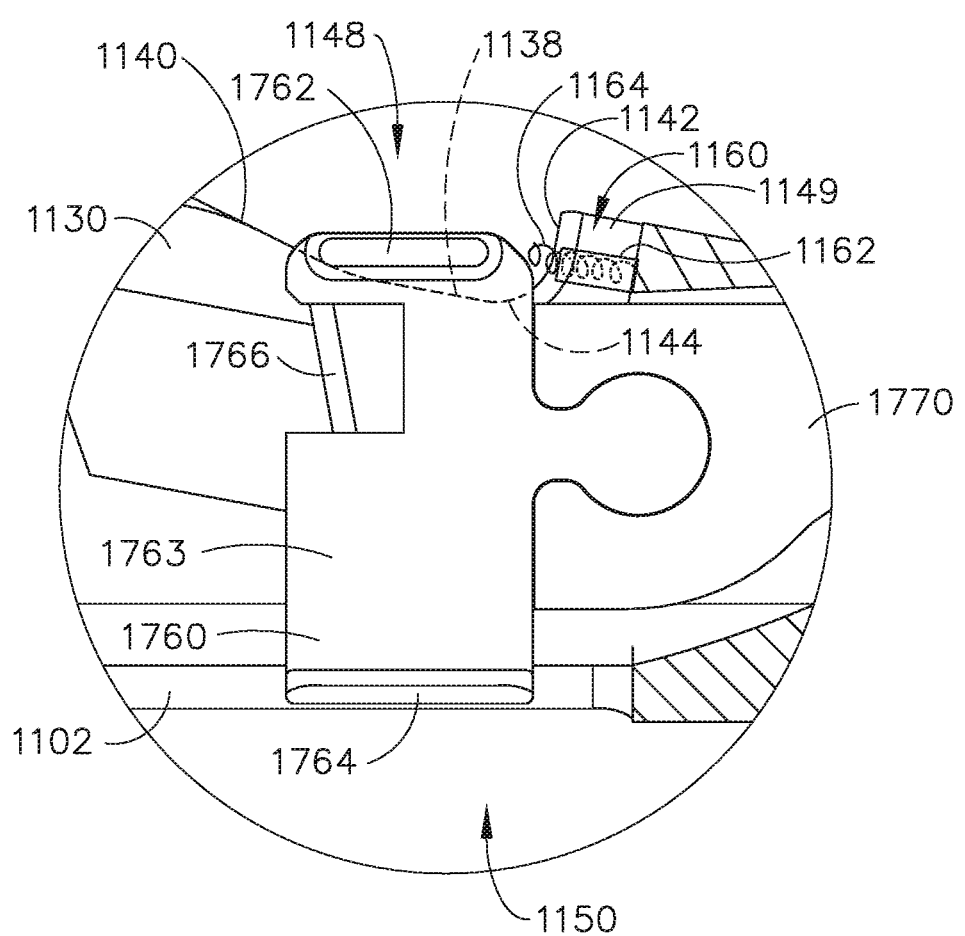
FIG. 54 is an elevation partial cross-sectional detail view of the pivot joint of FIG. 8 depicting the firing member at the pivot joint in an advanced position and further depicting a spring assembly.

Referring now to FIG. 54, a spring assembly 1160 is positioned proximal to the upper flange 1762 of the firing member 1760. The spring assembly 1160 includes a tubular member 1162 and a compression spring 1164 positioned partially within the tubular member 1162. The tubular member 1162 is positioned in a proximal notch or recess 1149 in the anvil 1130. For example, the anvil 1130 includes the proximal notch 1149 extending proximally from the open-close cavity 1148. The spring assembly 1160 is retained in the recess 1149 and positioned to operably engage the firing member 1760.

The spring assembly 1160 is configured to effect an opening motion of the anvil 1130 as the upper flange 1762 hovers above the intermediate surface 1138. The upper flange 1762 can be configured to move into contact with the compression spring 1164 when the anvil 1130 is in a closed configuration and the firing member 1760 is in a home position. As the firing member 1760 continues to be retracted proximally, the firing member 1760 can be configured to compress the compression spring 1164 into the tubular member 1162. Compression of the compression spring 1164 is configured to exert a force on the anvil 1130, which can correspond to an opening force on the anvil 1130. For example, the spring assembly 1160 can be configured to exert a proximal and downward force on a distal-facing surface of the notch 1149 to effect pivoting of the anvil 1130 upward toward an open configuration.

In various instances, the compression spring 1164 can be compressed by the firing member 1760 until the upper flange 1762 moves into engagement with the proximal closure surface 1142. The compression spring 1164 can define a spring force that is sufficient to initiate opening of the anvil 1130 before the upper flange 1762 moves into abutting engagement with the proximal closure surface 1142. In various instances, the spring force can be tuned to provide sufficient feedback during the dwell portion of the firing stroke. In certain instances, the compression spring 1164 can be compressed to the height of the tubular member 1162. When the compression spring 1164 is compressed entirely within the tubular member 1162, the opening motion can be proportional to the proximal displacement of the firing member 1760 and the corresponding actuation motion of the closure trigger 512.

In various instances, when the anvil 1130 is completely open with respect to the elongate channel 1102, a tissue aperture can be defined between the forming surface of the anvil 1130 and the deck 1115 of the staple cartridge 1110 positioned in the elongate channel 1102. The tissue aperture can be quantified as a vertical height between the anvil forming surface and the deck 1115 at the distal end of the end effector 1100 when the anvil 1130 is completely open. In certain instances, it can be desirable to increase the tissue aperture without increasing the angle between the anvil 1130 and the elongate channel 1102. In such instances, the proximal end of the anvil 1130 can be configured to move away from the elongate channel 1102 to increase the tissue aperture at the distal end.

Figure 55:
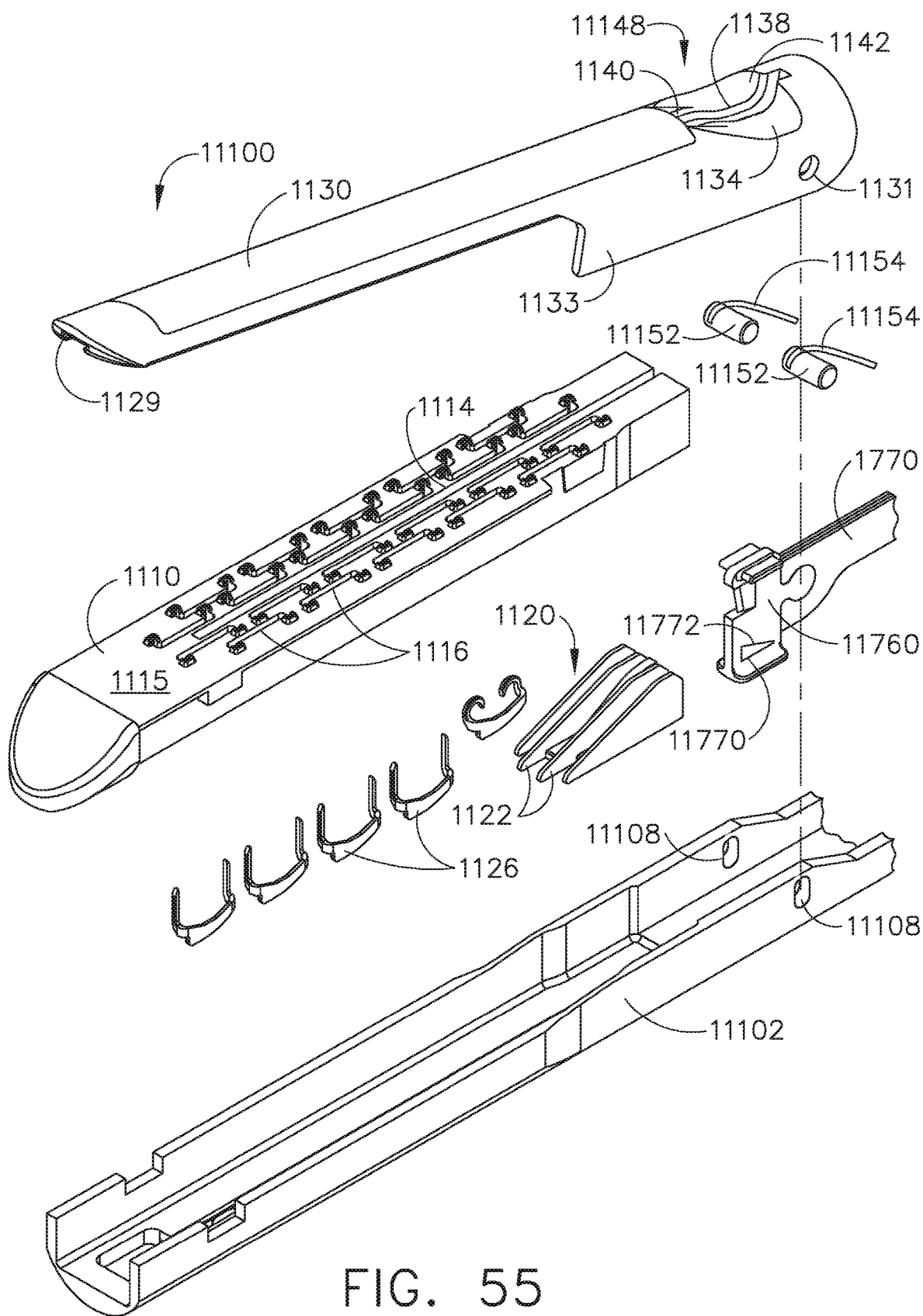
FIG. 55 is a perspective exploded assembly view of a distal portion of an interchangeable surgical tool assembly.

For example, referring now to FIG. 55, an elongate channel 11102 includes vertical slots 11108 for permitting vertical movement of the anvil 1130 relative to the elongate channel 11102. The elongate channel 11102 is similar in many respects to the elongate channel 1102; however, the elongate channel 11102 includes the vertical slots 11108 instead of the pin holes 1108 (see FIG. 5). The elongate channel 11102 can be utilized with an end effector 11100, which also includes the anvil 1130 and is configured to receive the staple cartridge 1110. The anvil 1130 is pivotably connected to the elongate channel 11102 by pivot pins 11152, which are operably engaged by springs 11154. The springs 11154 are configured to bias the pivot pins 11152 downward in the vertical slots 11108. The springs 11154 depicted in FIG. 55 are leaf springs; however, the reader will readily appreciate that alternative spring geometries and configurations can be utilized. When the pivot pins 11152 are positioned in the bottom of the vertical slots 11108, the end effector 11100 defines a first tissue aperture. When the pivot pins 11152 are permitted to move upwards to the top of the vertical slot 11108, the end effector 11100 defines a second, larger tissue aperture.

In various instances, the pivot pins 11152 can be permitted to overcome the springs 11154 and "pop" or spring upwards in the vertical slots 11108 when the firing member is retracted proximally out of engagement with the distal closure ramp 1140 on the anvil 1130. For example, the pivot pins 11152 are configured to shift upwards in the vertical slots 11108 when the firing member moves to dwell or hover above the intermediate surface 1138 on the anvil 1130. Referring still to FIG. 55, a firing member 11760 is configured to lift the pivot pins 11152 upwards. For example, the firing member 11760 is similar in many respects to the firing member 1760; however, the firing member 11760 includes wedged protrusions 11770 having a ramped surface 11772 for engaging and lifting the pivot pins 11152 upwards in the vertical slots 11108. Though only a single wedged protrusion 11170 is depicted in FIG. 55, the reader will readily appreciate that a pair of symmetrical wedges 11170 are positioned on opposing sides of the firing member 11760.

When the firing member 11760 is retracted proximally to exert an opening motion on the anvil 1130, the anvil 1130 is configured to shift vertically away from the elongate channel 11102 to increase the tissue aperture. Moreover, when the firing member 11760 is advanced distally during a subsequent closing motion, the wedged protrusions 11770 are configured to move out of engagement with the pivot pins 11152 such that the springs 11154 can return the pivot pins 11152 to their initial positions in the bottom of the vertical slots 11108. In various instances, the pivot pins 11152 are configured to return to the bottom of the vertical slots 11108 before the upper flanges of the firing member 11760 engage the distal closure ramp 1140 of the anvil 1130 to affect the closure thereof.

In certain instances, an end effector can be configured to clamp and staple tissue within a range of thicknesses. The end effector can clamp tissue having a first thickness during a first surgical function and can clamp tissue having a different thickness during a second surgical function. In certain surgical functions, the thickness of tissue clamped between the end effector jaws can be constant, or substantially constant. In other instances, the end effector can be configured to clamp and staple tissue having varying or changing thicknesses. For example, the thickness of tissue clamped between the end effector jaws can vary longitudinally along the length of the end effector.

As described herein, a firing member can include flanges for setting a tissue gap between the end effector jaws. For example, an upper flange can be configured to move along a channel in an anvil and a lower flange can be configured to move along a channel in an elongate channel during a firing stroke. The flanges of the firing member include camming surfaces that are configured to engage the inner surfaces of the respective channels to limit the tissue gap between the jaws. For example, the flanges can define a maximum and/or minimum spacing between the jaws, which amounts to a limitation to the spacing between a tissue-contacting deck on a staple cartridge installed in the end effector and a tissue-facing anvil of the end effector. In certain instances, the maximum and minimum spacing defined by the firing member flanges can be fixed. In other instances, one or both of the flanges can be configured to float or shift to accommodate variations in tissue thickness. The flange(s) can shift during the firing stroke or a portion thereof, for example.

Referring now to FIGS. 18-21, an upper portion of a firing member 8760 is depicted. The firing member 8760 is similar in many respects to the firing member 1760 (see FIGS. 4 and 5). For example, the firing member 8760 defines an I-beam structure that includes a lower flange (not shown), an upper flange 8762, and a support portion 8763 extending between the lower flange and the upper flange 8764. The upper flange 8762 is comprised of horizontal pins extending from the support portion 8763. The lower flange can be identical to the lower flange 1764 (see FIGS. 4 and 5), for example. A tissue cutting feature 8766 is supported by the support portion 8763 between the flanges.

The support portion 8763 is configured to travel though aligned slots in an elongate channel, a staple cartridge, and an anvil. For example, the firing member 8760 can be compatible with the end effector 1100 (see FIGS. 1-5) such that the support portion 8763 travels though aligned slots in the elongate channel 1102, the staple cartridge 1110, and the anvil 1130. Similar to the firing member 1760, when the firing member 8760 is fired or driven distally, the firing member 8760 is configured to drive a sled assembly distally as well. And, as the firing member 8760 moves distally through a staple cartridge, the tissue cutting feature 8766 is configured to cut the tissue that is clamped by the end effector 1100 as the sled assembly drives the staples upwardly in the staple cartridge 1110 and into forming contact with the anvil 1130.

The firing member 8760 includes a slot 8761 that extends along an upper portion of the support portion 8763. The slot 8761 is a wedge-shaped slot, and the height of the slot 8761 varies longitudinally along the length of the firing member 8760. More specifically, the height of the slot 8761 at the proximal end 8765 is greater than the height at the distal end 8767. In other instances, the height of the slot 8761 can be constant but the slot 8761 can be obliquely oriented, slanted, and/or non-horizontal along the length of the firing member 8760. The slot 8761 includes an upper edge 8768, which defines the maximum tissue gap. As described herein, the upper flange or pin 8762 is configured to move in the slot 8761 to adjust the tissue gap. Moreover, when a load is applied to the upper pin 8762, the upper pin 8762 is configured to slide along the upper edge 8768 as the upper pin 8762 moves in the slot 8761.

Figure 18:
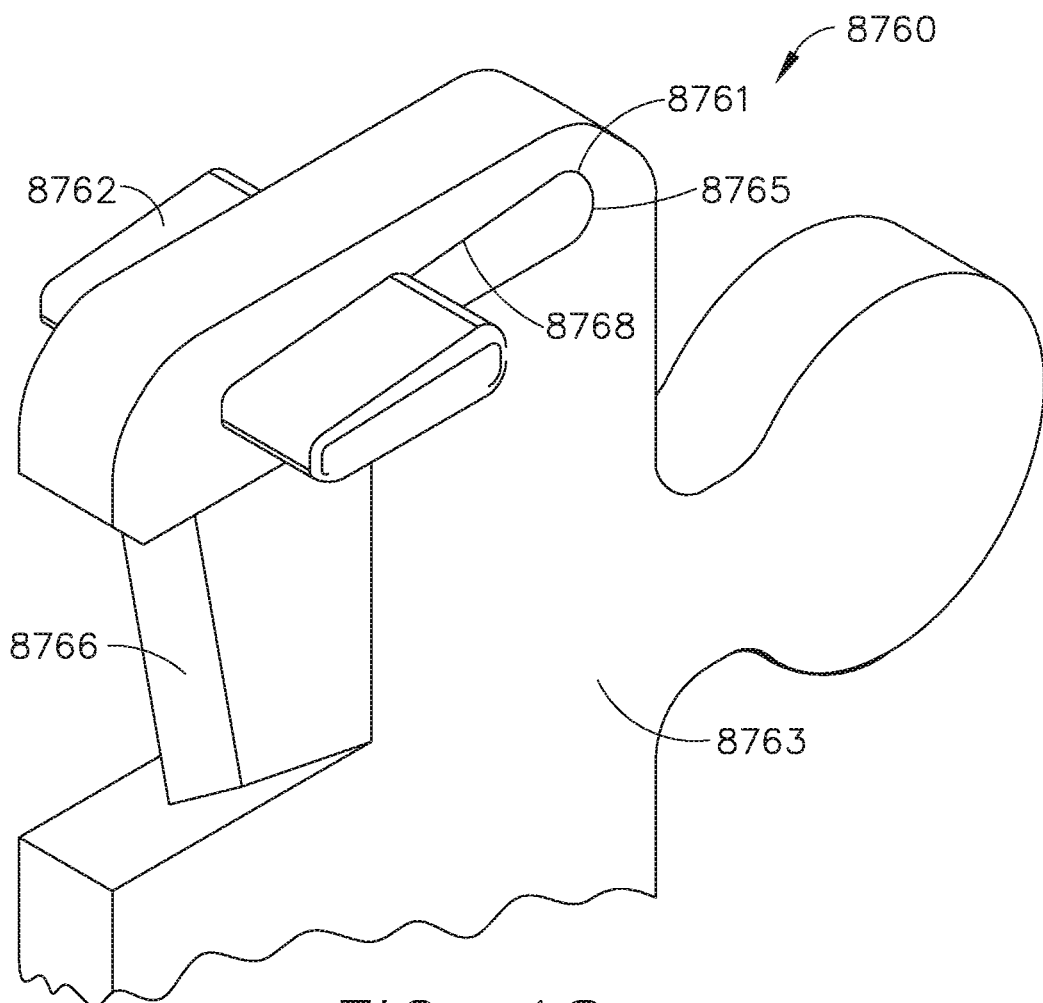
FIG. 18 is a perspective view of an upper portion of a firing member.
Figure 18A:
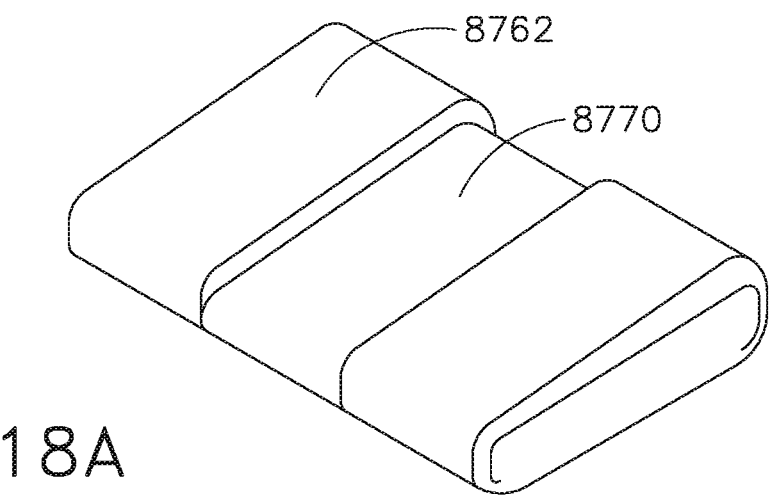
FIG. 18A is a perspective view of an upper flange of the firing member of FIG. 18.

Referring primarily to FIG. 18A, the upper pin 8762 includes a central groove 8770, which guides the upper pin 8762 within the slot 8761. For example, the upper edge 8768 is configured to extend into the groove 8770 when the upper pin 8762 is positioned in the slot 8761. In other embodiments, the upper pin 8762 can include guide blocks, which can be secured onto the pin 8762 on one or both sides of the support portion 8763. The central groove 8770 and/or the guide blocks can be configured to prevent twisting or torqueing of the upper pin 8762 during a firing stroke and as the upper pin 8762 moves in the slot 8761. The guide blocks can be welded onto the pin 8762, for example. In other instances, one or more guide blocks can be secured to the support portion 8763.

Figure 19:
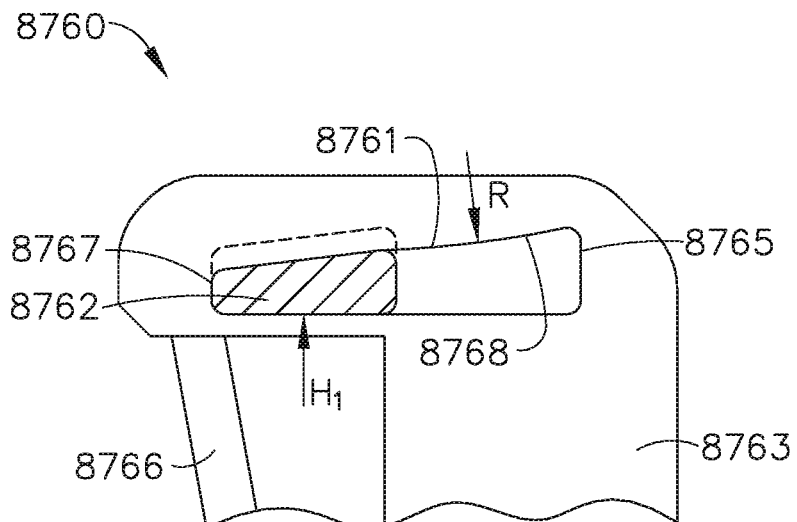
FIG. 19 is an elevation view of an upper portion of the firing member of FIG. 18 depicting the firing member in a first configuration.

A first or initial configuration of the firing member 8760 is depicted in FIG. 19. The upper pin 8762 is held in place by friction in the first configuration. For example, the upper pin 8762 can be compressed and press-fit within the slot 8761. In the first configuration, the upper pin 8762 is positioned adjacent to the distal end 8767 of the slot 8761. A first height $H_1$ is defined between the upper pin 8762 and the lower flange when the firing member 8760 is in the first configuration. More specifically, the first height $H_1$ is defined between the upper surface of the lower flange and the lower surface of the upper pin 8762. The first height $H_1$ corresponds to a minimum tissue gap defined by the firing member 8760.

Referring still to FIG. 19, the upper edge 8768 of the slot 8761 extends along an inward contour. In other words, the upper edge 8768 defines a compression radius R. The inward contour of the upper edge 8768 applies a compressive force to the upper pin 8762 that seeks to hold the upper pin 8762 in the distal-most position in the slot 8761 against the distal end 8767.

Figure 20:
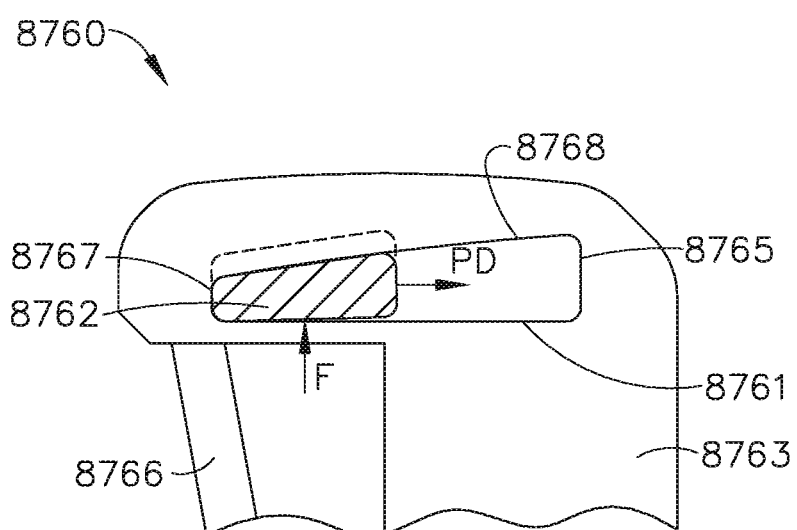
FIG. 20 is an elevation view of an upper portion of the firing member of FIG. 18 depicting the firing member in a stressed configuration.

Referring now to FIG. 20, during a firing stroke, a force F can be applied to the upper pin 8762. For example, when tissue is clamped between the jaws of an end effector, the tissue can be compressed by the jaws. As a result, the compressed tissue is configured to exert an opening force on the jaws, and such a force is applied to the upper pin 8762 and the lower flange of the firing member 8760. The force F is greater when the clamped tissue experiences increased compression, such as when thicker tissue is clamped between the jaws, for example. The force F in FIG. 20 is sufficient to deflect the inward contour of the upper edge 8768, which deflects the upper boundary of the firing member 8760 and relieves the compression on the upper pin 8762 in the slot 8761. The force F is equal to or greater than a threshold force that is required to deflect the upper edge 8768 and releases the upper pin 8762. In FIG. 20, the force F on the upper pin 8762 has moved the firing member 8760 to a stressed configuration.

Because the upper pin 8762 has been released by the force F, the upper pin 8762 is free to slide within the slot 8761 in the proximal direction (PD) (see FIG. 20). For example, the upper pin 8762 has moved to a proximal, upper position in FIG. 21. In the proximal, upper position of FIG. 21, a second height $H_2$ is defined between the upper pin 8762 and the lower flange. More specifically, the second height $H_2$ is defined between the upper surface of the lower flange and the lower surface of the upper pin 8762. The second height $H_2$ corresponds to a maximum tissue gap or the tissue gap when the firing member 8760 is in an adapted configuration. In such instances, the firing member 8760 is configured to allow a greater tissue gap during a second portion of the firing stoke. As described herein, in certain instances, it can be desirable to further limit the maximum tissue gap during an initial portion of the firing stroke when loads may be the highest to prevent jamming of the firing member 8760.

Figure 21:
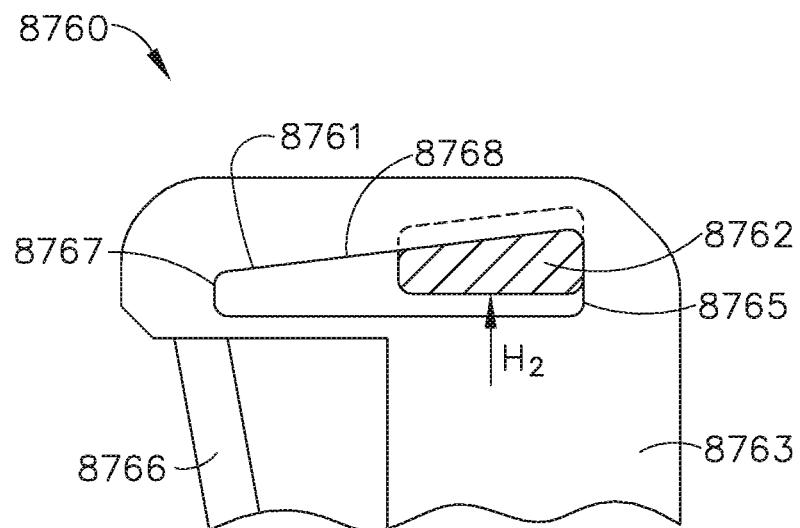
FIG. 21 is an elevation view of an upper portion of the firing member of FIG. 18 depicting the firing member in an adapted configuration.

The upper pin 8762 is configured to shift to the proximal, upper position depicted in FIG. 21 when a force equal to or greater than a threshold force is applied to the upper pin 8762. Because the force F is exerted upward on the upper pin 8762, the force F biases the upper pin 8762 along the upper edge 8768 of the slot 8761 and maintains the alignment of the groove 8770 and the upper edge 8768. As a result, the firing member 8760 is configured to adjust or adapt to accommodate variations in tissue thickness.

In other instances, the firing member 8760 can be configured to define a decreasing tissue gap during a distal portion of the firing stroke. In such instances, compression at the distal end of the end effector can be increased. For example, the upper surface 8768 of the slot 8761 can be angled downward toward the proximal end of the firing member 8760 such that the height of the slot 8761 is greatest at the distal end 8767 of the slot 8761, rather than as shown in FIGS. 19-23.

Figure 21A:
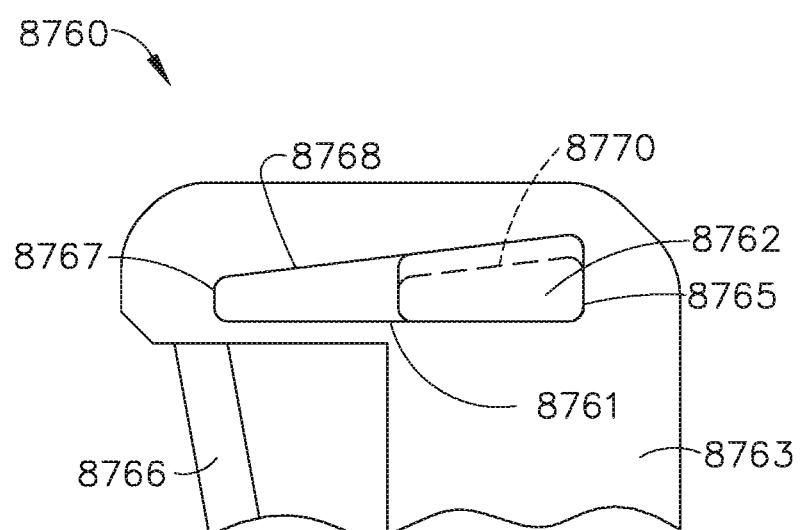
FIG. 21A is an elevation view of an upper portion of the firing member of FIG. 18 depicting the firing member in a loaded configuration.

Referring now to FIG. 21A, the upper pin 8762 is depicted in a loaded configuration. To load the upper pin 8762 into the slot 8761, the upper pin 8762 can be aligned with the largest or tallest portion of the slot 8761, which is at the proximal end 8765. From the proximal end 8765, the upper pin 8762 can be slid toward the distal end 8767 such that the upper edge 8768 protrudes into the central groove 8770 in the upper pin 8762 and restrains the upper pin 8762 in the slot 8761. For example, when the firing member 8760 is advanced distally, the upper pin 8762 is configured to slide toward the distal end 8767 and into the configuration depicted in FIG. 19. A first load on the upper pin 8762 can bias the upper pin 8762 distally and into a compressed state at the distal end 8767 and a second, greater load on the upper pin 8762 can deform the firing member 8760 to release the compression in the upper pin 8762 and permit it to slide proximally, as described herein.

Though the firing member 8760 has been described having a single floating flange, i.e. the upper flange 8762, in other instances, the lower flange can also be configured to float and/or shift when a force equal to or greater than a second threshold force is applied thereto. For example, the upper flange 8762 can be configured to shift when a first force is applied by the compressed tissue and the lower flange can be configured to shift when a second, greater force is applied by the compressed tissue. In other instances, only the lower flange can be configured to shift and/or float.

Figure 22:
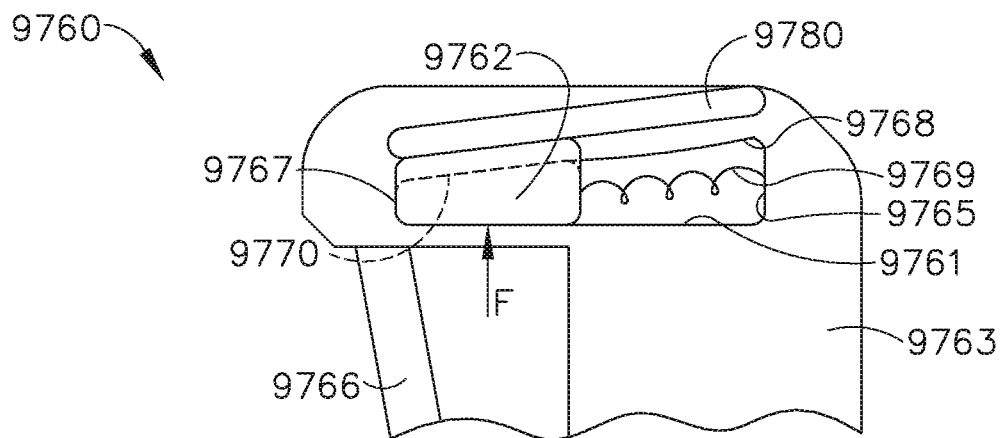
FIG. 22 is an elevation view of an upper portion of a firing member depicting the firing member in a first configuration.
Figure 23:
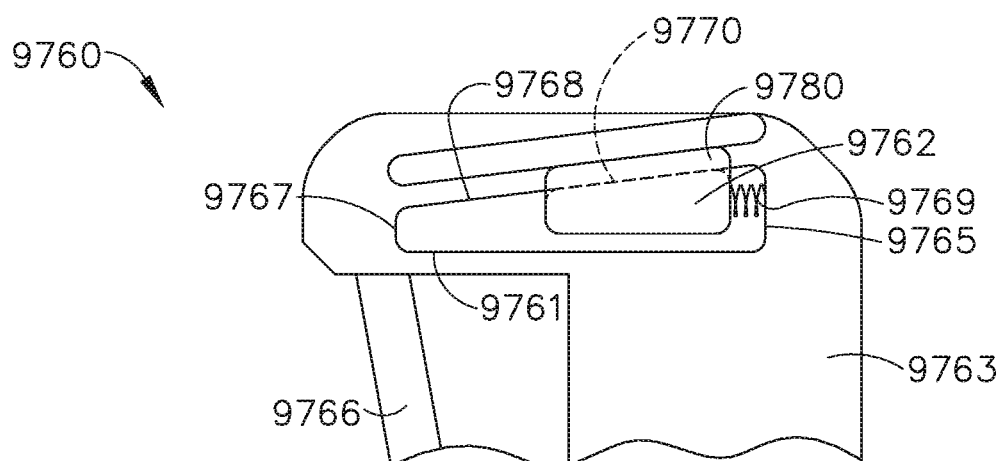
FIG. 23 is an elevation view of an upper portion of the firing member of FIG. 22 depicting the firing member in an adapted configuration.

Referring now to FIGS. 22 and 23, an upper portion of a firing member 9760 is depicted. The firing member 9760 is similar in many respects to the firing member 1760 (see FIGS. 4 and 5). For example, the firing member 9760 defines an I-beam structure that includes a lower flange, an upper flange 9762, and a support portion 9763 extending between the lower flange and the upper flange 9764. The upper flange 9762 is comprised of horizontal pins extending from the support portion 9763. The lower flange can be identical to the lower flange 1764 (see FIGS. 4 and 5), for example. A tissue cutting feature 9766 is supported by the support portion 9763 between the flanges.

The support portion 9763 is configured to travel though aligned slots in an elongate channel, a staple cartridge, and an anvil. For example, the firing member 9760 can be compatible with the end effector 1100 (see FIGS. 1-5) such that the support portion 9763 travels though aligned slots in the elongate channel 1102, the staple cartridge 1110, and the anvil 1130. Similar to the firing member 1760, when the firing member 9760 is fired or driven distally, the firing member 9760 is configured to drive a sled assembly distally as well. And, as the firing member 9760 moves distally through a staple cartridge, the tissue cutting feature 9766 is configured to cut the tissue that is clamped by the end effector as the sled assembly drives the staples upwardly in the cartridge and into forming contact with an anvil.

The firing member 9760 includes a slot 9761 that extends along an upper portion of the support portion 9763. The slot 9761 is a wedge-shaped slot, and the height of the slot 9761 varies longitudinally along the length of the firing member 9760. More specifically, the height of the slot 9761 at the proximal end 9765 is greater than the height at the distal end 9767. Additionally or alternatively, the slot 9761 can be obliquely oriented, slanted, and/or non-horizontal such that the distal end 9767 is higher than the proximal end 9765. The slot 9761 includes an upper edge 9768, which defines the maximum tissue gap. As described herein, the upper flange or pin 9762 is configured to move in the slot 9761 to adjust the tissue gap and the upper pin 9762 slides along the upper edge 9768 as the upper pin 9762 moves in the slot 9761. The firing member 9760 also includes a spring 9769 that is configured to exert a biasing force on the upper pin 9762.

The upper pin 9762 includes a central groove 9770, which guides the upper pin 9762 within the slot 9761. For example, the upper edge 9768 is configured to extend into the groove 9770 when the upper pin 9762 is positioned in the slot 9761. In the depicted embodiment, the upper pin 9762 includes guide blocks 9780, which are secured to both sides of the support portion 9763. The guide blocks 9780 are configured to prevent twisting or torqueing of the upper pin 9762 during a firing stroke and as the upper pin 9762 moves in the slot 9761. In other instances, one or more guide blocks can be secured to the upper pins 9762 and, in still other instances, the firing member 9760 may not include guide blocks.

A first or initial configuration of the firing member 9760 is depicted in FIG. 22. The upper pin 9762 is held in place by the spring 9769. For example, the spring 9769 is configured to bias the upper pin 9762 toward the distal end 9767 of the slot 9761. A first height $H_1$ is defined between the upper pin 9762 and the lower flange when the firing member 9760 is in the first configuration. More specifically, the first height $H_1$ is defined between the upper surface of the lower flange and the lower surface of the upper pin 9762. The first height $H_1$ corresponds to a minimum tissue gap.

Referring still to FIG. 22, when tissue is clamped between the jaws of an end effector, the tissue can be compressed by the jaws. As a result, the compressed tissue can exert an opening force on the jaws, and such a force is applied to the upper pin 9762 and the lower flange of the firing member 9760. The force F is greater when the clamped tissue experiences increased compression, such as when thicker tissue is clamped between the jaws, for example. When the force F is equal to or greater than a threshold force, the force F can be configured to overcome the bias of the spring 9769, as depicted in FIG. 23. For example, the force F is sufficient to deform the spring 9769 to a compressed configuration and permit the upper pin 9762 to move along the slot 9761 toward the proximal end 9765 thereof.

The upper pin 9762 has moved to a proximal, upper position in FIG. 23. In the proximal, upper position of FIG. 23, a second height $H_2$ is defined between the upper pin 9762 and the lower flange. More specifically, the second height $H_2$ is defined between the upper surface of the lower flange and the lower surface of the upper pin 9762. The second height $H_2$ corresponds to a maximum tissue gap or the tissue gap when the firing member 9760 is in an adapted configuration. Because the force F (FIG. 22) is exerted upward on the upper pin 9762, the force F biases the upper pin 9762 along the upper edge 9768 of the slot 9761 and maintains the alignment of the groove 9770 and the upper edge 9768. As a result, the firing member 9760 is configured to adjust or adapt to accommodate variations in tissue thickness.

Though the firing member 9760 has been described having a single floating flange, i.e. the upper flange 9762, in other instances, the lower flange can also be configured to float and/or shift when a force equal to or greater than a second threshold force is applied thereto. For example, the upper flange 9762 can be configured to shift when a first force is applied by the compressed tissue and the lower flange can be configured to shift when a second, greater force is applied by the compressed tissue. In other instances, only the lower flange can be configured to shift and/or float.

As described herein, a firing member can include at least one floating flange, which can be configured to shift or move when a threshold force is applied thereto to accommodate for variations in tissue thickness. In certain instances, the floating flange can be positioned in a slot and can be biased and/or retained in an initial configuration until the threshold force is applied thereto. In other instances, a portion of the firing member can include a deformable or compliant material, which can be configured to flex or otherwise deform when the threshold force is applied thereto. In certain instances, a compliant core of the firing member can support at least one flange that is configured to shift or move when the threshold force is applied thereto.

Figure 24:
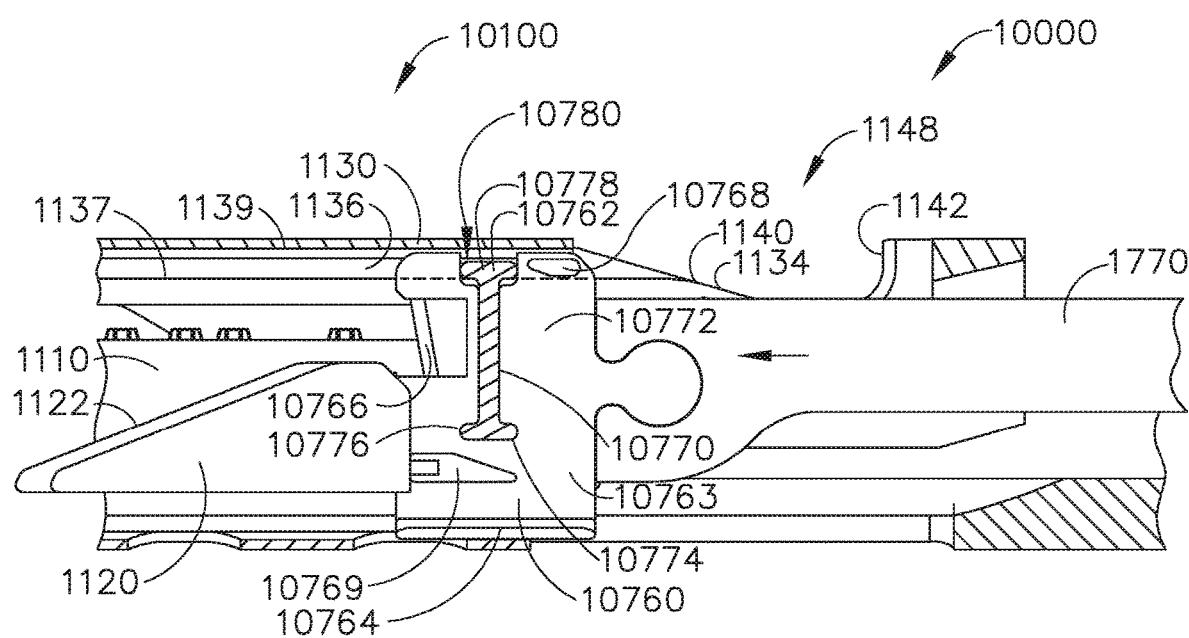
FIG. 24 is an elevation partial cross-sectional view of a portion of an interchangeable surgical tool assembly depicting a firing member displaced distally from a home position to a first intermediate position and having a first load applied to an upper flange of the firing member.
Figure 25:
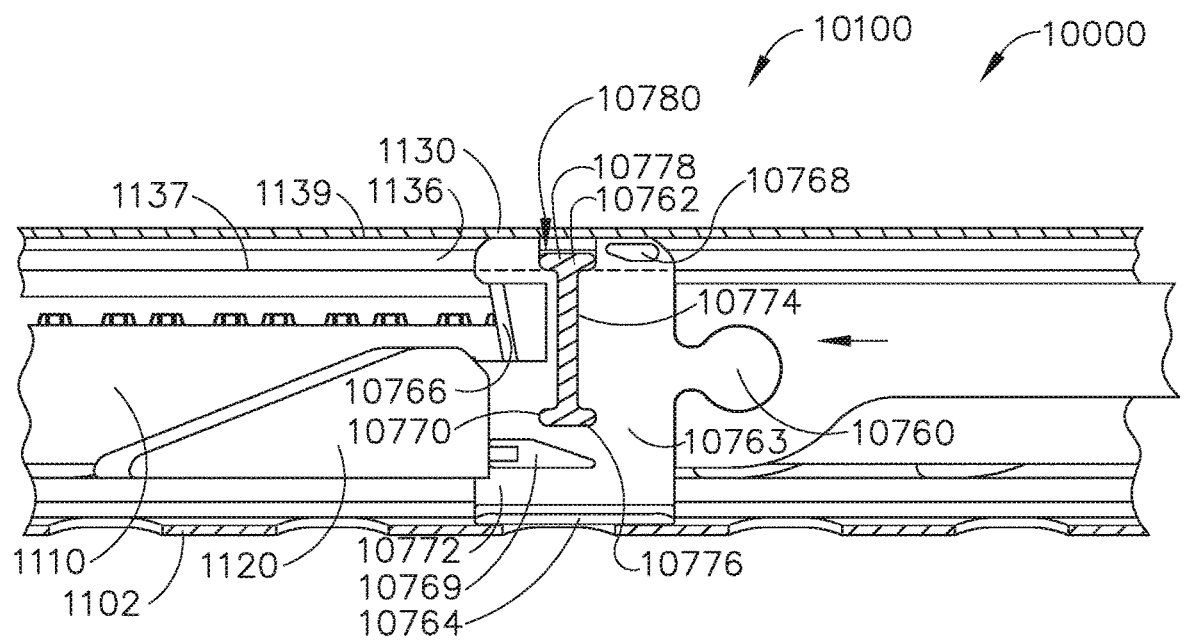
FIG. 25 is an elevation partial cross-sectional view of a portion of the interchangeable surgical tool assembly of FIG. 24 depicting the firing member displaced distally from the first intermediate position to a second intermediate position and having a decreased load applied to the upper flange.
Figure 26:
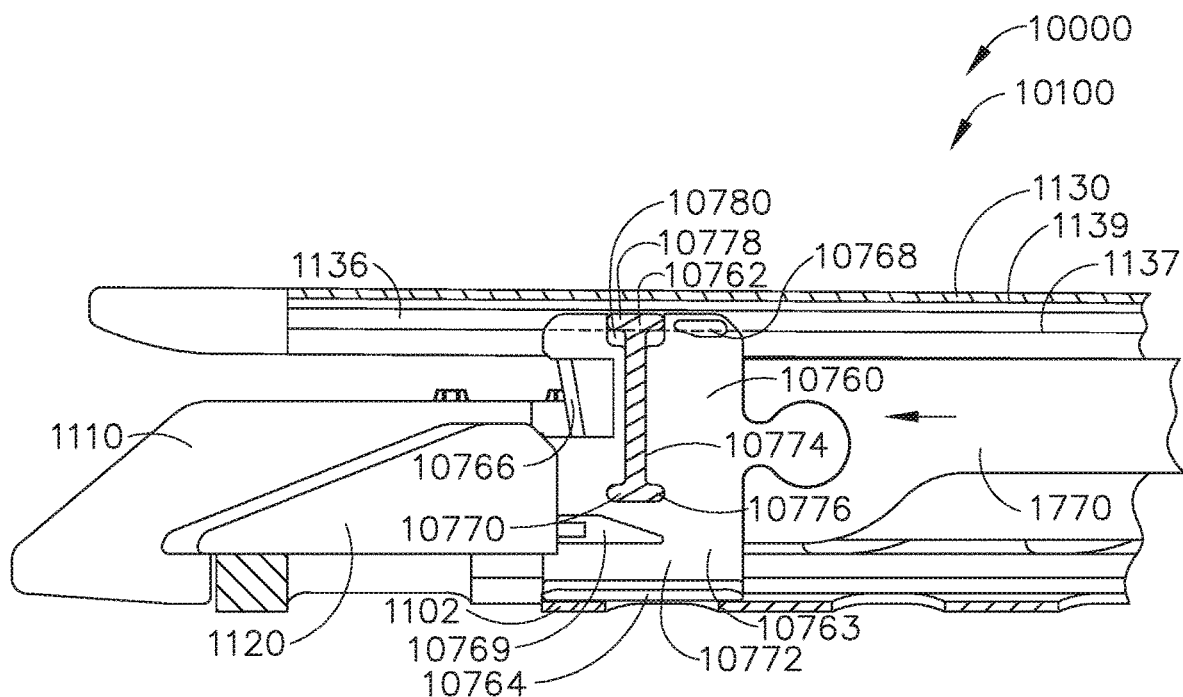
FIG. 26 is an elevation partial cross-sectional view of a portion of the interchangeable surgical tool assembly of FIG. 24 depicting the firing member displaced distally from the second intermediate position to a third intermediate position and having an increased load applied to the upper flange.

Referring now to FIGS. 24-26, a portion of an interchangeable surgical tool assembly 10000 including an end effector 10100 is depicted. The end effector 10100 includes the elongate channel 1102 and the anvil 1130, and the staple cartridge 1110 is installed in the elongate channel 1102. The end effector 10100 also includes a firing member 10760, which is similar in many respects to the firing member 1760 (see FIGS. 4 and 5). For example, the firing member 10760 defines an I-beam structure that includes a lower flange 10764, an upper flange 10762, and a support portion 10763 extending between the lower flange and the upper flange 10762. The upper flange 10762 is comprised of horizontal pins extending from the support portion 10763. The lower flange 10764 is comprised of an enlarged or widened foot at the base of the support portion 10763. A tissue cutting feature 10766 is supported by the support portion 10763 between the flanges 10762 and 10764.

The support portion 10763 is configured to travel though aligned slots in the elongate channel 1102, the staple cartridge 1110, and the anvil 1130. Similar to the firing member 1760, when the firing member 10760 is fired or driven distally, the firing member 10760 is configured to drive the sled assembly 1120 distally as well. And, as the firing member 10760 moves distally through a staple cartridge, the tissue cutting feature 10766 is configured to cut the tissue that is clamped by the end effector 10100 as the sled assembly 1120 drives the staples 1126 (see FIG. 5) upwardly in the staple cartridge 1110 and into forming contact with the anvil 1130.

Referring still to FIGS. 24-26, the firing member 10760 includes a body 10772 and a compliant portion or core 10770 embedded in the body 10772. For example, the body 10772 includes a cutout or cavity 10774, and the compliant portion 10770 is positioned in the cutout 10774. The compliant portion 10770 includes the upper flange 10762. As further described herein, the upper flange 10762 is configured to shift or move as the compliant portion 10770 deforms.

The elasticity of the body 10772 can be less than the elasticity of the compliant core 10770. In certain instances, the compliant core 10770 can be formed from a shape memory material, such as nitinol, which can provide a constant spring rate over the full range of vertical flexure thereof. Moreover, the body 10772 of the firing member 10760 can be formed from a non-compliant or substantially less compliant material, such as stainless steel or titanium, for example.

The compliant portion 10770 includes a first end 10776 and a second end 10778. The first end 10776 is held or fixed in the cutout 10774 in the body 10772. For example, the cutout 10774 can securely encapsulate the first end 10776 to prevent movement of the first end 10776 within the body 10772. The second end 10778 supports the upper flange 10762. For example, the upper flange 10762 can be integrally formed with the second end 10778 and/or can be securely connected thereto. The second end 10778 is provided with a clearance 10780 within the cutout 10774 to permit controlled deflection of the second end 10778 therein. For example, the second end 10778 and the upper flange 10762 supported thereon are configured to shift with respect to the first end 10776 and with respect to the lower flange 10764 in response to forces applied to the upper flange 10762. Movement of the upper flange 10762 is restrained by the geometry of the cutout 10774 and the passageway 1136 defined in the anvil 1130.

As described with respect to the firing member 1760 (see FIGS. 4 and 5), the firing member 10760 is configured to engage the open-close cavity 1148 of the anvil 1130 to move the anvil 1130 to a clamped position. For example, the upper flanges 10762 of the firing member 10760 are configured to move along the distal closure ramp 1140 of the anvil 1130 (see FIGS. 8-12) and into the passageway 1136. The passageway 1136 includes the lower ledge 1137 and the upper cap 1139 which define the lower and upper limits of the passageway 1136.

In FIG. 24, the firing member 10760 has been displaced distally from the home position to a first intermediate position. Between the home position and the first intermediate position, the upper flange 10762 has been moved along the distal closure ramp 1140 to pivot the anvil 1130 toward the staple cartridge 1110 and clamp tissue therebetween. Referring still to FIG. 24, a first load is applied to the upper flange 10762 of the firing member 10760. The first load can correspond to a first thickness, density, and/or toughness of tissue clamped by the end effector 10100.

When the first load is applied to the upper flange 10762, the compliant portion 10770 is configured to assume the configuration depicted in FIG. 24. In particular, the second end 10778 of the compliant portion 10770 is spaced between the lower ledge 1137 and the upper cap 1139 of the passageway 1136. A portion of the clearance 10780 is above the second end 10778 and another portion of the clearance 10780 is below the second end 10778. In such instances, the upper flange 10762 defines an intermediate tissue gap, which is between the minimum and maximum tissue gap permitted by the interchangeable surgical tool assembly 10000 at the first intermediate position.

In FIG. 25, the firing member 10760 has been advanced distally from the first intermediate position (see FIG. 24) to a second intermediate position, and a second load is applied to the upper flange 10762 of the firing member 10760. The second load is less than the first load and can correspond to a second thickness, density and/or toughness of tissue clamped by the end effector 10100, which is less than the first thickness, density and/or toughness, respectively. For example, the second load can be less than the first load because the tissue is thinner.

When the second load is applied to the upper flange 10762, the compliant portion 10770 is configured to assume the configuration depicted in FIG. 25. In particular, the second end 10778 of the compliant portion 10770 is positioned against the lower ledge 1137 of the passageway 1136 and the clearance 10780 is above the second end 10778. In such instances, the upper flange 10762 defines the minimum tissue gap. To assume the configuration of FIG. 25, the compliant portion 10770 has contracted to draw the second end 10778 toward the fixed, first end 10776. The contraction of the compliant portion 10770 can be limited by the material thereof, the position of the lower ledge 1137, and/or a limiting pin 10768, which is further described herein.

In FIG. 26, the firing member 10760 has been displaced distally from the second intermediate position (see FIG. 25) to a third intermediate position, and a third load is applied to the upper flange 10762 of the firing member 10760. The third load is greater than the first load and the second load and can correspond to a third thickness, density, and/or toughness of tissue clamped by the end effector 10100, which is greater than the first thickness, density, and/or toughness, respectively, and the second thickness, density, and/or toughness, respectively. For example, the third load can be greater than the first load and the second load because the tissue is thicker, denser, and/or tougher.

When the third load is applied to the upper flange 10762, the compliant portion 10770 is configured to assume the configuration depicted in FIG. 26. In particular, the second end 10778 of the compliant portion 10770 is positioned against the upper cap 1139 of the passageway 1136 and the clearance 10780 is below the second end 10778. In such instances, the upper flange 10762 defines the maximum tissue gap. To assume the configuration of FIG. 26, the compliant portion 10770 has been stretched or extended to draw the second end 10778 away from the fixed, first end 10776. The extension of the compliant portion 10770 can be limited by the material thereof, the position of the upper cap 1139, and/or the limiting pin 10768, which is further described herein.

The firing member 10670 also includes a first laterally protruding lug, or limiting pin, 10768, which is configured to move in the passageway 1136 of the anvil 1130. The limiting pin 10768 is configured to limit the tissue gap during a portion of the firing stroke. The limiting pin 10768 is fixed relative to the support portion 10763, and is configured to move in the passageway 1136 during at least a portion of the firing stroke. When the limiting pin 10768 rides along the anvil ledge 1137 (see FIG. 24), the limiting pin 10768 is configured to limit the maximum tissue gap. When the limiting pin 10768 rides along the upper cap 1139, the limiting pin 10768 is configured to limit the minimum tissue gap. For example, though the upper flange 10762 is moveable relative to the support portion 10763, the displacement of the upper flange 10762 is limited by the fixed location of the limiting pin 10768 within the passageway 1136.

In various instances, the limiting pin 10768 can protrude laterally a first distance, which can be less than the laterally-protruding distance of the upper flange 10762. In other words, the limiting pin 10768 can be narrower than the upper flange 10762. Additionally, the slot 1132 in the anvil 1130, which provides access to the passageway 1136, can be wider in a portion of the anvil 1130. In such instances, the shorter limiting pin 10768 can extend below the anvil ledge 1137 without limiting the maximum tissue gap for a portion of the firing stroke.

In the depicted embodiment, the limiting pin 10768 is positioned within the passageway 1136 during an initial, proximal portion of the firing stroke (see FIG. 24) and protrudes below the anvil ledge 1037 during a later, distal portion of the firing stroke (see FIG. 26). More specifically, between the proximal portion of the firing stroke and the distal portion of the firing stroke, the slot 1132 widens such that the fixed pin is not confined within the passageway 1136, however, the wider upper flange 1762 can remain confined within the passageway 1136. In various instances, the slot 1132 can widen to larger than the limiting pins 10768 at or about one-third of the distance from the proximal starting point. In other instances, the slot 1132 can widen to larger than the limiting pins 10768 before or after one-third of the distance from the proximal starting point.

In various instances, it can be desirable to limit the maximum tissue gap during an initial portion of the firing stroke. For example, at the outset of a firing stroke through thick, dense and/or tough tissue, the loads on the firing member 10760 can be large and can bias the upper flange 10762 a maximum distance away from the lower flange 10764. In such instances, to ensure that the firing member 10760 does not become jammed or otherwise disabled during the initial portion of the firing stroke when the highest loads are exerted on the firing member 10760, the maximum tissue gap can be controlled by the distance between the fixed limiting pin 10769 and the lower flange 10764. Thereafter, when the load on the firing member 10760 decreases as tissue is cut by the cutting edge 10766, the limiting pin 10768 can disengage the passageway 1136 and the anvil ledge 1137 thereof to permit an additional or increased maximum tissue gap, which can be controlled by the floating upper flange 10762.

The firing member 10760 also includes a second laterally-protruding lug 10769, which is operably configured to engage the elongate channel 1102. For example, the laterally-protruding lug 10769 is configured to ride along an inside surface in the elongate channel 1102 (e.g. along the cartridge-supporting base 1101) to further control the tissue gap. Additionally or alternatively, the laterally-protruding lug 10769 can be configured to engage a lockout arrangement, such as the lockout arrangement 6180 (see FIGS. 45-53), which is further described herein.

During a firing stroke, staples can be fired into tissue and the tissue can be cut by a cutting element. Upon the completion of the firing stroke, rows of staples can be positioned on both sides of the cutline and the staple rows can provide a tissue seal on both sides of the cutline. To minimize bleeding, the staples can be fired before the tissue is cut by the cutting element. In such instances, the staples can provide a tissue seal before the tissue between the seal is severed by the cutting element.

In certain instances, it is advantageous to prevent a surgical instrument from implementing a firing stroke. For example, if a staple cartridge is missing from the end effector, it can be advantageous to prevent the firing stroke because such a firing stroke can result in tissue being cut by the cutting element but not being sealed by the staples. Similarly, when an empty or spent staple cartridge is installed in an end effector, it can be advantageous to prevent a firing stroke because such a firing stroke would also result in tissue being cut by the cutting element but not being sealed by the staples.

Figure 27:
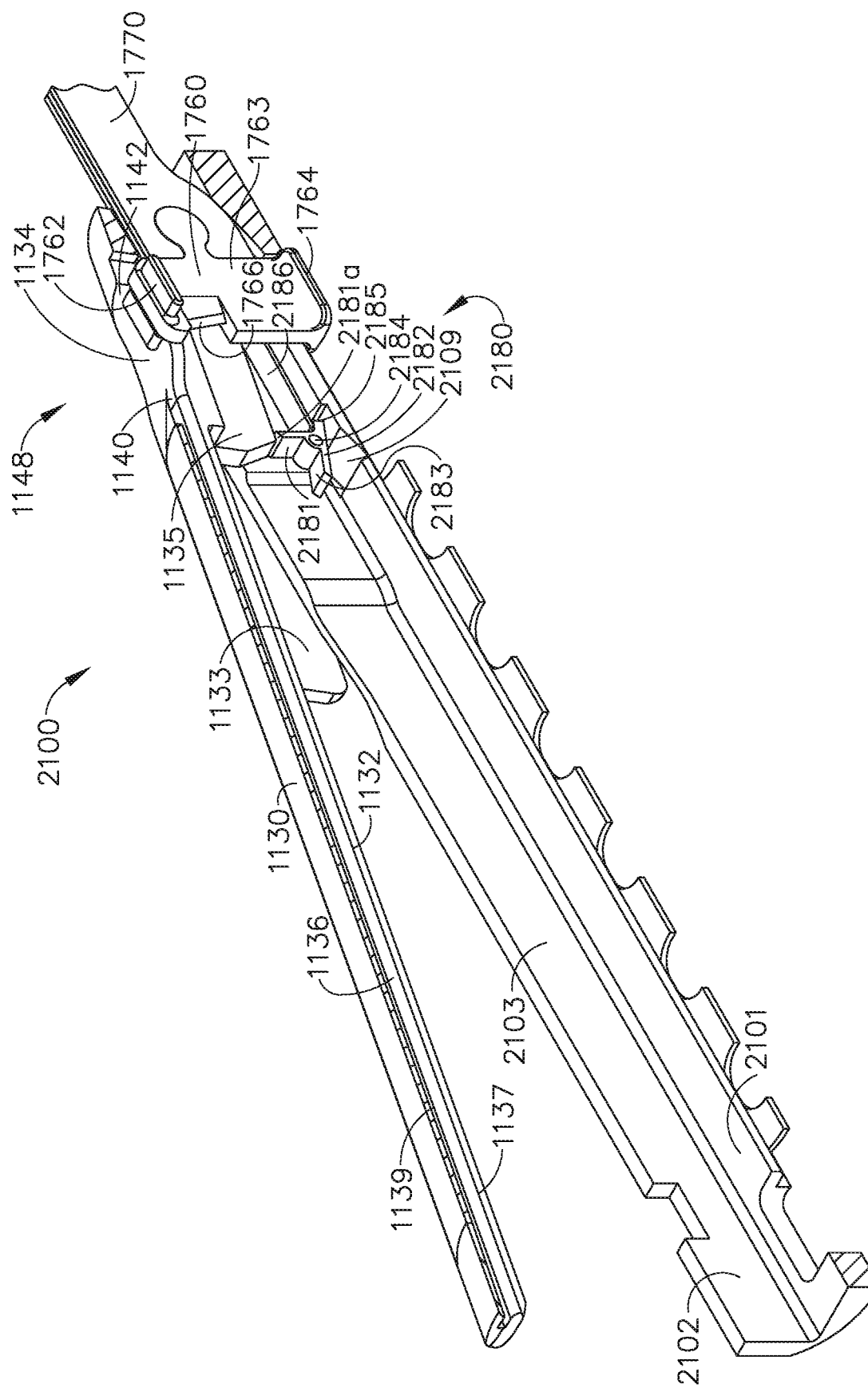
FIG. 27 is a perspective partial cross-sectional view of a distal portion of an interchangeable surgical tool assembly with portions thereof omitted for clarity.
Figure 28:
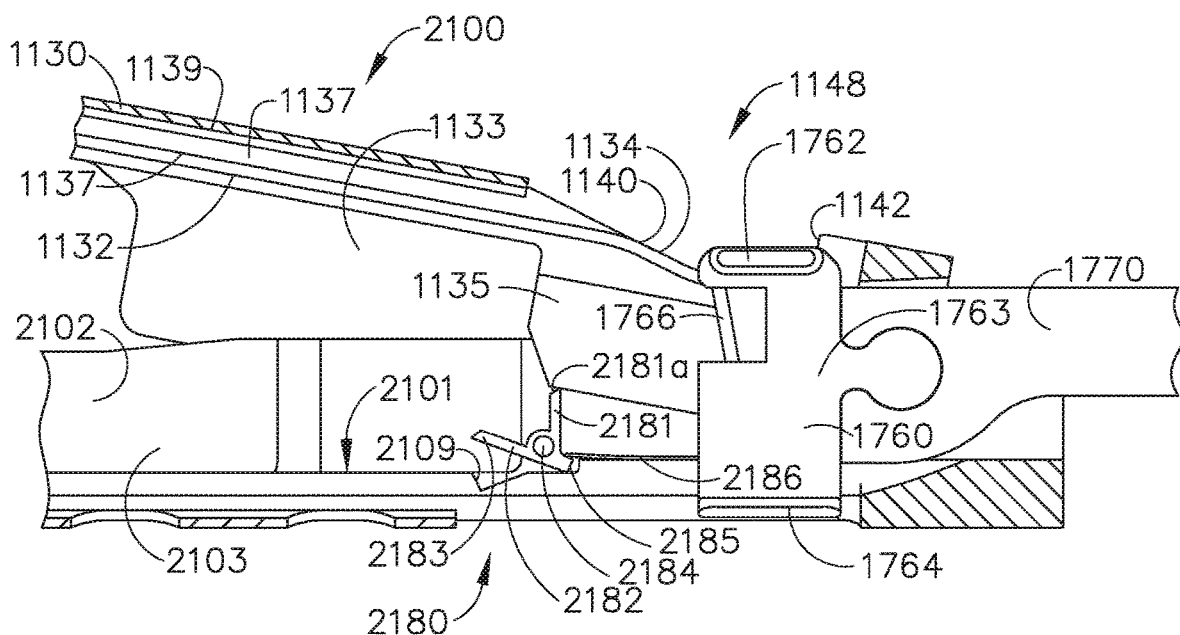
FIG. 28 is an elevation partial cross-sectional view of a portion of the interchangeable surgical tool assembly of FIG. 27 in which a staple cartridge is missing from the interchangeable surgical tool assembly.
Figure 29:
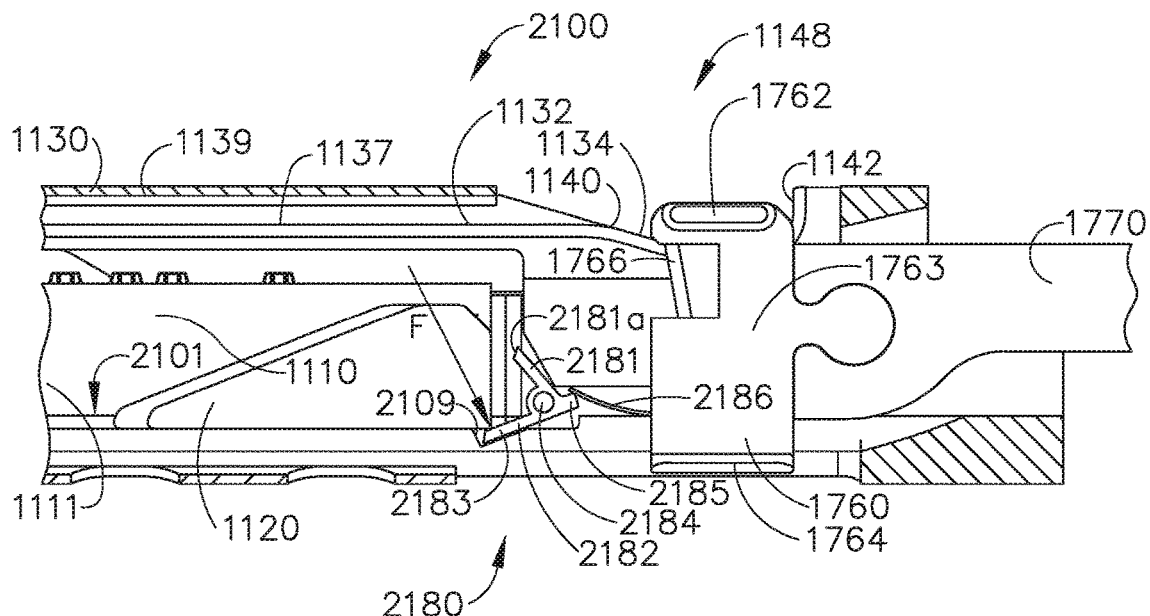
FIG. 29 is an elevation partial cross-sectional view of a portion of the interchangeable surgical tool assembly of FIG. 27 in which a staple cartridge is positioned in the interchangeable surgical tool assembly.

A surgical instrument can be provided with various features to prevent a firing stroke in certain instances. Such features are commonly referred to as "lockouts" and can be positioned in the handle, shaft, interchangeable surgical tool assembly, end effector, and/or staple cartridge, for example. Referring to FIGS. 27-29, an end effector 2100 having a lockout arrangement 2180 is depicted. The end effector 2100 includes an elongate channel 2102, which is similar in many respects to the elongate channel 1102 (see FIGS. 3-5). For example, the elongate channel 2102 includes a pair of sidewalls 2103 extending from a cartridge-supporting surface or base 2101. The elongate channel 2102 is configured to operably support a staple cartridge, such as the staple cartridge 1110 (see FIGS. 3-5) therein. The end effector 2100 also includes the anvil 1130 and the firing member 1760.

The lockout arrangement 2180 includes a lock 2182 having a first leg or prong 2181, a second leg or prong 2183, and a third leg or prong 2185. The first leg 2181 and the second leg 2183 form a V-shaped body of the lock 2182. The third leg 2185 extends proximally from the V-shaped body. A lockout pivot 2184 is positioned at a central hub portion intermediate the legs 2181, 2183, and 2185. The lock 2182 is configured to pivot about the lockout pivot 2184 between a locked position (see FIGS. 27 and 28) and an unlocked position (see FIG. 29). The lockout pivot 2184 can be pivotably mounted to the sidewall 2103 of the elongate channel 2102. The lockout arrangement 2180 also includes a lockout spring 2186 which is configured to act on the lock 2182. Although only one lock 2182 and one lockout spring 2186 are depicted in FIGS. 27-29, the reader will readily appreciate that the lockout arrangement 2180 can include symmetrical locks 2182 and lockout springs 2186. For example, each lock 2182-lockout spring 2186 pair can be positioned on one side of the firing member 1760. In other instances, the lockout arrangement 2180 can include a single lock 2182 and a single lockout spring 2186.

The first leg 2181 constitutes an anvil engagement leg, which acts as a support ledge for the anvil 1130 when the lock 2182 is in the first orientation. The second leg 2183 constitutes a cartridge engagement leg, which is biasable by a staple cartridge to pivot the lock 2182 to the unlocked position. The third leg 2185 constitutes a spring engagement leg, or nub, against which the lockout spring 2186 biases the lock 2182 toward the locked position. More specifically, the lockout arrangement 2180 includes the lockout spring 2186, which applies a downward force on the third leg 2185. The force on the third leg 2185 is configured to bias the first leg 2181 upward toward the anvil 1130 and proximally. A proximal portion of the lockout spring 2186 is fixedly secured to the elongate channel 2102 and a distal portion of the lockout spring 2186 is configured to deflect relative to the fixed proximal portion thereof. The lockout spring 2186 is a leaf spring; however, the reader will readily appreciate that alternative springs can be employed to bias the lock 2182 toward the locked position.

Referring primarily to FIG. 28, the lock 2182 is initially biased into the locked position by the lockout spring 2186. When in the locked position, the first leg 2181 abuts the anvil 1130. In particular, an end 2181a of the first leg 2181 is positioned against the inner rail 1135 of the anvil 1130. As a result of the engagement between the first leg 2181 and the inner rail 2135, the anvil 1130 is held in an open orientation relative to the elongate channel 2102. Even if a closure motion is applied to the anvil 1130 (e.g. by advancing the firing member 1760 distally), closing of the anvil 1130 is prevented by the first leg 2181 and the inner rail 1135 engagement.

The lock 2182 is configured to remain in the locked position until an unfired staple cartridge is installed in the elongate channel 2102. When the staple cartridge 1110 is positioned in the elongate channel 2102, as depicted in FIG. 29, a portion of the staple cartridge 1110 abuts the second leg 2183. More specifically, the sled assembly 1120 is in a proximal position when the staple cartridge 1110 is unfired, and the proximal end of the unfired sled assembly 1120 is positioned against the second leg 2183 of the lock 2182. The sled assembly 1120 applies a force F (see FIG. 29) to the second leg 2183, which displaces the second leg 2183 downward and into a lockout notch 2109 in the cartridge-supporting base 2101 of the elongate channel 2102. Because the second leg 2183 is nested in the lockout notch 2109, the installed staple cartridge 1110 can be positioned flush against the cartridge-supporting base 2101 of the elongate channel 2102. The force F exerted by the sled assembly 1120 on the second leg 2183 is sufficient to overcome the spring bias of the lockout spring 2186.

In other instances, another part of the staple cartridge 1110, such as the cartridge body 1111, can abut the lock 2182. In such instances, the lockout arrangement 1280 can be a missing or no-cartridge lockout, which prevents clamping of the end effector 2100 until a staple cartridge is installed therein. However, while a staple cartridge is installed in the end effector 2100, the lockout arrangement can be overcome even if the staple cartridge has already been fired. Such a missing cartridge lockout could be combined with an empty or spent cartridge lockout, for example. An empty cartridge lockout can be a sensor (e.g. an electronic contact sensor) that detects the proper position of the sled assembly 1120 within the staple cartridge 1110 and only permits the firing stroke when the sled assembly 1120 is in the proper, pre-fired position, for example.

Referring still to FIG. 29, as the second leg 2183 rotates into the lockout notch 2109, the lock 2182 pivots to the unlocked position. As a result, the first leg 2181 moves out of engagement with the inner rail 1135. When a closure motion is applied to the anvil 1130 (e.g. by advancing the firing member 1760 distally), the anvil 1130 is cleared to pivot downward toward the staple cartridge 1110. In other words, closure of the anvil 1130 is permitted when an unfired staple cartridge is positioned in the elongate channel 2102. For example, the firing member 1760 can be advanced distally, and the upper flanges 1762 can move along the distal closure ramp 1140 of the open-close cavity 1148 to cam the anvil 1130 toward the closed position.

The sled assembly 1120 holds the lock 2182 in the unlocked position while the sled assembly 1120 is positioned in the proximal position depicted in FIG. 29. When the sled assembly 1120 is advanced distally during a firing stroke, the lock 2182 is released; however, rotation of the lock 2182 back to the locked position is prevented by the inner rail 1135 while the anvil 1130 is clamped relative to the staple cartridge 1110. Thereafter, when the anvil 1130 is returned to an open position (e.g. by retracting the firing member 1760 proximally), the lockout spring 2186 is configured to bias the lock 2182 back toward the locked position (see FIGS. 27 and 28), which prevents a subsequent closing and firing stroke until the staple cartridge 1110 is removed from the elongate channel 2102 and replaced with a new staple cartridge having a proximally-positioned sled assembly positioned to overcome the lockout arrangement 1280.

The lockout arrangement 1280 prevents the pivoting of the anvil 1130 relative to the elongate channel 2102 unless an unfired staple cartridge 1110 is installed in the end effector 1000. In various instances, the anvil 1130 can be fixed or stationary, and the elongate channel 2102 can be configured to pivot relative to the fixed anvil 1130. In such instances, the reader will readily appreciate that the lockout arrangement 1280 can be configured to prevent the pivoting of the elongate channel 2102 relative to the anvil 1130 unless an unfired staple cartridge 1110 is installed in the end effector 2100.

In certain instances, a lockout can be positioned in an end effector. For example, the lock 2182 of the lockout arrangement 2180 is positioned in the elongate channel 2102 of the end effector 2100. In other instances, a lockout can be positioned in a shaft portion of a surgical instrument. For example, an interchangeable surgical tool assembly can include a shaft portion and an end effector portion, and a lockout can be positioned in the shaft portion.

Figure 30:
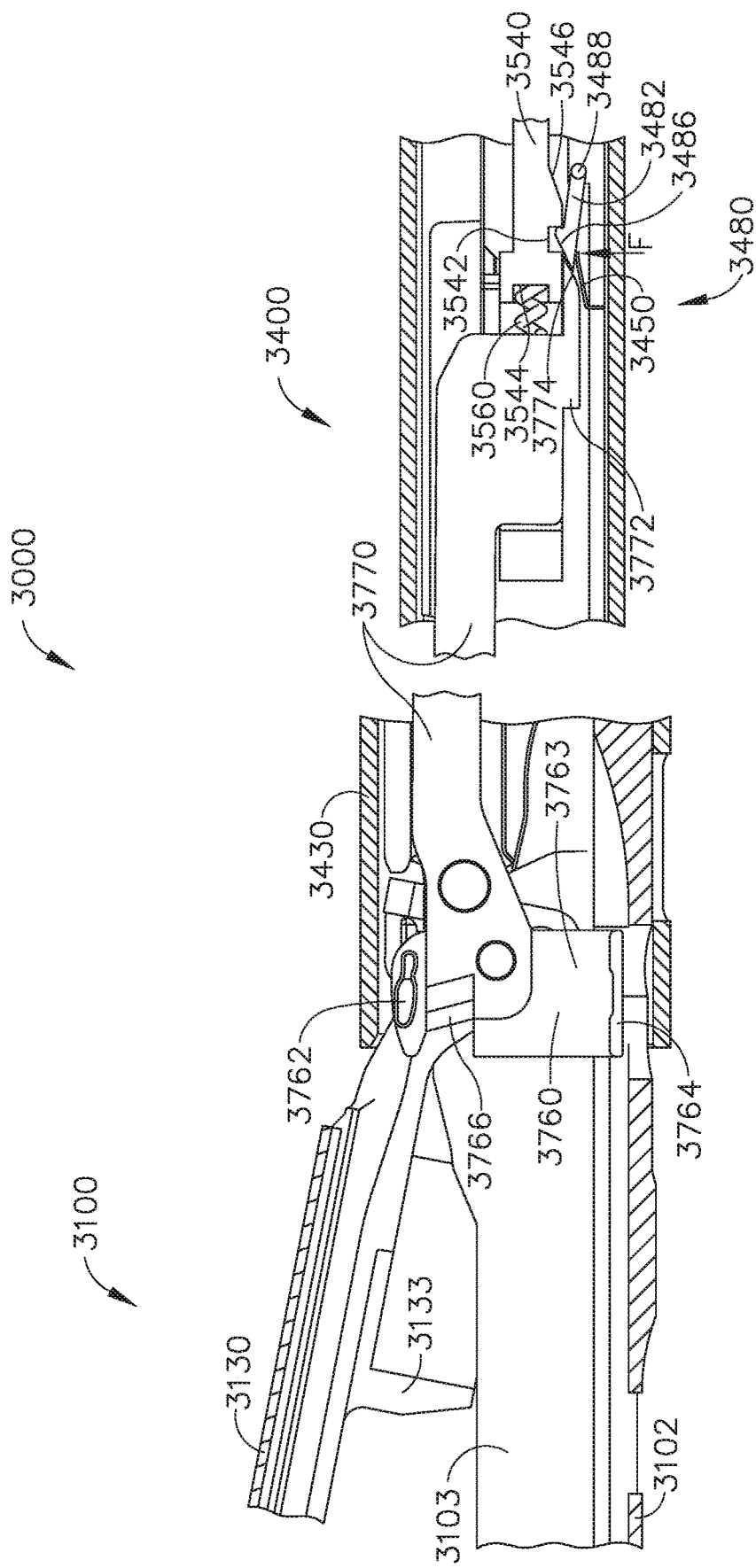
FIG. 30 is an elevation partial cross-sectional view of a portion of an interchangeable surgical tool assembly having a lockout, wherein the lockout arrangement is in a locked configuration.

FIG. 30 depicts an interchangeable surgical tool assembly 3000, which is similar in many respects to the interchangeable surgical tool assembly 1000. The interchangeable surgical tool assembly includes an end effector 3100 and a shaft portion 3400. A lockout arrangement 3480 is positioned in the shaft portion 3400. The interchangeable surgical tool assembly 3000 also includes a firing member 3760 coupled to a firing bar 3770.

The firing member 3760 is similar in many respects to the firing member 1760 (see FIGS. 4 and 5). For example, the firing member 3760 defines an I-beam structure that includes a lower flange 3764, an upper flange 3762, and a support portion 3763 extending between the flanges 3762 and 3764. The upper flange 3762 is comprised of horizontal pins extending from the support portion 3763. The lower flange 3764 is comprised of an enlarged or widened foot at the base of the support portion 3763. A tissue cutting feature 3766 is supported by the support portion 3763 between the flanges 3762 and 3764. The support portion 3763 travels though aligned slots in the elongate channel 3102, a staple cartridge, and an anvil 3130.

Unlike the anvil 1130, the anvil 3130 does not include the open-close cavity 1148 that is engageable by the firing member to open and close the jaws of the end effector 3100. Rather, to open and close the anvil 3130, a closure tube 3430 is configured to translate around a portion of the end effector 3100. Distal translation of the closure tube 3430 is configured to cam the jaws toward a clamped configuration, and proximal displacement of the closure tube 3430 is configured to cam the jaws toward an open configuration. Operation of a closure tube for opening and closing end effector jaws in further described herein.

The shaft portion 3400 includes a longitudinally-movable drive member 3540, which is similar in many respects to the drive member 1602. During a firing stroke, the drive member 3540 transfers a firing motion to the firing bar 3770 to fire the firing member 3760. For example, actuation of the drive member 3540 is configured to displace the firing bar 3770 and the firing member 3760 distally to cut tissue and effect firing of staples from a staple cartridge. Thereafter, the drive member 3540 can be retracted proximally to retract the firing bar 3770 and the firing member 3760 proximally.

In certain instances, the drive member 3540 can be directly coupled to the firing bar 3770. Other times, as depicted in FIG. 30, a bias spring 3560 is positioned between the drive member 3540 and the firing bar 3770. For example, the bias spring 3560 extends proximally from the firing bar 3770 toward the drive member 3540. In various instances, an end of the bias spring 3560 can be coupled to the firing bar 3770 and an opposite end of the bias spring 3560 can be coupled to the drive member 3540. The drive member 3540 includes a spring aperture 3544 at the distal end thereof. The spring aperture 3544 is configured to receive and constrain a portion of the bias spring 3560. The bias spring 3560 is a coil spring, but the reader will readily appreciate that alternative spring geometries can be configured to exert a proximal biasing force on the drive member 3540 and a corresponding distal biasing force on the firing bar 3770.

The lockout arrangement 3480 in the shaft portion 3400 includes a lockout lever 3482 having a detent 3484 (see FIGS. 33 and 35) and a distal nose 3486. The detent 3484 of the lockout lever 3482 is positioned to operably engage the drive member 3540, and the distal nose 3486 of the lockout lever 3482 is positioned to operably engage the firing bar 3770. In particular, the firing bar 3770 includes a proximal reset pawl 3772 having a proximal nose 3774. The proximal reset pawl 3772 extends toward the lockout arrangement 3480 from the proximal end of the firing bar 3770. The ramped surface of the distal nose 3486 on the lockout lever 3482 and the ramped surface of the proximal nose 3774 are slidingly engaged, as further described herein.

The lockout arrangement 3480 also includes a reset spring 3450, which operably engages the lockout lever 3482. The reset spring 3450 is positioned to exert a force F (see FIG. 30) on the lockout lever 3482 to bias the lockout lever 3482 toward the locked position depicted in FIG. 30. As further described herein, the lockout lever 3482 is configured to rotate about a pivot 3488 to move from the locked position to an unlocked position (see FIG. 31). When in the locked position, the detent 3484 (see FIGS. 33 and 35) of the lockout lever 3482 is engaged with the drive member 3540. More specifically, the detent 3484 is positioned in a lockout recess 3542 in the drive member 3540 such that longitudinal displacement of the drive member 3540 is prevented by the detent 3484.

Referring still to FIG. 30, a staple cartridge is missing from the end effector 3100. When a staple cartridge is not positioned in the end effector 3100, the force F from the reset spring 3450 pivots the lockout lever 3482 to the locked position such that the detent 3484 (see FIGS. 33 and 35) is positioned in the lockout recess 3542. As a result, distal displacement of the drive member 3540 is prevented. Though a firing motion may be applied to the drive member 3540 from an actuator in the handle (e.g. handle assembly 500 in FIGS. 1 and 2) of the surgical instrument, the drive member 3540 is not displaced and does not transfer the firing motion to the firing bar 3770 and the firing member 3760 because the detent 3484 holds and/or constrains the drive member 3540 to prevent distal displacement thereof.

Figure 31:
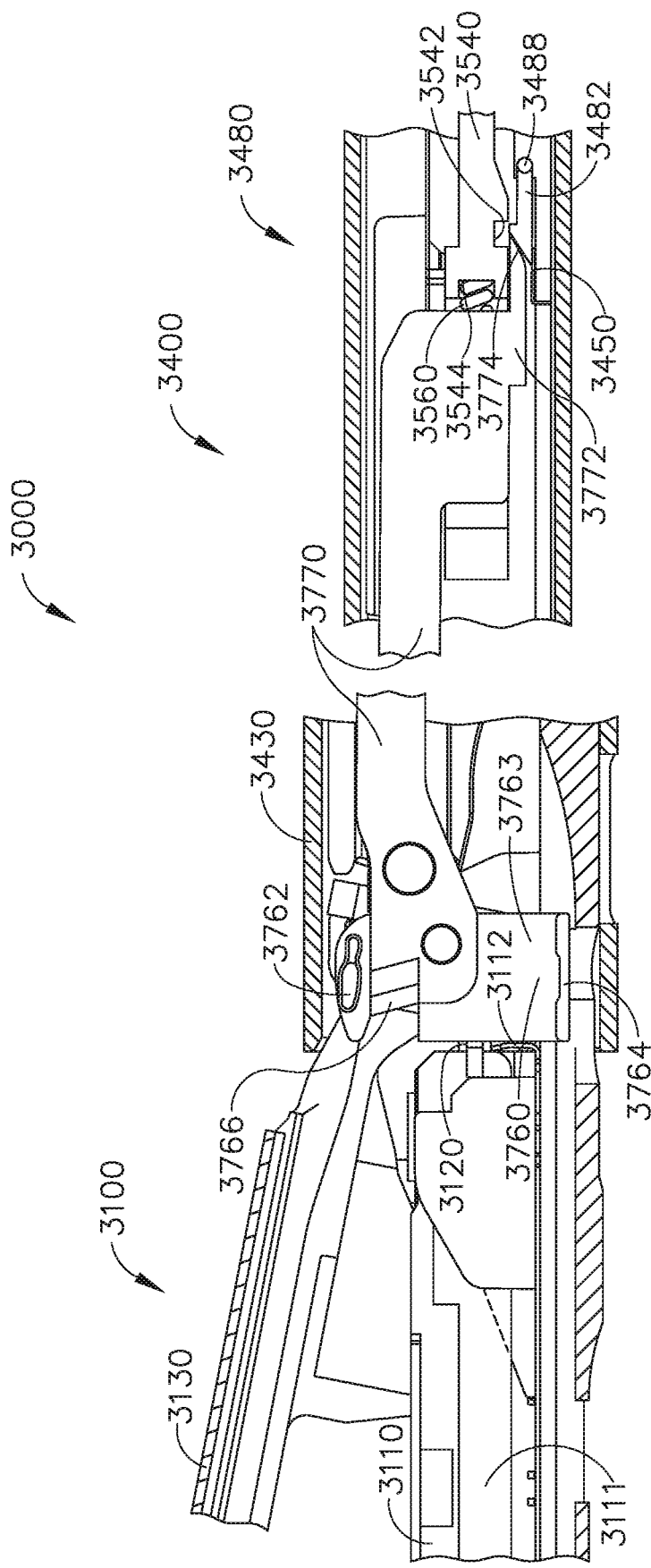
FIG. 31 is an elevation partial cross-sectional view of a portion of the interchangeable surgical tool assembly of FIG. 30 having a staple cartridge positioned therein, wherein the lockout arrangement is in an unlocked configuration and the staple cartridge is in a pre-fired state.
Figure 32:
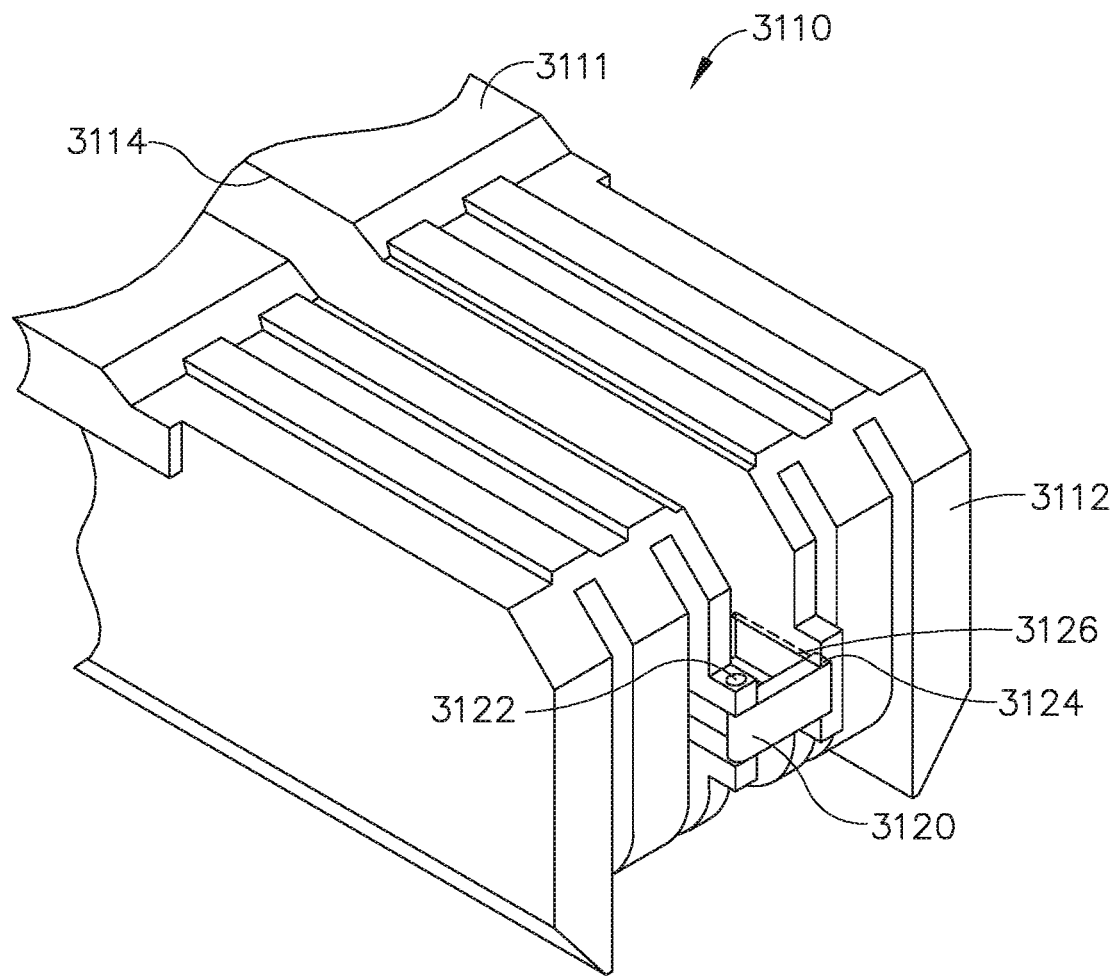
FIG. 32 is a perspective view of a proximal portion of the staple cartridge of FIG. 31 depicting the pre-fired state of the staple cartridge.

Referring to FIG. 31, a staple cartridge 3110 is positioned in the end effector 3100. The staple cartridge 3110 is similar in many respects to the staple cartridge 1110. However, the staple cartridge 3110 also includes a proximal gate 3120, which is operably configured to abut the firing member 3760. Referring primarily to FIG. 32, the staple cartridge 3110 includes a cartridge body 3111 and a longitudinal slot 3114 defined in the cartridge body 3111. The longitudinal slot 3114 extends from a proximal end 3112 of the staple cartridge 3110. At the proximal end 3112 of the staple cartridge 3110, the proximal gate 3120 extends across the longitudinal slot 3114. As a result, the proximal gate 3120 forms a frangible or breakable barrier for the firing member 3760.

Referring still to FIG. 32, the proximal gate 3120 is connected to the cartridge body 3111 by a hinge 3122 on a first side of the longitudinal slot 3114. The proximal gate 3120 abuts the cartridge body 3111 on the opposite side of the longitudinal slot 3114. In particular, the cartridge body 3111 includes a cutout 3124 that is dimensioned to fit and receive a portion of the gate 3120. In various instances, the gate 3120 can be press-fit or friction-fit into the cutout 3124. Additionally or alternatively, the cutout 3124 can define a stop 3126. The stop 3126 constitutes a distal abutment surface or shelf for the gate 3120. In various instances, the cartridge body 3111 can be molded from a plastic material, and the cutout 3124 and/or the stop 3126 can be molded-in features of the cartridge body 3111.

Referring again to FIG. 31, when the staple cartridge 3110 is positioned in the end effector 3100, the proximal gate 3120 is positioned against a distal end portion of the firing member 3760. As a result, the proximal gate 3120 is configured to shift the firing member 3760 and the firing bar 3770 proximally. As depicted in FIG. 31, the bias spring 3560 is configured to compress or otherwise deform to permit the proximal displacement of the firing member 3760 toward the drive member 3540. Though the proximal gate 3120 is frangible, the proximal gate 3120 is configured to withstand the biasing force generated by the compressed bias spring 3560.

Referring still to FIG. 31, proximal displacement of the firing member 3760 drives the proximal nose 3774 on the reset pawl 3772 proximally against the lockout lever 3482. The proximal nose 3774 is configured to overcome the reset spring 3450 such that the lockout lever 3482 can pivot toward the unlocked position depicted in FIG. 31. When in the unlocked position, the reset spring 3450 is compressed flush against an inner surface of the shaft portion 3400 and the detent 3484 (see FIGS. 33 and 35) on the lockout lever 3482 is disengaged from the lockout recess 3542. As a result, distal displacement of the drive member 3540 is permitted by the lockout arrangement 3480. Moreover, the firing force of the drive member 3540, transmitted to the firing bar 3770 and the firing member 3760, is configured to break the proximal gate 3120 on the staple cartridge 3110.

Figure 33:
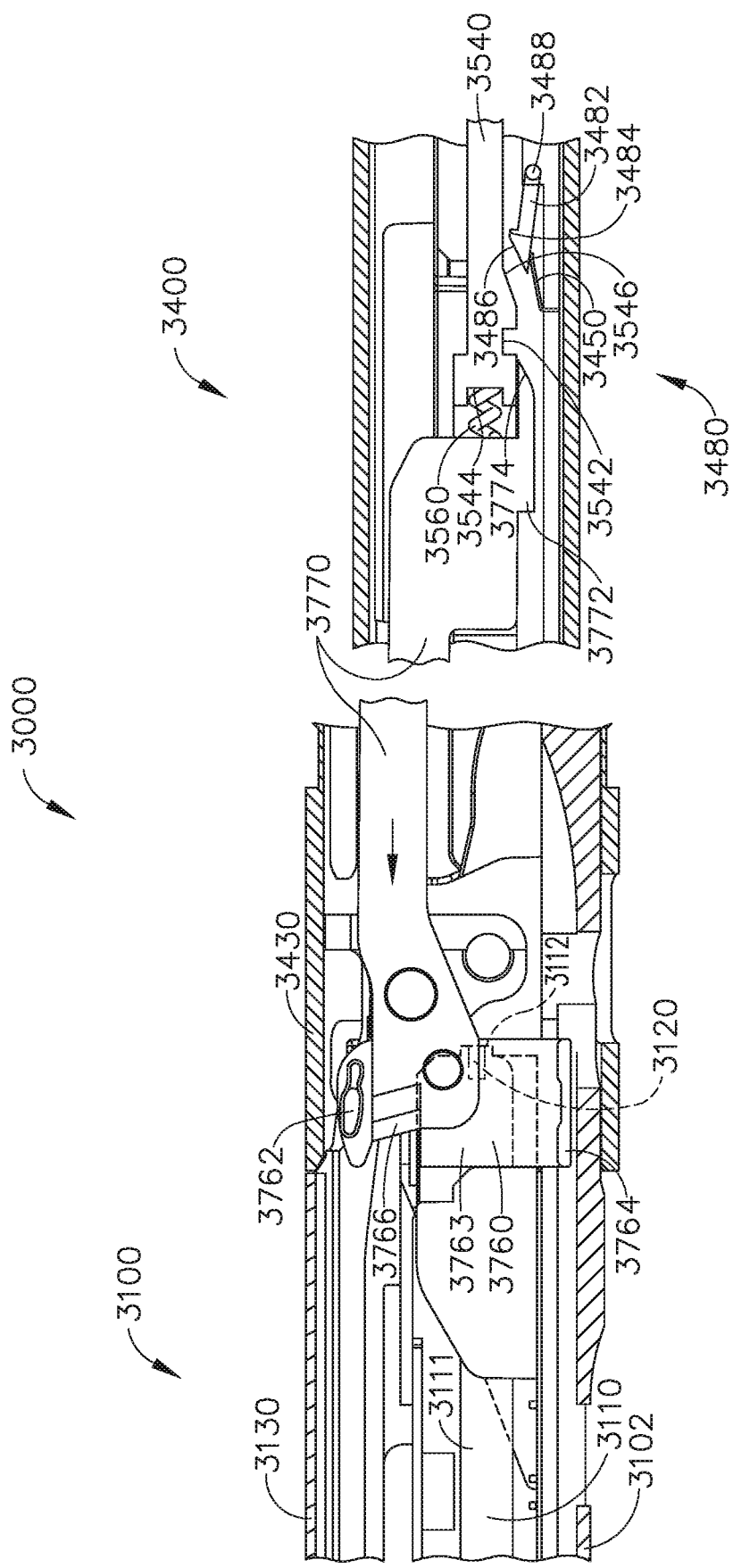
FIG. 33 is an elevation partial cross-sectional view of a portion of the interchangeable surgical tool assembly of FIG. 30 having the staple cartridge of FIG. 31 positioned therein, and depicting a firing assembly of the interchangeable surgical tool assembly advanced to an intermediate position during an initial portion of a firing stroke, wherein the staple cartridge is in a post-fired state.
Figure 34:
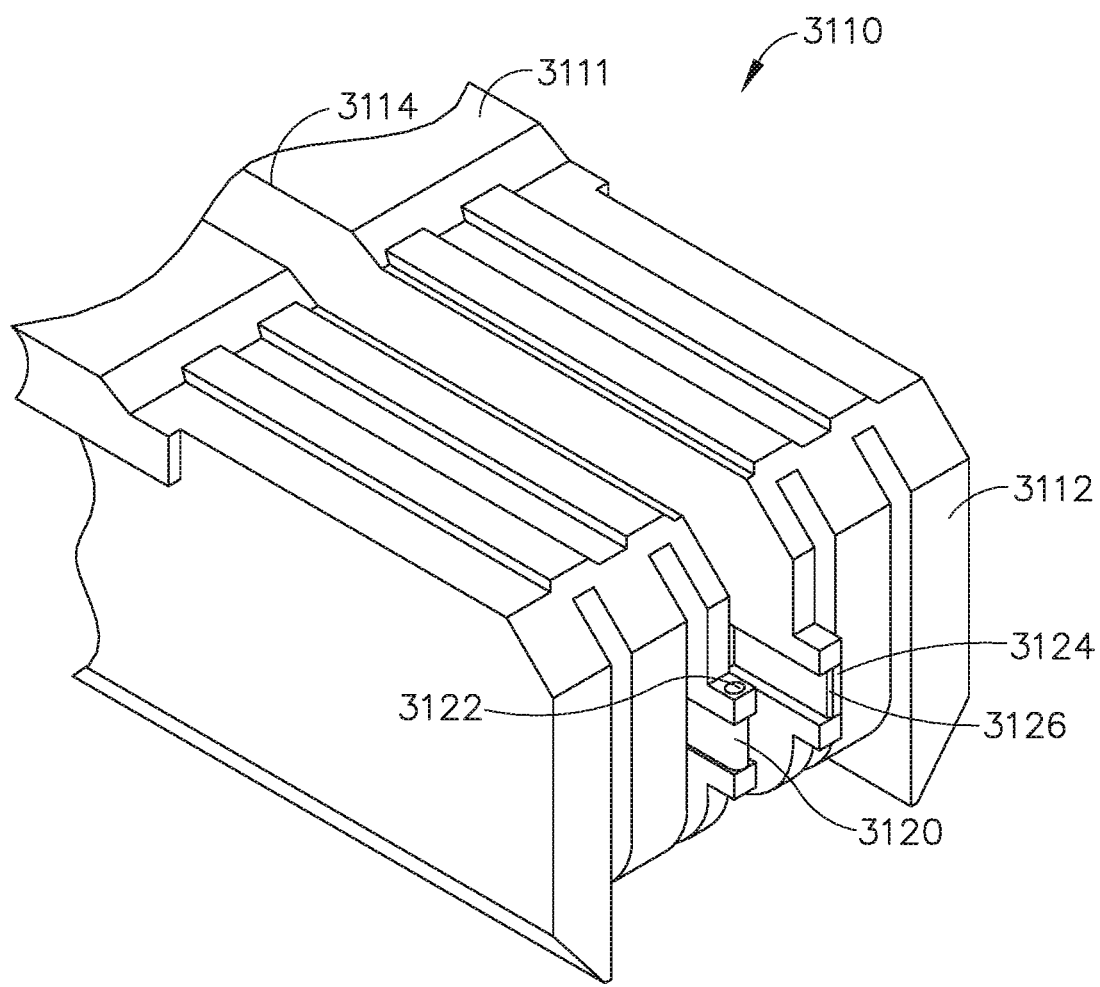
FIG. 34 is a perspective view of a proximal portion of the staple cartridge of FIG. 31 depicting the post-fired state of the staple cartridge.

Referring now to FIG. 33, the drive member 3540 has pushed the firing bar 3770 distally causing the firing member 3760 to break or otherwise release the proximal gate 3120. The threshold force required to break or otherwise release the proximal gate 3120 can be less than the force generated by the surgical instrument to implement a firing stroke. In other words, a firing stroke can be designed to break or otherwise overcome the proximal gate 3120. As depicted in FIG. 34, when the firing member 3760 pushes against the proximal gate 3120 with the force of a firing stroke, the proximal gate 3120 can be configured to pivot at the hinge 3122. In various instances, the stop 3126 of the cutout 3124 can deform or break to release the proximal gate 3120. For example, as depicted in FIG. 34, a corner of the stop 3126 is broken to accommodate the distally-pivoting gate 3120.

As the drive member 3540 moves distally during the firing stroke, referring again to FIG. 33, the firing bar 3770 and the reset pawl 3772 thereof also move distally. Distal displacement of the reset pawl 3772 moves the reset pawl 3772 out of engagement with the lockout lever 3482. Consequently, the force of the reset spring 3450 on the lockout lever 3482 is configured to bias the disengaged lockout lever 3482 back to the locked position. Though the lockout lever 3482 has returned to the locked position in FIG. 33, completion of the firing stroke is permitted because the lockout recess 3542 in the drive member 3540 is longitudinally offset from the detent 3484 on the lockout lever 3482.

Figure 35:
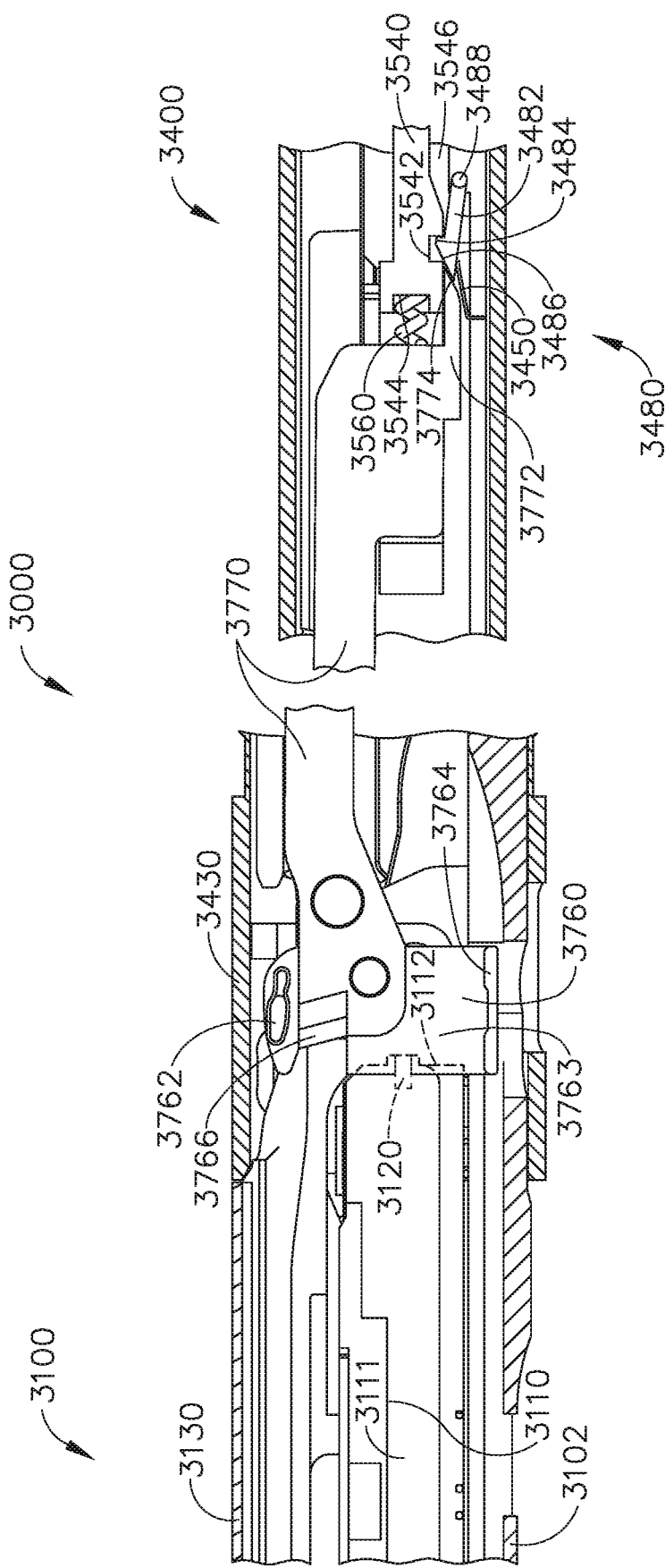
FIG. 35 is an elevation partial cross-sectional view of a portion of the interchangeable surgical tool assembly of FIG. 30 after the completion of the firing stroke and having the staple cartridge of FIG. 31 positioned therein.

At the completion of the firing stroke, the firing member 3760 can be retracted proximally. As the firing member 3760, the firing bar 3770, and the drive member 3540 move proximally, a ramped surface 3546 on the drive member 3540 engages the lockout lever 3482. For example, the ramped surface 3546 can slide along the distal nose 3486 of the lockout lever 3482 to temporarily compress the reset spring 3450 and pivot the lockout lever 3482 against the reset spring 3450. As the drive member 3540 continues to be retracted proximally and the ramped surface 3546 moves past the detent 3484 on the lockout lever 3482, the detent 3484 can spring into engagement with the lockout recess 3542 in the drive member 3540, as depicted in FIG. 35. The reset spring 3450 exerts the spring force on the lockout lever 3482 to reset the lockout arrangement 3480. Because the detent 3484 is reengaged with the lockout recess 3542 and biased into such a position by the reset spring 3450, the lockout arrangement 3480 has been reset in FIG. 35. In other words, a subsequent firing stroke is prevented by the lockout arrangement 3480.

Though the firing member 3760 has been retracted to its home position in FIG. 35, the firing member 3760 is slightly distal to the position depicted in FIG. 31. Because the proximal gate 3120 was overcome during the firing stroke, the gate 3120 no longer biases the firing member 3760, and thus the firing bar 3770, proximally. As a result, the lockout arrangement 3480 in the shaft portion 3400 cannot be overcome by the spent staple cartridge 3110 depicted in FIG. 35.

Although the lockout arrangement 3480 has been described with respect to the end effector 3100, the reader will readily appreciate that the lockout arrangement 3480 can also be utilized with other end effectors, such as the end effector 1100, which utilizes a multi-function firing member to open and close the end effector jaws, fire staples, and cut tissue.

In certain instances, an interchangeable surgical tool assembly can include a spring configured to urge the jaws of the end effector toward a closed position. Such a spring can be positioned distal to the pivot joint of the end effector, for example. In certain instances, the spring can interact with a lockout arrangement that prevents a firing stroke when a staple cartridge is not installed in the end effector, i.e., a missing cartridge or no-cartridge lockout.

Figure 36:
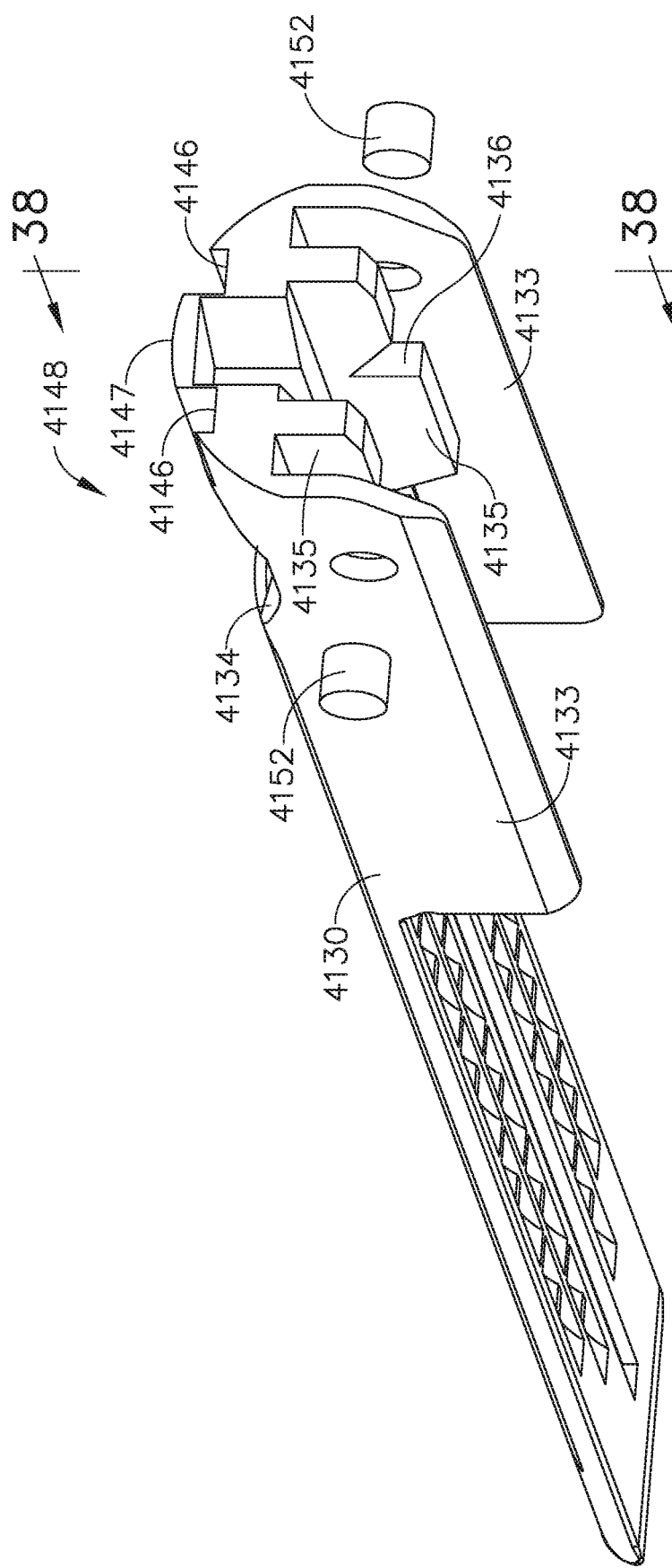
FIG. 36 is a perspective exploded assembly view of an anvil.
Figure 37:
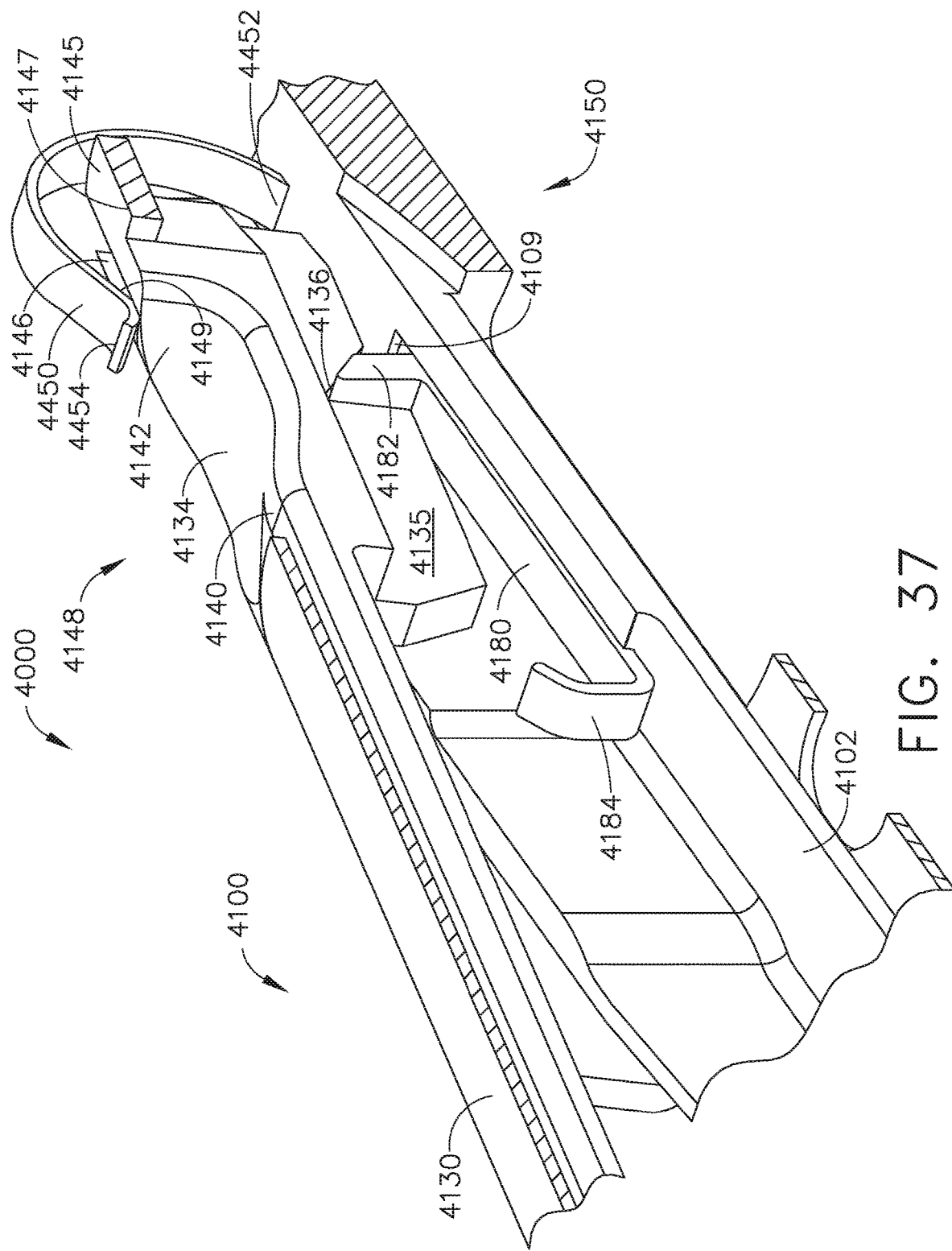
FIG. 37 is a perspective cross-sectional view of a portion of an interchangeable surgical tool assembly taken along a centerline of the interchangeable surgical tool assembly and depicting a portion of the anvil of FIG. 36, a portion of an elongate channel, and a lockout spring.
Figure 38:
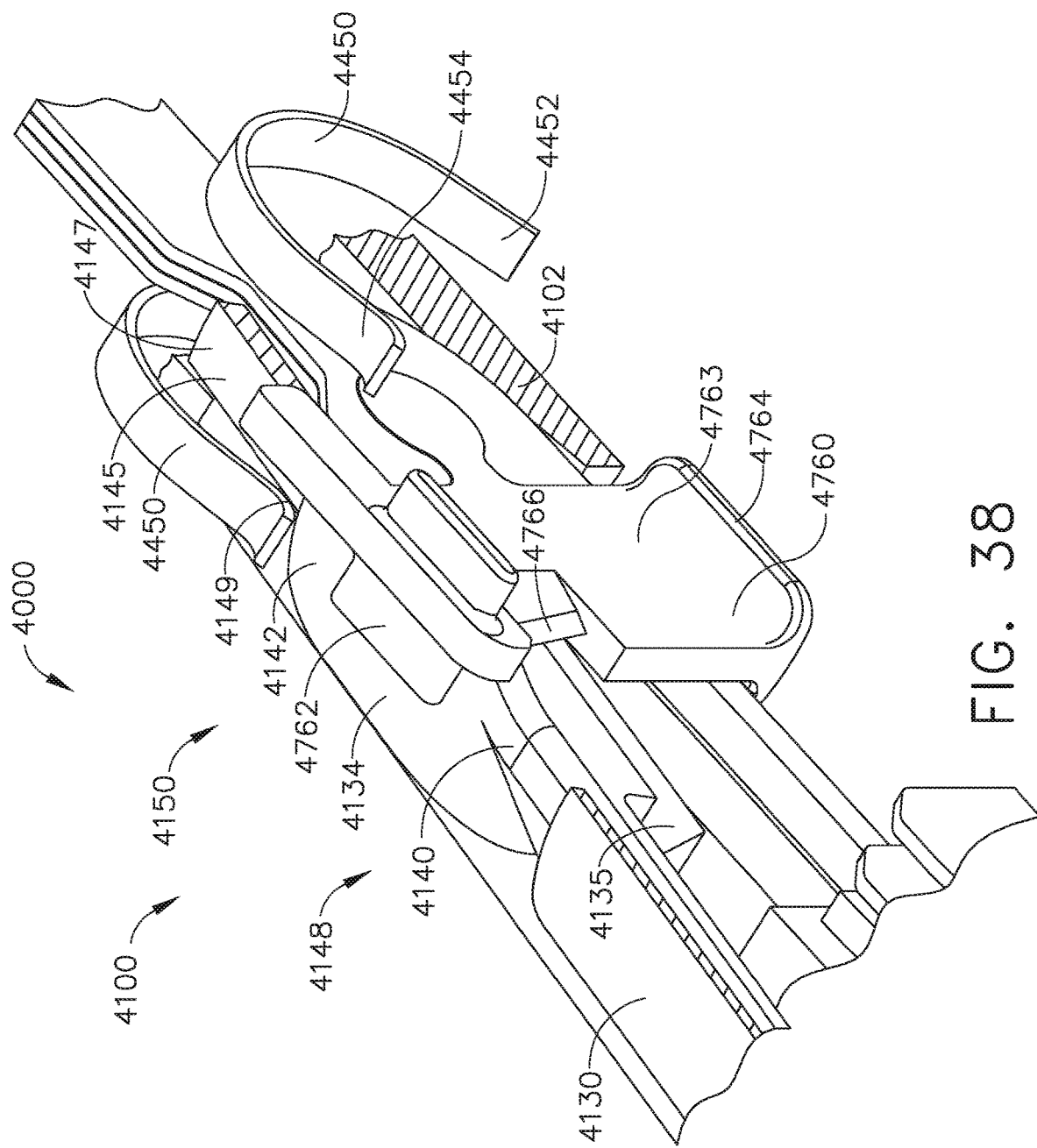
FIG. 38 is a perspective partial cross-sectional view of a portion of the interchangeable surgical tool assembly of FIG. 37 taken along the centerline of the interchangeable surgical tool assembly.

Referring to FIG. 36, an anvil 4130 is depicted. The anvil 4130 is similar in many respects to the anvil 1130 (see FIGS. 3-6), however, the anvil 4130 also includes spring slots 4146 and release notches 4136. The spring slots 4146 are defined in an outer proximal surface 4147 of the anvil 4130. For example, the anvil 4130 includes a ramped surface 4134 defining an open-close cavity 4148 similar to the ramped surface 1134 and the open-close cavity 1148 (see FIGS. 8-12), respectively. For example, the open-close cavity 4148 includes a distal closure ramp 4140 and a proximal opening surface 4142. The spring slots 4146 are located at the proximal end of the anvil 4130 proximal to the open-close cavity 4148. The anvil 4130 also includes inner rails 4135 positioned laterally inboard of the sidewall tissue stops 4133.

The inner rails 4135 are similar to the inner rails 1135 (see FIGS. 4 and 6) and include the release notches 4136 therein. The release notches 4136 are engaged by a lockout feature, as further described herein. The lockout arrangement of FIGS. 36-44 includes a pair of lockout springs 4450 and a pair of lock bars 4180. The lockout springs 4450 and the lock bars 4180 are symmetric with respect to a longitudinal axis of the anvil 4130. In other instances, the lockout arrangement can include a single lockout spring 4450 and a single lock bar 4180.

Referring primarily to FIGS. 33-40, an interchangeable surgical tool assembly 4000 includes an end effector 4100 having the anvil 4130, an elongate channel 4102, and lockout springs 4450 extending between the anvil 4130 and the elongate channel 4102. The anvil 4130 is configured to pivot relative to the elongate channel 4102 at a pivot joint 4150 at pivot pins 4152. The elongate channel 4102 is similar in many respects to the elongate channel 1102 (see FIGS. 3-5 and 7), however, the elongate channel 4102 also includes apertures 4107 (see FIGS. 24, 26, and 28) for the springs 4450 as well as recesses 4109 for the lock bars 4180, for example. The anvil 4130 is similar in many respects to the anvil 1130 (see FIGS. 3-6), however, the anvil 4130 also includes the spring slots 4146 for accommodating a portion of the lockout springs 4450, for example.

The lockout springs 4450 extend through the spring slots 4146 between the elongate channel 4102 and the anvil 4130. Each spring 4450 includes a first end 4452, which is held in an aperture 4107 in the elongate channel 4102, and a second end 4454, which engages the anvil 4130. The first ends 4452 of the springs 4450 can be embedded or otherwise secured to the elongate channel 4102. For example, the first ends 4452 of the springs 4450 can be held within the respective apertures 4107 in the elongate channel 4102. The second ends 4454 of the springs 4450 can be positioned against respective abutment surfaces 4149 on the outer proximal surface 4147 of the anvil 4130. For example, abutment surfaces 4149 are aligned with the spring slots 4146 directly adjacent to the open-close cavity 4148.

A firing member 4760 (see FIGS. 38-40) is positioned in the end effector 4100. The firing member 4760 is similar in many respects to the firing member 1760 (see FIGS. 4 and 5). For example, the firing member 4760 defines an I-beam structure that includes a lower flange 4764, an upper flange 4762, and a support portion 4763 extending between the flanges 4762 and 4764. The upper flange 4762 is comprised of horizontal pins extending from the support portion 4763. The lower flange 4764 is comprised of an enlarged or widened foot at the base of the support portion 4763. A tissue cutting feature 4766 is supported by the support portion 4763 between the flanges 4762 and 4764. The support portion 4763 travels though aligned slots in the elongate channel 4102, a staple cartridge, such as the staple cartridge 1110 (see FIGS. 3-5), and the anvil 4130.

The firing member 4760 also includes a proximal boss 4768, which extends proximally from a top portion of the firing member 4760. The proximal boss 4768 is operably configured to engage the anvil 4130 to facilitate an opening motion of the anvil 4130. More specifically, the proximal boss 4768 is positioned to engage a central crossover surface 4145 of the anvil 4130. The central crossover surface 4145 is positioned intermediate the spring slots 4146 and proximal to the open-close cavity 4148 and the pivot joint 4150 of the end effector 4100. When the firing member 4760 is retracted proximally beyond the pivot joint 4150, the proximal boss 4768 is configured to slidingly engage the central crossover surface 4145, which biases the central crossover surface 4145 downward to pivot the anvil 4130 toward an open position.

The end effector 4100 includes lock bars 4180 slidably positioned in a recess 4109 in the elongate channel 4102. Each lock bar 4180 includes a proximal end 4182 and a distal end 4184. The proximal end 4182 is operably positioned in the release notch 4136. The distal end 4184 is positioned to engage a staple cartridge when a staple cartridge is inserted in the elongate channel 4102. The engaged surfaces at the proximal end 4182 of the lock bar 4180 and the notch 4136 are configured to bias the lock bar 4180 distally. For example, the notch 4136 defines a ramped surface that pushes the proximal end 4182 of the lock bar 4180 distally. Additionally or alternatively, the lockout arrangement can include a bias spring 4186 (see FIG. 40) for biasing the lock bar 4180 toward a distal position. The bias spring 4186 is positioned in abutting contact with the proximal end 4182 of the lock bar 4180. In various instances, a recess in the elongate channel 4102 can be configured to receive and support the bias spring 4186.

Figure 39:
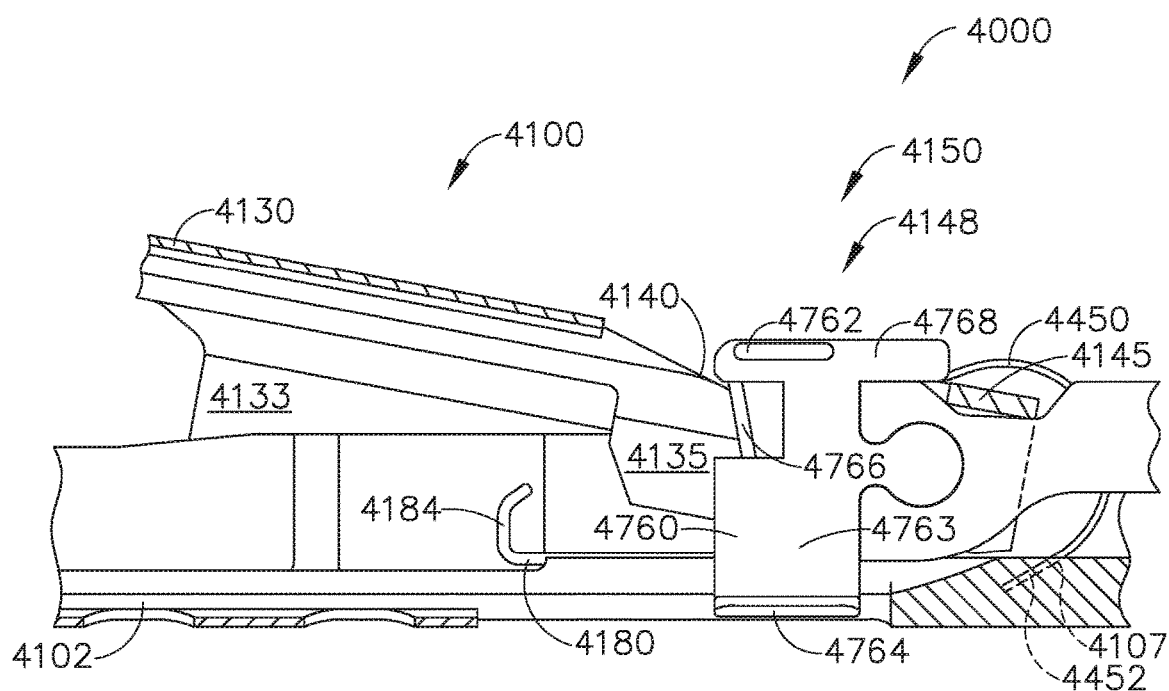
FIG. 39 is an elevation partial cross-sectional view of a portion of the interchangeable surgical tool assembly of FIG. 37 taken along the centerline of the interchangeable surgical tool assembly and depicting the anvil in an open position.
Figure 40:
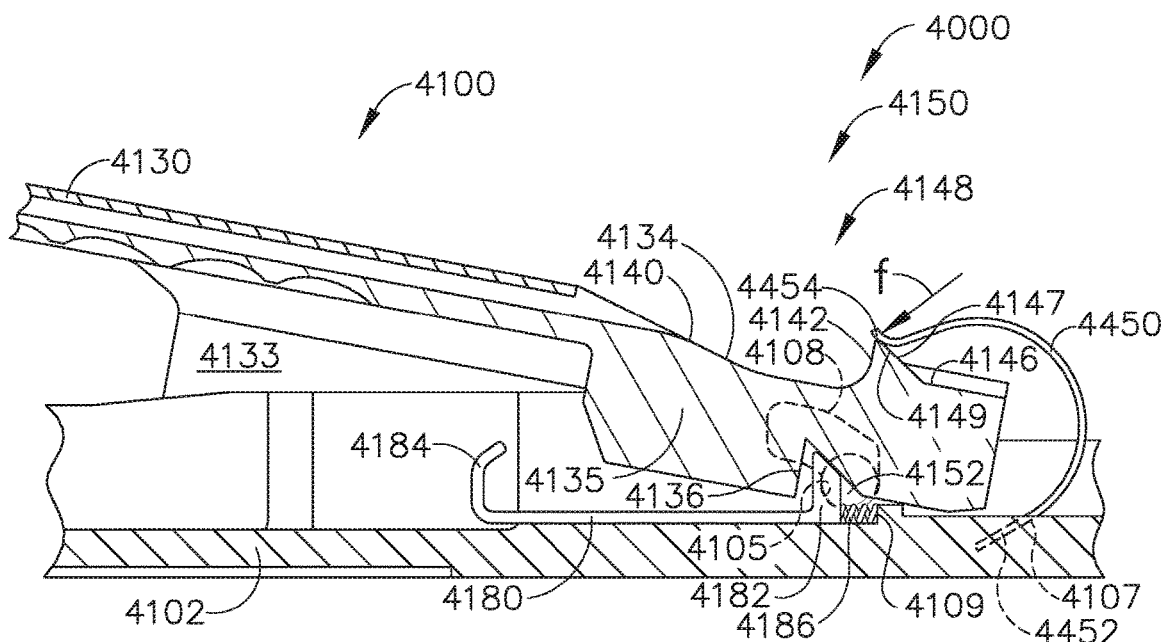
FIG. 40 is an elevation partial cross-sectional view of a portion of the interchangeable surgical tool assembly of FIG. 37 taken along the plane indicated in FIG. 36 and depicting the anvil in the open position.

Referring primarily to FIGS. 39 and 40, the end effector 4100 is shown in an unclamped or open configuration. Moreover, a staple cartridge has not been installed in the elongate channel 4102. Though the anvil 4130 is not clamped with respect to a staple cartridge, the lockout springs 4450 are configured to exert a closure force on the anvil 4130. For example, the lockout springs 4450 are configured to bias the anvil 4130 downward and forward. Referring primarily to FIG. 40, the second end 4454 of the spring 4450 is positioned against the abutment surface 4149 on the outer proximal surface 4147 and the spring 4450 is configured to exert a force f (see FIG. 40) on the abutment surface 4149; the force f biases the anvil 4130 toward a closed position.

The force f from the lockout spring 4450 is also configured to bias the anvil pin 4152 into a lockout notch 4105 in the elongate channel 4102. More specifically, the elongate channel 4102 includes a pair of contoured slots 4108 defined in a proximal portion of each sidewall. The contoured slots 4108 are commonly referred to as "kidney slots" or "banana slots" due to their geometry. The lockout notch 4105 extends from a lower proximal portion of the contoured slot 4108. When the anvil pin 4152 is positioned in the lockout notch 4105, rotation of the anvil 4130 from the open position (see FIGS. 39-42) to a closed position (see FIGS. 43 and 44) is prevented. For example, wherein the proximal end 4182 of the lock bar 4180 is positioned in the release notch 4136, a ramped surface at the proximal end 4182 can be positioned flush against a ramped surface in the release notch 4136 such that movement of the anvil 4130 is restrained.

Figure 41:
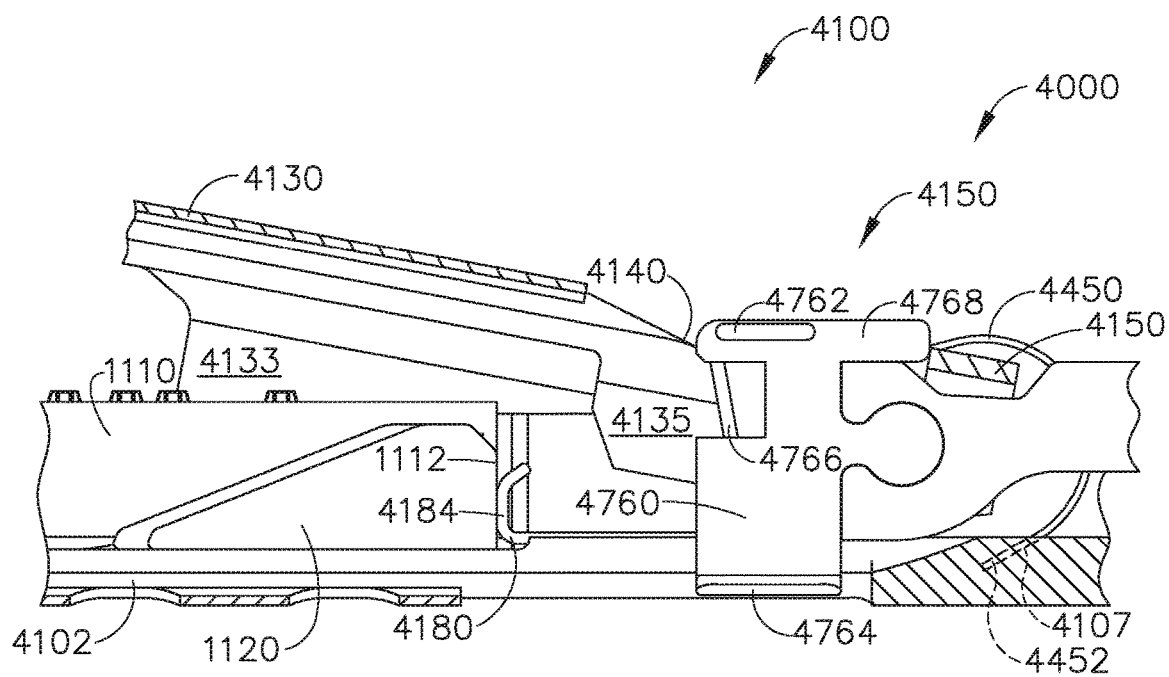
FIG. 41 is an elevation partial cross-sectional view of a portion of the interchangeable surgical tool assembly of FIG. 37 taken along the centerline of the interchangeable surgical tool assembly and depicting a staple cartridge installed in the elongate channel and the anvil in the open position.
Figure 42:
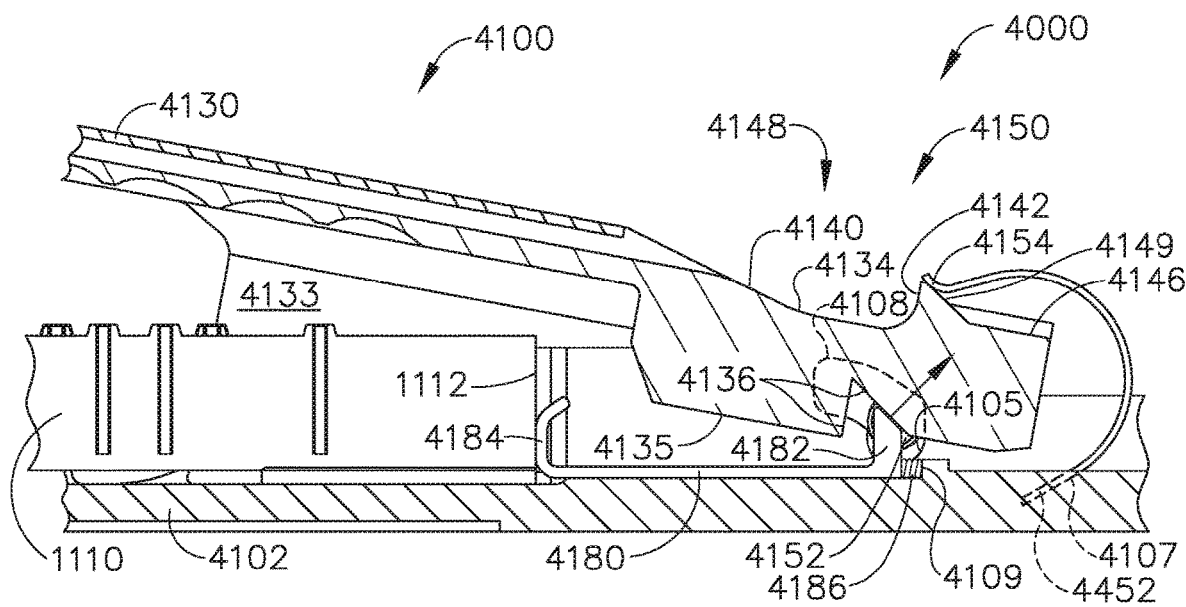
FIG. 42 is an elevation partial cross-sectional view of a portion of the interchangeable surgical tool assembly of FIG. 37 taken along the plane indicated in FIG. 36 and depicting the staple cartridge installed in the elongate channel and the anvil in the open position.

Referring now to FIGS. 41 and 42, the staple cartridge 1110 has been installed in the elongate channel 4102. When the staple cartridge 1110 is inserted in the end effector 4100, the proximal end 1112 of the staple cartridge 1110 is positioned against the distal end 4184 of the lock bar 4180 and shifts the lock bar 4180 proximally in the recess 4109. For example, the distal end 4184 of the lock bar 4180 can include a cartridge-facing surface against which the proximal end 1112 of the staple cartridge abuts. The proximal displacement of the lock bar 4180 also moves the proximal end 4182 of the lock bar within the release notch 4136. The proximal end 4182 includes a ramped surface, which engages a ramped surface of the release notch 4136 to lift the anvil 4130 upward away from the elongate channel 4102. As the anvil 4130 moves upward, the anvil pins 4152 also move upward out of the lockout notch 4105 and into the contoured slot 4108. Though the springs 4450 continue to bias the anvil 4130 downward and, thus, bias the anvil pins 4152 into the lockout notch 4105, the proximal displacement of the lock bar 4180 by the installed staple cartridge 1110 is sufficient to overcome the bias of the lockout springs 4450. When the anvil pins 4152 are positioned within the contoured slots 4108, as shown in FIG. 42, the anvil 4130 is operably configured to pivot about the pivot joint 4150 at the anvil pins 4152 toward the closed position.

Figure 43:
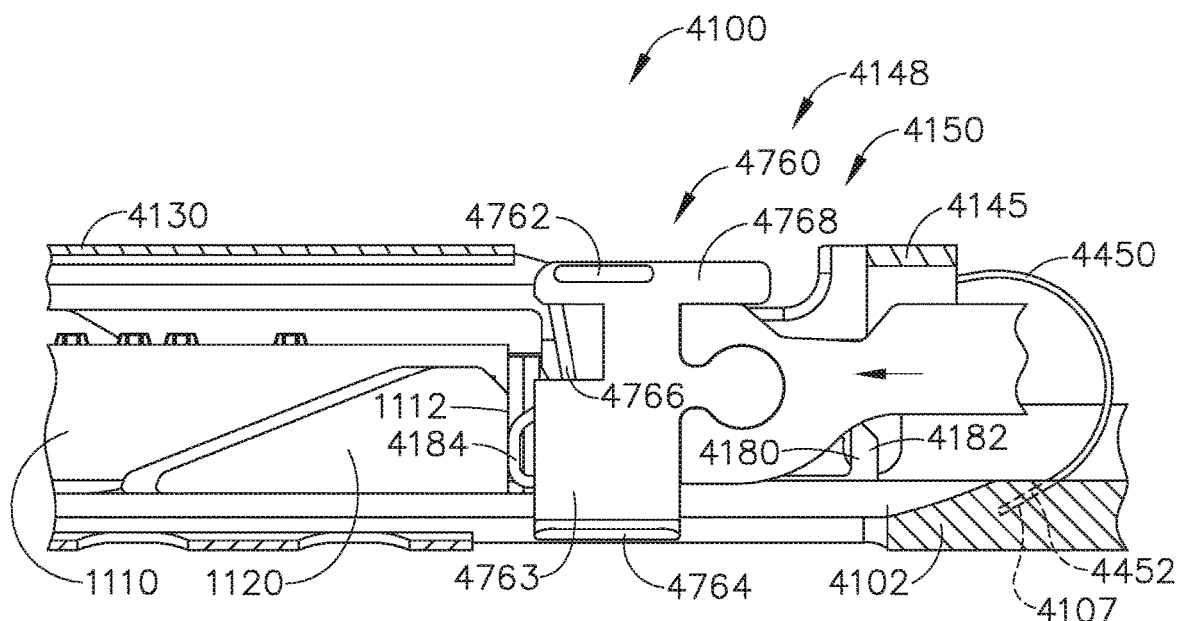
FIG. 43 is an elevation partial cross-sectional view of a portion of the interchangeable surgical tool assembly of FIG. 37 taken along the centerline of the interchangeable surgical tool assembly and depicting the staple cartridge installed in the elongate channel and the anvil moved to a closed position by the firing member.
Figure 44:
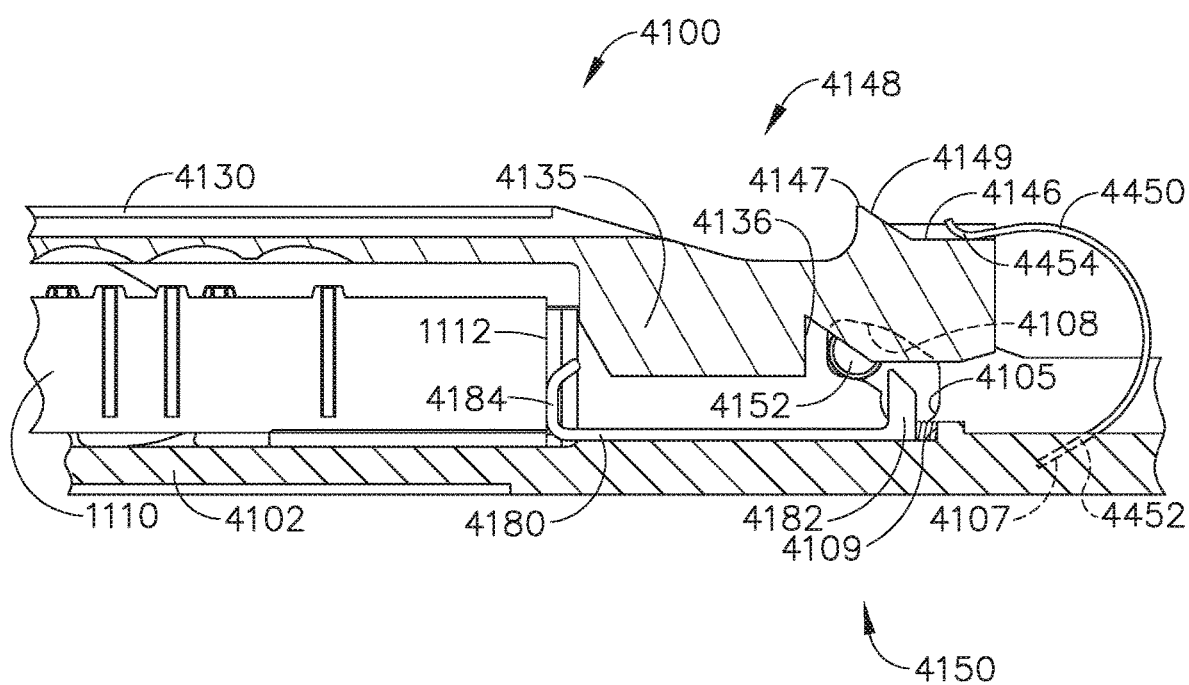
FIG. 44 is an elevation partial cross-sectional view of a proximal portion of the interchangeable surgical tool assembly of FIG. 37 taken along the plane indicated in FIG. 36 and depicting the staple cartridge installed in the elongate channel and the anvil moved to the closed position by the firing member.

Referring now to FIGS. 43 and 44, the firing member 4760 has been advanced distally to close the anvil 4130. For example, the upper flanges 4762 of the anvil 4130 are configured to cam against a distal closure ramp, similar to the distal closure ramp 1140 (see FIGS. 8-12) on the anvil 1130, for example, on the anvil 4130 as the firing member 4760 moves distally. The camming force generated by the firing member 4760 is sufficient to pivot the anvil 4130 toward the closed position, and the anvil pins 4152 are configured to move along the contoured slots 4108 as the anvil 4130 pivots relative to the elongate channel 4102. Thereafter, the firing member 4760 can continue to move distally along the firing path in the end effector 4100 to complete the firing stroke.

Upon completion of the firing stroke, the firing member 4760 is retracted toward the proximal end 1112 of the spent staple cartridge 1110. Though the firing member 4760 is retracted proximally, the sled assembly 1120 is configured to remain at the distal end 1113 of the spent staple cartridge 1110. In such instances, the proximal end 1112 of the spent staple cartridge 1110 can continue to bias the lock bar 4180 proximally such that the anvil pin 4152 remains in the contoured slot 4108.

In other instances, the sled assembly 1120 can operably engage the lock bar 4180 such that the lock bar 4180 is biased proximally only when the sled assembly 1120 is in the proximal, pre-fired position in the staple cartridge 1110. In such instances, at the outset of the firing stroke, the lock bar 4180 can be permitted to shift distally and reengage the lockout arrangement such that a subsequent firing stroke is prevented until a new staple cartridge is installed in the end effector 4100.

As described herein, in certain instances, the elongate channel of an end effector can include contoured slots (e.g. "kidney" or "banana" slots) for facilitating the opening and closing of the anvil. In other instances, the elongate channel can include a pin hole for facilitating the opening and closing of the anvil. In such instances, the anvil is configured to pivot about a single pivot axis at the pivot joint. The lockout arrangement including the lock bar 4180 can be modified for a single pivot axis closure of an anvil.

Figure 90:
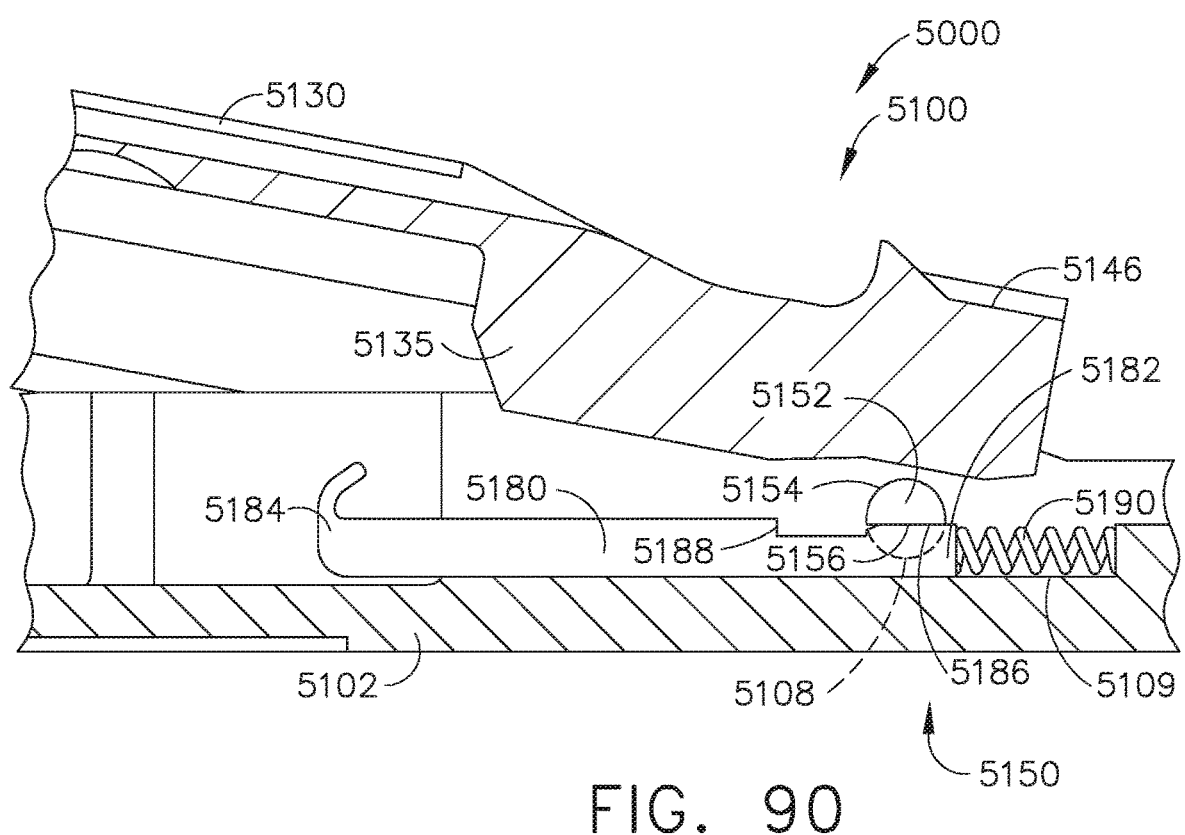
FIG. 90 is an elevation cross-sectional view of a portion of an interchangeable surgical tool assembly depicting an anvil thereof in an open position.
Figure 91:
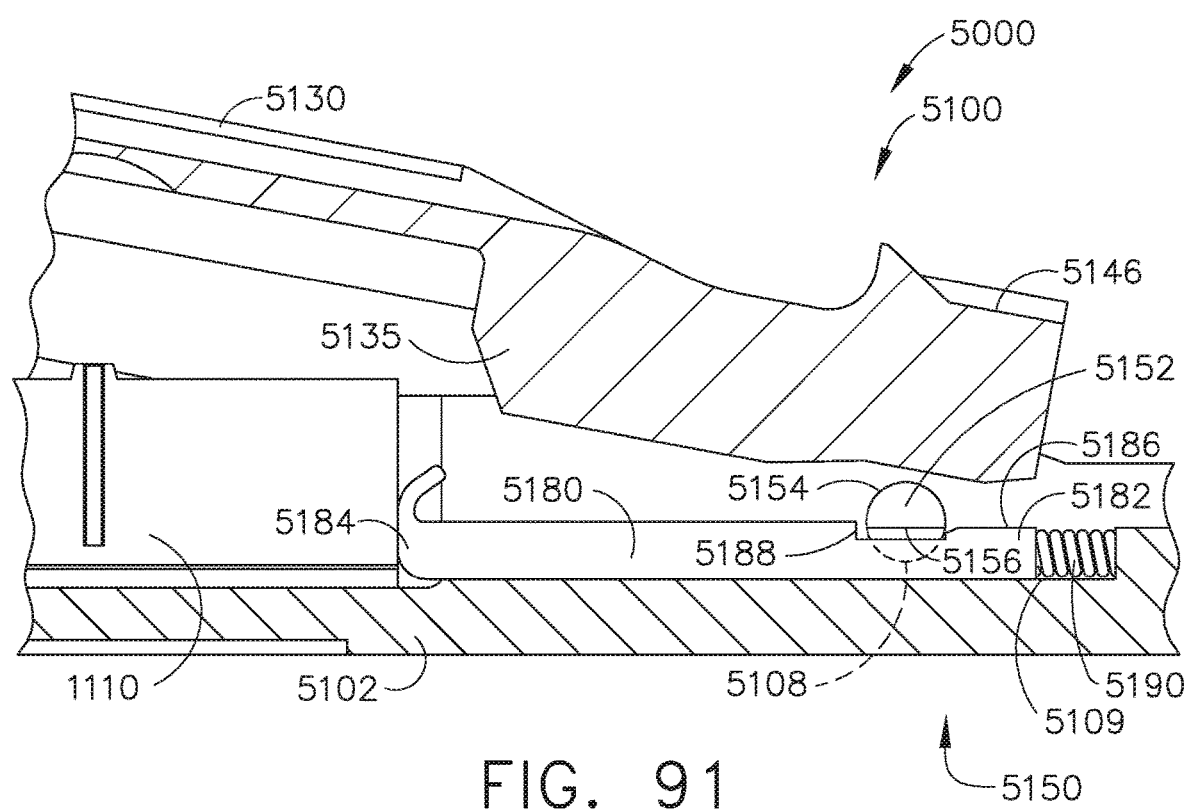
FIG. 91 is an elevation cross-sectional view of a portion of the interchangeable surgical tool assembly of FIG. 90 depicting a staple cartridge installed in an elongate channel and the anvil in the open position.
Figure 92:
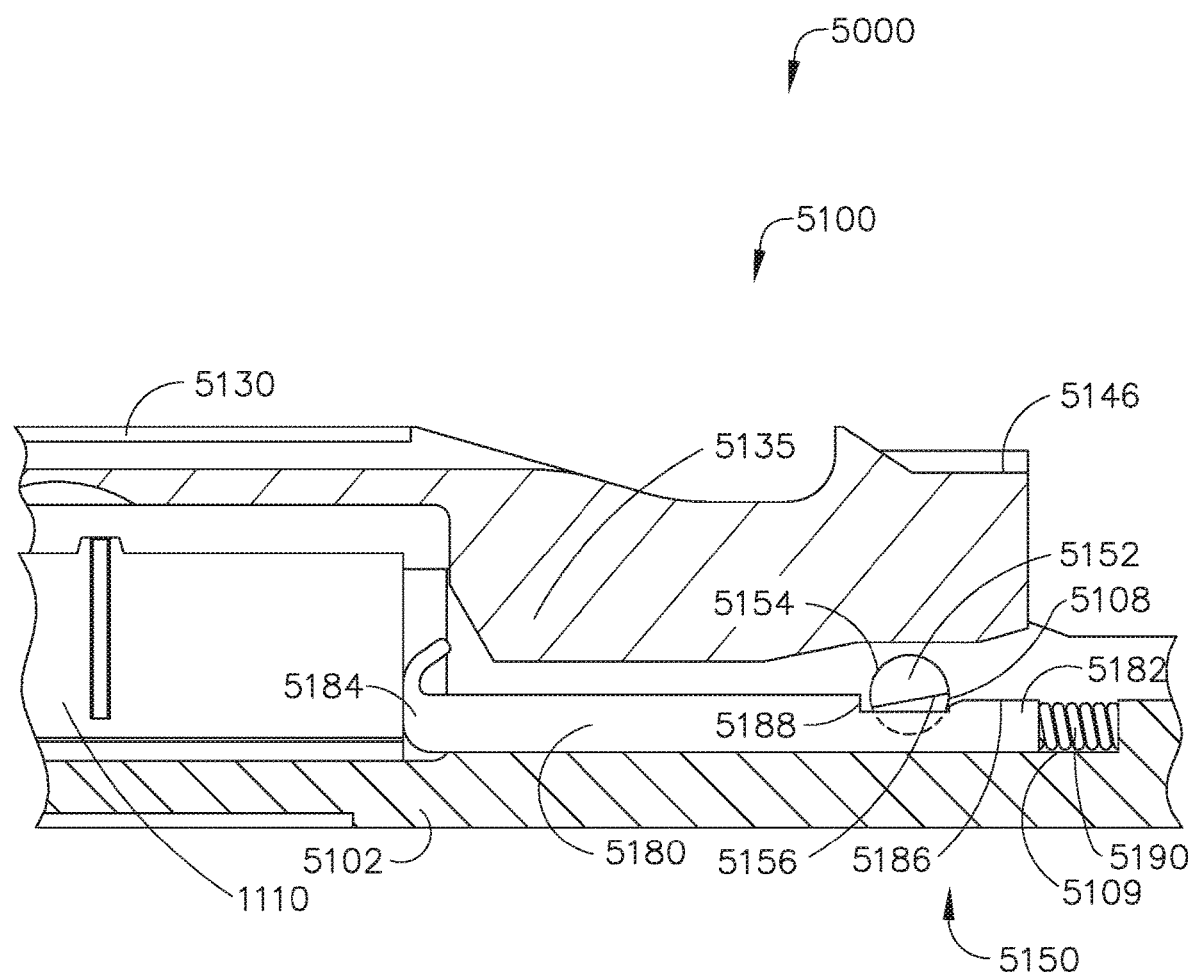
FIG. 92 is an elevation cross-sectional view of a portion of the interchangeable surgical tool assembly of FIG. 90 depicting the staple cartridge installed in the elongate channel and the anvil moved to a closed position.

For example, referring now to FIGS. 90-92, an interchangeable surgical tool assembly 5000 includes an end effector 5100 having an anvil 5130 and an elongate channel 5102. The anvil 5130 is configured to pivot relative to the elongate channel 5102 about a pivot joint 5150 at pivot pins 5152. The elongate channel 5102 is similar in many respects to the elongate channel 4102 (see FIGS. 37-44), however, the elongate channel 5102 includes pin holes 5108 for receiving the pivot pins 5152 instead of contoured slots. The anvil 5130 is similar in many respects to the anvil 4130 (see FIGS. 36-44), however, the anvil 5130 does not include a notch in the inner rail 5135 for engagement with a lock bar.

Although a firing member is not depicted in FIGS. 90-92, the reader will readily appreciate that the firing member in the end effector 5100 can be identical to the firing member 4760 (see FIG. 38), for example. The firing member for the end effector 5100 can be configured to engage a ramped surface defining an open-close cavity similar to the ramped surface 1134 and the open-close cavity 1148 (see FIGS. 8-12), respectively. For example, the open-close cavity includes a distal closure ramp and a proximal opening surface. In certain instances, lockout springs can extend through spring slots 5146 between the elongate channel 5102 and the anvil 5130. Such lockout springs can be identical to the lockout springs 4450, for example. In other instances, the end effector 5100 may not include lockout springs extending between the anvil 5130 and the elongate channel 5102.

The end effector 5100 includes lock bars 5180 slidably positioned in a recess 5109 in the elongate channel 5102. Each lock bar 5180 includes a proximal end 5182 and a distal end 5184. The proximal end 5182 is positioned in abutting contact with a compression spring 5190, which is also positioned in the recess 5109. The distal end 5184 is positioned to engage a staple cartridge when a staple cartridge is inserted in the elongate channel 5102. Although only a single lock bar 5180 is depicted in FIGS. 90-92, the reader will readily appreciate that symmetrical lock bars 5180 can be positioned on each lateral side of the end effector 5100. In other instances, the lockout arrangement of the end effector 5100 can be asymmetrical relative to the firing member, and may only include a single lock bar 5180, for example.

Referring primarily to FIG. 90, the end effector 5100 is shown in an unclamped or open configuration. Moreover, a staple cartridge has not been installed in the elongate channel 5102. Though the anvil 5130 is not clamped with respect to a staple cartridge, in certain instances, lockout springs can be configured to exert a closure force on the anvil 5130. For example, the lockout springs can be configured to bias the anvil 5130 downward and forward. Though the anvil 5130 may be biased toward a clamped configuration, the pivot pin 5152 can be configured to prevent pivoting of the anvil 5130.

The pivot pin 5152 has a semicircular perimeter or cross-section including a circular, rounded, or otherwise contoured portion 5154 and a flat or linear portion 5156. When the anvil 5130 is in the unclamped configuration, the pivot pin 5152 is oriented such that the flat portion 5156 is positioned flush against a top surface 5186 of the lock bar 5180. When the flat portion 5156 is flush against the top surface 5186, rotation of the pivot pin 5152 and, thus, rotation of the anvil 5130 from the open position to a closed position (see FIG. 92) is restrained or entirely prevented. For example, when the firing member is advanced distally from a home position in the open-close cavity toward the distal closure ramp, the attempted distal displacement of the firing member can be insufficient to overcome the rotational resistance between the flat surface 5156 of the pivot pin 5152 and the top surface 5186 of the lock bar 5180. As result, the anvil 5130 can be prevented from moving toward the closed configuration until a staple cartridge is positioned in the elongate channel 5102 and, thus, the lockout arrangement is overcome.

Referring now to FIG. 91, the staple cartridge 1110 has been installed in the elongate channel 5102. When the staple cartridge 1110 is inserted in the end effector 5100, the proximal end 1112 of the staple cartridge 1110 is positioned against the distal end 5184 of the lock bar 5180 and shifts the lock bar 5180 proximally in the recess 5109. For example, the distal end 5184 of the lock bar 5180 can include a cartridge-facing surface against which the proximal end 1112 of the staple cartridge abuts.

The proximal displacement of the lock bar 5180 also moves a notch 5188 in the lockout bar 5180 proximally. The notch 5188 is defined downward from the top surface 5186 intermediate the proximal end 5182 and the distal end 5184. When the compression spring 5190 compresses to permit proximal shifting of the lock bar 5180 within the recess 5109, the notch 5188 is configured to move into longitudinal alignment with the pivot pin 5152. As depicted in FIG. 91, when the notch 5188 is aligned with the pivot pin 5152, the flat portion 5156 of the pivot pin 5152 can be spaced apart from the lock bar 5180. As a result, the anvil 5130 is operably permitted to pivot at the pivot joint 5150 about the anvil pins 5152 toward the closed position.

Referring now to FIG. 92, a closure motion has been applied to the anvil 5130. For example, the firing member can be advanced distally to close the anvil 5130. The distal advancement of the firing member is configured to cam the upper flanges thereof against the distal closure ramp on the anvil 5130. The camming force generated by the firing member is sufficient to pivot the pins 5152 within the pin holes 5108. Thereafter, the firing member can continue to move distally along the firing path in the end effector 5100 to complete the firing stroke.

Upon completion of the firing stroke, the firing member can be retracted toward the proximal end 1112 of the spent staple cartridge 1110. Though the firing member is retracted proximally, the sled assembly 1120 is configured to remain at the distal end 1113 of the spent staple cartridge 1110. In such instances, the proximal end 1112 of the spent staple cartridge 1110 can continue to bias the lock bar 5180 proximally such that the anvil pin 5152 remains aligned with the notch 5188.

In other instances, the sled assembly 1120 can operably engage the lock bar 5180 such that the lock bar 5180 is biased proximally only when the sled assembly 1120 is in the proximal, pre-fired position in the staple cartridge 1110. In such instances, at the outset of the firing stroke, the lock bar 5180 can be permitted to shift distally and reengage the lockout arrangement such that a subsequent firing stroke is prevented until a new staple cartridge is installed in the end effector 5100.

Referring now to FIGS. 45-53, a surgical end effector 6100 is depicted. The surgical end effector 6100 includes an elongate channel 6102 and the anvil 1130. The elongate channel 6102 is similar in many respects to the elongate channel 1102 (see FIGS. 3-5 and 7), however, the elongate channel 6102 also includes a recess 6109 dimensioned and positioned to operably receive a portion of a lockout spring 6182. In other instances, the surgical end effector 6100 can include the elongate channel 1102 instead of the elongate channel 6102, as further described herein.

A firing member 6760 is positioned in the end effector 6100. The firing member 6760 is similar in many respects to the firing member bar 1760 (see FIGS. 4 and 5). For example, the firing member 6760 defines an I-beam structure that includes a lower flange 6764, an upper flange 6762, and a support portion 6763 extending between the flanges 6762 and 6764. The upper flange 6762 is comprised of horizontal pins extending from the support portion 6763. The lower flange 6764 is comprised of an enlarged or widened foot at the base of the support portion 6763. A tissue cutting feature 6766 is supported by the support portion 6763 between the flanges 6762 and 6764. The support portion 6763 travels though aligned slots in the elongate channel 6102, a staple cartridge 6110, and the anvil 1130.

Similar to the firing member 1760, the firing member 6760 is configured to exert a closure camming force on the end effector 6100 to clamp the anvil 1130 relative to the elongate channel 6102 during a portion of the firing stroke and is configured to exert an opening camming force on the end effector 6100 to pivot the anvil 1130 away from the elongate channel 6102 upon completion of the firing stroke. For example, the firing member 6730 is positioned to operably engage the open-close cavity 1148 in the anvil 1130 to facilitate the pivoting of the anvil 1130.

The surgical end effector 6100 includes a lockout arrangement 6180, which can operably prevent a firing stroke and/or prevent rotational movement of the anvil 1130 toward the elongate channel 6102 unless an unfired staple cartridge is positioned in the first jaw. In other words, the lockout arrangement 6180 is a missing and empty cartridge lockout and can also be considered to be a clamping lockout. Because the firing member 6760 is a multi-function firing member, the firing member is configured to implement a combination of surgical functions with a single actuation system. Consequently, when the lockout arrangement 6180 prevents the actuation of the firing member 6760, the lockout arrangement 6180 effectively prevents the combination of surgical functions implemented by the firing member 6760 including the clamping of the end effector 6100 and the advancement of the cutting edge 6766.

In other instances, the lockout arrangement 6180 can be configured to engage the firing member 6760 after the firing member 6760 has closed the end effector jaws. For example, the lockout arrangement 6180 can be positioned farther distally such that the firing member 6760 engages the lockout arrangement 6180 after engaging the distal closure ramp 1140 of the open-close cavity 1148. In such instances, the firing member 6760 can be configured to clamp the anvil 1130 relative to the elongate channel 6102 before the lockout arrangement 6180 is potentially engaged.

The lockout arrangement 6180 includes the lockout spring 6182 as well as lockout lugs 6770 on the firing member 6760. The lockout spring 6182 is positioned in the recess 6109 in the elongate channel 6102. The lockout spring 6182 defines a U-shaped member having a fixed end and a pair of deflectable ends. The lockout spring 6182 is a leaf spring, however, the reader will readily appreciate that various alternative springs can be configured to operably engage the lockout lugs 6770. For example, the lockout spring 6182 can be comprised of two separate leaf springs on either side of the firing member 6760.

The fixed end of the lockout spring 6182 is a proximal end 6184, which is fixed to the elongate channel 6102. For example, the proximal end 6184 can be welded to the elongate channel 6102 at the spot welds 6196 (see FIG. 47). The deflectable or free ends of the lockout spring 6182 define the distal ends 6186 thereof. A spring arm 6188 extends between the proximal end 6184 and each free distal end 6186 of the lockout spring 6182.

Figure 47:
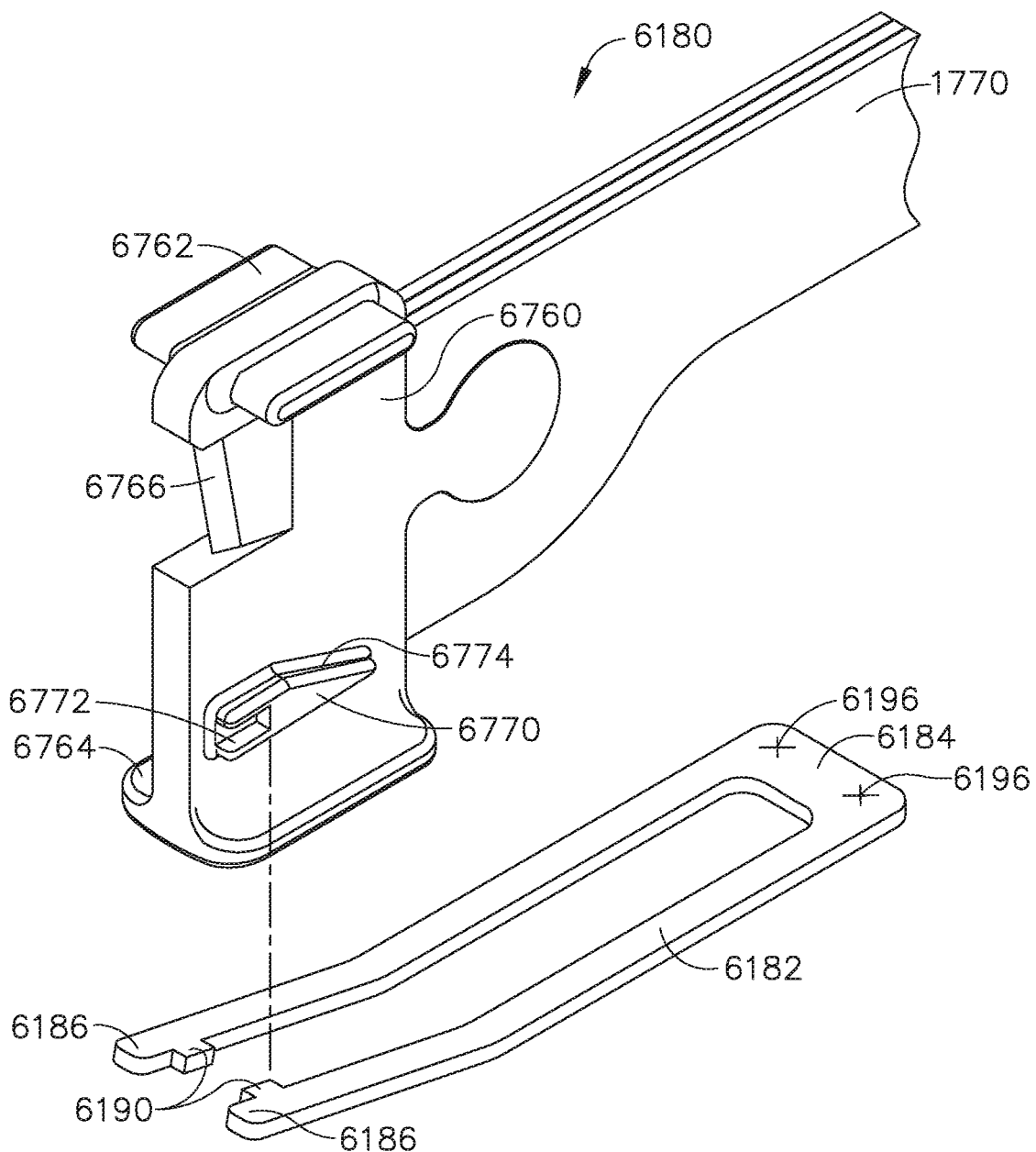
FIG. 47 is a perspective exploded assembly view of a lockout arrangement in the interchangeable surgical tool assembly of FIG. 45.

Referring primarily to FIG. 47, a pair of laterally-extending tabs or hooks 6190 extend inward from the distal ends 6186 toward a centerline of the lockout spring 6182. The hooks 6190 are laterally inboard of the spring arms 6188. The hooks are operably configured to catch or engage the lockout lugs 6770, as further described herein. Referring still to FIG. 47, the lockout spring 6182 is depicted in a non-stressed, or non-flexed, default configuration. In the non-stressed configuration, the spring arms 6188 define a bend or contour such that the distal ends 6186 are offset upward from the proximal end 6184. Though the lockout spring 6182 is configured to flex or otherwise deform during operation of the end effector 6100, the lockout spring 6182 is configured to seek to resume the non-stressed configuration of FIG. 47.

The lockout lugs 6770 define laterally-protruding lugs on the support portion 6763 of the firing member 6760. A lock or notch 6772 is defined in each laterally-protruding lug 6770. The locks 6772 are rectangular cutouts that are dimensioned and aligned to receive the hooks 6190 on the lockout spring 6182 when the lockout spring 6182 is in the non-stressed configuration of FIG. 47 and the firing member 6760 is advanced distally into engagement with the hooks 6190. For example, each lock 6772 includes a distally-facing opening which is configured to receive the hook 6190 when the hook 6190 is aligned with the distally-facing opening and the firing member 6760 is advanced distally. When the hooks 6190 are retained in the locks 6772, distal advancement of the firing member 6760 is prevented. As a result, clamping of the anvil 1130 and advancement of the knife edge 6766 is prevented by the lockout arrangement 6180.

In use, the lockout spring 6182 can initially be in the non-stressed configuration of FIG. 47 in the elongate channel 6102. In the non-stressed configuration, the hooks 6190 on the distal ends 6186 of the lockout spring 6182 are biased upward and into alignment with the locks 6772 in the firing member 6760. As a result, when the firing member 6760 is advanced distally, the hooks 6190 slide into locks 6772 on the advancing firing member 6760 such that distal displacement of the firing member 6760 past the hooks 6190 is prevented.

Figure 48:
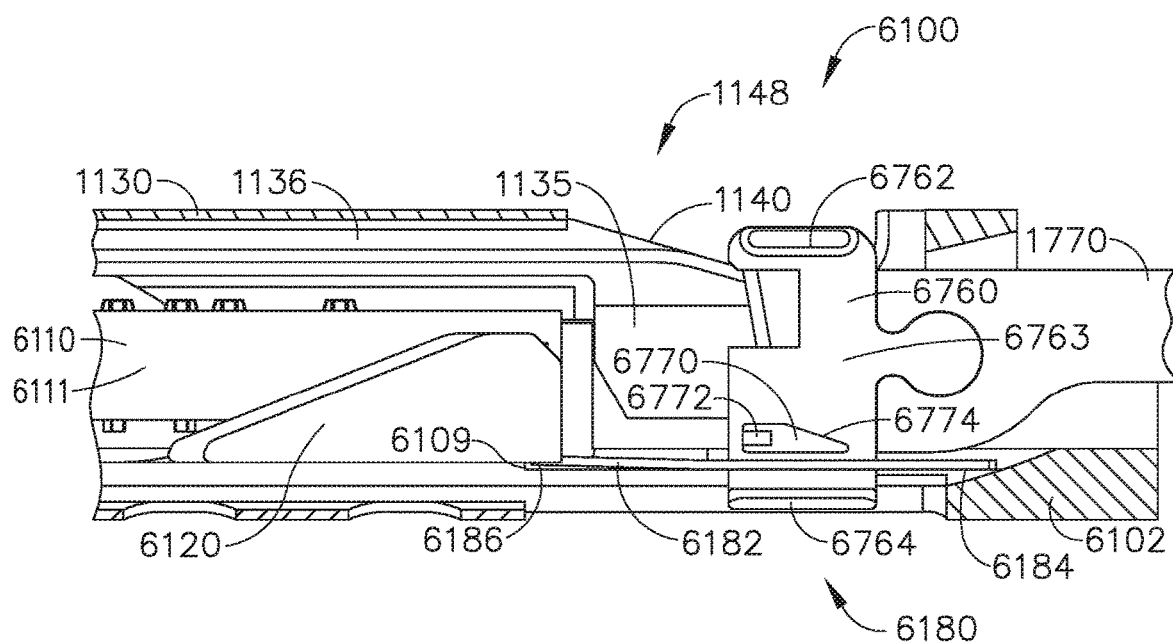
FIG. 48 is an elevation partial cross-sectional view of a portion of the interchangeable surgical tool assembly of FIG. 45 depicting the unfired staple cartridge installed therein and the firing member in a proximal, home position.
Figure 49:
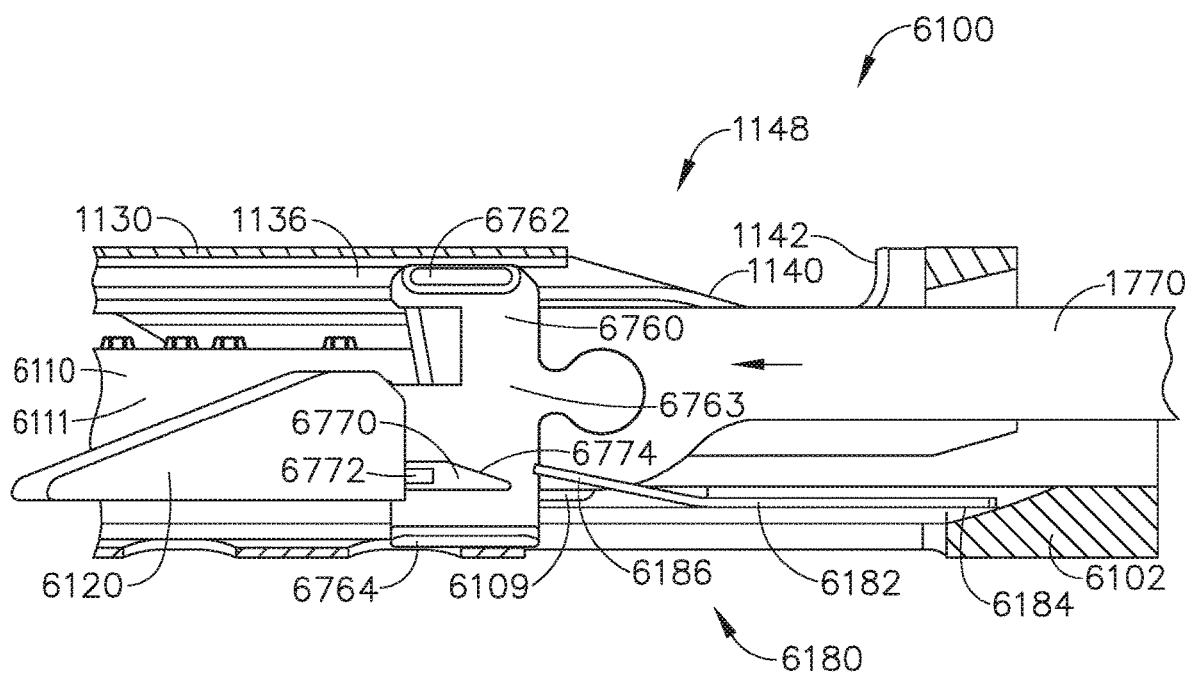
FIG. 49 is an elevation partial cross-sectional view of a portion of the interchangeable surgical tool assembly of FIG. 45 depicting the firing member displaced distally from the proximal, home position during an initial portion of a firing stroke.

Referring now to FIG. 48, when a staple cartridge 6110 is installed in the end effector 6100, a part of the staple cartridge 6110 is configured to engage the lockout spring 6182. The staple cartridge 6110 is similar in many respects to the staple cartridge 1110 (see FIGS. 3-5). The staple cartridge 6110 includes a sled assembly 6120, which is similar in many respects to the sled assembly 1120 (see FIGS. 4 and 5), however, the sled assembly 6120 has a cutout or recess 6122 at a proximal end 6112 of the staple cartridge 6110. The cutout 6122 is defined in a channel-facing surface of the sled assembly 6120 and is configured to receive the distal end 6186 of the lockout spring 6182 including the hooks 6190 thereof when the sled assembly 6120 is in the proximal, home position (see FIG. 48) in the staple cartridge 6110. The sled assembly 6120 engages the distal ends 6186 of the lockout spring 6182 to deflect the hooks 6190 into the cutout 6122 and out of alignment with the locks 6772.

In other instances, the staple cartridge 1110 (see FIGS. 3-5) can be installed in the elongate channel 6102, and the sled assembly 1120 thereof can be configured to deflect the hooks 6190 downward into the lockout recess 6109 in the elongate channel 6102. In such instances, the lockout recess 6109 can be sized to accommodate the height of the lockout spring 6182 such that the staple cartridge 1110 can be positioned flush against a cartridge-supporting surface of the elongate channel 6102. In still other instances, the elongate channel 6102 may not include the lockout recess 6109, similar to the elongate channel 1102 (see FIGS. 3-5). In such instances, the cutout 6122 in the sled assembly 6120 can be sized to accommodate the height of the lockout spring 6182 such that the staple cartridge 6110 can be positioned flush against a cartridge-supporting surface of the elongate channel 6102.

During a firing stroke, the sled assembly 6120 is advanced distally though the cartridge body 6111 by the firing member 6760. The sled assembly 6120 is left in the distal portion of the staple cartridge 6110 when the firing member 6760 is retracted proximally after the firing stroke. For example, referring now to FIG. 49, the firing member 6760 has been advanced distally from the proximal, home position during an initial portion of a firing stroke. As the firing member 6760 moves distally away from the lockout spring 6182, the lockout spring 6182 is configured to resume the non-stressed orientation of FIG. 47 in which the hooks 6190 are deflected upwards with respect to the fixed proximal end 6184 of the lockout spring 6182.

Figure 50:
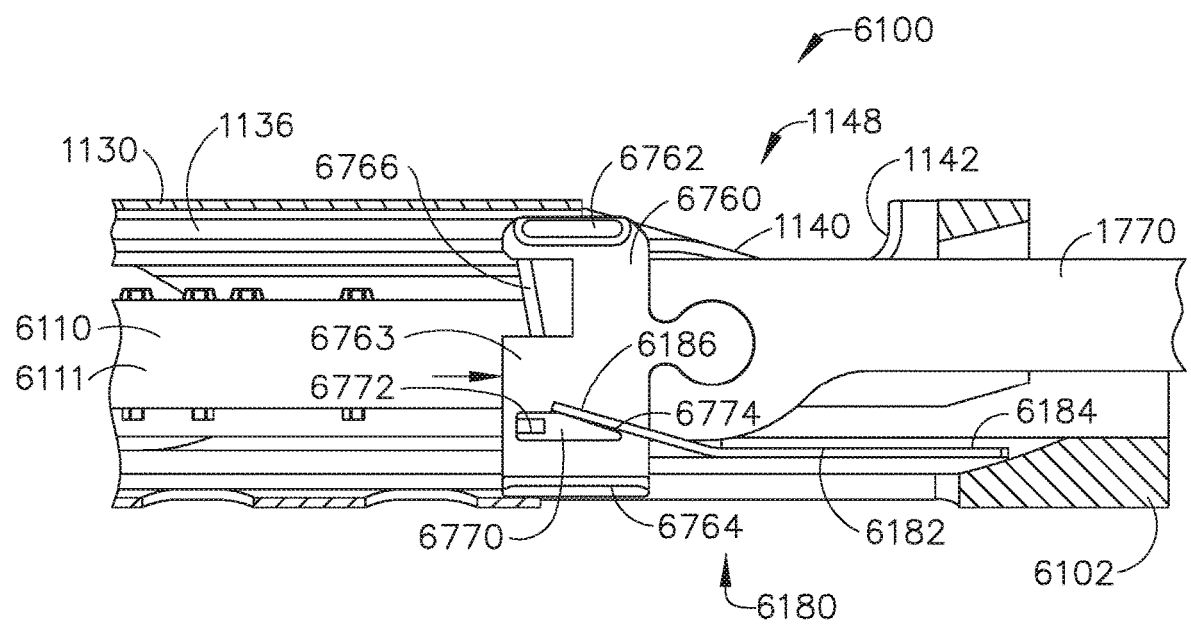
FIG. 50 is an elevation partial cross-sectional view of a portion of the interchangeable surgical tool assembly of FIG. 45 depicting the firing member returning to the proximal, home position upon completion of the firing stroke.

Referring now to FIG. 50, upon completion of the firing stroke, the firing member 6760 is retracted proximally toward the proximal, home position. As the firing member 6760 moves proximally past the distal end 6186 of the lockout spring 6182, the hooks 6190 on the lockout spring 6182 are configured to ride or slide along ramped surfaces 6774 on the laterally-protruding lugs 6770. The hooks 6190 are engaged with the ramped surfaces 6774 in FIG. 50 such that the ramped surfaces 6774 cam or lift the hooks 6190 and the distal end 6186 of the lockout spring 6182 upward over the locks 6772 and along a top surface of the laterally-protruding lugs 6770. As the hooks 6190 bypass the locks 6772, the lockout arrangement 6180 is effectively reset.

Figure 45:
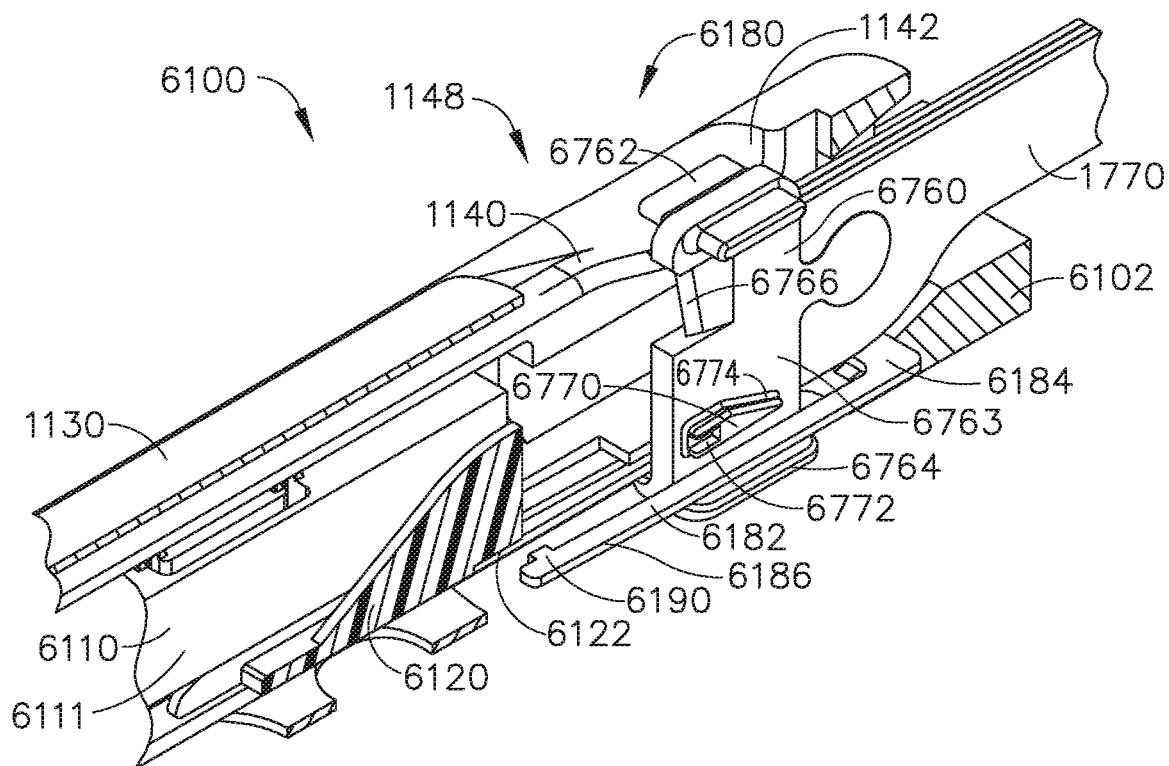
FIG. 45 is a perspective partial cross-sectional view of a portion of an interchangeable surgical tool assembly depicting an unfired staple cartridge installed therein and a firing member in a proximal position.
Figure 46:
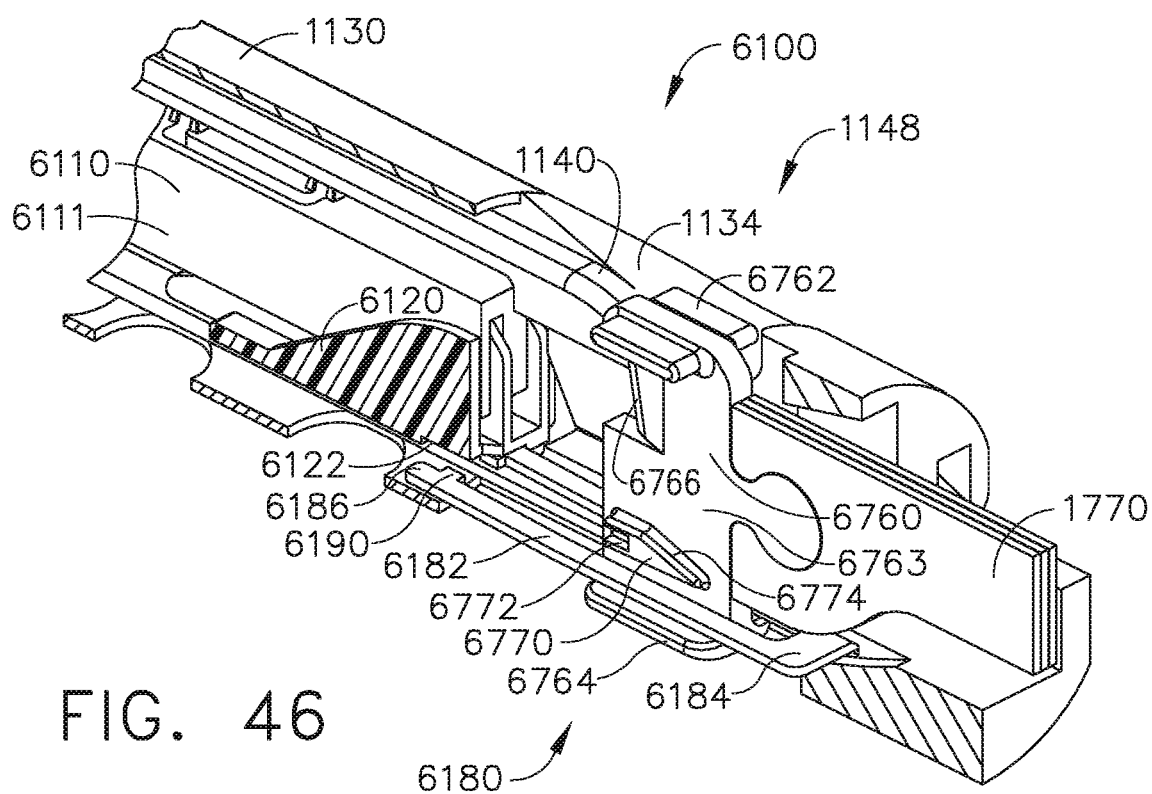
FIG. 46 is another perspective partial cross-sectional view of a portion of the interchangeable surgical tool assembly of FIG. 45 depicting the unfired staple cartridge installed therein and the firing member in the proximal position.
Figure 51:
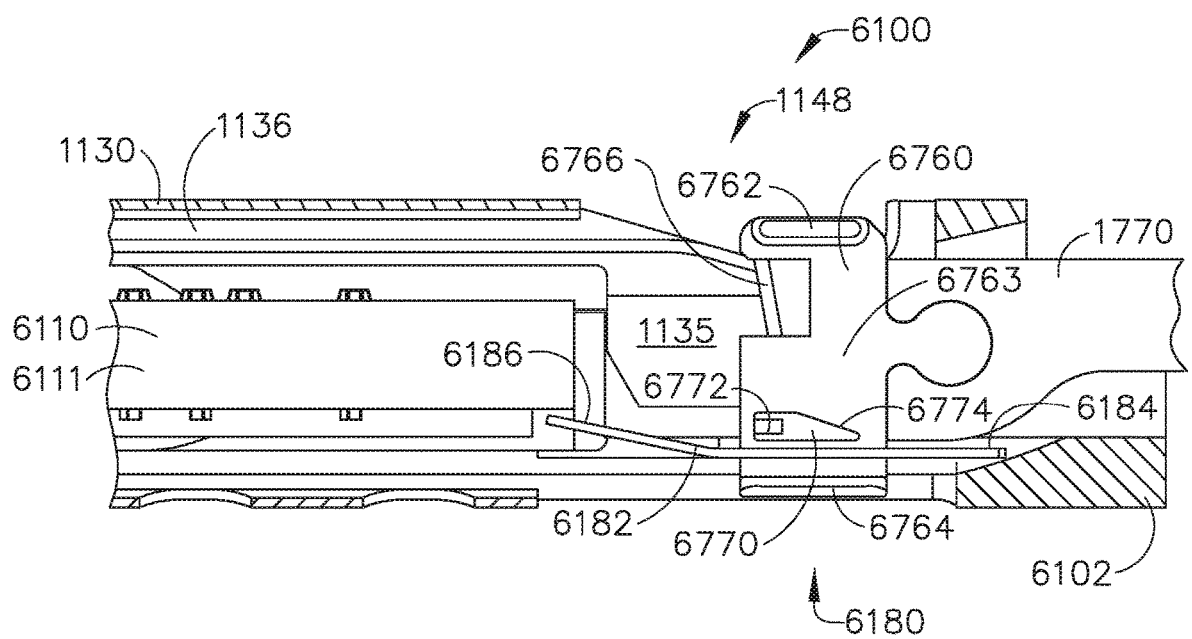
FIG. 51 is an elevation partial cross-sectional view of a portion of the interchangeable surgical tool assembly of FIG. 45 depicting the firing member returned to the proximal, home position.

Referring now to FIG. 51, the firing member 6760 has returned to the proximal, home position and the lockout spring 6182 has returned to the non-stressed configuration. As a result, the hooks 6190 on the lockout spring 6182 are aligned with the locks 6772 on the firing member 6760. For example, the locks 6772 are configured to move along respective lock paths in the end effector 6100 as the firing member 6760 is advanced distally, and each hook 6190 is in the lock path of the corresponding lock 6772. Though the staple cartridge 6110 remains in the elongate channel 6102 in FIG. 51, because the staple cartridge 6110 has already been fired, or spent, the sled 6120 (see FIGS. 33 and 34) remains in a distal end portion of the staple cartridge 6110. The distally-displaced sled 6120 is not positioned to engage the distal ends 6186 of the lockout spring 6182 to overcome the lockout arrangement 6180 as depicted in FIG. 45.

Figure 52:
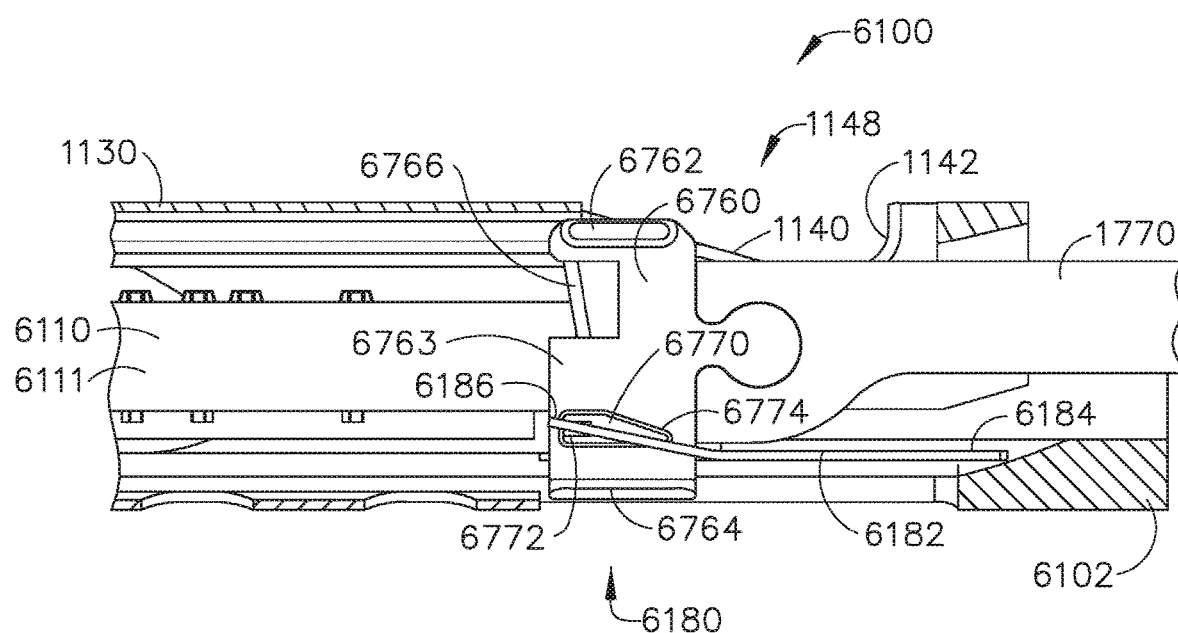
FIG. 52 is an elevation partial cross-sectional view of a portion of the interchangeable surgical tool assembly of FIG. 45 depicting the firing member displaced distally from the proximal, home position during a subsequent attempted firing stroke.
Figure 53:
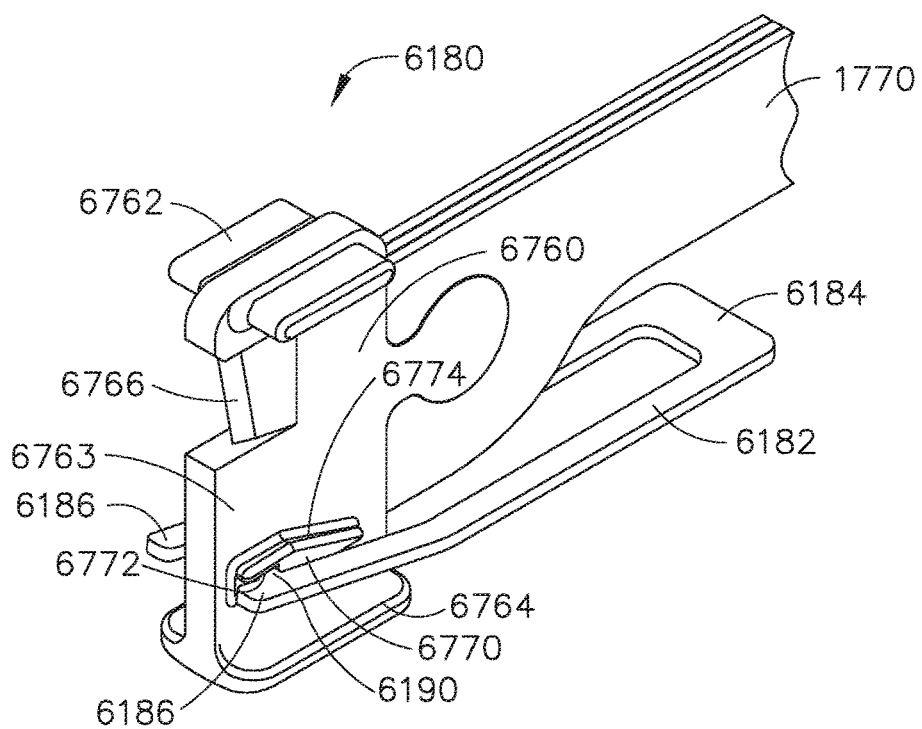
FIG. 53 is a perspective view of the lockout arrangement of FIG. 47.

Distal displacement of the firing member 6170 past the reset lockout arrangement 6180 is prevented, as shown in FIG. 52. In particular, the firing member 6760 has been displaced distally from the proximal, home position during a subsequent attempted firing stroke. However, as the firing member 6760 moves distally, the locks 6772 move along their respective lock paths into engagement with the hooks 6190. The hooks 6190 slide into the locks 6772 to prevent further distal movement of the firing member 6760.

The lockout arrangement 6180 includes symmetrical locks 6772 and symmetrical hooks 6190. For example, the locks 6772 and the hooks 6190 are symmetrical about a longitudinal axis of the end effector 6100 such that a firing force generated by the firing member is restrained by the lockout arrangement 6180 in a balanced and symmetrical manner. In other instances, the lockout arrangement 6180 can be asymmetrical, and can include a single lock 6772 and a single hook 6190, for example.

In various instances, an interchangeable surgical tool assembly for a surgical instrument can be fired upon actuation of a firing trigger on the handle assembly thereof, as described herein. In certain instances, multiple actuations of the firing trigger can be configured to fire the interchangeable surgical tool assembly. For example, each actuation of the firing trigger can implement a portion of a firing stroke. In other instances, a single actuation of the firing stroke can be configured to implement a series of successive firing strokes. In certain instances, each successive firing stroke can contribute to the distal advancement and/or proximal retraction of a firing member, a cutting edge and/or a sled assembly. For example, a firing rod in an interchangeable surgical tool assembly can be extended and retracted multiple times in a series of successive firing strokes to complete the firing of the end effector.

In certain instances, it can be desirable to advance a firing member distally to an intermediate portion of the end effector. The firing member can fire a sled assembly and/or a cutting element to the intermediate portion of the end effector. Moreover, in various instances, a pusher plate can be advanced distally to complete the firing of the sled assembly and/or the cutting element. As described herein, the firing member can include an upper flange that is configured to travel through the anvil of the interchangeable surgical tool assembly. In instances in which the distal advancement of the firing member terminates at an intermediate portion of the end effector, the distal portion of the anvil can be passageway-free. For example, the distal portion of the anvil can be solid such that the upper flange of the firing member cannot travel therethrough. When the distal portion of an anvil is solid, the rigidity of the anvil can be greater than an anvil having a passageway that extends to the distal end thereof. Increased rigidity of the anvil can be configured to limit deformation and/or bowing of the anvil.

An interchangeable surgical tool assembly 12000 configured to execute a series of successive firing strokes is depicted in FIGS. 56-70. The interchangeable surgical tool assembly 12000 can be mounted to the handle assembly 500 (see FIGS. 1 and 2). In certain instances, each firing stroke in the series of successive firing strokes can be affected by a single actuation of the firing trigger 532 (see FIGS. 1 and 2). In other instances, a single actuation of the firing trigger 532 can affect one or more of the firing strokes. For example, a single actuation of the firing trigger 532 can affect the complete series of successive firing strokes to fire the staples and incise the target tissue clamped between the end effector jaws.

The interchangeable surgical tool assembly 12000 includes an end effector 12100, a shaft portion 12400, a firing member 12760, and a firing bar 12770. The end effector 12100 includes an elongate channel 12102 that is configured to operably support a staple cartridge 11210 therein. The elongate channel 12102 is operably attached to the shaft portion 12400. The end effector 12100 also includes an anvil 12130 that is pivotally supported relative to the elongate channel 12102.

The firing member 12760 is configured to operably interface with a sled assembly 12120 that is operably supported within the body 12111 of the surgical staple cartridge 12110. The sled assembly 12120 is slidably displaceable within the surgical staple cartridge body 12111 from a proximal starting position adjacent the proximal end 12112 of the cartridge body 12111 to an ending position adjacent a distal end 12113 of the cartridge body 12111. The sled assembly 12120 includes a plurality of sloped or wedge-shaped cams 12122 wherein each cam 12122 corresponds to a particular line of staples 1126. The sled assembly 12120 also includes a cutting edge 12124. The cutting edge 12124 is configured to travel through the end effector 12100 with the sled assembly 12120. For example, the cutting edge 12124 is integrally formed on the sled assembly 12120.

Direct-drive surgical staples 1126 (see also FIG. 5) are positioned in staple cavities in the body 12111. When the sled assembly 12120 is driven distally, the tissue cutting edge 12124 is configured to cut the tissue that is clamped between the anvil assembly 12130 and the staple cartridge 12110, and the sled assembly 12120 drives the staples 1126 upwardly in the staple cartridge 12110 and into forming contact with the anvil assembly 12130. As further described herein, the sled assembly 12120 can be driven distally by the firing member 12760 and/or by a pusher plate 12780. For example, the firing member 12760 is configured to push the sled assembly 12120 distally to an intermediate location in the end effector 12100, and the pusher plate 12780 is configured to bypass the firing member 12760 to further advance the sled assembly 12120 distally to a distal location in the end effector 12100.

During a firing stroke, a drive member in the shaft portion 12400, such as the drive member 1602 (see FIG. 2), for example, is configured to transfer a firing motion to the firing bar 12770. For example, displacement of the drive member 1602 is configured to displace the firing bar 12770. As described herein, the firing bar 12770 can be operably configured to fire the firing member 12760. For example, the firing bar 12770 can push the firing member 12760 distally during at least a portion of the firing sequence.

The firing member 12760 is similar in many respects to the firing member 1760 (see FIGS. 4 and 5). For example, the firing member 12760 defines an I-beam structure that includes a lower flange 12764, an upper flange 12762, and a support portion 12763 extending between the lower flange 12764 and the upper flange 12762. The upper flange 12762 is comprised of horizontal pins extending from the support portion 12763. The lower flange 12764 is comprised of an enlarged or widened foot at the base of the support portion 12763. The firing member 12760 can be configured to engage an open-close cavity, such as the open-close cavity 1148 (see FIGS. 8-12) on the anvil 12130 to effect opening and closing of the anvil 12130 relative to the staple cartridge 12110. Additionally, the upper flange 12762 can be configured to travel through a passageway 12136 in the anvil 12130 and the lower flange 12764 can be configured to travel through a passageway 12106 in the elongate channel 12102. Unlike the firing member 1760, the firing member 12760 does not include a cutting edge. Rather, the firing member 12760 is configured to selectively engage the sled assembly 12120, which includes the cutting edge 12124.

Figure 56:
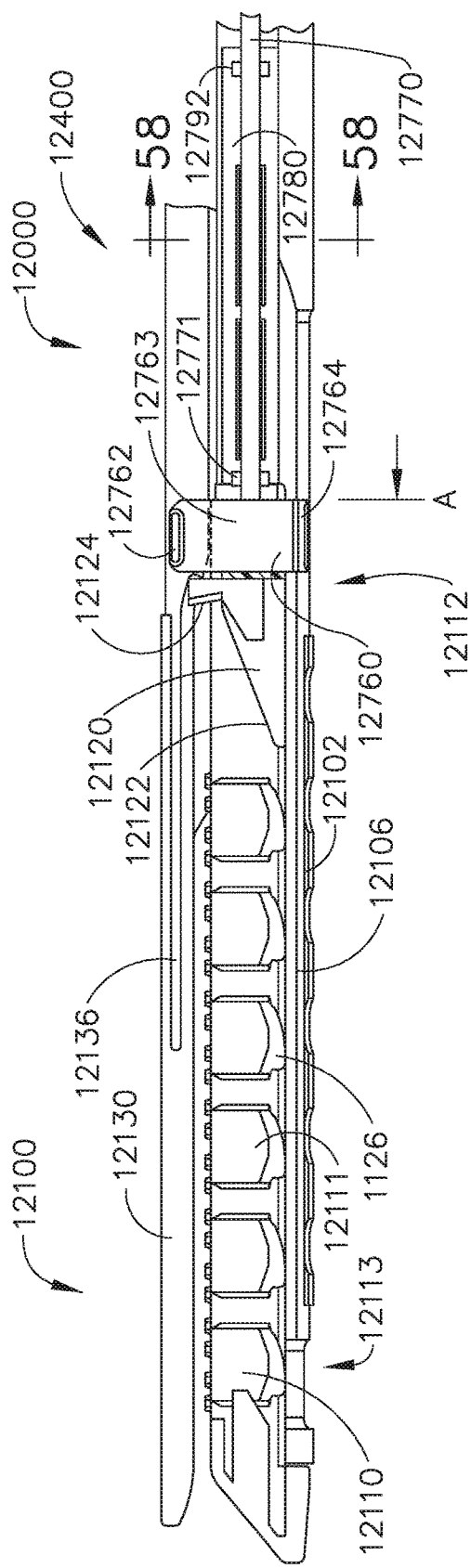
FIG. 56 is an elevation cross-sectional view of a distal portion of an interchangeable surgical tool assembly.
Figure 58:
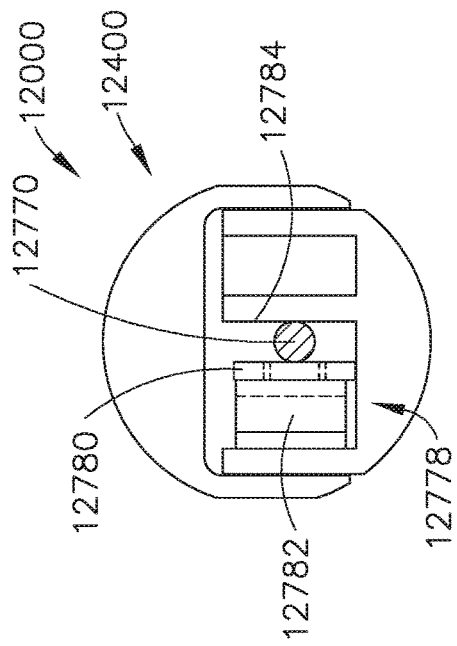
FIG. 58 is an elevation cross-sectional view of the interchangeable surgical tool assembly of FIG. 56 taken along the plane indicated in FIG. 56.
Figure 57:
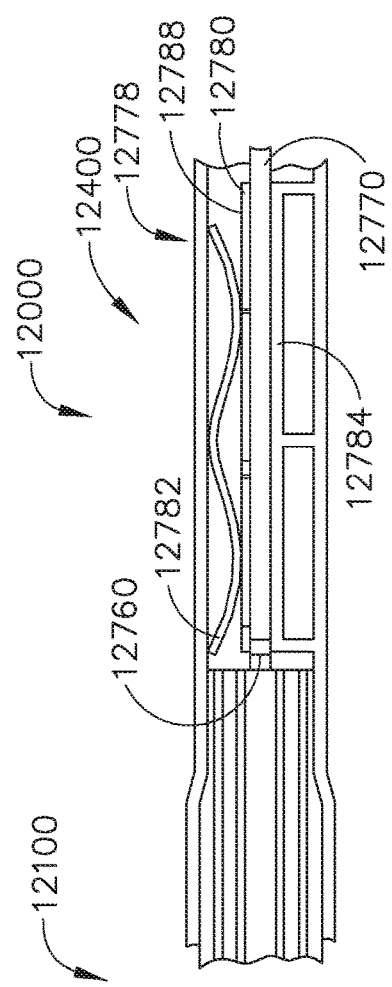
FIG. 57 is a plan view of a portion of the interchangeable surgical tool assembly of FIG. 56.

The interchangeable surgical tool assembly 12000 also includes a pusher assembly 12778 having the pusher plate 12780 and a spring 12782. Referring primarily to FIGS. 56-58, when the interchangeable surgical tool assembly 12000 is in an unfired configuration, the spring 12782 is configured to bias the pusher plate 12780 laterally toward the firing bar 12770. For example, the spring 12782 is positioned intermediate the pusher plate 12780 and a sidewall of the shaft assembly 12400. The pusher plate 12780 is biased against the firing bar 12770, which is positioned against a stop plate 12784 in the shaft portion 12400. The spring 12782 is a linear wave spring, however, the reader will readily appreciate that alternative spring designs can be configured to bias the pusher plate 12780 laterally toward the firing bar 12770. As further described herein, the pusher plate 12780 is retained in the shaft portion 12400 of the interchangeable surgical tool assembly 12000 until the firing bar 12770 is retracted to a more proximal position, which permits the pusher plate 12780 to spring laterally into engagement with the firing bar 12770.

Figure 59:
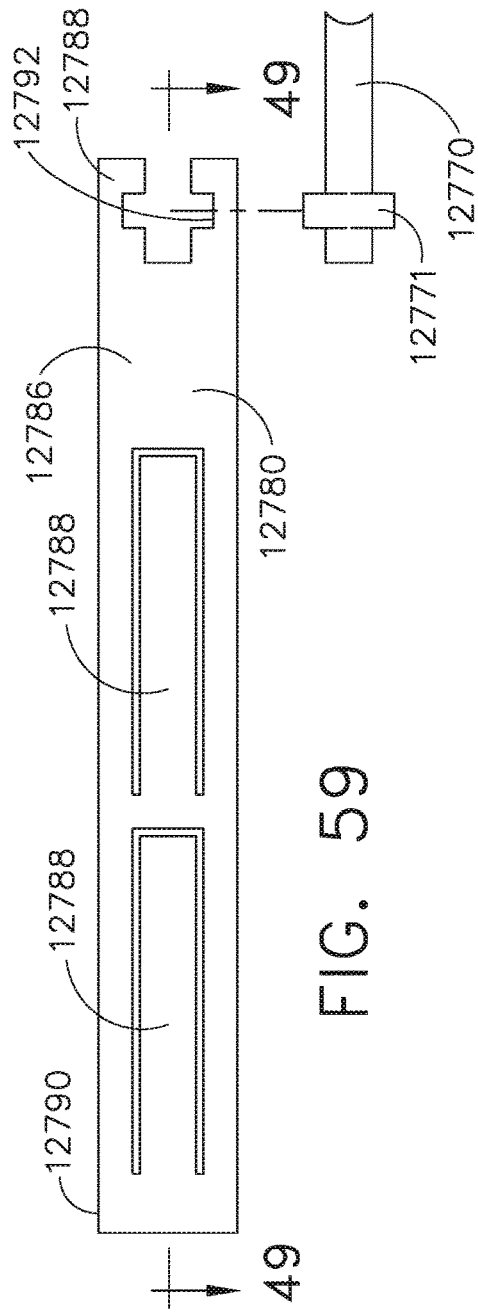
FIG. 59 is an elevation exploded assembly view of a pusher plate and a firing rod of the interchangeable surgical tool assembly of FIG. 56.
Figure 60:
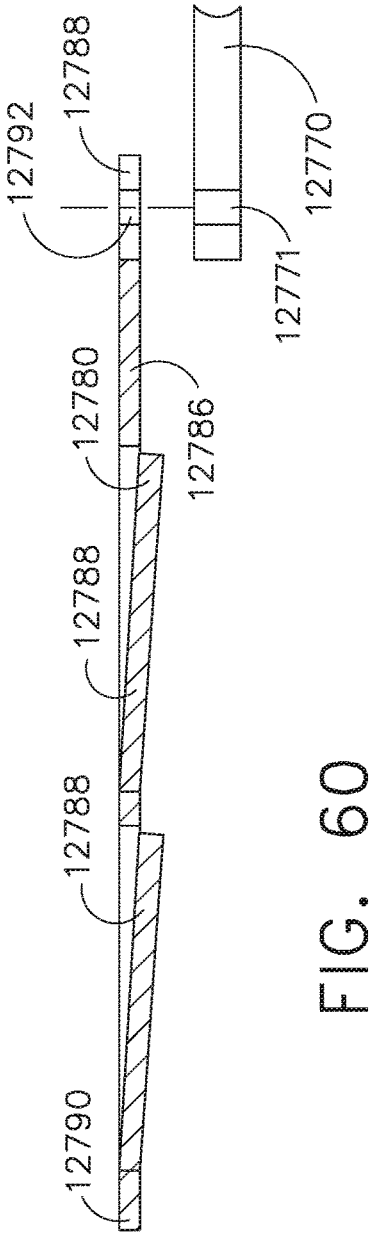
FIG. 60 is a plan cross-sectional view of the pusher plate and the firing rod of FIG. 59 taken along the plane indicated in FIG. 59.
Figure 61:
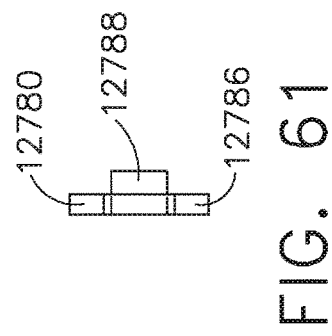
FIG. 61 is an elevation view of the pusher plate of FIG. 59.

Referring now to FIGS. 59-61, the pusher plate 12780 comprises a linear body 12786 having a plurality of leaf springs 12788 along the body 12786. The leaf springs 12788 are depicted in a non-stressed or undeformed configuration in FIGS. 60 and 61, which depict the leaf springs 12788 biased outward laterally from the linear body 12786. The linear body 12786 extends between a proximal end 12788 and a distal end 12790. A T-slot 12792 is defined in the proximal end 12788. The T-slot 12792 is configured to operably receive a distal key or nub 12771 on the firing bar 12770. The distal key 12771 can comprise a disk-shaped key (see FIG. 63), for example, protruding from the firing bar 12770. When the key 12771 is positioned in the T-slot 12792, proximal and distal translation of the firing bar 12770 is transferred to the pusher plate 12780. The reader will readily appreciate that alternative complementary slot and key geometries can be employed to transfer the firing motions between the firing bar 12770 and the pusher plate 12780.

At the outset of a first firing stroke, referring primarily to FIGS. 62 and 63, a distal end of the firing bar 12770 is positioned in abutting and driving contact with the firing member 12760. Moreover, the firing bar 12770 is configured to restrain the pusher plate 12780 and the leaf springs 12788 thereof. In such instances, the firing bar 12770 can be advanced distally to push the firing member 12760 distally. As the firing member 12760 moves distally, the firing member 12760 pushes the sled assembly 12120 distally. In FIG. 62, a ramped surface 12122 of the sled assembly 12120 has engaged the proximal-most staple 1126 in the depicted row and started to lift the staple 1126 toward the anvil 12130.

Though the firing bar 12770 has moved distally in FIG. 62, the pusher plate 12780 is configured to remain in a proximal position in the shaft portion 12400 of the interchangeable surgical tool assembly 12000. Referring primarily to FIG. 63, the firing member 12760 includes a notch 12766, which is dimensioned to allow the pusher plate 12780 to bypass the firing member 12760 at a later stage in the firing stroke sequence, as further described herein.

Figure 64:
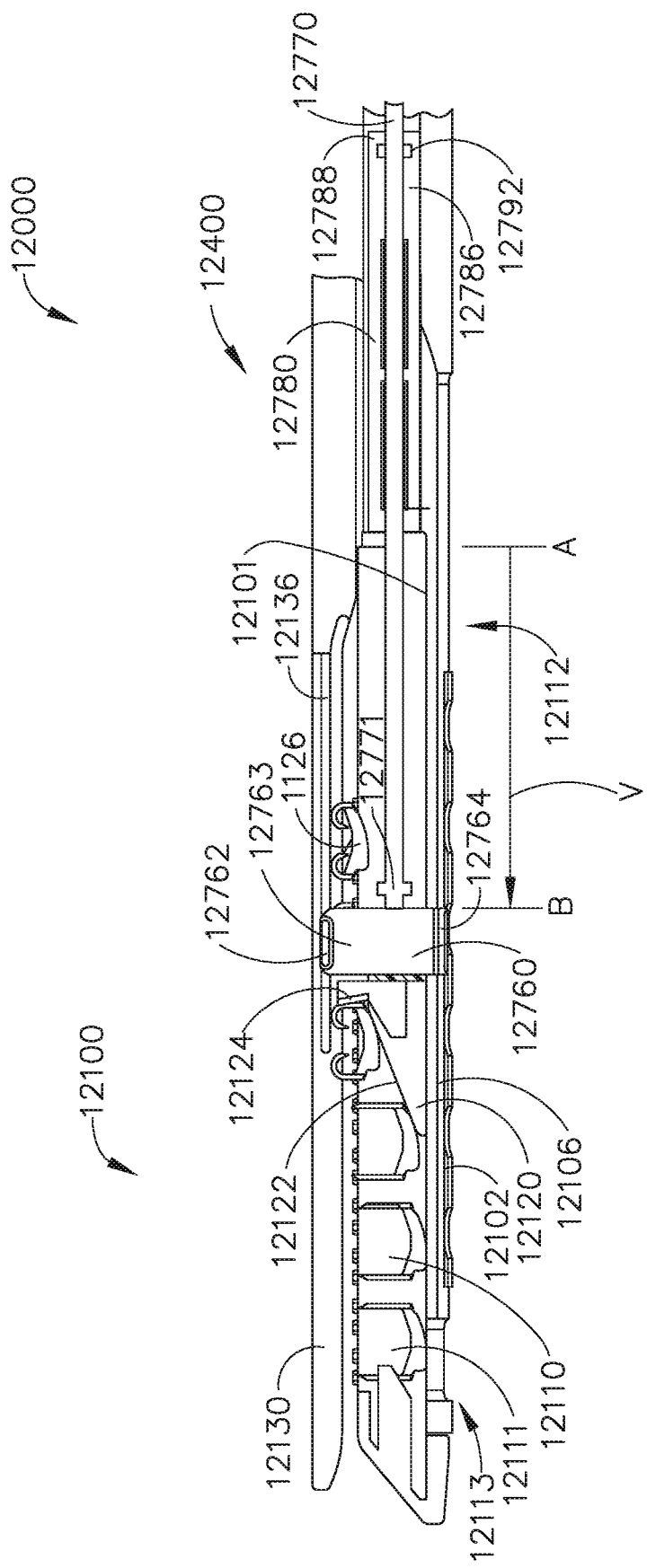
FIG. 64 is an elevation cross-sectional view of a distal portion of the interchangeable surgical tool assembly of FIG. 56 at the completion of the first firing stroke.

The interchangeable surgical tool assembly 12000 is depicted at the completion of the first firing stroke in FIG. 64. Upon comparing FIG. 58 to FIG. 64, the reader will readily appreciate that the firing member 12760 has been moved distally by the firing bar 12770 a distance V from a point A to a point B. The point B is approximately one-third of the distance between the proximal end 12112 and the distal end 12113 of the staple cartridge 12110. In other instances, the point B can be less than or more than one-third of the distance between the proximal end 12112 and the distal end 12113. For example, the point B can be approximately one-fourth or one-sixth of the distance between the proximal end 12112 and the distal end 12113. In other instances, the point B can be farther than halfway between the proximal end 12112 and the distal end 12113.

Upon reaching the point B, the sled assembly 12120 has moved two staples 1126 in the depicted row into a forming position and has moved a third staple in the depicted row toward the forming position. Thereafter, the firing bar 12770 is configured to be retracted proximally during a second firing stroke. Because the firing bar 12770 is merely in abutting, driving contact with the firing member 12760 and is not coupled thereto, when the firing bar 12770 is retracted proximally, the firing member 12760 is configured to remain in the intermediate position (point B) in the end effector 12100.

Figure 65:
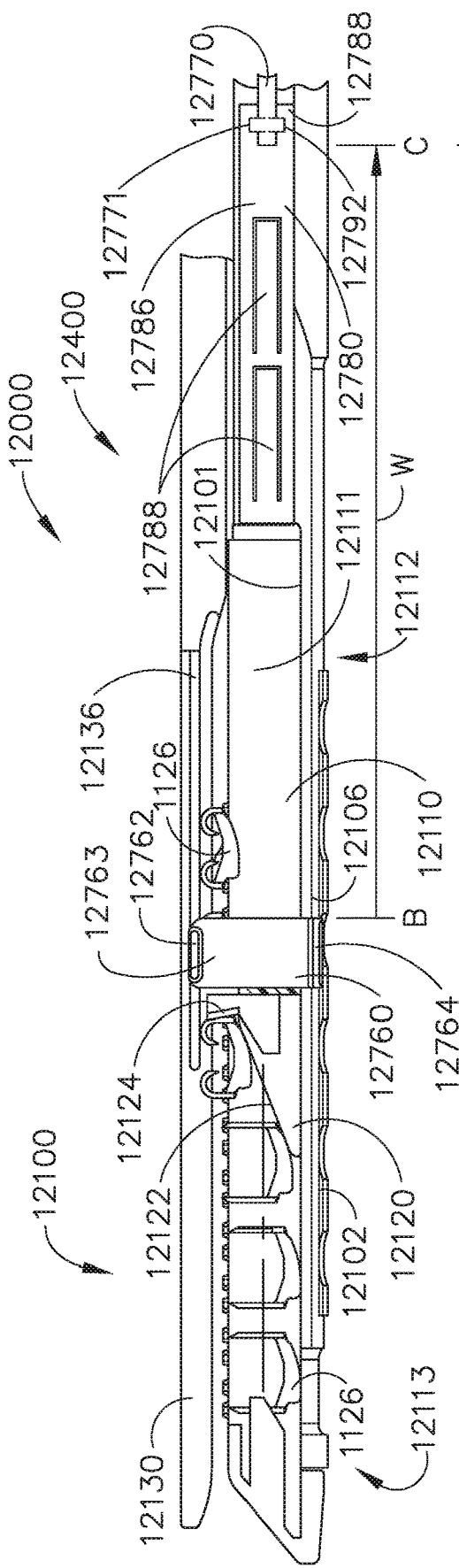
FIG. 65 is an elevation cross-sectional view of a distal portion of the interchangeable surgical tool assembly of FIG. 56 at the completion of a second firing stroke.
Figure 66:
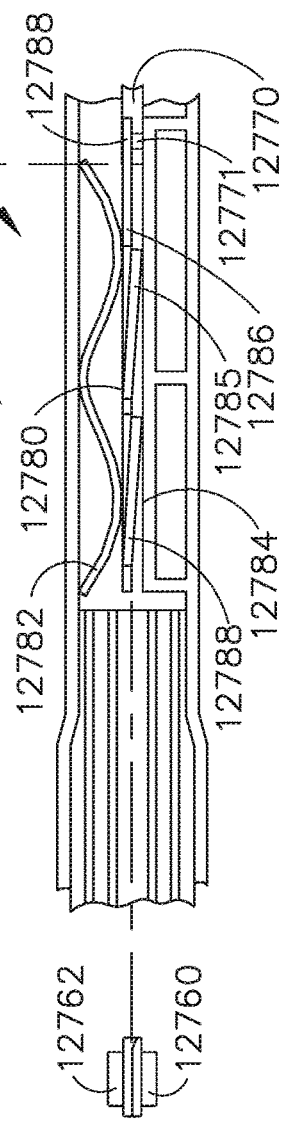
FIG. 66 is a plan view of a portion of the interchangeable surgical tool assembly of FIG. 56 at the completion of the second firing stroke.

Referring primarily to FIGS. 65 and 66, the interchangeable surgical tool assembly 12000 is depicted at the completion of the second firing stroke. Upon comparing FIG. 64 to FIG. 66, the reader will readily appreciate that the firing bar 12770 has been moved proximally a distance W from the point B to a point C. The point C is proximal to the point A. In other words, the distance W is greater than the distance V (see FIG. 64). Moreover, the point C is proximal to the pusher assembly 12778. More specifically, when the firing bar 12770 is retracted to the point C, the firing bar 12770 is retracted proximally such that the T-slot 12792 in the proximal end 12788 of the pusher plate 12780 is aligned with the distal key 12771 on the firing bar 12770. When the distal key 12771 is aligned with the T-slot 12792, the T-slot 12792 is configured to receive the distal key 12771 therein. For example, referring primarily to FIG. 66, the spring 12782 is configured to bias the pusher plate 12780 laterally into engagement with the firing bar 12770. Moreover, the leaf springs 12788 are permitted to resume the non-stressed configuration (see FIGS. 60 and 61) when the firing bar 12770 has been retracted proximally thereof.

Figure 67:
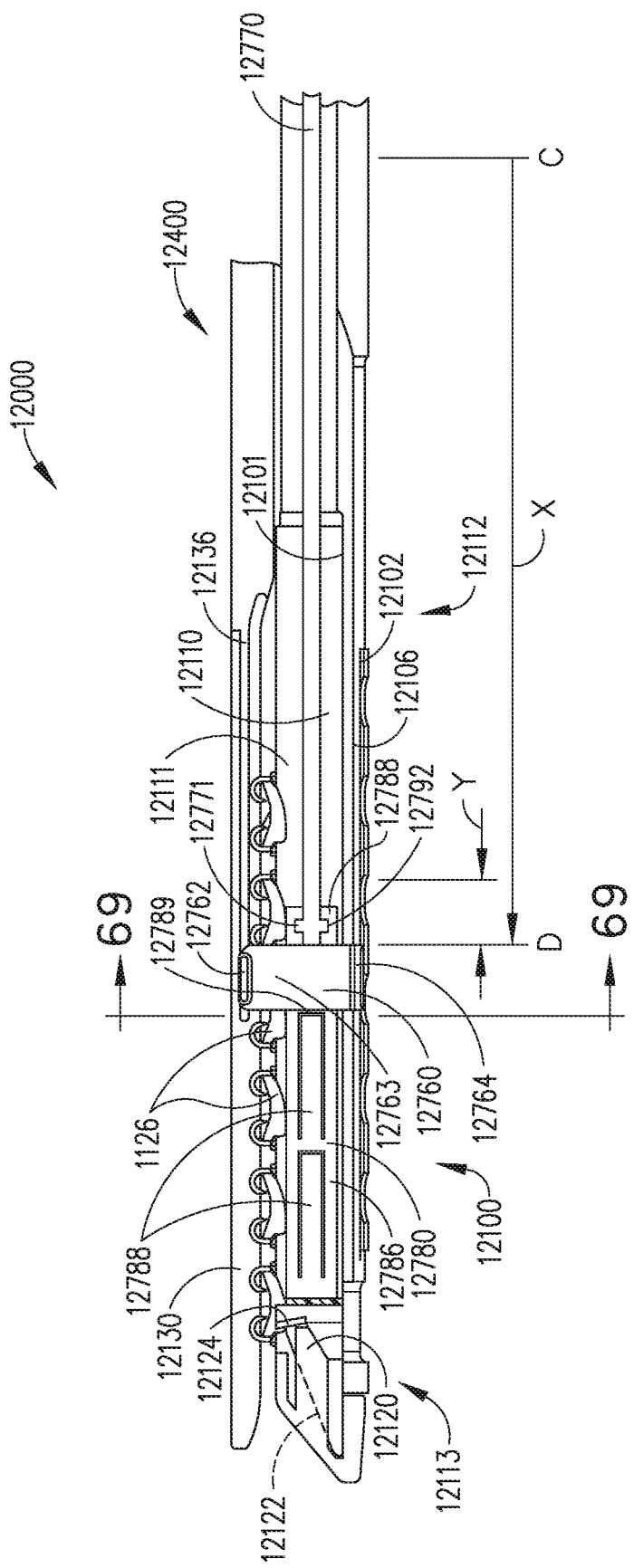
FIG. 67 is an elevation cross-sectional view of a distal portion of the interchangeable surgical tool assembly of FIG. 56 at the completion of a third firing stroke.
Figure 68:
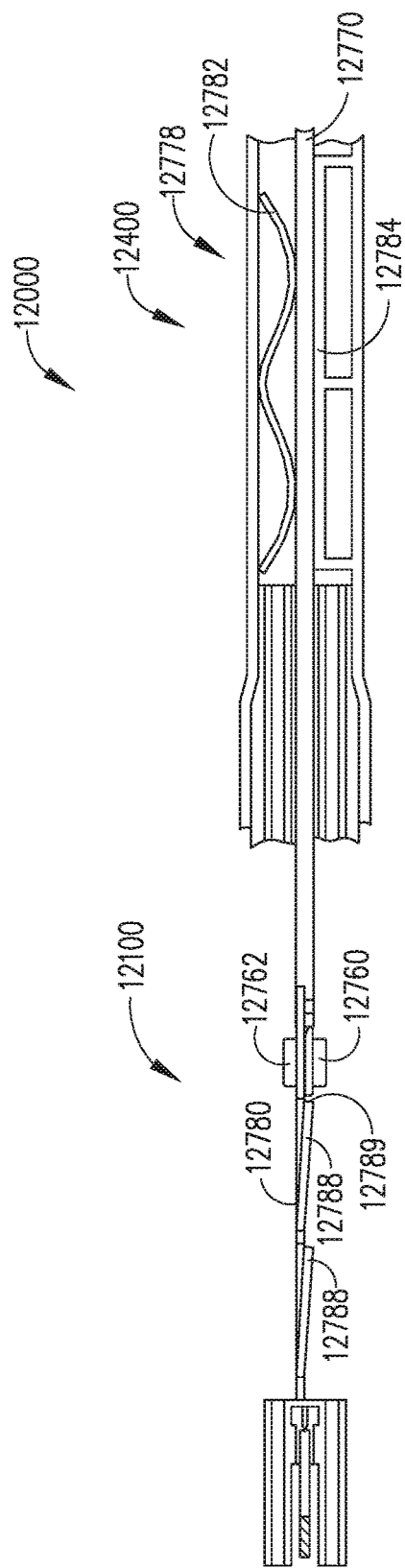
FIG. 68 is a plan view of a portion of the interchangeable surgical tool assembly of FIG. 56 at the completion of the third firing stroke.
Figure 69:
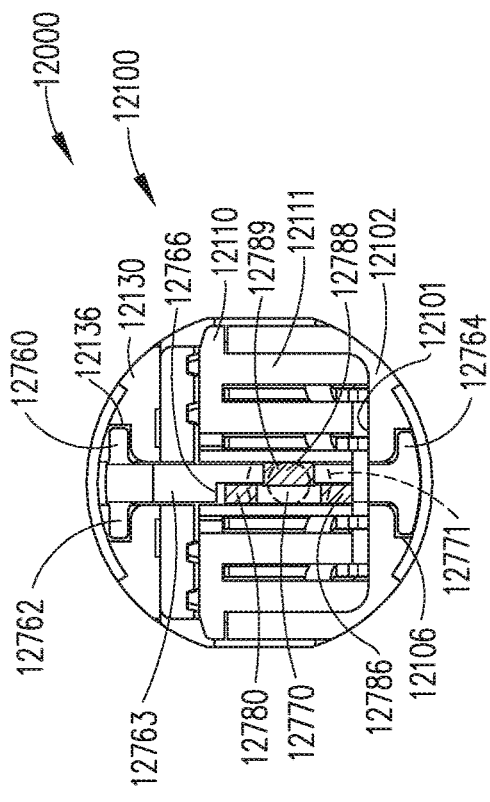
FIG. 69 is an elevation cross-sectional view of the interchangeable surgical tool assembly of FIG. 56 taken along the plane indicated in FIG. 67 at the completion of the third firing stroke.
Figure 70:
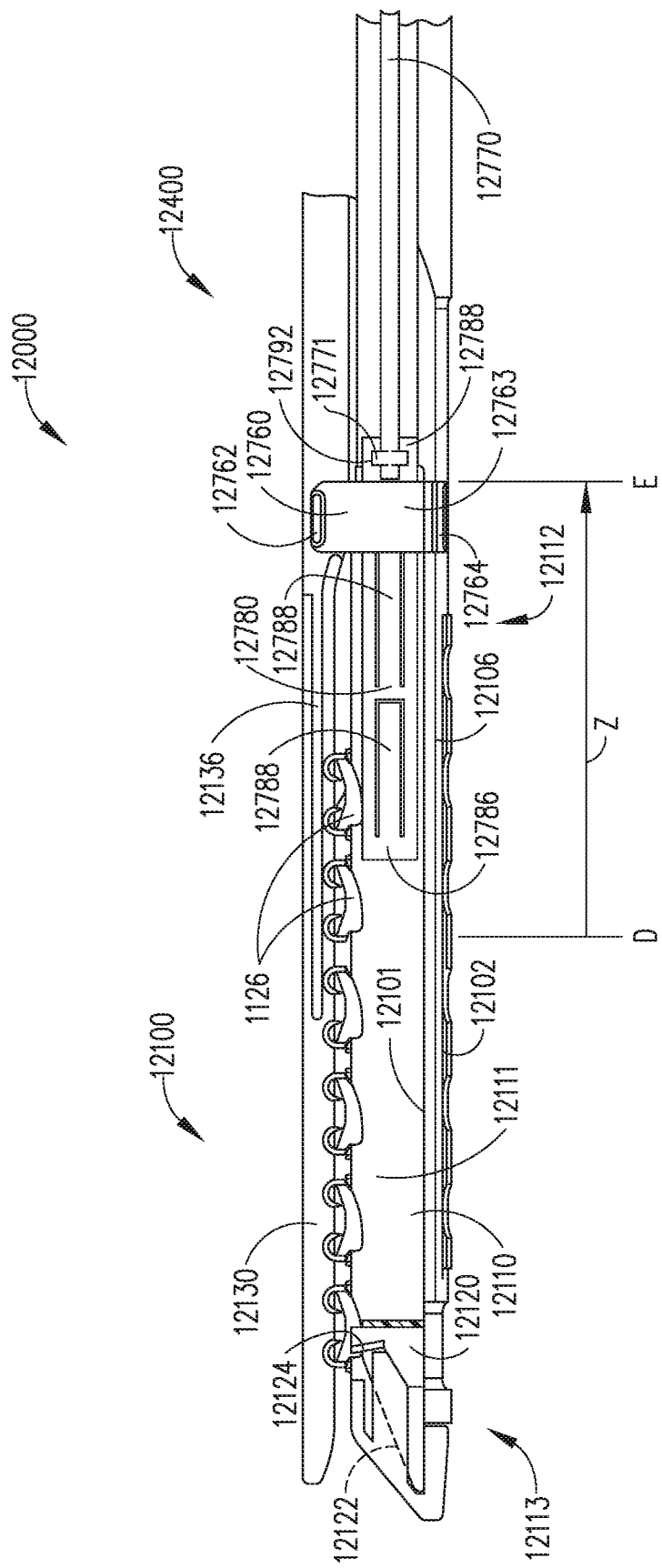
FIG. 70 is an elevation cross-sectional view of a distal portion of the interchangeable surgical tool assembly of FIG. 56 at the completion of a fourth firing stroke.
Figure 71:
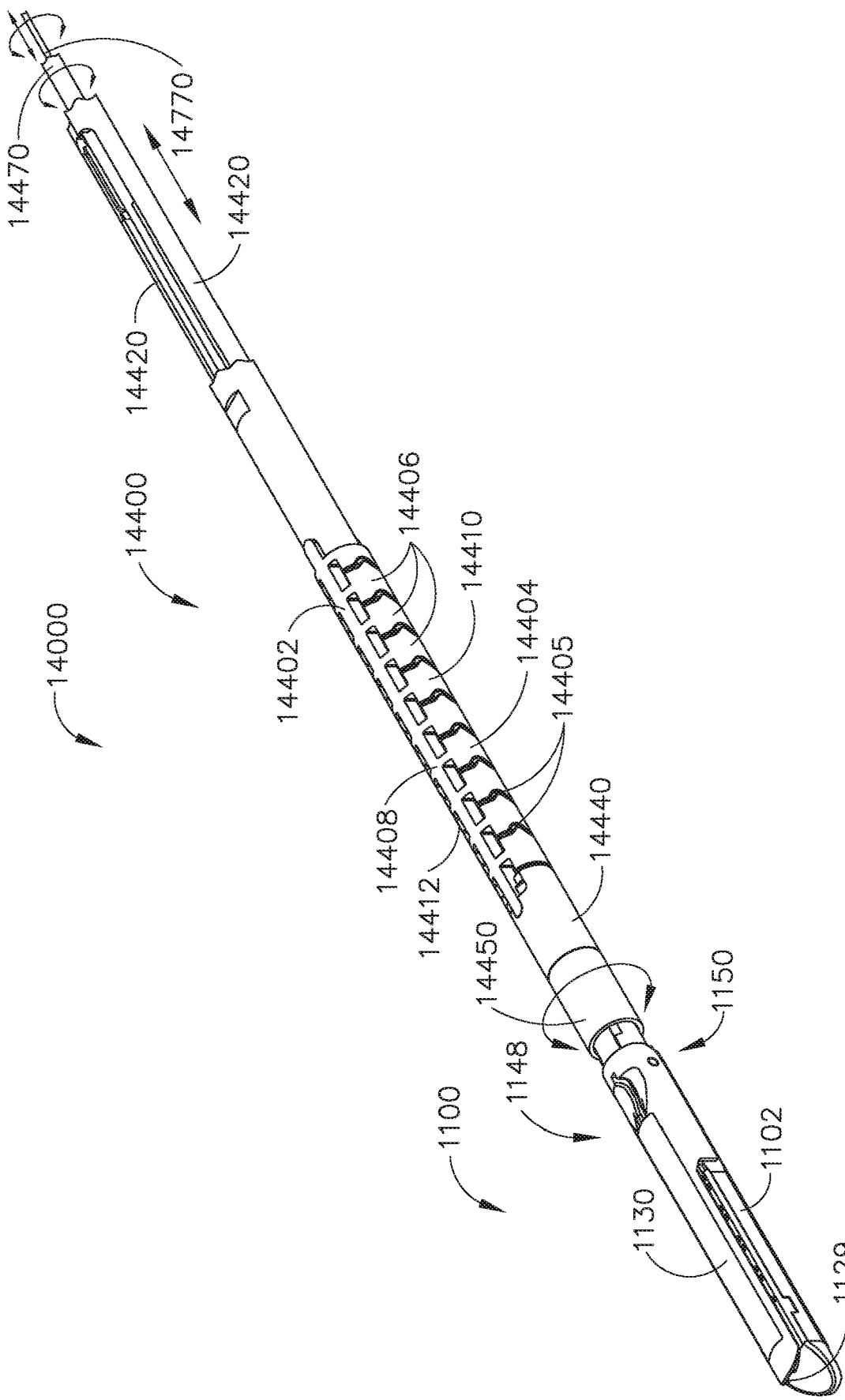
FIG. 71 is a perspective view of a distal portion of an interchangeable surgical tool assembly.

The interchangeable surgical tool assembly 12000 is depicted at the completion of a third firing stroke in FIGS. 67-69. Upon comparing FIG. 66 to FIG. 67, the reader will readily appreciate that the firing bar 12770 has been moved distally a distance X from the point C to a point D. The point D is also distal to the point B (see FIG. 64). The distal displacement of the firing bar 12770 the distance X is configured to move the firing member 12760 a distance Y and the sled assembly 12120 to the distal end 12113 of the staple cartridge 12110. The pusher plate 12780 is advanced distally by the firing bar 12770 during the third firing stroke.

During the third firing stroke, the pusher plate 12780 pushes the firing member 12760 distally until the firing member 12760 reaches the end of the passageway 12136. When the upper flange 12762 of the firing member 12760 abuts the distal end of the passageway 12136 (or the firing member 12760 is otherwise prevented from traveling farther distally), the pusher plate 12780 is configured to bypass the firing member 12760. For example, the leaf springs 12788 are configured to deflect toward the body 12786, which permits the pusher plate 12780 to fit within the notch 12766 in the firing member 12760. When the pusher plate 12780 is positioned within the notch 12766, the pusher plate 12780 is configured to travel distally past the firing member 12760. In certain instances, the pusher plate 12780 may not displace the firing member distally during the third firing stroke. For example, the point B can be aligned with the distal end of the passageway 12136.

At the completion of the third firing stroke, the sled assembly 12120 is positioned at the distal end 12113 of the staple cartridge 12110 and all of the staples 1126 in the depicted row having been moved into a forming position with the anvil 12130. Moreover, the sled assembly 12120 is configured to sink or move downward toward a cartridge-supporting surface 12101 of the elongate channel 12102 at the completion of the third firing stroke. The sunken sled assembly 12120 depicted in FIG. 67 is configured to shift the cutting edge 12124 downward. For example, the cutting edge 12124 can be positioned below the deck of the staple cartridge 12110. In such instances, when the firing member 12760 is retracted and the anvil 12130 is pivoted to an open configuration, the cutting edge 12124 can be concealed within or shielded by the cartridge body 12111, which can prevent inadvertent cutting and/or injury with the cutting edge 12124. In certain instances, the body 12111 of the staple cartridge 12110 includes a distal cavity into which the sled assembly 12120 is configured to fall or shift at the completion of the third firing stroke.

Referring still to FIGS. 67-69, the leaf springs 12788 are in the non-stressed configuration such that they extend laterally outboard of the body 12786. When in the non-stressed configuration, a proximal, outwardly-positioned end 12789 of one of the leaf springs 12788 extends in front of the support portion 12763 of the firing member 12760 (see FIG. 69). In other words, the end 12789 of the leaf spring 12788 extends beyond the notch 12766 and laterally overlaps the support portion 12763 of the firing member 12760. As a result, the end 12789 acts as a spring-loaded barb that catches the firing member 12760 when the pusher plate 12780 is subsequently retracted proximally.

During the fourth firing stroke, the pusher plate 12780 is retracted proximally. Upon comparing FIG. 67 to FIG. 70, the reader will readily appreciate that the firing bar 12770 has been moved proximally a distance Z from the point D to a point E. The firing bar 12770 is engaged with the pusher plate 12780 via the lock 12771 and the T-slot 12792 and, thus, the pusher plate 12780 is also withdrawn proximally with the firing bar 12770. Moreover, because the end 12789 of one of the leaf springs 12788 is caught or otherwise engaged with the firing member 12760, the retraction of the pusher plate 12780 also retracts the firing member 12760. The firing member 12760 in FIG. 70 has been retracted such that the upper flange 12762 is withdrawn from the passageway 12136 in the anvil 12130. In certain instances, the upper flange 12762 can be configured to engage an open-close cavity to open the anvil 12130 toward an open configuration when withdrawn to the point E. Moreover, the sled assembly 12120 including the cutting edge 12124 thereof remains shielded in the drop down cavity at the distal end 12113 of the staple cartridge 12110.

In certain instances, an interchangeable surgical tool assembly can include a flexible spine, which can permit flexing of at least a portion of the shaft away from a linear configuration. The flexible spine is configured to move the end effector of the interchangeable surgical tool assembly vertically and/or horizontally with respect to a longitudinal axis of the shaft. Additionally or alternatively, in certain instances, the end effector and/or a distal portion of the interchangeable surgical tool assembly can be configured to rotate with respect to the longitudinal axis of the shaft. The flexibility and rotatability of an interchangeable surgical tool assembly is configured to increase the range of motion such that the end effector can be manipulated to assume different positions with respect to target tissue. Additionally, flexibility and rotatability can be configured to increase the operator's viewability at the surgical site.

An interchangeable surgical tool assembly 14000 is depicted in FIGS. 71-74. The interchangeable surgical tool assembly 14000 includes the end effector 1100 including the elongate channel 1102, the anvil 1130, and the firing member 1760. The staple cartridge 1110 (see FIGS. 72 and 74) is removably positioned in the elongate channel 1102. The interchangeable surgical tool assembly 14000 also includes a shaft portion 14400 including a flexible spine 14402. A flexible spine for a surgical instrument is further described in U.S. patent application Ser. No. 14/138,554, entitled SURGICAL INSTRUMENTS WITH ARTICULATABLE SHAFT ARRANGEMENTS, filed Dec. 23, 2013, now U.S. Patent Application Publication No. 2015/0173789, which is hereby incorporated by reference herein in its entirety.

Figure 74:
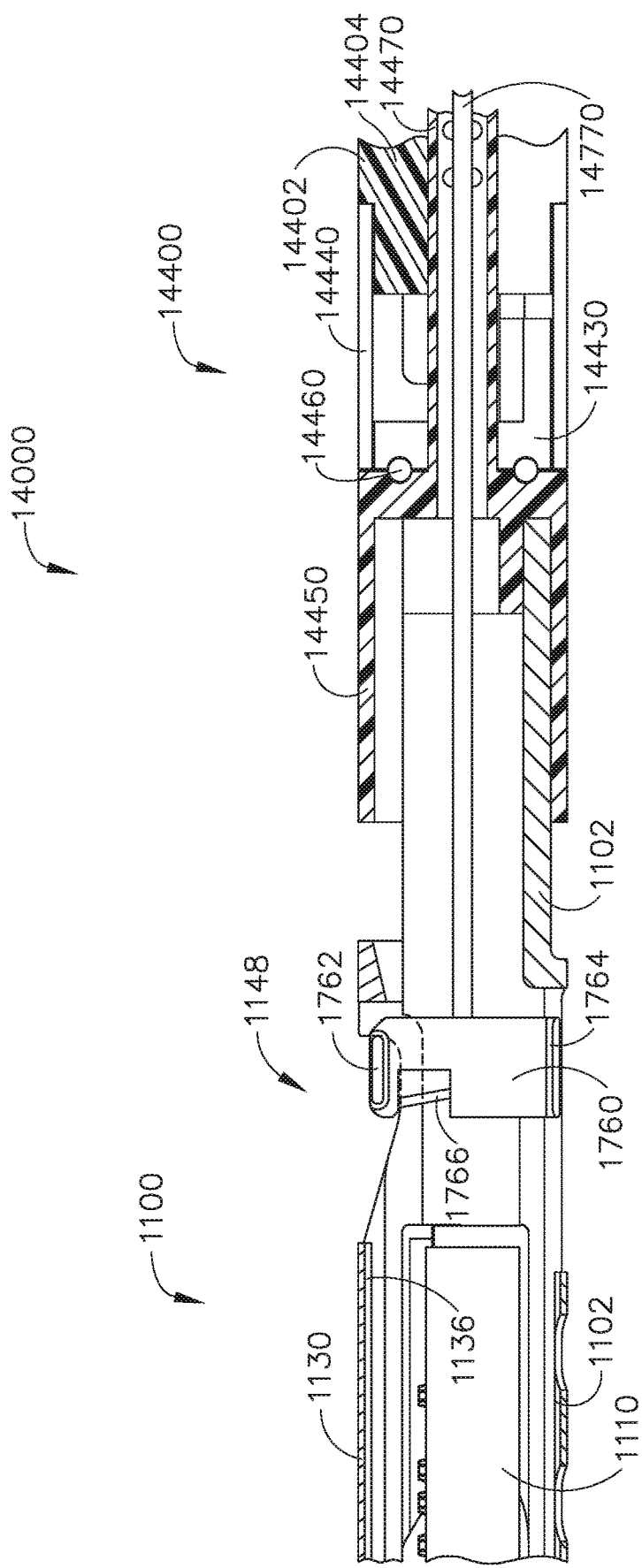
FIG. 74 is an elevation cross-sectional view of a portion of the interchangeable surgical tool assembly of FIG. 71.

The flexible spine 14402 comprises a vertebral body 14404 and a distal tube segment 14440 mounted to the vertebral body 14404 (see FIG. 74). The vertebral body 14404 includes a central portion 14408 and laterally-symmetric pairs of vertebrae 14406 extending from the central portion 14408. The vertebrae 14406 are positioned along each lateral side 14410, 14412 of the vertebral body 14404. The vertebrae 14406 along the length of the vertebral body 14404 are nested. For example, each vertebra 14406 includes a protrusion and the adjacent vertebra 14406 includes a corresponding recess into which the protrusion protrudes. The interlocking protrusions and recesses are configured to limit torqueing or twisting of the vertebral body 14404.

Adjacent vertebra 14406 in the vertebral body 14404 are separated by a gap 14405 when the vertebral body 14404 is in a linear orientation. For example, the gaps 14405 can extend between the interlocking protrusions and recesses. The gaps 14405 between adjacent vertebrae 14406 are configured to permit the articulation of the vertebral body 14404 in an articulation plane.

Figure 72:
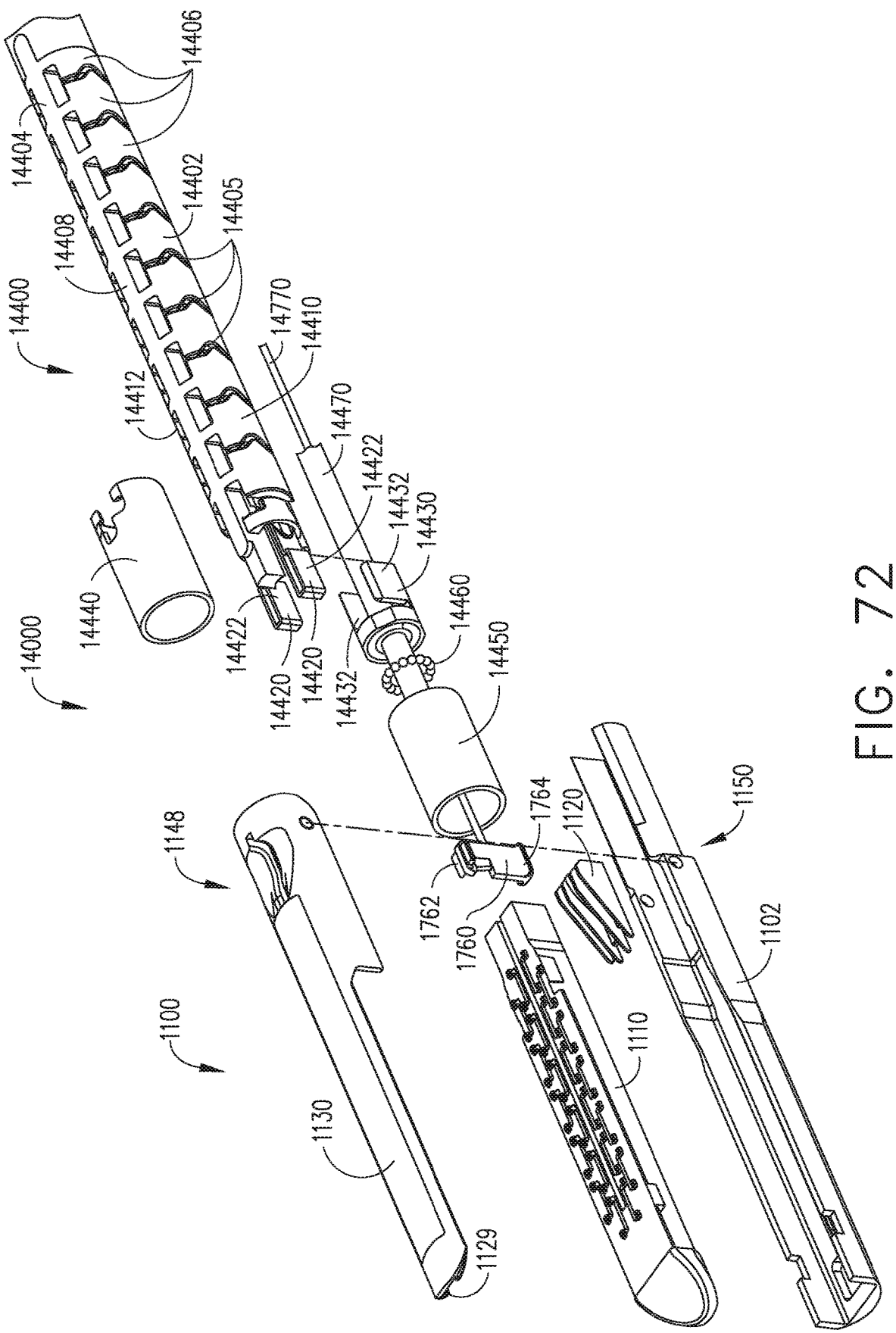
FIG. 72 is a perspective exploded assembly view of a distal portion of the interchangeable surgical tool assembly of FIG. 71.
Figure 73:
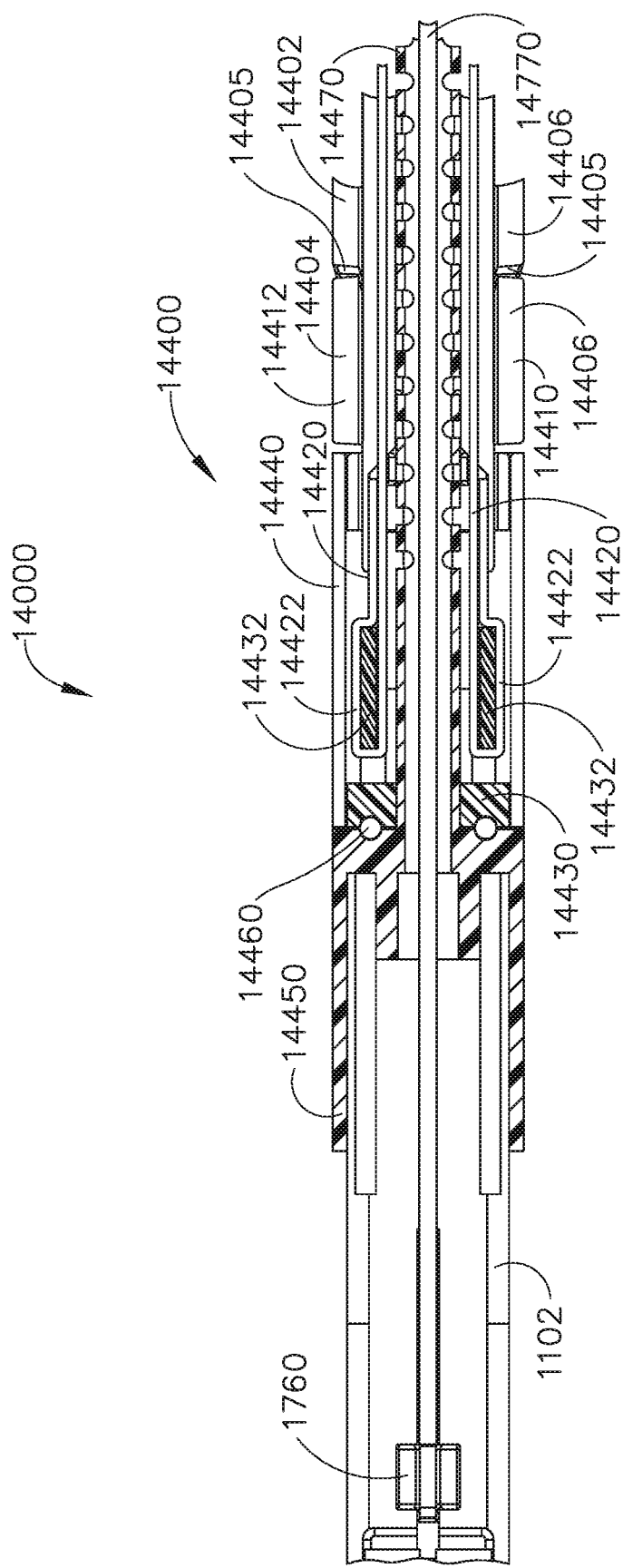
FIG. 73 is a plan cross-sectional view of a portion of the interchangeable surgical tool assembly of FIG. 71.

Referring primarily to FIGS. 72 and 73, to articulate the flexible spine 14402 and the distal tube segment 14440 mounted thereto, the respective lateral sides 14410, 14412 of the vertebral body 14404 are simultaneously compressed and expanded by selective movement of articulation bands 14420 that longitudinally pass through passages along each respective lateral side 14410, 14412 of the vertebral body 14404. The distal ends of the articulation bands 14420 are anchored to an articulation head 14430, which is mounted or otherwise secured to the distal tube segment 14440. For example, the articulation bands 14420 terminate at distal loops 14422, which are positioned around attachment tabs 14432 on the articulation head 14430. Thus, the reciprocating motions of the articulation bands 14420 are configured to cause the articulation head 14430 and the distal tube segment 14440 to articulate relative to the flexible spine 14402. The articulation bands 14420 can be comprised of metal bands, which can be at least partially enclosed or encased in plastic, for example. In various instances, the articulation bands can be actuated (i.e. displaced proximally or distally) by levers or other actuators on the handle assembly, such as the handle assembly 500 (see FIGS. 1 and 2) of the surgical instrument.

As the vertebral body 14404 flexes and the distal tube segment 14440 articulates, the end effector 1100 is also configured to articulate. More specifically, the end effector 1100 includes a proximal mounting portion 14450. Referring primarily to FIG. 74, the proximal mounting portion 14450 is mounted to the elongate channel 1102. For example, the proximal mounting portion 14450 can be fixed to the elongate channel 1102 and/or integrally formed with the elongate channel 1102. The proximal mounting portion 14450 is positioned adjacent to the distal tube segment 14440 and the articulation head 14430 therein. As further described herein, a thrust bearing 14460 is positioned intermediate the proximal mounting portion 14450 and the distal tube segment 14440 such that the proximal mounting portion 14450 can rotate relative to the distal tube segment 14440. When the distal tube segment 14440 articulates, the proximal mounting portion 14450 and the end effector 1100 extending therefrom are also configured to articulate.

In various instances, the end effector 1100 can also be configured to rotate about the longitudinal axis of the shaft portion 14000. For example, the end effector 1100 can be rotated relative to the flexible spine 14402. The interchangeable surgical tool assembly 14000 includes a rotation shaft 14470, which extends proximally from the proximal mounting portion 14450. The rotation shaft 14470 can extend proximally through the distal tube segment 14440 and the flexible spine 14402 and can be secured at a rotational coupling in the handle assembly. The rotation shaft 14470 and the proximal mounting portion 14450 can be connected such that rotation of the rotation shaft 14470 causes a rotation of the proximal mounting portion 14450 and, thus, the end effector 1100, as well. For example, the rotation shaft 14470 can be fixed and/or integrally formed with the proximal mounting portion 14450. In other instances, rotation transmitting features, such as gear teeth, for example, can be configured to transmit rotation of the rotation shaft 14470 to the proximal mounting portion 14450.

The rotation shaft 14470 extends through the flexible spine 14402. For example, the rotation shaft 14470 can be concentric with the flexible spine 14402 and the vertebral body 14404 thereof. Though the rotation shaft 14470 extends through the flexible spine 14402 and rotates therein, rotation of the rotation shaft 14470 is not transferred to the flexible spine 14402. For example, the thrust bearing 14460 intermediate the proximal mounting portion 14450 and the articulation head 14430 is configured to permit rotation of the proximal mounting portion 14450 relative to the articulation head 1430. In other instances, the flexible spine 14402 can be configured to rotate with the rotation shaft 14470 and the thrust bear 14460 can be positioned intermediate the flexible spine 14402 and a non-rotatable portion of the shaft 14400.

Referring primarily to FIG. 73, the rotation shaft 14470 can be serrated or notched. The serrations and/or notches are configured to permit flexing of the rotation shaft 14470 within the flexible spine 14402. Though the rotation shaft 14470 is permitted to flex, the serrations can be configured to limit twisting or torqueing of the rotation shaft 14470 such that rotational movement generated at the proximal end thereof can be efficiently transferred to the distal end of the rotation shaft 14470 and, thus, to the proximal mounting portion 14450.

Referring primarily to FIGS. 73 and 74, the shaft portion 14400 includes a longitudinally-movable firing bar 14770, which is similar in many respects to the firing bar 1770 (see FIGS. 3-5). During a firing stroke, a drive member in the handle assembly (e.g. the drive member 540 in the handle assembly 500, see FIGS. 1 and 2) transfers a firing motion to the firing bar 1770 via a drive member (e.g. the drive member 1602, see FIG. 2) to fire the firing member 1760. For example, actuation of the drive member 540 can be configured to displace the firing bar 14770 and the firing member 1760 distally to cut tissue and effect firing of staples from the staple cartridge 1110. Thereafter, the drive member 540 can be retracted proximally to retract the firing bar 14770 and the firing member 1760 proximally. The firing bar 14770 is configured to flex within the flexible spine 14402.

The firing bar 14770 is concentric with the rotation shaft 14470. Moreover, as the rotation shaft 14470 rotates within the flexible spine 14402, the firing bar 14770 is configured to rotate as well. For example, the firing bar 14770 extends distally to the firing member 1760 having the upper flange 1462 restrained by the anvil 1130 and the lower flange 1464 restrained by the elongate channel 1102. As the end effector 1100 rotates with the rotation shaft 14470, as described herein, the firing member 1760 positioned in the end effector 1100 is also configured to rotate.

As described herein, the rotational joint between the proximal mounting portion 14450 and the distal tube segment 14440 is distal to the articulating vertebral body 14404. Therefore, the rotation of the end effector 1100 occurs distal to the articulation region of the shaft portion 14400. In other instances, the interchangeable surgical tool assembly 14000 can include alternative and/or additional articulation joints and/or regions. For example, various additional articulation joints are further described herein. In such instances, the rotational joint between the proximal mounting portion 14450 and the distal tube segment 14440 can be positioned distal to the distal-most articulation joint.

In various instances, translation of the firing member 1760 and/or firing bar 14770 can be prevented until an unfired staple cartridge is positioned in the end effector 1100. For example, the various lockout arrangements disclosed herein can be incorporated into the end effector 1100 and/or the interchangeable surgical tool assembly 14000. Through translation of the firing member 1760 and/or the firing bar 14770 can be prevented in such instances, the rotation of the firing member and the firing bar 14770 along with the rotation shaft 14470 and the end effector 1100 can be permitted by such lockout arrangements.

Turning next to FIGS. 75-81, there is shown a portion of another surgical instrument embodiment 15010 of the present invention. In the illustrated arrangement, the surgical instrument 15010 comprises a shaft assembly 15100 that may be operably coupled to a housing (not shown) in the form of a handle assembly or a portion of a robotic system. For example, the shaft assembly 15100 may be operably coupled to, or otherwise configured for use in connection with the handle assembly and other drive arrangements disclosed above and/or in connection with the various handle assemblies, firing and articulation drive systems disclosed in U.S. Patent Application Publication No. 2014/0246471, entitled ARTICULATABLE SURGICAL INSTRUMENTS WITH CONDUCTIVE PATHWAYS FOR SIGNAL COMMUNICATION, the entire disclosure of which is hereby incorporated by reference herein.

Figure 75:
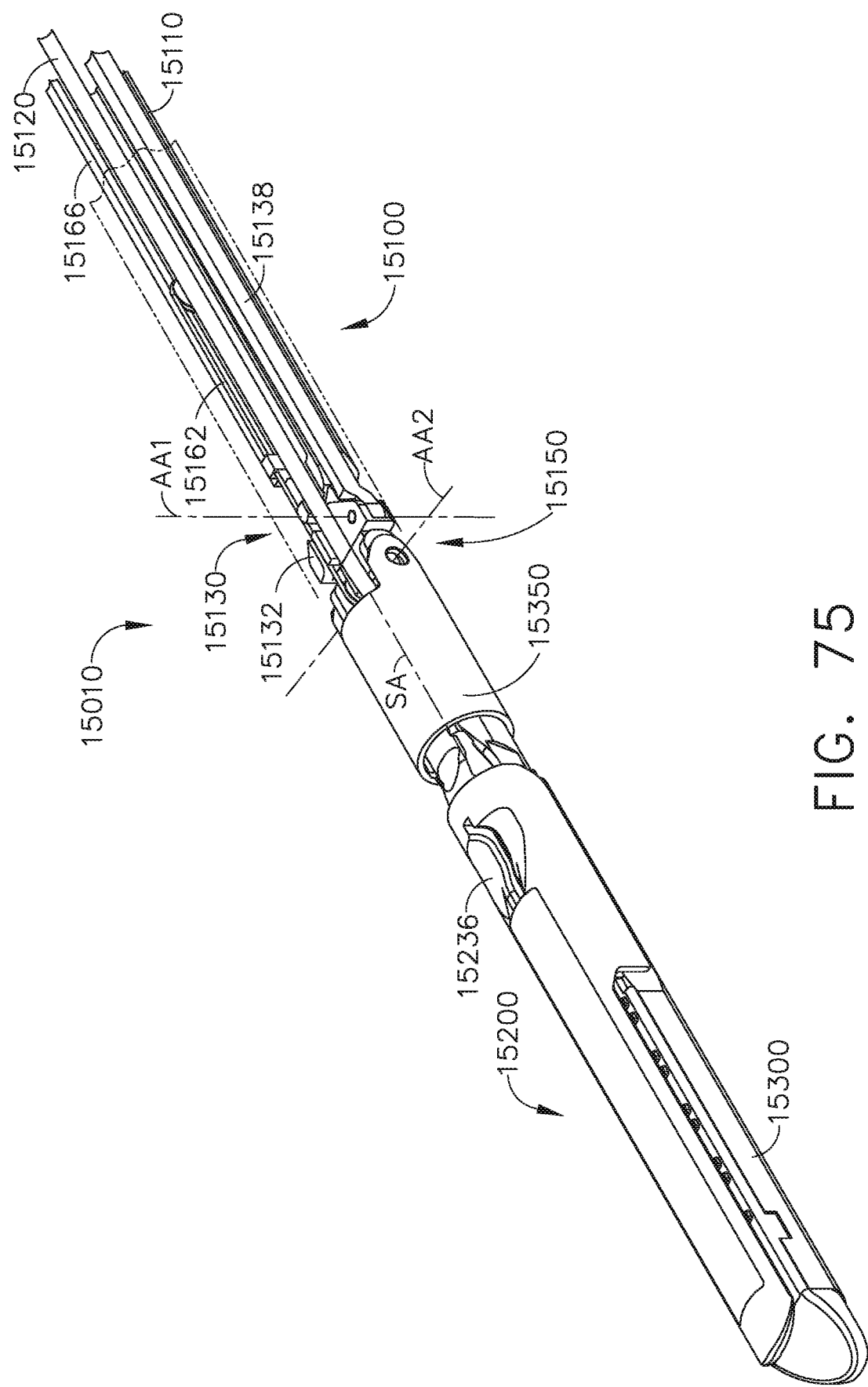
FIG. 75 is perspective view of a portion of another surgical instrument embodiment.

As can be seen in FIG. 75, the shaft assembly 15100 includes a spine member 15110 that operably supports a proximal rotary drive shaft 15120 that operably interfaces with a source of rotary motion (e.g., a motor or motor arrangement supported in the handle assembly or robotic system). In the illustrated arrangement, the proximal rotary drive shaft 15120 is flexible to accommodate articulation of a portion of the shaft assembly 15100. For example, the rotary drive shaft may comprise a cable that is somewhat flexible. The spine member 15110 defines a shaft axis SA and may, for example, be coupled to the handle assembly or robotic system in various known manners to facilitate selective rotation of the spine member 15110 about the shaft axis SA relative to the handle assembly or robotic system. In the illustrated embodiment, the shaft assembly 15100 includes a proximal or "first" articulation joint 15130 that defines a first articulation axis AA1 that is transverse to the shaft axis SA and a distal or "second" articulation joint 15150 that defines a second articulation axis AA2 that is also transverse to the shaft axis SA as well as to the first articulation axis AA1.

Figure 76:
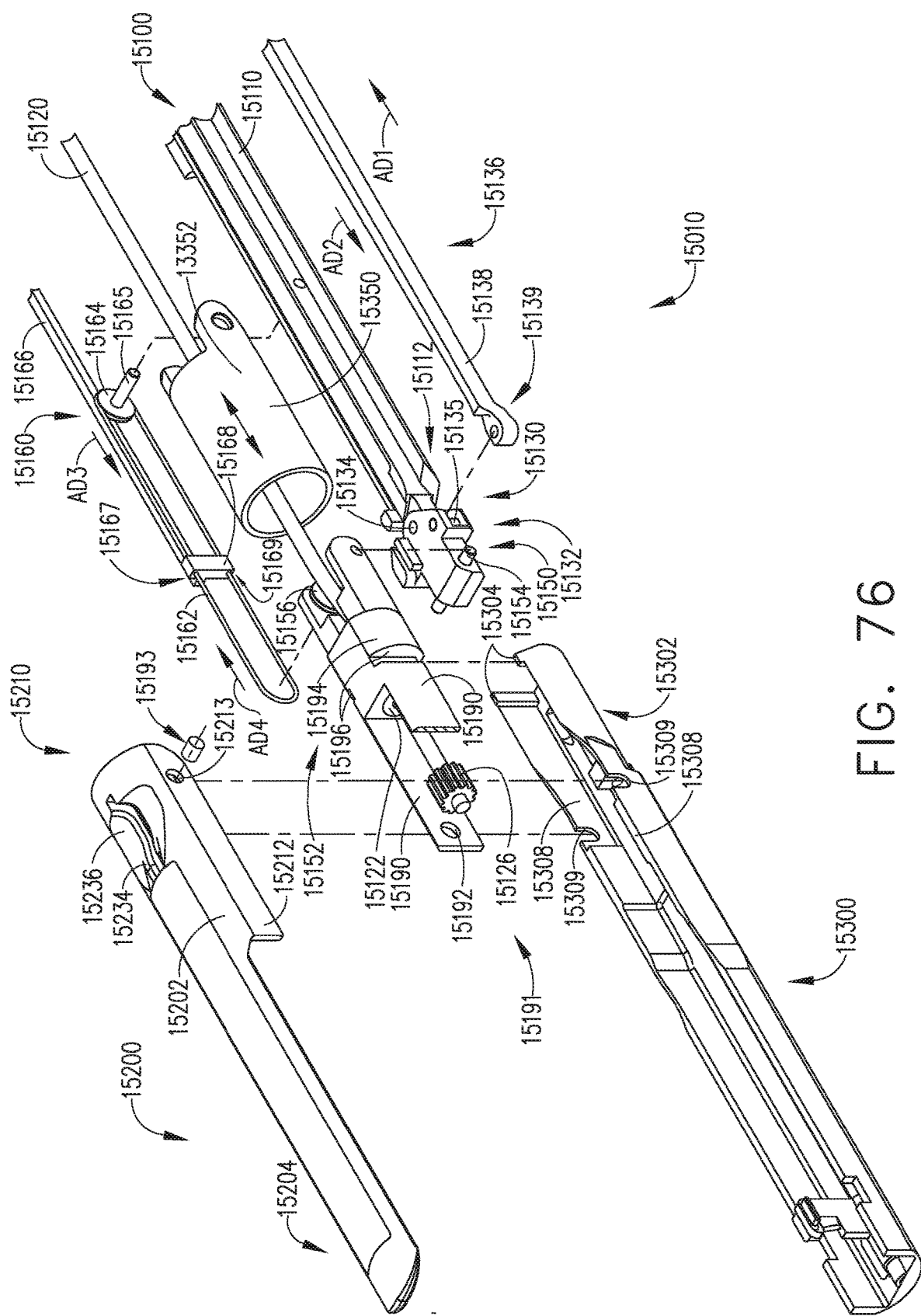
FIG. 76 is an exploded perspective assembly view of the surgical instrument portion of FIG. 75.

Referring now to FIG. 76, the proximal or first articulation joint 15130 comprises a first channel mounting assembly 15132 that is pivotally coupled to a distal end 15112 of the spine member 15110 by a first articulation pin 15134. The first articulation pin 15134 defines the first articulation axis AA1 about which the first channel mounting assembly 15132 may pivot. The illustrated shaft assembly 15100 comprises a first articulation system 15136 that comprises a first axially movable articulation actuator 15138 that operably interfaces with a source of first axial articulation motions in the handle assembly or robotic system. Such first axial articulation motions are represented by arrows AD1 and AD2 in FIG. 76. As can be seen in FIG. 76, a distal end 15139 of the first axially movable articulation member 15138 is pivotally pinned to the first channel mounting assembly 15132 by an attachment pin 15135. Axial movement of the first articulation actuator 15138 in the first and second articulation directions AD1, AD2 will result in the pivotal travel of the first channel mounting assembly 15132 relative to the spine member 15110 about the first articulation axis AA1.

Still referring to FIG. 76, the distal or second articulation joint 15150 comprises a second channel mounting member 15152 that is pivotally coupled to the first channel mounting assembly 15132 by a second articulation pin 15154. The second articulation pin 15154 defines the second articulation axis AA2 about which the second channel mounting member 15152 may pivot relative to the first channel mounting assembly 15132. See FIG. 75. The illustrated shaft assembly 15100 further comprises a second articulation system 15160 that comprises a second endless articulation member 15162 that is journaled on a proximal idler pulley 15164 that is rotatable supported on a pulley shaft 15165 that is attached to the spine member 15110. The second endless articulation member 15162 is also attached to an articulation pulley 15156 that is non-movably attached to or formed on the second channel mounting member 15152 such that rotation of the second endless articulation member 15162 on the idler pulley 15164 will cause the second channel mounting member 15152 to pivot relative to the first channel mounting assembly 15132 about the second articulation axis AA2. The second articulation system 15160 further comprises a second axially movable articulation actuator 15166 that operably interfaces with a source of second axial articulation motions in the handle assembly or robotic system. Such second axial articulation motions are represented by arrows AD3 and AD4 in FIG. 76. As can be seen in FIG. 76, a distal end 15167 of the second axially movable articulation member 15166 is clamped to a portion of the second endless articulation member 15162 by a clamp member 15168. The clamp member 15168 includes a cable guide hole 15169 therethrough for slidably supporting another portion of the second endless articulation member 15162 during application of second articulation motions thereto.

In the illustrated embodiment, an anvil member 15200 is movably coupled to the shaft assembly 15100. The anvil 15200 may be similar to the anvil 1130 described above. For example, the anvil 15200 is pivotally coupled to the second channel mounting member 15162 for selective pivotal travel relative thereto. As can be seen in FIG. 76, the anvil 15200 includes an anvil body 15202 that includes a staple forming portion 15204 and an anvil mounting portion 15210. The anvil mounting portion 15210 includes downwardly extending side walls 15212 that are commonly referred to as tissue stops, the purpose of which was previously described herein.

In the illustrated example, the second channel mounting member 15152 includes two distally protruding anvil mounting portions 15190 that each have a pin hole 15192 therein that is adapted to receive therein a corresponding anvil attachment pin 15193. The anvil attachment pins 15193 are received in the pin holes 15192 and in corresponding apertures 15213 in the side walls 15212 of the anvil 15200. As discussed above, the pins may be pressed into the apertures 15213. Such arrangement forms a pivot joint 15191 that facilitates pivotal travel of the anvil 15200 relative to the second channel mounting member 15152 while remaining attached thereto. In such arrangement, the anvil 15200 is not intended to be detached from the shaft assembly 15100 or more particularly, the second channel mounting member 15152 during normal use. Thus, as used in this context of describing the attachment of the anvil 15200 to the shaft assembly 15100, the term, "non-removably attached" means that the anvil 15200 remains attached to the shaft assembly 15100 during operation of the surgical instrument as well as when operably installing other surgical staple cartridges as will be discussed in further detail below.

Figure 77:
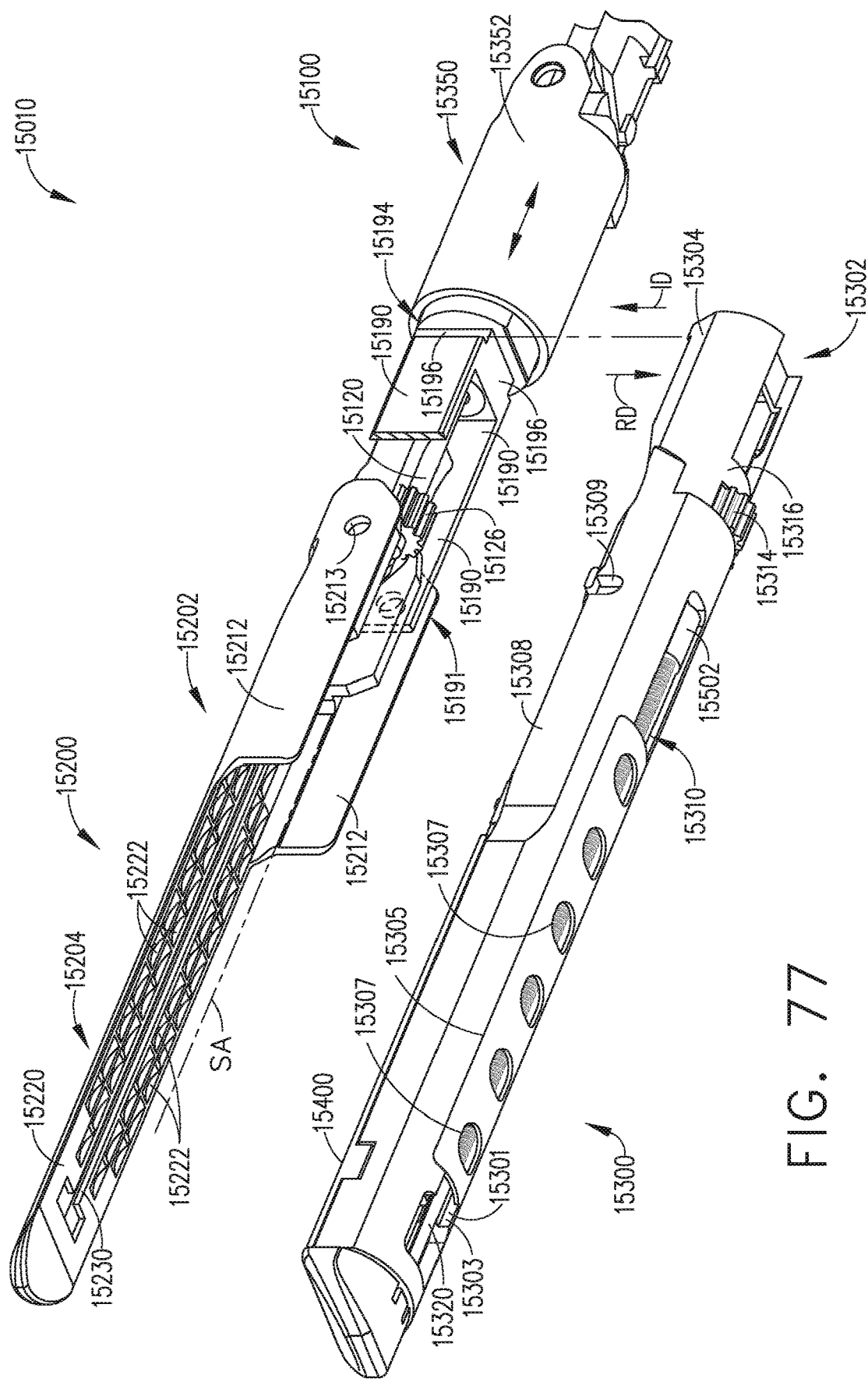
FIG. 77 is another exploded assembly view of the surgical instrument of FIGS. 75 and 76 with a channel portion thereof detached from a shaft assembly thereof.

As can be seen in FIGS. 76 and 77, the surgical instrument 15010 further includes a channel 15300 that is configured to operably support a surgical staple cartridge 15400 therein. In the illustrated embodiment, the channel 15300 includes a proximal attachment portion 15302 that is configured to be removably attached to the second channel mounting member 15152. For example, the second channel mounting member 15152 includes a mounting body or mounting hub portion 15194 that has two channel attachment slots 15196 formed therein that are configured to receive corresponding channel rails 15304 that are formed on the proximal attachment portion 15302 of the channel 15300. As can be seen in FIG.

77, the channel 15300 is removably attached to the shaft assembly 15100 by inserting the channel rails 15304 into the corresponding channel attachment slots 15196 in the second channel mounting member 15152 in an installation direction ID that is transverse to the shaft axis SA. In the illustrated example, the channel 15300 is removably locked to the shaft assembly 15100 by a lock member 15350.

Still referring to FIGS. 76 and 77, in the illustrated example, the lock member 15350 comprises a distal tube segment 15352 that is axially movably supported on the mounting hub portion 15194 of the second channel mounting member 15152. The distal tube segment 15352 may be pivotally attached to a flexible proximal tube segment (not shown) of the shaft assembly 15100 to facilitate articulation about the first and second articulation axes. The distal tube segment 15352 is configured to axially move between a distal-most "locked" position wherein the distal tube segment 15352 prevents the channel 15300 from being detached from the shaft assembly 15100 in removal direction RD and a proximal "unlocked" position whereby the distal tube segment 15352 is proximal of the channel attachment slots 15196 to enable the channel 15300 to be detached from the shaft assembly 15100. Thus, the distal tube segment 15352 is coupled to the proximal tube segment to facilitate axial movement relative thereto or the entire assembly (distal tube segment 15352 and proximal tube segment) is axially movable. As can be seen in FIGS. 76-79, clearance slots 15309 are provided in upstanding side walls 15308 of the elongate channel 15300 to accommodate the anvil attachment pins 15193 that attach the anvil 15200 to the second channel mounting member 15152. The anvil side walls 15212 are spaced from each of the corresponding anvil mounting portions 15190 to accommodate the corresponding side wall 15308 of the elongate channel 15300 when the anvil 15200 is closed and the elongate channel 15300 is attached to the second channel mounting member 15152.

In one arrangement, the surgical staple cartridge 15400 includes a cartridge body 15402 that is configured to be snapped or otherwise removably retained within the channel 15200 to facilitate easy replacement after use. The cartridge body 15402 includes a centrally disposed elongate slot 15404 that is configured to accommodate axial travel of a firing member 15500 therethrough. The cartridge body 15402 further includes a plurality of staple pockets 15406 therein. In the illustrated example, the staple pockets 15406 are arranged in two lines on each side of the elongate slot 15404. The staple pockets 15406 in one line are staggered with respect to the staple pockets 15406 in the adjacent line of staple pockets. In the illustrated example, each staple pocket 15406 contains a "direct drive" surgical staple 1126 therein. In the arrangement depicted in FIG. 79, the surgical staples 1126 are movably supported within the staple pockets 15406 and are configured such that a separate movable staple driver is not employed. FIG. 80 illustrates an alternative arrangement wherein conventional surgical staples 1126' are each supported on a staple driver 15412 that are supported within the staple pockets 15406' in the cartridge body 15402'. The staple drivers 15412 are driven upward in the surgical staple cartridge 15400' as the firing member 15500' is driven distally therethrough. Further details concerning the operation of the firing member 15500' and the staple drivers 15412 may be found in U.S. patent application Ser. No. 14/308,240, entitled SURGICAL CUTTING AND STAPLING INSTRUMENTS AND OPERATING SYSTEMS THEREFOR, now U.S. Patent Application Publication No. 2014/0299648, the entire disclosure of which is hereby incorporated by reference herein.

Figure 78:
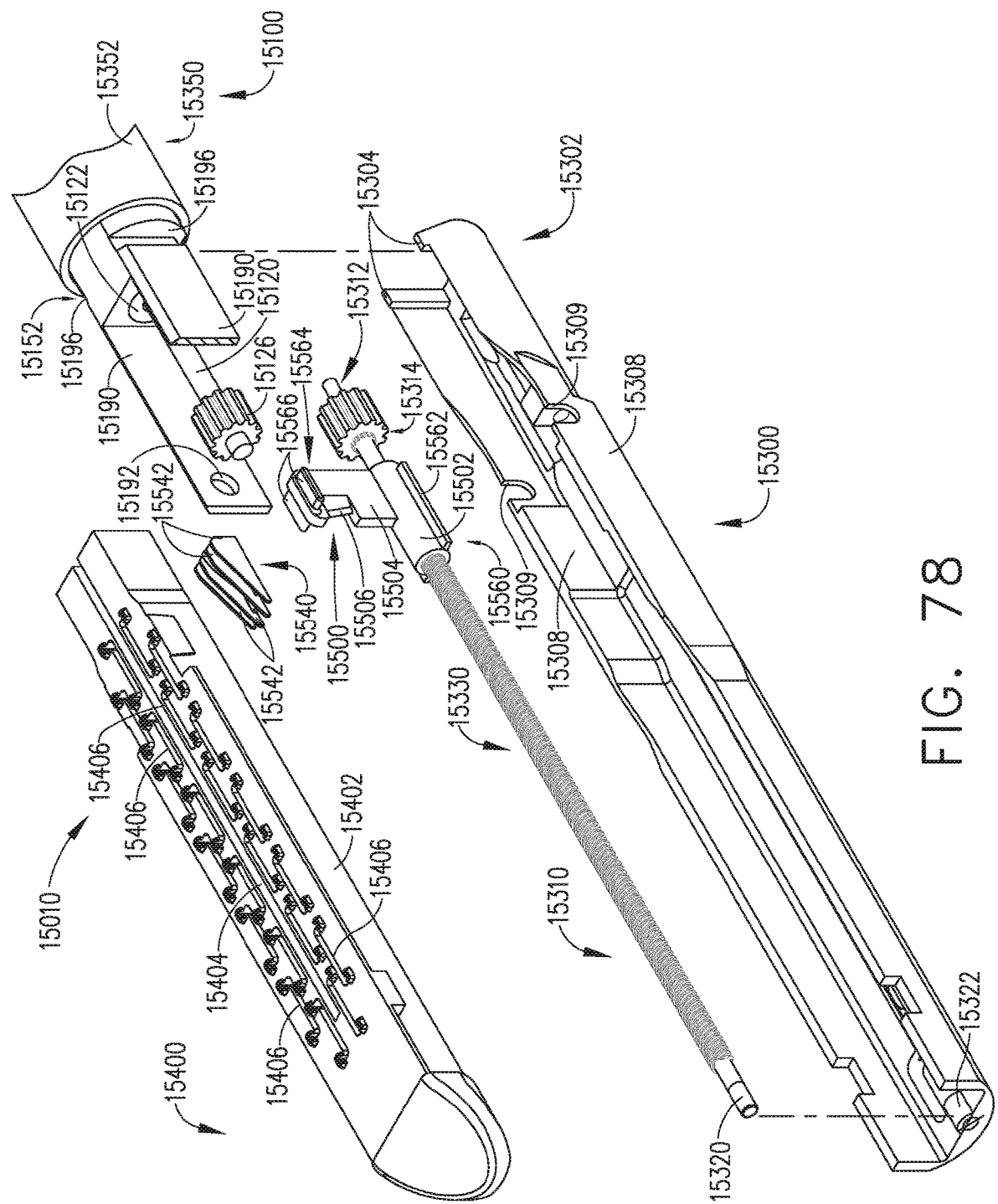
FIG. 78 is another exploded assembly view of portions of the channel and shaft assembly of the surgical instrument of FIGS. 75-77.

Turning next to FIGS. 78 and 81, in the illustrated example, the proximal rotary drive shaft 15120 extends through the second channel mounting member 15152 and is rotatably supported therein by a bearing assembly 15122. A distal end 15124 of the proximal rotary drive shaft 15120 has a firing member drive gear 15126 attached thereto that is configured for operable engagement with a distal rotary drive shaft assembly 15310 mounted within the elongate channel 15300. The distal rotary drive shaft assembly 15310 includes a proximal shaft end 15312 that has a firing member driven gear 15314 attached thereto. The proximal shaft end 15312 is rotatably supported in a proximal shaft bearing 15316 that is mounted in the proximal attachment portion 15302 of the channel 15300. See FIGS. 77 and 81. The distal rotary drive shaft assembly 15310 further includes a distal shaft end 15320 that is rotatably supported in a distal shaft bearing 15322 that is supported in a distal end 15306 of the channel 15300. See FIG. 78. A central portion 15330 of the distal rotary drive shaft assembly 15310 is threaded for threaded driving engagement with a threaded drive nut portion 15502 of the firing member 15500.

In one example, the firing member 15500 includes an upstanding body 15504 that extends upward from the threaded drive nut portion 15502 and has a tissue cutting surface 15506 formed thereon or attached thereto. In at least one embodiment, the firing member body 15504 has a sled assembly 15540 formed thereon or attached thereto. In other arrangements, the sled assembly may not be attached to the firing member 15500 but is configured to be driven distally through the surgical staple cartridge 15400 as the firing member 15500 is driven distally therethrough. The sled assembly 15540 includes a series of wedge-shaped cams 15542 that are configured to cammingly engage the staples 1126 or the drivers 15412 to cammingly drive the staples upward into forming contact with the staple forming undersurface 15220 on the anvil 15200. See FIG. 79. As can be seen in FIG. 77, for example, the staple forming undersurface 15220 comprises a series of staple forming pockets 15222 corresponding to each staple within the surgical staple cartridge 15400. As the staple legs contact the forming pockets, the staple is formed or closed. See e.g., the staples 1126' illustrated in FIG. 80. In the illustrated embodiment, the firing member driven gear 15314 is configured to meshingly engage the firing member drive gear 15126 on the proximal drive shaft 15120 when the channel 15300 is attached to the second channel mounting member 15152 of the shaft assembly 15100. Thus, rotation of the proximal drive shaft 15120 will result in rotation of the distal drive shaft assembly 15310. Rotation of the proximal drive shaft 15120 in a first rotary direction will cause the firing member 15500 to be driven distally within the channel 15300 and rotation of the proximal drive shaft 15120 in a second rotary direction will cause the firing member 15500 to be driven in a proximal direction within the channel 15300.

The firing member 15500 defines an I-beam like structure and includes a lower flanged portion 15560 that is formed from two laterally extending flanges 15562 that extend from the threaded drive nut portion 15502. In addition, the firing member includes an upper flanged portion 15564 that is formed from two laterally extending flanges 15566. The firing member body 15504 extends through an elongate channel slot 15301 in the elongate channel 15300, the elongate slot 15404 in the surgical staple cartridge 15400 and an anvil slot 15230 in the anvil 15200. For example, the firing member body 15504 extends through the centrally-disposed channel slot 15301 in the elongate channel 15300 such that the lower flanges 15562 are movably positioned within a passageway 15303 defined by the elongate channel 15300. In the embodiment depicted in FIG. 77, the bottom of the channel 15300 is open. A plate 15305 is attached thereto to provide added rigidity thereto. The plate 15305 has a series of windows 15307 therein to enable the surgeon to view therethrough the position of the firing member 15500 during firing and retraction.

In the illustrated embodiment, the anvil member 15200 is moved between an open position and closed positions by the firing member 15500. As indicated above, the firing member body 15504 extends through the elongate slot 15404 in the cartridge body. A top end 15505 of the firing member body 15504 is configured to extend into an anvil slot 15230 in the staple forming portion 15204 of the anvil body 15202. See FIG. 77. The top end 15505 extends through the anvil slot 15230 such that the upper flanges 15566 are movably positioned within a passageway 15232 (see FIG. 79) defined by the anvil 15200. For example, the passageway 15232 can be defined through the anvil 15200. The I-beam flanges 15562 and 15566 provide camming surfaces, which interact with the elongate channel 15300 and the anvil 15200, respectively, to open and clamp, or close, the jaws, as further described herein. Moreover, the firing member 15500 is configured to maintain a constant distance between the elongate channel 15300 and the anvil 15200 along the length of the end effector 1100.

At the outset of the firing stroke, the firing member 15500 is configured to move distally from an initial position. As the firing member 15500 moves distally, the anvil 15200 is pivoted toward a clamped configuration by the I-beam structure of the firing member 15500. More specifically, the lower flanges 15562 of the firing member 15500 move through the passageway 15303 defined by the elongate channel 15300 and the upper flanges 15566 move along a ramped surface 15234 of the anvil 15200 and then through the passageway 15232 defined by the anvil 15200.

Figure 79:
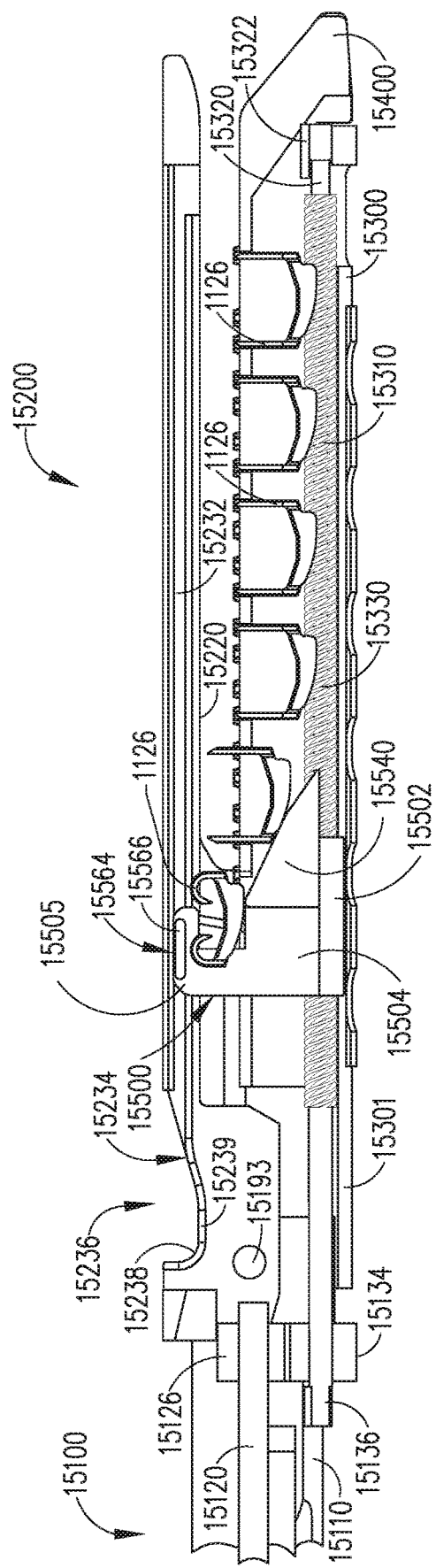
FIG. 79 is a partial cross-sectional elevational view of portions of the surgical instrument of FIGS. 75-78 with the channel thereof supporting a surgical staple cartridge therein and being attached to the shaft assembly, with an anvil thereof in a closed position and a firing member being distally advanced to fire staples within the surgical staple cartridge.
Figure 80:
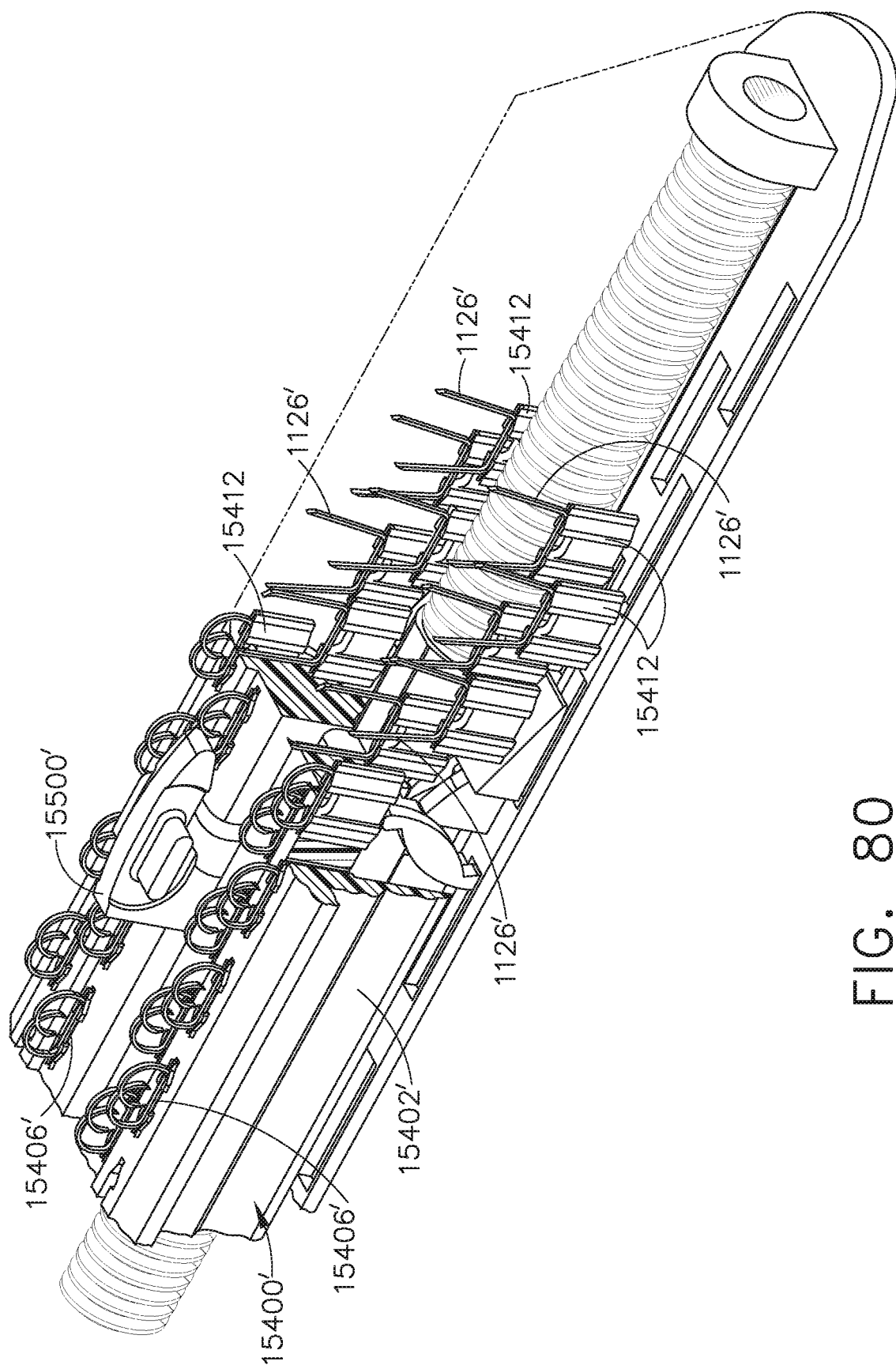
FIG. 80 is a partial perspective view of a portion of another surgical instrument embodiment.

Referring primarily to FIGS. 79 and 81, the ramped surface 15234 defines an open-close cavity 15236 in the anvil 15200 through which a portion of the firing member 15500 extends during a portion of the firing stroke. For example, the upper flanges 15566 protrude from the anvil 15200 via the open-close cavity 15236. The ramped surface 15234 slopes downward along a proximal opening surface 15238, extends along an intermediate portion 15239, and slopes upward along a distal closure ramp 15234. When the firing member 15500 is in an initial position or home position, the upper flanges 15566 are spaced apart from the intermediate portion 15239. In other words, the upper flanges 15566 are not cammingly engaged with the open-close cavity 15236. In the home position, the firing member 15500 can dwell with respect to the open-close cavity 15234 such that neither an opening force nor a closing force is applied to the anvil 15200 by the firing member 15500.

From the home position, the firing member 15500 can be retracted proximally. As the firing member 15500 continues to move proximally, the upper flanges 15566 of the firing member 15500, which are engaged with the proximal opening surface 15238, are configured to exert an opening force on the proximal opening surface 15238. As the upper flanges 15566 move against the proximal opening surface 15238, the proximal opening surface 15238 pivots, which causes the anvil 15200 to pivot open. As the upper flanges 15566 exert a downward force on the proximal opening surface 15238, the anvil 15200 is pushed upward by the leveraging action on the proximal opening surface 15238.

From the retracted position, the firing member 15500 can be advanced distally to return to the home position. To close the end effector, the firing member 15500 can be further advanced from the home position to an advanced position. For a portion of the firing motion intermediate the home position and the advanced position, the upper flanges 15566 are spaced apart from the ramped surface 15234. For example, the upper flanges 15566 hover or dwell above the intermediate portion 15239 as the firing member 15500 shifts between a closure motion and an opening motion. The dwell portion of the firing motion can be configured to prevent jamming of the opening and/or closing motions, for example.

As the firing member 15500 moves distally, the flanges 15566 contact the ramp surface 15234 to exert a downward force on the anvil 15200 to pivot it closed. As the firing member 15500 continues to move in the distal direction, the upper flanges 15566 move through the passageway 15232 to ensure a constant distance exists between the anvil 15200 and the elongate channel 15300 along the length of the end effector. For example, the passageway 15232 includes a lower ledge and an upper cap, which define the lower and upper limits of the passageway 15232. The upper flanges 15566 are constrained within those lower and upper limits during the firing stroke. The upper flanges 15566 can be dimensioned to fit snuggly within the confines of the passageway 15232. In other instances, as further described herein, the upper flanges 15566 can be configured to float and/or adjust vertically within the passageway 15232.

Figure 85:
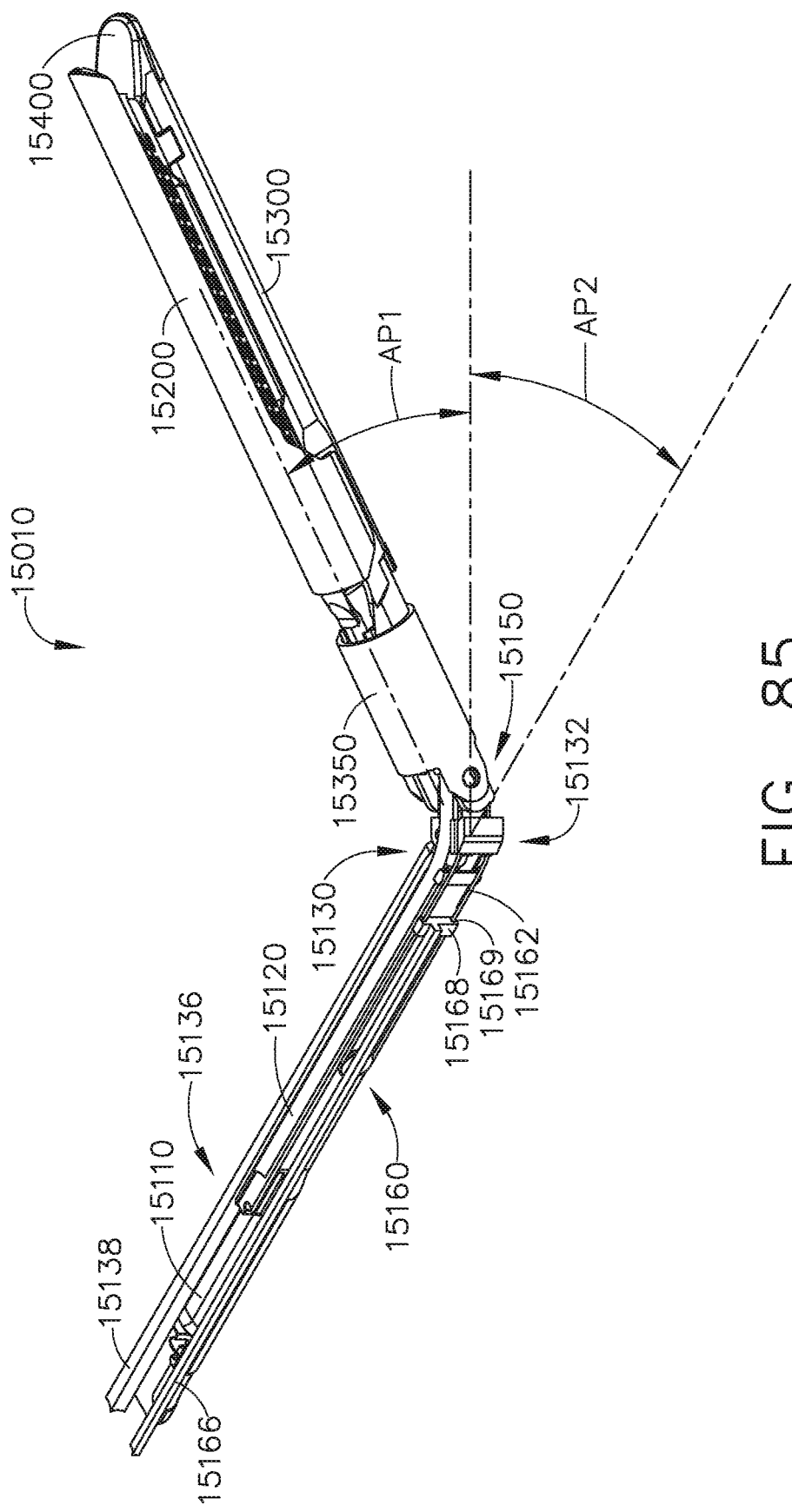
FIG. 85 is another perspective view of the surgical instrument of FIGS. 83 and 84 showing the end effector r articulated in the first and second articulation planes.
Figure 86:
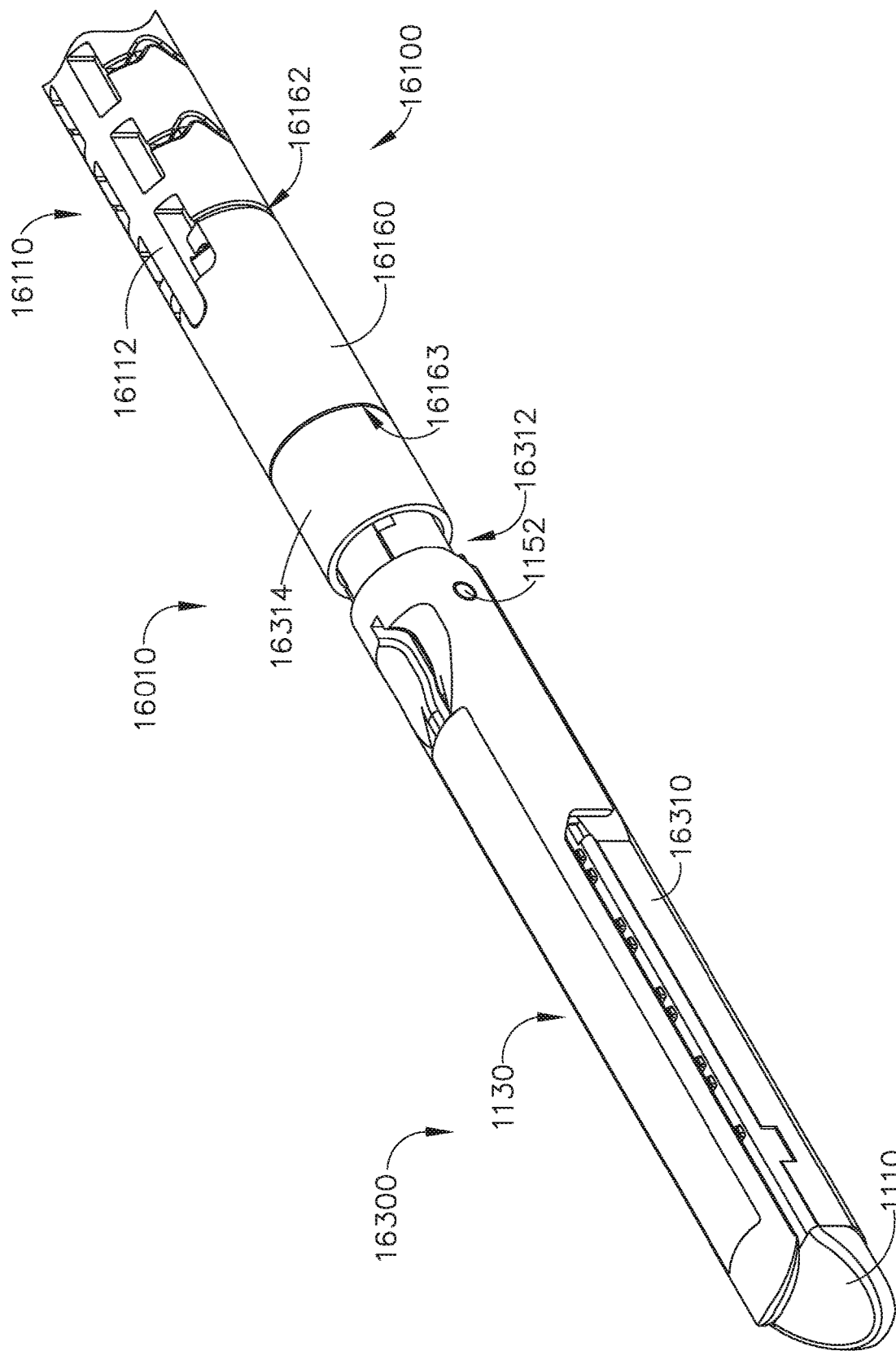
FIG. 86 is perspective view of a portion of another surgical instrument embodiment.

The firing member 15500 is a multi-function firing member. For example, the firing member 15500 is configured to drive the sled assembly 15540 to fire the staples 1126 from the surgical staple cartridge 15400, cut tissue clamped between the jaws 15200 and 15300, cam the jaw 15200 into a clamped configuration at the outset of the firing stroke, and cam the jaw 15200 into an open configuration at the completion of the firing stroke. The firing member 15500 can implement combination surgical functions with a single actuation system. As a result, the independent actuations systems required to fit within the footprint of the end effector may be minimized by the multi-function firing member 15500. In addition, the elongate channel and surgical staple cartridge 15400 can be replaced as a unit without detaching or replacing the anvil 15200. In alternative arrangements, the surgical staple cartridge 15400 may be replaced without replacing the elongate channel 15300 whether the elongate channel 15300 remains attached to the shaft assembly 15100 or has been detached therefrom. In addition, as can be seen in FIGS. 83-85, the elongate channel 15300, as well as the surgical staple cartridge 15400 and the anvil 15200, may be selectively pivoted in multiple articulation planes AP1, AP2 that are perpendicular to each other.

FIGS. 86-89 illustrate portions of another surgical instrument embodiment 16010 of the present invention. In the illustrated arrangement, the surgical instrument 16010 comprises a shaft assembly 16100 that may be operably coupled to a housing (not shown) in the form of a handle assembly or a portion of a robotic system. For example, the shaft assembly 16100 may be operably coupled to, or otherwise configured for use in connection with the various drive arrangements disclosed herein and/or in connection with the various handle assemblies, firing and articulation drive systems disclosed in U.S. Patent Application Publication No. 2015/0173789, entitled SURGICAL INSTRUMENTS WITH ARTICULATABLE SHAFT ARRANGEMENTS, the entire disclosure of which is hereby incorporated by reference herein.

As shown in FIGS. 86-89, the illustrated shaft assembly includes a flexible shaft portion 16110. The flexible shaft portion 16110 may be of the type and construction disclosed in greater detail in U.S. Patent Application Publication No. 2015/0173789. Thus, for the sake of brevity, specific details of the flexible shaft portion 16110 will not be discussed herein beyond what is necessary to understand the construction and operation of the surgical instrument 16010. In various arrangements, the flexible shaft portion 16110 may comprise a segment of the shaft assembly 16100 and be attached to, for example, an attachment stem portion (not shown) that is coupled to the housing (handle, robot system, etc.) as described in the aforementioned U.S. Patent Application or those interchangeable shaft arrangements disclosed herein. The flexible shaft portion 16110 may be fabricated from, for example, rigid thermoplastic polyurethane sold commercially as ISOPLAST grade 2510 by the Dow Chemical Company and include a centrally disposed, vertically extending articulation spine 16112. The articulation spine 16112 includes a centrally disposed component or knife slot 16114 for facilitating the passage of various control components therethrough. See FIG. 87. In the illustrated arrangement, the knife slot 16114 movably supports a central firing beam or bar 16200 therein. The flexible shaft portion 16110 further includes a plurality of right ribs 16116 and a plurality of left ribs 16118 that may be integrally-formed with, and laterally protrude from, the articulation spine 16112. The right and left ribs 16116, 16118 have an arcuate shape to provide the flexible shaft portion 16110 with a substantially-circular cross-sectional shape. Such shape may facilitate easy passage of the flexible shaft portion 16110 through a circular passage such as, for example, an appropriately sized trocar.

In various arrangements, each of the right ribs 16116 serves to define a right articulation passage for movably receiving a right articulation band 16120 therethrough. The right articulation band 16120 may extend through the right articulation passage and be coupled to a connector assembly 16150. For example, a distal end 16122 of the right articulation band 16120 may have a right hook portion 16124 that is adapted to be coupled to a right attachment portion 16152 of the connector assembly 16150. See FIG. 89. Similarly, each of the left ribs 16118 serves to define a left articulation passage for movably receiving a left articulation band 16130 therethrough. The left articulation band 16130 may extend through the left articulation passage and be coupled to the connector assembly 16150. For example, a distal end 16132 of the left articulation band 16130 may have a left hook portion 16134 that is adapted to be coupled to a left attachment portion 16154 of the connector assembly 16150. In the illustrated example, the right and left articulation bands 16120, 16130 operably interface with an articulation system in the handle or housing such as the one disclosed in, for example, U.S. Patent Application Publication No. 2015/0173789 or the articulation systems of the interchangeable shaft arrangements disclosed herein.

Figure 87:
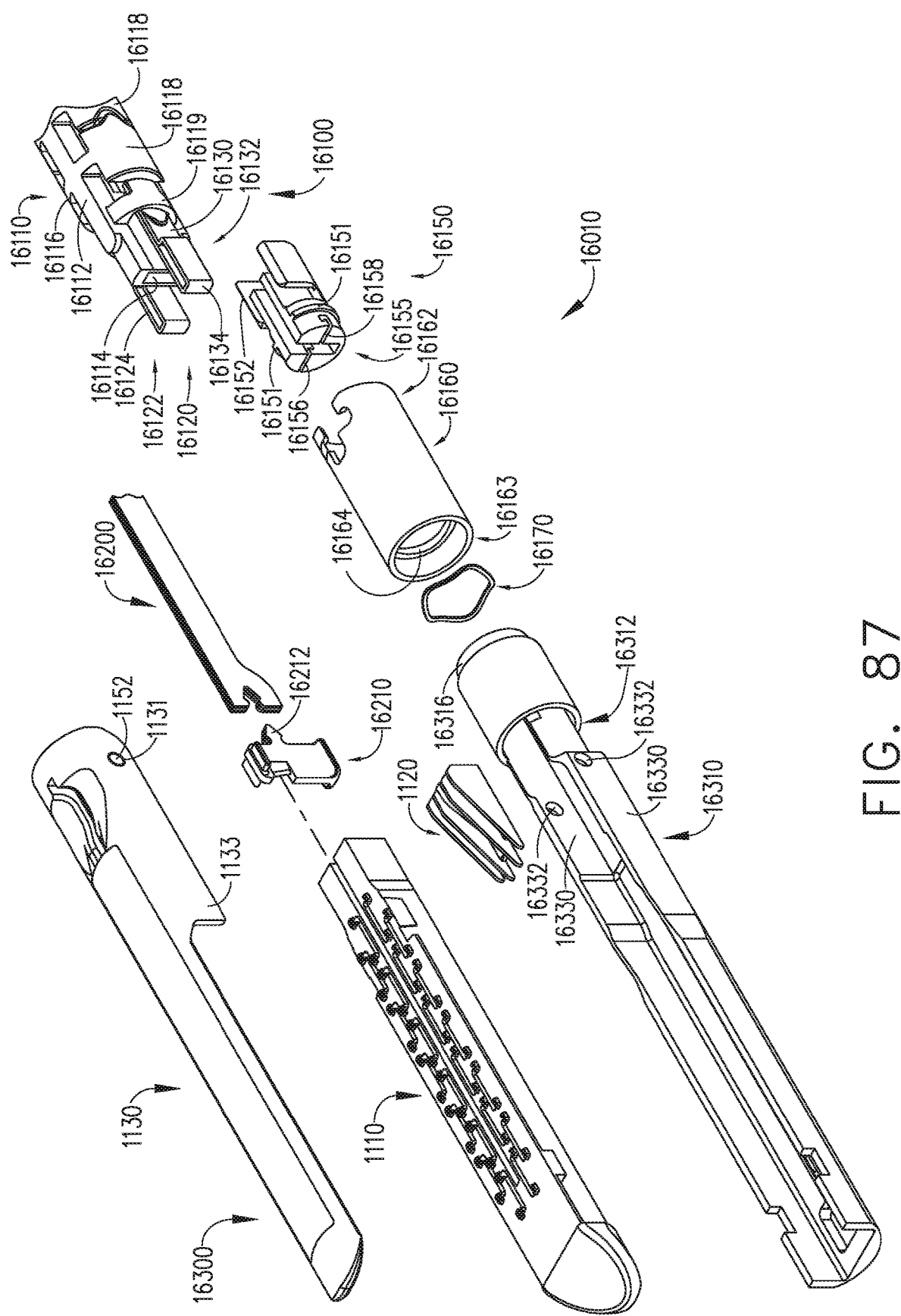
FIG. 87 is an exploded perspective assembly view of the surgical instrument portion of FIG. 86.
Figure 88:
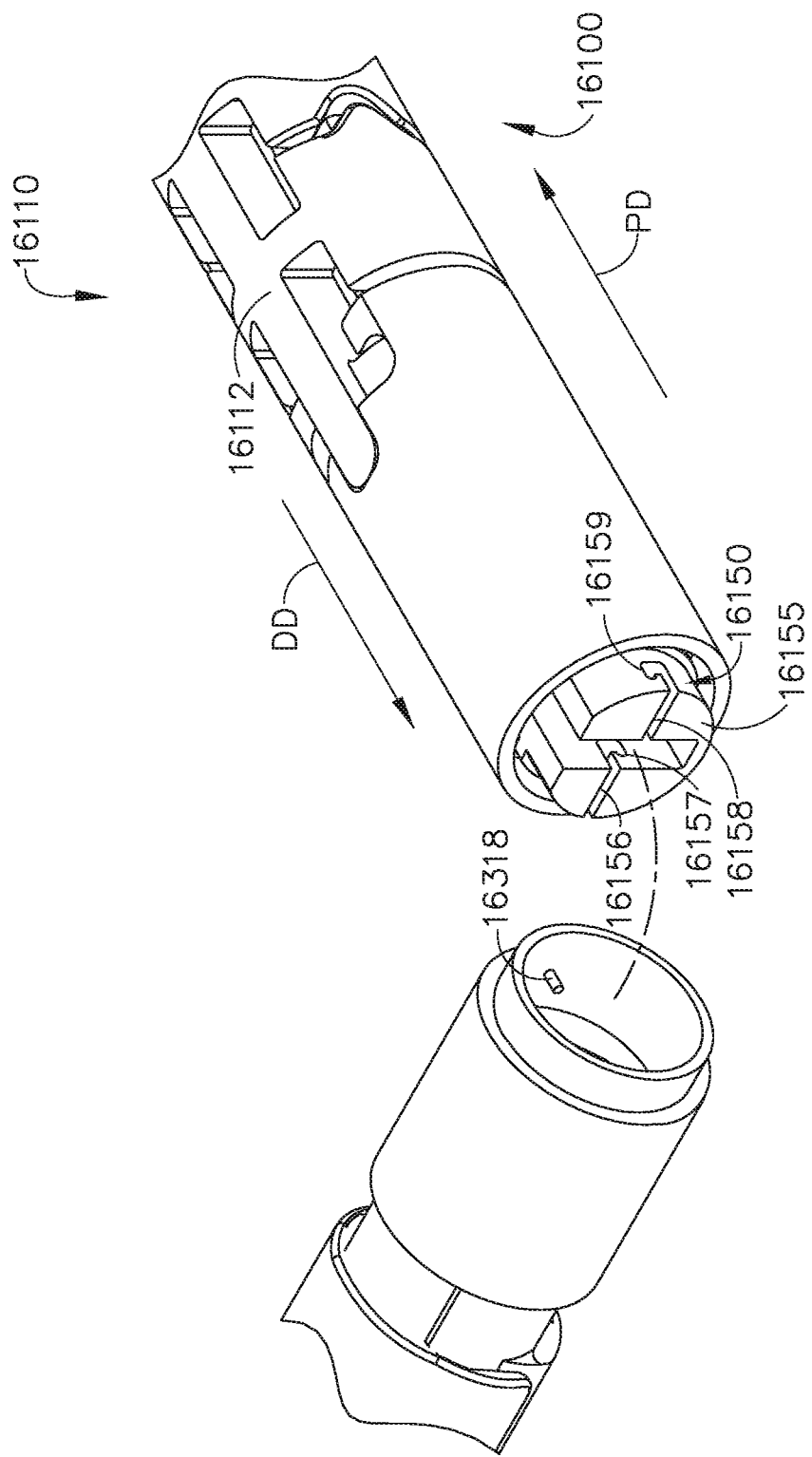
FIG. 88 is a perspective view of a coupler arrangement for removably coupling an end effector portion to a shaft assembly portion of the surgical instrument of FIGS. 86 and 87.
Figure 89:
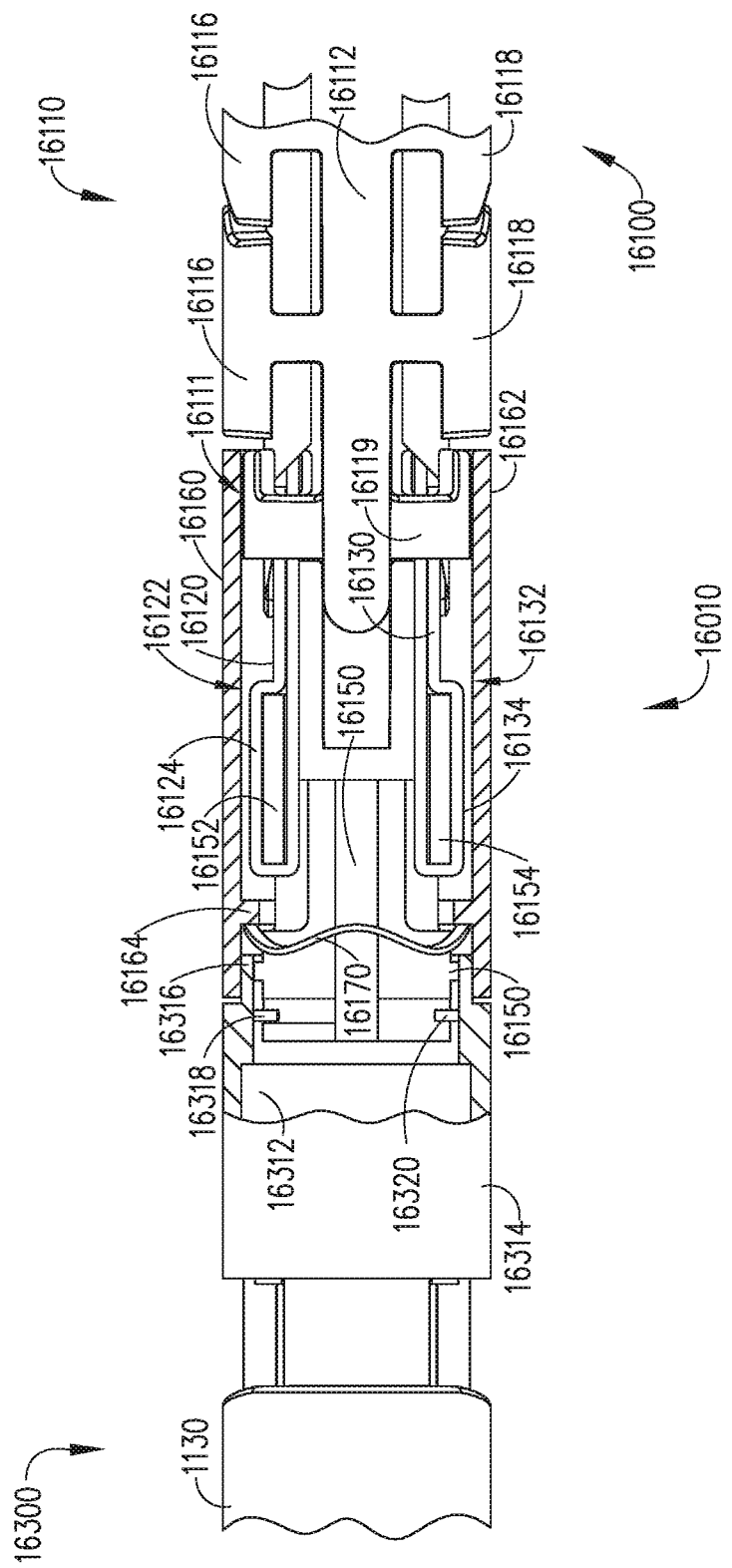
FIG. 89 is a top view of the end effector attached to the shaft assembly of FIGS. 86-88 with portions of the end effector and shaft assembly shown in cross-section for clarity.

Referring now to FIG. 87, in the illustrated example, the connector assembly 16150 has a proximal outer tube member 16160 mounted thereon. As can be seen in FIG. 89, the proximal outer tube member 16160 may have an outer diameter that is the same as the outer diameter of the flexible shaft portion 16110 to facilitate insertion thereof through a trocar cannula or other passage. An open proximal end 16162 is sized to be non-movably received on a distal mounting hub 16119 on a distal end 16111 of the flexible shaft portion 16110. The proximal outer tube member 16160 has an open distal end 16163 and an internal flange 16164 formed therein. As can be seen in FIG. 89, the right and left articulation bands 16120, 16130 are free to axially move within the proximal outer tube member 16160. The connector assembly 16150 is configured to facilitate quick attachment and detachment of a surgical end effector 16300 to the shaft assembly 16100.

In the illustrated example, the end effector 16300 comprises an elongate channel 16310 that is configured to operably support a surgical staple cartridge 1110 therein. The elongate channel 16310 may be substantially similar to the elongate channel 1102 described in detail above except that the elongate channel 16310 includes a proximal end portion 16312 that has a distal tube connector 16314 non-movably attached thereto. The distal tube connector 16314 protrudes proximally from the proximal end portion 16312 of the channel 16310 and includes a proximal mounting hub portion 16316 that is sized to be received within the opened distal end 16163 of the proximal outer tube member 16160. See FIG. 89. In addition, the distal tube connector 16314 includes a pair of diametrically opposed, inwardly extending bayonet pins 16318 and 16320. Bayonet pin 16318 is configured to be received within a corresponding slot 16156 in a distal end 16155 of the connector assembly 16150 and the bayonet pin 16320 is configured to be received within a corresponding slot 16158 in the distal end 16155 of the connector assembly 16150. See FIG. 88. In addition, a biasing member 16170 is received within the open distal end 16163 of the proximal outer tube member 16160 in butting engagement with the internal flange 16164. In the illustrated arrangement, for example, the biasing member 16170 comprises a wave spring. See FIGS. 87 and 89. To attach the surgical end effector 16300 to the shaft assembly 16100, the proximal mounting hub portion 16316 of the distal connector tube is inserted into the open distal end 16163 of the proximal outer tube member 16160 so that the bayonet pin 16318 is aligned with the slot 16156 in the connector assembly 16150 and the bayonet pin 16320 is aligned with the slot 16158. The end effector 16300 is then moved in the proximal direction PD and rotated about the shaft axis until the bayonet pin 16318 is seated in a retention groove 16157 in the connector assembly 16150 and the bayonet pin 16320 is seated in a retention groove 16159. See FIG. 88. The biasing member 16170 applies a biasing motion to the distal tube connector 16314 to retain the bayonet pins 16318, 16320 seated in their respective retention grooves 16157, 16159. To detach the end effector 16300 from the shaft assembly 16100, the user applies a force in the proximal direction to the surgical end effector 16300 to compress the biasing member 16170 and then rotates the surgical end effector 16300 in an opposite direction to unseat the bayonet pins 16318, 16320 from their respective retention grooves 16157, 16159 and then pulls the surgical end effector 16300 in the distal direction DD away from the connector assembly 16150.

In at least one embodiment, the surgical end effector 16300 includes an anvil 1130 as was described in detail above. The elongate channel 16310 includes upstanding side walls 16330 that each has a pin hole 16332 therein. See FIG. 87. The anvil 1130 is pivotally attached to the elongate channel 16310 by pivot pins 1152 that extend through apertures 1131 on each side of the anvil 1130 and into the pin holes 16332 in the manner discussed in detail above.

As can be seen in FIG. 87, the elongate channel 16310 is configured to operably support a staple cartridge 1110 therein. The surgical instrument 16010 also includes a firing member 16210 that is similar to firing member 1760 described above, except that the firing member 16210 is configured for quick axial attachment to and detachment from the firing beam 16200. The firing beam 16200 may be comprised of a plurality of laminated plates and be configured to sufficiently flex to accommodate articulation of the end effector relative to the shaft assembly. In the illustrated example, the firing member 16210 includes a proximally protruding coupler 16212 that is configured to be removably inserted into a corresponding retention cavity 16204 formed on a distal end 16202 of the firing beam 16200. In one arrangement, the coupler 16212 comprises a somewhat arrow-shaped member and the retention cavity 16204 is correspondingly shaped so as to retain the firing member in coupled engagement during normal operations (e.g., firing and retraction) of the surgical instrument 16010, yet facilitate detachment of the firing member 16210 from the firing beam 16200 when the surgical end effector 16300 is detached from the shaft assembly 16100. Actuation of the firing member 16210 otherwise facilitates opening and closing of the anvil 1130 in the various manners disclosed herein. Such arrangement facilitates easy attachment and detachment of the surgical end effector from the shaft assembly. Thus, such arrangement can serve to provide the user with a fresh (unused) firing member and tissue cutting surface as well as a new anvil and staple cartridge when the entire end effector is replaced. However, if desired, the user may simply replace the cartridge without replacing the entire end effector. The firing member 16210 is otherwise operated in a similar manner as firing member 1760 described above and serves to interact with sled 1120 in the manners described herein to eject staples from the staple cartridge 1110.

EXAMPLES

Example 1

An interchangeable surgical tool assembly, comprising an end effector, wherein the end effector comprises a sled and a cutting edge. The interchangeable tool assembly also comprises a firing bar operably configured to fire the sled and the cutting edge, wherein the firing bar comprises a distal engagement portion, and wherein the firing bar is movable from a first proximal position to a first distal position to a second proximal position to a second distal position. The interchangeable tool assembly further comprises a pusher assembly, wherein the pusher assembly comprises a plate comprising a proximal engagement portion, wherein the proximal engagement portion is selectively coupled to the distal engagement portion, and a spring configured to bias the proximal engagement portion laterally into engagement with the distal engagement portion when the firing bar is moved from the first distal position to the second proximal position.

Example 2

The interchangeable surgical tool assembly of Example 1, further comprising a firing member, wherein the firing bar is configured to push the firing member distally when the firing bar moves from the first proximal position to the first distal position.

Example 3

The interchangeable surgical tool assembly of Example 2, wherein the firing member comprises a first flange configured to engage a first jaw of the end effector, a second flange configured to engage a second jaw of the end effector, and a support portion extending between the first flange and the second flange. A notch is defined in the support portion, and the plate is configured to slide distally through the notch when the firing bar is moved from the second proximal position to the second distal position.

Example 4

The interchangeable surgical tool assembly of Example 3, wherein the plate comprises a spring-loaded catch configured to engage the support portion when the plate is retracted proximally by the firing bar.

Example 5

The interchangeable surgical tool assembly of Examples 1, 2, 3, or 4, wherein the first proximal position is distal to the second proximal position.

Example 6

The interchangeable surgical tool assembly of Examples 1, 2, 3, 4, or 5, wherein the first distal position is proximal to the second distal position.

Example 7

The interchangeable surgical tool assembly of Examples 1, 2, 3, 4, 5, or 6, wherein the cutting edge is integrally formed with the sled.

Example 8

The interchangeable surgical tool assembly of Examples 1, 2, 3, 4, 5, 6, or 7, wherein the proximal engagement portion comprises a t-shaped slot, and wherein the distal engagement portion comprises a key.

Example 9

An interchangeable surgical tool assembly comprising an end effector, wherein the end effector comprises a first jaw, a second jaw rotatably coupled to the first jaw; and a sled configured to translate relative to the first jaw and the second jaw. The interchangeable surgical tool assembly also comprises a firing member, wherein the firing member comprises a first flange configured to engage the first jaw, and a second flange configured to engage the second jaw. The interchangeable surgical tool assembly further comprises a pusher plate, and a firing bar selectively coupled to the pusher plate, wherein the firing bar is configured to move through a plurality of successive firing strokes. The plurality of successive firing strokes comprises a first distal firing stroke in which the firing bar is configured to push the firing member distally, and a first proximal firing stroke in which the firing bar is configured to retract proximally into engagement with the pusher plate. The plurality of successive firing strokes further comprises a second distal firing stroke in which the firing bar is configured to advance the pusher plate distally past the firing member, and a second proximal firing stroke in which the firing bar is configured to retract the pusher plate and the firing member proximally.

Example 10

The interchangeable surgical tool assembly of Example 9, wherein the firing member is configured to push the sled distally during the first distal firing stroke.

Example 11

The interchangeable surgical tool assembly of Examples 9 or 10, wherein the pusher plate is configured to push the sled distally during the second distal firing stroke.

Example 12

The interchangeable surgical tool assembly of Examples 9, 10, or 11, wherein the pusher plate comprises a leaf spring comprising an end, and wherein the end is configured to engage the firing member when the pusher plate is retracted proximally during the second proximal firing stroke.

Example 13

The interchangeable surgical tool assembly of Examples 9, 10, 11, or 12, wherein the sled comprises a cutting edge.

Example 14

The interchangeable surgical tool assembly of Example 13, further comprising a staple cartridge removably positioned in the first jaw, wherein the first jaw comprises a distal cavity configured to receive the cutting edge at the completion of the second distal firing stroke.

Example 15

The interchangeable surgical tool assembly of Example 9, further comprising a spring configured to bias the pusher plate laterally into engagement with the firing bar during the first proximal firing stroke.

Example 16

An interchangeable surgical tool assembly comprising an end effector, wherein the end effector comprises a first jaw comprising a proximal end, and a second jaw rotatably coupled to the first jaw. The interchangeable surgical tool assembly also comprises a distal mounting portion fixedly attached to the proximal end, and a proximal mounting portion rotatably attached to the distal mounting portion. The interchangeable surgical tool assembly also comprises a rotational bearing intermediate the proximal mounting portion and the distal mounting portion, and a rotational shaft extending from the distal mounting portion through the proximal mounting portion, wherein a rotation of the rotational shaft is configured to rotate the distal mounting portion. The interchangeable surgical tool assembly further comprises a flexible spine extending from the proximal mounting portion, wherein the flexible spine comprises a plurality of laterally-symmetrical vertebrae.

Example 17

The interchangeable surgical tool assembly of Example 16, further comprising a firing member configured to translate with the rotational shaft, wherein the firing member comprises a first flange configured to cammingly engage an open-close cavity in the first jaw, and a second flange configured to cammingly engage the second jaw.

Example 18

The interchangeable surgical tool assembly of Examples 16 or 17, wherein the rotational shaft comprises a plurality of perforations for permitting flexing of the rotational shaft within the flexible spine.

Example 19

The interchangeable surgical tool assembly of Examples 16, 17, or 18, wherein the flexible spine comprises a plurality of gaps positioned intermediate adjacent the laterally-symmetrical vertebrae.

Example 20

The interchangeable surgical tool assembly of Examples 16, 17, 18, or 19, wherein the flexible spine comprises an articulation head mounted to the proximal mounting portion, wherein the articulation head comprises a pair of attachment tabs, and a pair of flexible attachment bands extending distally to a respective attachment tab.

Example 21

A surgical instrument comprising a shaft assembly defining a shaft axis wherein the shaft assembly comprises a proximal articulation joint defining a first articulation axis that is transverse to the shaft axis, and a distal articulation joint defining a second articulation axis that is transverse to the shaft axis and the first articulation axis. The surgical instrument also comprises a drive shaft configured to transmit rotary drive motions from a source of rotary drive motions, and a movable anvil. The surgical instrument further comprises a channel that is configured to operably support a surgical staple cartridge therein, the channel being configured to be removably attached to the shaft assembly. The surgical instrument further comprises a firing member movably supported in the channel and configured to operably interface with the drive shaft when the channel is operably coupled to the shaft assembly, wherein the firing member is operably movable between a first proximal position, wherein the firing member applies an opening motion to the anvil, and closing positions wherein the firing member applies closing motions to the anvil.

Example 22

The surgical instrument of Example 21, wherein the channel is configured to be attached to the shaft assembly in an installation direction that is transverse to the shaft axis.

Example 23

The surgical instrument of Examples 21 or 22, wherein the shaft assembly further comprises a spine member and wherein the proximal articulation joint comprises a first channel mounting assembly pivotally coupled to the spine member for selective articulation relative thereto about the first articulation axis and wherein the distal articulation joint comprises a second channel mounting member pivotally coupled to the first channel mounting assembly for selective pivotal travel relative to the first channel mounting assembly about the second articulation axis.

Example 24

The surgical instrument of Examples 21, 22, or 23, further comprising a first articulation system operably interfacing with the first channel mounting assembly for selectively applying first articulation motions thereto, and a second articulation system operably interfacing with the second channel mounting member for selectively applying second articulation motions thereto.

Example 25

The surgical instrument of Example 24, wherein the first articulation system comprises a first axially movable articulation actuator operably coupled to the first channel mounting assembly and wherein the second articulation system comprises a second endless articulation member operably interfacing with the second channel mounting member and configured to apply the second articulation motions thereto as the second endless articulation member is rotated, and means for rotating the second articulation member.

Example 26

The surgical instrument of Example 25, wherein the means for rotating comprises a second axially movable articulation actuator operably interfacing with the second endless articulation member.

Example 27

The surgical instrument of Examples 21, 22, 23, 24, 25, or 26, wherein portions of the channel are configured to be slidably received within corresponding slots in the second channel mounting member.

Example 28

The surgical instrument of Examples 21, 22, 23, 24, 25, 26, or 27, wherein the portions of the channel are configured to be slidably inserted into the corresponding slots in the second channel mounting member in an installation direction that is transverse to the shaft axis.

Example 29

The surgical instrument of Examples 21, 22, 23, 24, 25, 26, 27, or 28, further comprising means for releasably retaining the portions of the channel in the corresponding slots.

Example 30

The surgical instrument of Example 29, wherein the means for releasably retaining comprises a lock member that is selectively axially movable between a locked position wherein the portions of the channel are retained within the corresponding slots and an unlocked position wherein the portions of the channel are removable from the corresponding slots in a removal direction that is opposite to the installation direction.

Example 31

The surgical instrument of Example 30, wherein the lock member is axially movable in locking directions that are transverse to the installation directions and the removal directions.

Example 32

A surgical instrument, comprising a shaft assembly wherein the shaft assembly comprises a spine member defining a shaft axis, a first channel mounting assembly movably coupled to the spine member for selective articulation relative thereto in a first articulation plane, and a second channel mounting member movably coupled to the first channel mounting assembly for selective articulation relative thereto in a second articulation plane that is perpendicular to the first articulation plane. The surgical instrument also comprises a flexible rotary drive shaft, and an anvil pivotally coupled to the second channel mounting member. The surgical instrument also comprises a channel that is configured to operably support a surgical staple cartridge therein, wherein the channel is configured to be removably detached from the second channel mounting member apart from the anvil. The surgical instrument further comprises a firing member movably supported in the channel and configured to operably interface with the flexible rotary drive shaft when the channel is operably coupled to the second channel mounting member, the firing member operably movable between a first proximal position wherein the firing member applies an opening motion to the anvil and closing positions wherein the firing member applies closing motions to the anvil.

Example 33

The surgical instrument of Example 32, wherein the firing member comprises a tissue cutting portion, and means for ejecting surgical staples from a surgical staple cartridge supported in the channel as the firing member is driven between the first proximal position and an ending position within the channel.

Example 34

The surgical instrument of Examples 32 or 33, wherein the channel is configured to be attached to the second channel mounting member in an installation direction that is transverse to the shaft axis.

Example 35

The surgical instrument of Examples 32, 33, or 34, wherein the shaft assembly further comprises a lock member movably supported on the spine member and being selectively axially movable thereon between a locked position wherein the channel is locked to the second channel mounting member and an unlocked position wherein the channel is detachable from the second channel mounting member.

Example 36

A surgical instrument, comprising a shaft assembly, wherein the shaft assembly comprises a spine assembly, and an axially movable firing bar. The surgical instrument also comprises a surgical end effector comprising a channel configured to operably support a surgical staple cartridge therein, wherein the channel is configured to be removably coupled to the spine assembly by a connector assembly. The surgical instrument further comprises a firing member supported for axial travel within a surgical staple cartridge supported within the channel. The firing member comprises a proximally protruding coupler sized to be removably inserted into a corresponding retention cavity formed in a distal end of the axially movable firing bar. The corresponding retention cavity is sized relative to the proximally protruding coupler to snappingly receive the proximally protruding coupler therein when the channel is removably coupled to the spine assembly.

Example 37

The surgical instrument of Example 36, wherein the connector assembly comprises a channel retainer operably coupled to the spine assembly, and a distal channel coupler comprising a pair of inwardly extending, diametrically opposed attachment pins configured to be axially inserted into corresponding coupling slots in the channel retainer that are transverse to the shaft axis.

Example 38

The surgical instrument of Examples 36 or 37, wherein the spine assembly comprises a flexible articulation segment movably coupled to the channel retainer.

Example 39

The surgical instrument of Example 38, wherein the channel retainer is movably coupled to the flexible articulation segment by at least one axially movable articulation bar that is movably supported by the flexible articulation segment.

Example 40

The surgical instrument of Examples 36, 37, 38 or 39, wherein the axially moving firing bar comprises a plurality of laminated plates.

Example 41

A surgical end effector, comprising a first jaw, a second jaw rotatably coupled to the first jaw, and a firing member configured to translate during a firing stroke, wherein the firing member comprises a notch. The surgical end effector further comprises a lockout spring comprising a hook, wherein the notch is aligned to receive the hook during the firing stroke unless an unfired staple cartridge is positioned in the first jaw, and wherein a sled assembly of the unfired staple cartridge is positioned to deflect the hook out of alignment with the notch.

Example 42

The surgical end effector of Example 41, wherein the lockout spring comprises a leaf spring. The leaf spring comprises a proximal portion fixed to the first jaw, and a distal portion comprising the hook.

Example 43

The surgical end effector of Examples 41 or 42, wherein the firing member comprises a cutting edge, an intermediate portion supporting the cutting edge, and a lug protruding laterally from the intermediate portion, wherein the notch is defined in the lug.

Example 44

The surgical end effector of Examples 41, 42 or 43, wherein the firing member further comprises a first flange configured to cammingly engage the first jaw, and a second flange configured to cammingly engage the second jaw.

Example 45

The surgical end effector of Examples 41, 42, 43, or 44, wherein the lockout spring is configured to prevent translation of the firing member distally past the hook unless the unfired staple cartridge is positioned in the first jaw.

Example 46

The surgical end effector of Examples 41, 42, 43, 44, or 45, wherein the first jaw comprises a cartridge support surface, wherein a recess is defined in the cartridge support surface, and wherein the hook is deflected at least partially into the recess when the unfired staple cartridge is positioned in the first jaw.

Example 47

The surgical end effector of Examples 41, 42, 43, 44, 45, or 46, wherein the lockout spring comprises a spring arm supporting the hook, and wherein the spring arm is laterally offset from the firing member.

Example 48

The surgical end effector of Examples 41, 42, 43, 44, 45, 46, or 47, wherein the lockout spring comprises a second hook, and wherein the firing member comprises a second notch aligned to receive the second hook during the firing stroke unless the unfired staple cartridge is positioned in the first jaw.

Example 49

A surgical end effector, comprising a first jaw, a second jaw rotatably coupled to the first jaw, and a firing member configured to translate during a firing stroke. The firing member comprises a laterally-protruding lug, and a lock defined in the laterally-protruding lug. The surgical end effector further comprises a lockout spring comprising a laterally-protruding tab, wherein the lock is positioned to receive the laterally-protruding tab during the firing stroke unless an unfired staple cartridge is positioned in the first jaw.

Example 50

The surgical end effector of Example 49, further comprising the unfired staple cartridge, comprising a sled assembly configured to translate distally during the firing stroke.

Example 51

The surgical end effector of Example 50, wherein the lock is configured to translate along a lock path during the firing stroke, and wherein the sled assembly in the unfired staple cartridge is configured to deflect the laterally-protruding tab out of the lock path.

Example 52

The surgical end effector of Examples 49, 50, or 51, wherein the first jaw comprises a cartridge support surface, wherein a recess is defined in the cartridge support surface, and wherein the laterally-protruding tab is deflected into the recess when the unfired staple cartridge is positioned in the first jaw.

Example 53

The surgical end effector of Examples 49, 50, 51, or 52, wherein the lockout spring comprises a leaf spring. The leaf spring comprises a first portion fixed to the first jaw, a second portion supporting the laterally-protruding tab, and a spring arm extending intermediate the first portion and the second portion, wherein the spring arm is laterally offset from the firing member.

Example 54

The surgical end effector of Examples 49, 50, 51, 52, or 53, wherein the firing member further comprises a support comprising a cutting edge. The firing member further comprises a first flange extending from the support, wherein the first flange is configured to cammingly engage the first jaw, and a second flange extending from the support, wherein the second flange is configured to cammingly engage the second jaw.

Example 55

The surgical end effector of Examples 49, 50, 51, 52, 53, or 54, wherein the firing member further comprises a second laterally-protruding lug and a second lock defined in the second laterally-protruding lug, wherein the lockout spring further comprises a second laterally-protruding tab, and wherein the second lock is positioned to receive the second laterally-protruding tab during the firing stroke unless the unfired staple cartridge is positioned in the first jaw.

Example 56

A surgical end effector comprising a first jaw, a second jaw rotatably coupled to the first jaw, and a lockout arrangement. The lockout arrangement comprises a lock configured to translate along a lock path during a firing stroke, and a lockout spring comprising an inwardly-protruding tab, wherein the lock is positioned to receive the inwardly-protruding tab during the firing stroke unless an unfired staple cartridge is positioned in the first jaw.

Example 57

The surgical end effector of Example 56, further comprising the unfired staple cartridge, wherein the unfired staple cartridge comprises a sled assembly configured to translate distally during the firing stroke, wherein the lock is configured to translate along a lock path during the firing stroke, and wherein the sled assembly in the unfired staple cartridge is configured to deflect the inwardly-protruding tab out of the lock path.

Example 58

The surgical end effector of Examples 56 or 57, wherein the first jaw comprises a cartridge support surface, wherein a recess is defined in the cartridge support surface, and wherein the inwardly-protruding tab is deflected into the recess when the unfired staple cartridge is positioned in the first jaw.

Example 59

The surgical end effector of Examples 56, 57, or 58, wherein the lockout spring comprises a leaf spring. The leaf spring comprises a first portion fixed to the first jaw, and a second portion supporting the laterally-protruding tab. The leaf spring further comprises a spring arm extending intermediate the first portion and the second portion, wherein the spring arm is laterally offset from the firing member.

Example 60

The surgical end effector of Examples 56, 57, 58, or 59, further comprising a firing member, wherein the firing member comprises a support comprising a cutting edge and the lock. The firing member further comprises a first flange extending from the support, wherein the first flange is configured to cammingly engage the first jaw, and a second flange extending from the support, wherein the second flange is configured to cammingly engage the second jaw.

Example 61

A surgical end effector comprising a first jaw, a second jaw comprising a closure surface and an opening surface, and a pivot joint, wherein the second jaw is configured to pivot relative to the first jaw at the pivot joint, wherein the closure surface is positioned distal to the pivot joint and wherein the opening surface is positioned proximal to the pivot joint. The surgical end effector further comprises a firing member configured to move distally during a firing stroke. The firing member comprises a first flange positioned to engage the first jaw, and a second flange positioned to engage the second jaw, wherein the second flange is configured to engage the closure surface to pivot the second jaw toward a closed position, and wherein the second flange is configured to engage the opening surface to pivot the second jaw toward an open position.

Example 62

The surgical end effector of Example 61, wherein the firing member is movable distally from a home position to pivot the second jaw toward the closed position, and wherein the firing member is movable proximally from the home position to pivot the second jaw toward the open position.

Example 63

The surgical end effector of Examples 61 or 62, wherein the second jaw comprises an intermediate surface between the closure surface and the opening surface, and wherein the second flange is spaced apart from the intermediate surface when the firing member is in the home position.

Example 64

The surgical end effector of Examples 61, 62, or 63, wherein the firing member further comprises a knife intermediate the first flange and the second flange.

Example 65

The surgical end effector of Examples 61, 62, 63, or 64, wherein the first jaw is configured to receive a staple cartridge.

Example 66

The surgical end effector of Examples 61, 62, 63, 64, or 65, wherein the second jaw comprises a staple-forming anvil.

Example 67

The surgical end effector of Examples 61, 62, 63, 64, 65, or 66, wherein the first jaw comprises a first passageway for the first flange, and wherein the second jaw comprises a second passageway for the second flange.

Example 68

The surgical end effector of Examples 61, 62, 63, 64, 65, 66, or 67, further comprising a spring configured to bias the second jaw toward the open position when the firing member is proximal to a home position.

Example 69

A surgical end effector comprising a first jaw, a second jaw comprising a closure surface and an opening surface, and a pivot joint, wherein the second jaw is configured to pivot relative to the first jaw at the pivot joint. The surgical end effector further comprises a firing member configured to move distally from a home position during a firing stroke. The firing member comprises a first flange positioned to engage the first jaw, and a second flange positioned to engage the second jaw, wherein the second flange is configured to engage the closure surface when the firing member is moved distally from the home position, and wherein the second flange is configured to engage the opening surface when the firing member is moved proximally from the home position.

Example 70

The surgical end effector of Example 69, wherein the second flange is configured to engage the closure surface to pivot the second jaw toward a closed position, and wherein the second flange is configured to engage the opening surface to pivot the second jaw toward an open position.

Example 71

The surgical end effector of Examples 69 or 70, wherein the second jaw comprises an intermediate surface between the closure surface and the opening surface, and wherein the second flange is spaced apart from the intermediate surface when the firing member is in the home position.

Example 72

The surgical end effector of Examples 69, 70, or 71, wherein the firing member further comprises a knife intermediate the first flange and the second flange.

Example 73

The surgical end effector of Examples 69, 70, 71, or 72, wherein the first jaw is configured to receive a staple cartridge.

Example 74

The surgical end effector of Examples 69, 70, 71, 72, or 73, wherein the second jaw comprises an anvil.

Example 75

The surgical end effector of Examples 69, 70, 71, 72, 73, or 74, wherein the first jaw comprises a first passageway for the first flange, and wherein the second jaw comprises a second passageway for the second flange.

Example 76

The surgical end effector of Examples 69, 70, 71, 72, 73, 74, or 75, further comprising a spring configured to bias the second jaw away from the first jaw when the firing member is in the home position.

Example 77

A surgical end effector, comprising a first jaw, a second jaw comprising a first camming means and a second camming means, and a pivot joint, wherein the second jaw is configured to pivot relative to the first jaw at the pivot joint. The surgical end effector further comprises a firing member configured to move distally from a home position during a firing stroke. The firing member comprises a first flange positioned to engage the first jaw, and a second flange positioned to engage the second jaw, wherein the second flange is configured to engage the first camming means when the firing member is moved distally from the home position, and wherein the second flange is configured to engage the second camming means when the firing member is moved proximally from the home position.

Example 78

The surgical end effector of Example 77, wherein the first camming means is configured to cam the second jaw toward a closed position, and wherein the second camming means is configured to cam the second jaw toward an open position.

Example 79

The surgical end effector of Examples 77 or 78, wherein the first camming means comprises a distal closure ramp extending upward from an intermediate surface into a passageway in the second jaw, and wherein the second camming means comprises a proximal closure surface extending upward from the intermediate surface.

Example 80

The surgical end effector of Examples 77, 78, or 79, wherein the home position comprises a range of positions.

Example 81

A surgical end effector comprising a first jaw, a second jaw rotatably coupled to the first jaw, and a lockout arrangement configured to prevent rotational movement of the second jaw toward the first jaw unless an unfired staple cartridge is positioned in the first jaw, wherein the lockout arrangement comprises a pivotable lock configured to pivot between a locked orientation and an unlocked orientation. The pivotable lock comprises a first leg configured to engage the second jaw when the pivotable lock is in the locked orientation, and a second leg configured to engage the unfired staple cartridge when the unfired staple cartridge is positioned in the first jaw.

Example 82

The surgical end effector of Example 81, further comprising a spring comprising a distal end, wherein the distal end is engaged with the pivotable lock, and wherein the spring is configured to bias the pivotable lock toward the locked orientation.

Example 83

The surgical end effector of Example 82, wherein the spring comprises a leaf spring.

Example 84

The surgical end effector of Examples 81, 82, or 83, wherein the pivotable lock comprises a third leg, and wherein the distal end is positioned against the third leg.

Example 85

The surgical end effector of Examples 81, 82, 83, or 84, wherein a lockout notch is defined in the first jaw, and wherein the second leg is positioned at least partially in the lockout notch when the pivotable lock is in the unlocked orientation.

Example 86

The surgical end effector of Examples 81, 82, 83, 84, or 85, wherein the first jaw comprises an elongate channel, wherein the second jaw comprises an anvil comprising an inner rail extending into the elongate channel, and wherein an end portion of the first leg abuts the inner rail when the pivotable lock is in the locked orientation.

Example 87

The surgical end effector of Examples 81, 82, 83, 84, 85, or 86, wherein the lockout arrangement comprises a second pivotable lock.

Example 88

The surgical end effector of Examples 81, 82, 83, 84, 85, 86, or 87, further comprising the unfired staple cartridge comprising a sled assembly, wherein the sled assembly is configured to engage the second leg when the sled assembly is in a pre-fired position.

Example 89

An interchangeable surgical tool assembly comprising an end effector configured to receive a staple cartridge, and a shaft. The shaft comprises a firing assembly, wherein the firing assembly comprises a distal portion, a proximal portion comprising a notch, and a spring intermediate the proximal portion and the distal portion. The shaft further comprises a lockout lever movable between an unlocked orientation and a locked orientation, wherein the lockout lever extends into the notch when the lockout lever is in the locked orientation, and wherein a displacement of the distal portion of the firing assembly is configured to move the lockout lever to the unlocked orientation.

Example 90

The interchangeable surgical tool assembly of Example 89, further comprising the staple cartridge, wherein the staple cartridge comprises a proximal end, a longitudinal slot extending distally from the proximal end, and a frangible gate extending across the longitudinal slot at the proximal end. The frangible gate is configured to shift the distal portion of the firing assembly proximally when the staple cartridge is installed in the end effector.

Example 91

The interchangeable surgical tool assembly of Examples 89 or 90, wherein the spring is configured to compress between the proximal portion and the distal portion when the staple cartridge is installed in the end effector.

Example 92

The interchangeable surgical tool assembly of Examples 89, 90, or 91, wherein the distal portion comprises a proximally-extending wedge configured to move the lockout lever to the unlocked orientation when the distal portion is shifted proximally.

Example 93

The interchangeable surgical tool assembly of Examples 90, 91, or 92, wherein the staple cartridge comprises a cartridge body comprising a cutout, and wherein the frangible gate comprises a first end pivotably coupled to the cartridge body, and a second end friction-fit in the cutout.

Example 94

The interchangeable surgical tool assembly of Examples 90, 91, 92, or 93, wherein the firing assembly is configured to break the frangible gate during a firing stroke.

Example 95

The interchangeable surgical tool assembly of Examples 89, 90, 91, 92, 93, or 94, wherein the shaft further comprises a reset spring configured to bias the lockout lever toward the locked orientation.

Example 96

The interchangeable surgical tool assembly of Examples 89, 90, 91, 92, 93, 94, or 95, wherein the distal portion of the firing assembly is advanced from a pre-fired proximal position to a distal position during a firing stroke and is retracted from the distal position to a post-fired proximal position after the firing stroke, and wherein the post-fired proximal position is distal to the pre-fired proximal position.

Example 97

A surgical end effector comprising a first jaw, and a second jaw rotatably coupled to the first jaw, wherein the second jaw comprises a pin movable between a locked configuration and an unlocked configuration. The surgical end effector further comprises a lockout arrangement configured to prevent rotational movement of the second jaw toward the first jaw unless a staple cartridge is positioned in the first jaw, wherein the lockout arrangement comprises a lock bar configured to translate within the first jaw from a distal position to a proximal position when the staple cartridge is positioned in the first jaw, and wherein the lock bar is configured to move the pin to the unlocked configuration when the lock bar moves to the proximal position.

Example 98

The surgical end effector of Example 97, further comprising a spring extending between the first jaw and the second jaw, wherein the spring is configured to bias the second jaw toward the first jaw.

Example 99

The surgical end effector of Example 98, wherein the first jaw comprises a contoured slot, wherein the pin is configured to move along the contoured slot when the second jaw rotates toward the first jaw, wherein the first jaw further comprises a lockout notch extending from the contoured slot, and wherein the spring biases the pin into the lockout notch.

Example 100

The surgical end effector of Examples 97, 98, or 99, wherein the pin comprises a semicircular perimeter.

Example 101

A surgical end effector comprising a first jaw, a second jaw, and a firing member configured to translate relative to the first jaw and the second jaw during a firing stroke. The firing member comprises a support portion comprising a slot, a first flange extending from the support portion, wherein the first flange is configured to engage the first jaw during the firing stroke. The firing member further comprises a second flange positioned in the slot, wherein the second flange is configured to engage the second jaw during the firing stroke, and wherein the second flange is configured to move in the slot away from the first flange when a threshold force is applied to the second flange.

Example 102

The surgical end effector of Example 101, wherein the slot comprises a wedge-shaped slot.

Example 103

The surgical end effector of Examples 101 or 102, wherein the slot comprises a proximal end and a distal end, and wherein the second flange is friction-fit in the distal end of the slot.

Example 104

The surgical end effector of Example 103, wherein the threshold force is configured to overcome the friction securing the second flange in the distal end.

Example 105

The surgical end effector of Examples 101, 102, 103, or 104, wherein the slot comprises a contoured upper edge, and wherein the second flange is configured to slide along the contoured upper edge when the threshold force is applied to the second flange.

Example 106

The surgical end effector of Examples 101, 102, 103, 104, or 105, wherein the second flange comprises a groove aligned with the slot.

Example 107

The surgical end effector of Examples 101, 102, 103, 104, 105, or 106, wherein the firing member further comprises a guide secured to the second flange.

Example 108

The surgical end effector of Examples 101, 102, 103, 104, 105, 106, or 107, wherein the second jaw is rotatably coupled to the first jaw.

Example 109

A surgical end effector comprising a first jaw, a second jaw, and a firing member configured to translate relative to the first jaw and the second jaw during a firing stroke. The firing member comprises a fixed flange configured to engage the first jaw during the firing stroke, a floating flange configured to engage the second jaw during the firing stroke, and a spring configured to bias the floating flange toward a first position.

Example 110

The surgical end effector of Example 109, wherein a slot is defined in the firing member, and wherein the floating flange is configured to slide along the slot when a threshold force is applied to the floating flange.

Example 111

The surgical end effector of Example 110, wherein the slot comprises a proximal end, a distal end, wherein the distal end is closer to the fixed flange than the proximal end, and an upper edge extending from the proximal end to the distal end.

Example 112

The surgical end effector of Example 111, wherein the first position is adjacent to the distal end.

Example 113

The surgical end effector of Examples 111 or 112, wherein the spring comprises a coil spring extending between the floating flange and the proximal end of the slot.

Example 114

The surgical end effector of Examples 110, 111, 112, or 113, wherein the floating flange comprises a groove aligned with the slot.

Example 115

The surgical end effector of Examples 109, 110, 111, 112, 113, or 114, wherein the firing member further comprises a guide.

Example 116

A surgical end effector comprising a first jaw, a second jaw, and a firing member configured to translate relative to the first jaw and the second jaw during a firing stroke. The firing member comprises a fixed flange configured to engage the first jaw during the firing stroke, and a compliant portion comprising a floating flange, wherein the floating flange is configured to engage the second jaw during the firing stroke.

Example 117

The surgical end effector of Example 116, wherein the compliant portion is comprised of nitinol.

Example 118

The surgical end effector of Examples 116 or 117, wherein a cutout is defined in the firing member, and wherein the compliant portion is embedded in the cutout.

Example 119

The surgical end effector of Example 118, wherein the cutout comprises a lower portion, and wherein the compliant portion comprises a foot positioned in the lower portion.

Example 120

The surgical end effector of Examples 116, 117, 118, or 119, wherein the floating flange is configured to move away from the fixed flange when a threshold force is applied to the floating flange.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical end effector, comprising:
   a first jaw;
   a second jaw rotatably coupled to said first jaw;
   a firing member configured to translate along an axis during a firing stroke, wherein said firing member comprises a notch defined laterally into said firing member toward the axis; and
   a lockout spring comprising a hook, wherein said notch is aligned to receive said hook during the firing stroke unless an unfired staple cartridge is positioned in said first jaw, wherein said firing member applies a tensile force on said lockout spring when said firing stroke is initiated and said hook is received by said notch, and wherein a sled assembly of the unfired staple cartridge is positioned to deflect said hook out of alignment with said notch.

2. The surgical end effector of claim 1, wherein said lockout spring comprises a leaf spring comprising:
   a proximal portion fixed to said first jaw; and
   a distal portion comprising said hook.

3. The surgical end effector of claim 1, wherein said firing member comprises:
   a cutting edge;
   an intermediate portion supporting said cutting edge; and
   a lug protruding laterally from said intermediate portion, wherein said notch is defined in said lug.

4. The surgical end effector of claim 3, wherein said firing member further comprises:
   a first flange configured to cammingly engage said first jaw; and
   a second flange configured to cammingly engage said second jaw.

5. The surgical end effector of claim 4, wherein said lockout spring is configured to prevent translation of said firing member distally past said hook unless the unfired staple cartridge is positioned in said first jaw.

6. The surgical end effector of claim 1, wherein said first jaw comprises a cartridge support surface, wherein a recess is defined in said cartridge support surface, and wherein said hook is deflected at least partially into said recess when the unfired staple cartridge is positioned in said first jaw.

7. The surgical end effector of claim 1, wherein said lockout spring comprises a spring arm supporting said hook, and wherein said spring arm is laterally offset from said firing member.

8. The surgical end effector of claim 1, wherein said lockout spring comprises a second hook, and wherein said firing member comprises a second notch aligned to receive said second hook during the firing stroke unless the unfired staple cartridge is positioned in said first jaw.

9. A surgical end effector, comprising:
   a first jaw;
   a second jaw rotatably coupled to said first jaw;
   a firing member configured to translate along an axis during a firing stroke, wherein said firing member comprises:

a laterally-protruding lug; and
a lock defined in said laterally-protruding lug; and
a lockout spring comprising a laterally-protruding tab, wherein said laterally-protruding tab protrudes laterally relative to the axis, wherein said lock is positioned to receive said laterally-protruding tab during the firing stroke unless an unfired staple cartridge is positioned in said first jaw, and wherein said firing member applies a tensile force on said lockout spring when said firing stroke is initiated and said laterally-protruding tab is received by said lock.

10. The surgical end effector of claim 9, further comprising said unfired staple cartridge comprising a sled assembly configured to translate distally during the firing stroke.

11. The surgical end effector of claim 10, wherein said lock is configured to translate along a lock path during the firing stroke, and wherein said sled assembly in said unfired staple cartridge is configured to deflect said laterally-protruding tab out of said lock path.

12. The surgical end effector of claim 11, wherein said first jaw comprises a cartridge support surface, wherein a recess is defined in said cartridge support surface, and wherein said laterally-protruding tab is deflected into said recess when the unfired staple cartridge is positioned in said first jaw.

13. The surgical end effector of claim 9, wherein said lockout spring comprises a leaf spring comprising:
a first portion fixed to said first jaw;
a second portion supporting said laterally-protruding tab; and
a spring arm extending intermediate said first portion and said second portion, wherein said spring arm is laterally offset from said firing member.

14. The surgical end effector of claim 9, wherein said firing member further comprises:
a support comprising a cutting edge;
a first flange extending from said support, wherein said first flange is configured to cammingly engage said first jaw; and
a second flange extending from said support, wherein said second flange is configured to cammingly engage said second jaw.

15. The surgical end effector of claim 9, wherein said firing member further comprises a second laterally-protruding lug and a second lock defined in said second laterally-protruding lug, wherein said lockout spring further comprises a second laterally-protruding tab, and wherein said second lock is positioned to receive said second laterally-protruding tab during the firing stroke unless the unfired staple cartridge is positioned in said first jaw.

16. A surgical end effector, comprising:
a first jaw;
a second jaw rotatably coupled to said first jaw; and
a lockout arrangement, comprising:
a lock configured to translate along a lock path during a firing stroke; and
a lockout spring comprising an inwardly-protruding tab, wherein said inwardly-protruding tab protrudes inwardly toward the lock path, wherein said lock is positioned to receive said inwardly-protruding tab during the firing stroke unless an unfired staple cartridge is positioned in said first jaw, and wherein said lockout spring is under tension when said firing stroke is initiated and said inwardly-protruding tab is received by said lock.

17. The surgical end effector of claim 16, further comprising said unfired staple cartridge comprising a sled assembly configured to translate distally during the firing stroke, wherein said lock is configured to translate along a lock path during the firing stroke, and wherein said sled assembly in said unfired staple cartridge is configured to deflect said inwardly-protruding tab out of said lock path.

18. The surgical end effector of claim 17, wherein said first jaw comprises a cartridge support surface, wherein a recess is defined in said cartridge support surface, and wherein said inwardly-protruding tab is deflected into said recess when said unfired staple cartridge is positioned in said first jaw.

19. The surgical end effector of claim 16, wherein said lockout spring comprises a leaf spring comprising:
a first portion fixed to said first jaw;
a second portion supporting said inwardly-protruding tab; and
a spring arm extending intermediate said first portion and said second portion, wherein said spring arm is laterally offset from a firing member.

20. The surgical end effector of claim 16, further comprising a firing member comprising:
a support comprising a cutting edge and said lock;
a first flange extending from said support, wherein said first flange is configured to cammingly engage said first jaw; and
a second flange extending from said support, wherein said second flange is configured to cammingly engage said second jaw.

* * * * *